United States Patent
Gurney

(10) Patent No.: US 10,232,017 B2
(45) Date of Patent: Mar. 19, 2019

(54) METHOD OF TREATING CANCER BY ADMINISTERING TUMOR NECROSIS FACTOR RECEPTOR LIGAND SUPERFAMILY (TNFRSF) SINGLE-CHAIN POLYPEPTIDES

(71) Applicant: OncoMed Pharmaceuticals, Inc., Redwood City, CA (US)

(72) Inventor: Austin L Gurney, San Francisco, CA (US)

(73) Assignee: ONCOMED PHARMACEUTICALS, INC., Redwood City, CA (US)

(*) Notice: Subject to any disclaimer, the term of this patent is extended or adjusted under 35 U.S.C. 154(b) by 0 days.

(21) Appl. No.: 15/636,711

(22) Filed: Jun. 29, 2017

(65) Prior Publication Data

US 2018/0021407 A1 Jan. 25, 2018

Related U.S. Application Data

(62) Division of application No. 15/014,134, filed on Feb. 3, 2016, now Pat. No. 9,724,390.

(60) Provisional application No. 62/259,129, filed on Nov. 24, 2015, provisional application No. 62/218,956, filed on Sep. 15, 2015, provisional application No. 62/154,008, filed on Apr. 28, 2015, provisional application No. 62/153,272, filed on Apr. 27, 2015, provisional application No. 62/111,404, filed on Feb. 3, 2015.

(51) Int. Cl.
| | | |
|---|---|---|
| *A61K 38/19* | (2006.01) | |
| *C12Q 1/68* | (2018.01) | |
| *C07K 14/00* | (2006.01) | |
| *C07K 14/52* | (2006.01) | |
| *C07K 16/18* | (2006.01) | |
| *C12N 15/00* | (2006.01) | |
| *C12N 15/62* | (2006.01) | |
| *C07K 14/525* | (2006.01) | |
| *C07K 14/715* | (2006.01) | |
| *A61K 39/395* | (2006.01) | |
| *A61K 45/06* | (2006.01) | |
| *A61K 39/00* | (2006.01) | |
| *A61K 39/295* | (2006.01) | |

(52) U.S. Cl.
CPC ........ *A61K 38/19* (2013.01); *A61K 39/39558* (2013.01); *A61K 45/06* (2013.01); *C07K 14/00* (2013.01); *C07K 14/52* (2013.01); *C07K 14/525* (2013.01); *C07K 14/7151* (2013.01); *C07K 16/18* (2013.01); *C12N 15/00* (2013.01); *C12N 15/62* (2013.01); *C12Q 1/68* (2013.01); *A61K 2039/505* (2013.01); *C07K 2317/31* (2013.01); *C07K 2317/55* (2013.01); *C07K 2317/622* (2013.01); *C07K 2317/73* (2013.01); *C07K 2319/30* (2013.01)

(58) Field of Classification Search
CPC .. A61K 38/19; A61K 39/39558; A61K 45/06; A61K 2039/505; C07K 14/00; C07K 14/52; C07K 14/525; C07K 14/7151; C07K 16/18; C07K 2317/31; C07K 2317/55; C07K 2317/622; C07K 2317/73; C07K 2319/30; C12N 15/00; C12N 15/62; C12Q 1/68
See application file for complete search history.

(56) References Cited

U.S. PATENT DOCUMENTS

| | | |
|---|---|---|
| 5,155,027 A | 10/1992 | Sledziewski et al. |
| 5,457,035 A | 10/1995 | Baum et al. |
| 5,716,805 A | 2/1998 | Srinivasan et al. |
| 5,783,665 A | 7/1998 | Baum et al. |
| 5,962,406 A | 10/1999 | Armitage et al. |
| 5,998,171 A | 12/1999 | Yu et al. |
| 6,087,329 A | 7/2000 | Armitage et al. |
| 6,242,566 B1 | 6/2001 | Godfrey et al. |
| 6,312,700 B1 | 11/2001 | Weinberg |
| 6,406,867 B1 | 6/2002 | Yu et al. |
| 6,521,742 B2 | 2/2003 | Yu et al. |
| 7,078,027 B2 | 7/2006 | Yu et al. |
| 7,087,225 B2 | 8/2006 | Yu et al. |
| 7,268,116 B2 | 9/2007 | Liang |
| 7,300,774 B1 | 11/2007 | Kornbluth |
| 7,332,298 B2 | 2/2008 | Kornbluth |
| 7,514,081 B2 | 4/2009 | Yu et al. |

(Continued)

FOREIGN PATENT DOCUMENTS

| | | |
|---|---|---|
| EP | 0672141 B1 | 5/2003 |
| EP | 1196186 B1 | 10/2007 |

(Continued)

OTHER PUBLICATIONS

Baltz, K.M., et al., "Cancer Immunoediting by GITR (Glucocorticoid-induced TNF-related Protein) Ligand in Humans: NK Cell/tumor Cell Interactions," FASEB Journal 21(10):2442-2454, The Federation, United States (2007).

(Continued)

*Primary Examiner* — Robert S Landsman
(74) *Attorney, Agent, or Firm* — Sterne, Kessler, Goldstein & Fox P.L.L.C.

(57) ABSTRACT

Polypeptides and agents that bind a TNF receptor superfamily protein are disclosed, particularly agents that specifically bind GITR, OX40, or CD40. The polypeptides or agents may include fusion polypeptides, particularly polypeptides comprising GITRL, OX40L, or CD40L and/or bispecific agents. Also disclosed are methods of using the polypeptides or agents for inducing and/or enhancing the immune response, as well as methods for the treatment of diseases such as cancer.

18 Claims, 36 Drawing Sheets

Specification includes a Sequence Listing.

(56) References Cited

U.S. PATENT DOCUMENTS

| | | |
|---|---|---|
| 7,622,444 B2 | 11/2009 | Weinberg |
| 7,666,837 B2 | 2/2010 | Liang |
| 7,691,815 B2 | 4/2010 | Liang |
| 7,722,868 B2 | 5/2010 | Freeman et al. |
| 7,758,852 B2 | 7/2010 | Soto-Jara et al. |
| 7,794,710 B2 | 9/2010 | Chen et al. |
| 7,812,135 B2 | 10/2010 | Smith et al. |
| 7,858,765 B2 | 12/2010 | Soto-Jara et al. |
| 7,892,540 B2 | 2/2011 | Chen et al. |
| 7,959,925 B2 | 6/2011 | Weinberg et al. |
| 8,168,179 B2 | 5/2012 | Honjo et al. |
| 8,207,130 B2 | 6/2012 | Epstein et al. |
| 8,388,967 B2 | 3/2013 | Smith et al. |
| 8,431,350 B2 | 4/2013 | Baldwin et al. |
| 8,450,460 B2 | 5/2013 | Hill et al. |
| 8,460,927 B2 | 6/2013 | Chen |
| 8,461,311 B2 | 6/2013 | Hawkins et al. |
| 8,586,023 B2 | 11/2013 | Shiku et al. |
| 8,591,886 B2 | 11/2013 | Ponath et al. |
| 8,652,465 B2 | 2/2014 | Freeman et al. |
| 8,664,366 B2 | 3/2014 | Hill et al. |
| 8,669,350 B2 | 3/2014 | Chou et al. |
| 8,709,424 B2 | 4/2014 | Schebye et al. |
| 8,747,833 B2 | 6/2014 | Chen et al. |
| 8,779,108 B2 | 7/2014 | Queva et al. |
| 8,981,063 B2 | 3/2015 | Chen |
| 9,241,992 B2 | 1/2016 | Ponte et al. |
| 9,724,390 B2 | 8/2017 | Gurney |
| 2004/0197876 A1 | 10/2004 | Tschopp et al. |
| 2005/0014224 A1 | 1/2005 | Collins et al. |
| 2005/0152872 A1 | 7/2005 | Gaide et al. |
| 2005/0158831 A1 | 7/2005 | Kornbluth |
| 2006/0051350 A1 | 3/2006 | Van Oosterhout et al. |
| 2006/0105376 A1 | 5/2006 | Isogai et al. |
| 2006/0216270 A1 | 9/2006 | Ashkenazi et al. |
| 2007/0010658 A1 | 1/2007 | Holtet et al. |
| 2007/0015271 A1 | 1/2007 | Rosen et al. |
| 2007/0286843 A1 | 12/2007 | Pfizenmaier et al. |
| 2008/0038264 A1 | 2/2008 | Bodary et al. |
| 2008/0050809 A1 | 2/2008 | Abuin et al. |
| 2008/0221016 A1 | 9/2008 | Byrne et al. |
| 2009/0136446 A1 | 5/2009 | Nishikawa et al. |
| 2009/0263348 A1 | 10/2009 | Kornbluth |
| 2010/0015143 A1 | 1/2010 | Hussell et al. |
| 2010/0080809 A1 | 4/2010 | Collins et al. |
| 2010/0199364 A1 | 8/2010 | Hill et al. |
| 2011/0162095 A1 | 6/2011 | Hill et al. |
| 2011/0212086 A1 | 9/2011 | Shankara et al. |
| 2012/0121640 A1 | 5/2012 | Tykocinski et al. |
| 2012/0251537 A1 | 10/2012 | Ahmed et al. |
| 2012/0282184 A1 | 11/2012 | Waldmann et al. |
| 2013/0039911 A1 | 2/2013 | Bedi et al. |
| 2013/0122014 A1 | 5/2013 | Korman et al. |
| 2013/0251720 A1 | 9/2013 | Clark et al. |
| 2013/0280265 A1 | 10/2013 | Rolland et al. |
| 2013/0309250 A1 | 11/2013 | Cogswell et al. |
| 2014/0120124 A1 | 5/2014 | Shiku et al. |
| 2014/0178370 A1 | 6/2014 | Freeman et al. |
| 2014/0242077 A1 | 8/2014 | Choi et al. |
| 2014/0314714 A1 | 10/2014 | Honjo et al. |
| 2014/0335050 A1 | 11/2014 | Haggerty et al. |
| 2014/0341906 A1 | 11/2014 | Taylor et al. |
| 2015/0004129 A1 | 1/2015 | Tschopp et al. |
| 2015/0004175 A1 | 1/2015 | Kaech et al. |
| 2015/0044165 A1 | 2/2015 | Chen et al. |
| 2015/0071910 A1 | 3/2015 | Kowanetz et al. |
| 2015/0110734 A1 | 4/2015 | Hill et al. |
| 2015/0152160 A1 | 6/2015 | Gao et al. |
| 2016/0009783 A1 | 1/2016 | Teitelbaum et al. |
| 2016/0122412 A1 | 5/2016 | Stone et al. |
| 2016/0159874 A1 | 6/2016 | Tavernier et al. |
| 2016/0199487 A1 | 7/2016 | Gu et al. |
| 2016/0200833 A1 | 7/2016 | Amann et al. |
| 2016/0340399 A1 | 11/2016 | Amann et al. |
| 2017/0022284 A1 | 1/2017 | Timmer et al. |
| 2017/0073386 A1 | 3/2017 | Stewart et al. |
| 2017/0081386 A1 | 3/2017 | Hill et al. |

FOREIGN PATENT DOCUMENTS

| | | |
|---|---|---|
| EP | 1032672 B1 | 12/2008 |
| EP | 2025682 A2 | 2/2009 |
| EP | 2133365 A2 | 12/2009 |
| EP | 2206517 A1 | 7/2010 |
| EP | 2243493 A1 | 10/2010 |
| EP | 1539228 B1 | 12/2010 |
| EP | 1891107 B1 | 7/2011 |
| EP | 1060247 B2 | 10/2011 |
| EP | 2397155 A1 | 12/2011 |
| EP | 2397156 A1 | 12/2011 |
| EP | 2399932 A1 | 12/2011 |
| EP | 1492813 B1 | 5/2012 |
| EP | 1907000 B1 | 10/2012 |
| EP | 1671097 B1 | 8/2013 |
| EP | 2650020 A1 | 10/2013 |
| EP | 1877090 B1 | 1/2014 |
| EP | 2310509 B1 | 1/2015 |
| EP | 2604693 B1 | 2/2016 |
| WO | WO-0050620 A2 | 8/2000 |
| WO | WO-0103720 A2 | 1/2001 |
| WO | WO-0125277 A1 | 4/2001 |
| WO | WO-2004084942 A2 | 10/2004 |
| WO | WO-2004107618 A2 | 12/2004 |
| WO | WO-2005007190 A1 | 1/2005 |
| WO | WO-2005103077 A1 | 11/2005 |
| WO | WO-2005115451 A2 | 12/2005 |
| WO | WO-2006042237 A2 | 4/2006 |
| WO | WO-2006050172 A3 | 1/2007 |
| WO | WO-2007084559 A2 | 7/2007 |
| WO | WO-2008025516 A2 | 3/2008 |
| WO | WO-2009000538 A1 | 12/2008 |
| WO | WO-2009007120 A2 | 1/2009 |
| WO | WO-2009126688 A2 | 10/2009 |
| WO | WO-2010010051 A1 | 1/2010 |
| WO | WO-2010063011 A1 | 6/2010 |
| WO | WO-2010078966 A1 | 7/2010 |
| WO | WO-2011051726 A2 | 5/2011 |
| WO | WO-2011109789 A2 | 9/2011 |
| WO | WO-2012027328 A2 | 3/2012 |
| WO | WO-2012130471 A1 | 10/2012 |
| WO | WO-2013107413 A1 | 7/2013 |
| WO | WO-2013119202 A1 | 8/2013 |
| WO | WO-2014022758 A1 | 2/2014 |
| WO | WO-2014083178 A1 | 6/2014 |
| WO | WO-2014089113 A1 | 6/2014 |
| WO | WO-2014106839 A1 | 7/2014 |
| WO | WO 2014/145355 A1 | 9/2014 |
| WO | WO-2015007903 A1 | 1/2015 |
| WO | WO-2015009856 A2 | 1/2015 |
| WO | WO-2015026684 A1 | 2/2015 |
| WO | WO-2015038583 A1 | 3/2015 |
| WO | WO-2015197874 A2 | 12/2015 |
| WO | WO-2016029043 A1 | 2/2016 |
| WO | WO 2017/068185 A1 | 4/2016 |
| WO | WO-2016057841 A1 | 4/2016 |
| WO | WO-2016075174 A1 | 5/2016 |
| WO | WO-2016113395 A1 | 7/2016 |
| WO | WO 2016/126781 A1 | 10/2016 |
| WO | WO-2016156291 A1 | 10/2016 |
| WO | WO-2016164480 A1 | 10/2016 |

OTHER PUBLICATIONS

Berg, D., et al., "Enforced Covalent Trimerization Increases the Activity of the TNF Ligand Family Members Trail and CD95L," Cell Death and Differentiation 14(12):2021-2034, Nature Publishing Group, England (2007).

Bodmer, J.L., et al., "The Molecular Architecture of the TNF Superfamily," Trends in Biochemical Sciences 27(1):19-26, Elsevier Trends Journals, England (2002).

(56) References Cited

OTHER PUBLICATIONS

Bremer, E., "Targeting of the Tumor Necrosis Factor Receptor Superfamily for Cancer Immunotherapy," ISRN Oncology 2013: 25 pages, Hindawi (2013).

Chattopadhyay, K., et al, "Assembly and Structural Properties of Glucocorticoid-induced TNF Receptor Ligand: Implications for Function," Proceedings of the National Academy of Sciences USA 104(49):19452-19457, National Academy of Sciences, United States (2007).

Chattopadhyay, K., et al, "Evolution of GITRL Immune Function: Murine GITRL Exhibits Unique Structural and Biochemical Properties within the TNF Superfamily," Proceedings of the National Academy of Sciences USA 105(2):635-640, National Academy of Sciences, United States (2008).

Cho, J.S., et al., "Localized Expression of GITR-L in the Tumor Microenvironment Promotes CD8+ T Cell Dependent Anti-tumor Immunity," Cancer Immunology, Immunotherapy 58(7):1057-1069, Springer Verlag, Germany (2009).

Cohen, A.D., et al., "Agonist Anti-GITR Antibody Enhances Vaccine-induced CD8(+) T-cell Responses and Tumor Immunity," Cancer Research 66(9):4904-4912, American Association for Cancer Research, United States (2006).

Cohen, A.D., et al., "Agonist Anti-GITR Monoclonal Antibody Induces Melanoma Tumor Immunity in Mice by Altering Regulatory T Cell Stability and Intra-tumor Accumulation," PLoS One 5(5):e10436, Public Library of Science, United States (2010).

Croft, M., et al., "Clinical Targeting of the TNF and TNFR Superfamilies," Nature Reviews. Drug discovery 12(2):147-168, Nature Publishing Group, England (2013).

Curti, B.D., et al.,"OX40 is a Potent Immune-stimulating Target in Late-stage Cancer Patients," Cancer Research 73(24):7189-7198, American Association for Cancer Research, United States (2013).

Elgueta, R., et al., "Molecular Mechanism and Function of CD40/CD4OL Engagement in the Immune System," Immunological Reviews 229 (1): 31 pages, Munksgaard, England (2009).

Gieffers, C., et al., "APG350 Induces Superior Clustering of TRAIL Receptors and Shows Therapeutic Antitumor Efficacy Independent of Cross-linking via FCγ Receptors," Molecular Cancer Therapeutics 12(12):2735-2747, American Association for Cancer Research, United States (2013).

Guiducci, C., et al., "CD40/CD40L Interaction Regulates CD4+ CD25+ T reg Homeostasis Through Dendritic Cell-Produced IL-2," European Journal of Immunology 35 (2): 557-567, Verlag Chemie GmbH, Germany (2005).

Gurney, A.L., et al., "Identification of a New Member of the Tumor Necrosis Factor Family and its Receptor, a Human Ortholog of Mouse GITR," Current Biology 9(4):215-218, Cell Press, England (1999).

Hassan, S.B., et al., "Anti-CD40-mediated Cancer Immunotherapy: an Update of Recent and Ongoing Clinical Trials," Immunopharmacol Immunotoxicol 36 (2): 96-104, Marcel Dekker, England (2014).

Hornig, N., et al., "Evaluating Combinations of Costimulatory Antibody-ligand Fusion Proteins for Targeted Cancer Immunotherapy," Cancer Immunology, Immunotherapy 62(8):1369-1380, Springer Verlag, Germany (2013).

Hu, P., et al., "Construction and Preclinical Characterization of Fc-mGITRL for the Immunotherapy of Cancer," Clinical Cancer Research 14(2):579-588, The Association, United States (2008).

International Search Report for International Application No. PCT/US16/16306, ISA/US, Alexandria, Virginia, United States, dated Jul. 15, 2016, 7 pages.

Khalil, M., et al., "Anti-CD40 Agonist Antibodies: Preclinical and Clinical Experience," Update on Cancer Therapeutics 2 (2): 61-65, Elsevier, England (2007).

Knee, D.A., et al., "Rationale for Anti-GITR Cancer Immunotherapy," European Journal of Cancer 67: 1-10, Elsevier Science (2016).

Ko, K., et al., "Treatment of Advanced Tumors with Agonistic Anti-GITR Mab and Its Effects on Tumor-infiltrating Foxp3+Cd25+ Cd4+ Regulatory T Cells," The Journal of Experimental Medicine 202(7):885-891, Rockefeller University Press, United States (Oct. 2005).

Kornbluth, R.S., et al., "Design of CD40 Agonists and their Use in Growing B Cells for Cancer Immunotherapy," International Reviews of Immunology 31(4):279-288, Informa Healthcare, England (2012).

Korniluk, A., et al., "Multifunctional CD40L: Pro- and Antineoplastic Activity," Tumour Biology 35(10):9447-9457, Springer Netherlands, Netherlands (2014).

Krippner-Heidenreich, A., et al., "Single-chain TNF, a TNF Derivative with Enhanced Stability and Antitumoral Activity," Journal of Immunology 180(12):8176-8183, American Association of Immunologists, United States (2008).

Leyland, R., et al., "A Mouse GITR Ligand Fusion Protein Drives T-Cell Activation and Antitumor Activity in Preclinical Mouse Models of Cancer," AACR 2016 Annual Meeting in New Orleans, Apr. 16-20, 2016, Poster #203, 1 page (2016).

Liao, G., et al., "GITR Engagement Preferentially Enhances Proliferation of Functionally Competent CD4+ CD25+ FoxP3+ Regulatory T Cells," International Immunology 22(4):259-270, University Press, England (2010).

Loskog, A., et al., "CD40L—A Multipotent Molecule for Tumor Therapy," Endocrine, Metabolic & Immune Disorders—Drug Targets 7: 23-28, Bentham Science Publishers, United Arab Emirates (2007).

Loskog, A., et al., "The Janus Faces of CD40 in Cancer," Seminars in Immunology 21 (5): 301-307, Saunders, England (2009).

Lu, L., et al., "Combined PD-1 Blockade and GITR Triggering Induce a Potent Antitumor Immunity in Murine Cancer Models and Synergizes with Chemotherapeutic Drugs," Journal of Translational Medicine 12: 11 pages, BioMed Central, England (2014).

Melero, I., et al., "Agonist Antibodies to TNFR Molecules that Costimulate T and NK Cells," Clinical Cancer Research 19(5):1044-1053, The Association, United States (2013).

Moran, A.E., et al., "The TNFRs OX40, 4-1BB, and CD40 as Targets for Cancer Immunotherapy," Current Opinion in Immunology 25(2):230-237, Elsevier, England (2013).

Morris, N.P., et al., "Development and Characterization of Recombinant Human Fc:OX40L Fusion Protein Linked via a Coiled-coil Trimerization Domain," Molecular Immunology 44(12):3112-3121, Pergamon Press, England (2007).

Murphy, J.T., et al., "Anaphylaxis Caused by Repetitive Doses of a GITR Agonist Monoclonal Antibody in Mice," Blood 123(14):2172-2180, American Society of Hematology, United States (2014).

Nocentini, G. and Riccardi, C., "GITR: A Modulator of Immune Response and Inflammation," Advances in Experimental Medicine and Biology 647:156-173, Kluwer Academic/Plenum Publishers, United States (2009).

Nocentini, G., et al., "Pharmacological Modulation of GITRL/GITR System: Therapeutic Perspectives," British Journal of Pharmacology 165(7):2089-2099, Wiley, England (2012).

OMED Transcript—Thomson Reuters Streetevents Edited Transcript, "OMED—OncoMed Pharmaceuticals Inc 2015 Research and Development Day," Apr. 29, 2015, 54 pages (2015).

"OncoMed Pharmaceuticals 2015 R&D Day" presentation from Apr. 29, 2015, 9 slides.

Ostrand-Rosenberg, S. and Sinha, P., "Myeloid-derived Suppressor Cells: Linking Inflammation and Cancer," Journal of Immunology 182(8):4499-4506, American Association of Immunologists, United States (2009).

Pan, P.Y., et al., "Immune Stimulatory Receptor CD40 Is Required for T-Cell Suppression and T Regulatory Cell Activation Mediated by Myeloid-Derived Suppressor Cells in Cancer," Cancer Research 70(1):99-108, American Association for Cancer Research, United States (2010).

Pedroza-Gonzalez, A., et al., "T-cell Suppression Mediated by Regulatory T Cells Infiltrating Hepatic Tumors can be Overcome by GITRL Treatment," Oncoimmunology 2(1):e22450, Taylor and Francis, United States (2013).

Placke, T., et al., "Glucocorticoid-induced Tnfr-related (GITR) Protein and Its Ligand in Antitumor Immunity: Functional Role and Therapeutic Modulation," Clinical and Developmental Immunology, 10 pages, Hindawi Publishing Corporation, Egypt (2010).

(56) References Cited

OTHER PUBLICATIONS

R&D Day Presentation—"OncoMed Pharmaceuticals 2015 R&D Day," Presentation by Paul J. Hastings on Apr. 29, 2015, 146 slides (2015).

Richman, L.P., et al., "Anti-Human CD40 Monoclonal Antibody Therapy is Potent Without FcR Crosslinking," Oncoimmunology 3: e28610-1 to e28610-2, Taylor & Francis, United States (2014).

Sanmamed, M.F., et al., "Agonists of Co-stimulation in Cancer Immunotherapy Directed AgainstCD137,OX40,GITR,CD27, CD28, and ICOS," Seminars in oncology 42 (4): 640-655, Saunders, United States (2015).

Schaer, D.A., et al., "GITR Pathway Activation Abrogates Tumor Immune Suppression Through Loss of Regulatory T Cell Lineage Stability," Cancer Immunology Research 1(5):320-331, American Association for Cancer Research, United States (2013).

Schaer, D.A., et al., "Modulation of GITR for Cancer Immunotherapy," Current Opinion in Immunology 24(2):217-224, Elsevier Ltd., England (Apr. 2012).

Shevach., E.M. and Stephens, G,L., "The GITR-GITRL Interaction: Co-stimulation or Contrasuppression of Regulatory Activity?," Nature Reviews Immunology 6(8):613-618, Nature Publishing Group, England (2006).

Shimizu, J., et al., "Stimulation of CD25(+)CD4(+) Regulatory T Cells through GITR Breaks Immunological Self-Tolerance," Nature Immunology 3(2):135-142, Nature America Inc., United States (2002).

Siegemund, M., et al., "Superior Antitumoral Activity of Dimerized Targeted Single-chain Trail Fusion Proteins Under Retention of Tumor Selectivity," Cell Death & Disease 3: e295, 11 pages, Nature Pub, England (2012).

Stone, G.W., et al., "Multimeric Soluble CD40 Ligand and GITR Ligand as Adjuvants for Human Immunodeficiency Virus DNA Vaccines," Journal of Virology 80 (4): 1762-1772, American Society for Microbiology, United States (2006).

Tone., M., et al., "Mouse Glucocorticoid-induced Tumor Necrosis Factor Receptor Ligandi Is Costimulatory for T Cells," Proceedings of the National Academy of Sciences USA 100(25):15059-15064, National Academy of Sciences, United States (2003).

Tong, A.W. and Stone, M.J., "Prospects for CD40-directed Experimental Therapy of Human Cancer," Cancer Gene Therapy 10(1):1-13, Nature Publishing Group, England (2003).

Van Kooten, C. and Banchereau, J,, "CD40-CD40 Ligand," Journal of Leukocyte Biology 67(1):2-17, Society for Leukocyte Biology, United States (2000).

Vonderheide R.H., et al., "Agonistic CD40 Antibodies and Cancer Therapy," Clinical Cancer Research 19 (5): 1035-1043, The Association, United States (2013).

Vonderheide R.H., et al., "Phase I Study of Recombinant Human CD40 Ligand in Cancer Patients," Journal of Clinical Oncology 19 (13): 3280-3270, American Society of Clinical Oncology, United States (2001).

Voo, K.S., et al., "Antibodies Targeting Human OX40 Expand Effector T Cells and Block Inducible and Natural Regulatory T Cell Function," Journal of Immunology 191(7):3641-3650, American Association of Immunologists, United States (2013).

Weinberg, A.D., et al., "Science Gone Translational: the OX40 Agonist Story," Immunological Reviews 244(1):218-231, Blackwell, England (2011).

Written Opinion for International Application No. PCT/US16/16306, ISA/US, Alexandria, Virginia, United States, dated Jul. 15, 2016, 10 pages.

Wyzgol, A., et al., "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand," Journal of Immunology 183(3):1851-1861, American Association of Immunologists, United States (2009).

Xiao, X., et al., "GITR subverts Foxp3 Tregs to Boost Th9 Immunity Through Regulation of Histone Acetylation," Nature Communications 6: 8266, 13 pages, Nature Pub England (2015).

Zhou, Z., et al., "Human Glucocorticoid-induced TNF Receptor Ligand Regulates Its Signaling Activity Through Multiple Oligomerization States," Proceedings of the National Academy of Sciences USA 105(14):5465-5470, National Academy of Sciences, United States (2008).

Office Action dated Dec. 20, 2016, in U.S. Appl. No. 15/014,134, Gurney, A.L. et al., filed Feb. 3, 2016, 7 pages.

GITRL Trimer

"stalk"

Cell membrane

SEQ ID NO:1  MTLHPSPITCEFLFSTALISPK|MCLSHLENMPLSHSRTQGAQRSSWKLWL
    cytoplasmic region
|FCSIVMLLFLCSFSWLIFIF|LQLETAKEPCMAKFGPLPSKWQMASSEPPC
 signal-anchor        extracellular domain

VNKVSDWKLEILQNGLYLIYGQVAPNANYNDVAPFEVRLYKNKDMIQTLT

NKSKIQNVGGTYELHVGDTIDLIFNSEHQVLKNNTYWGIIILLANPQFIS

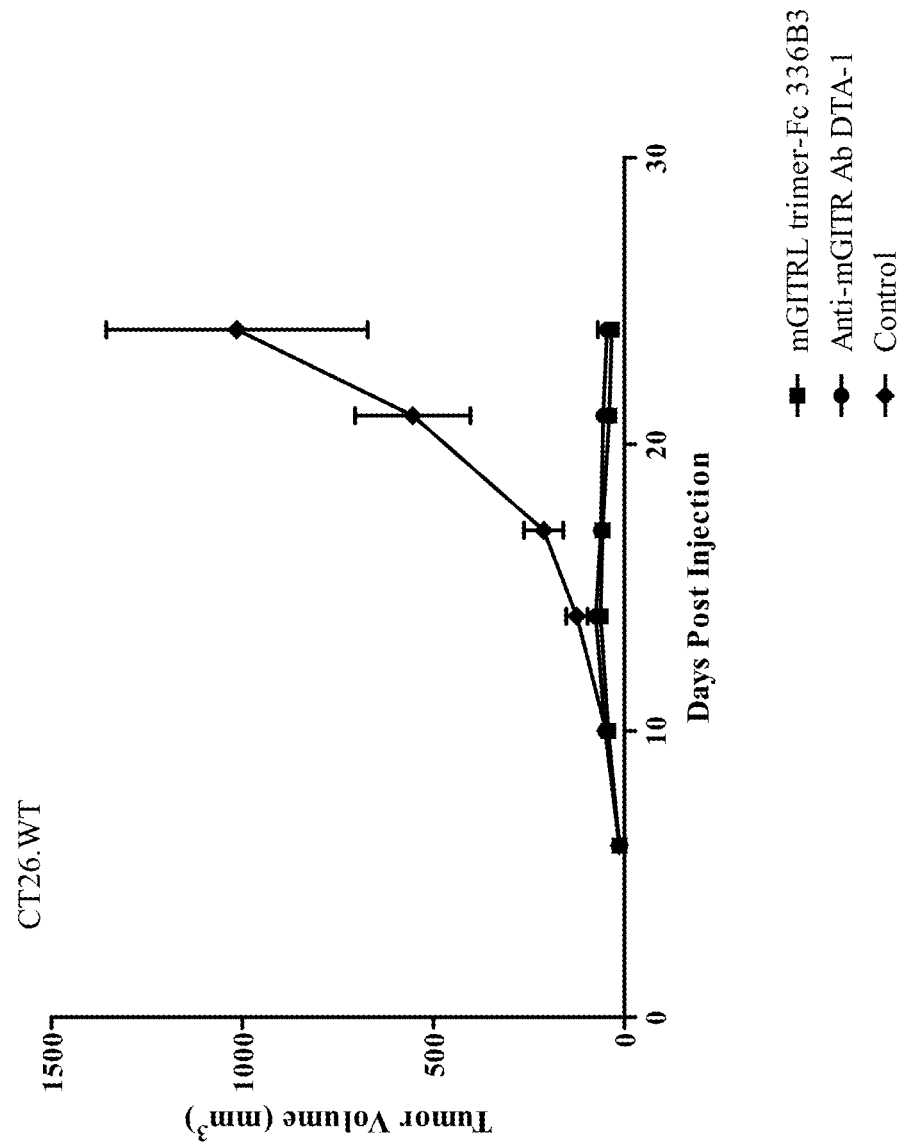

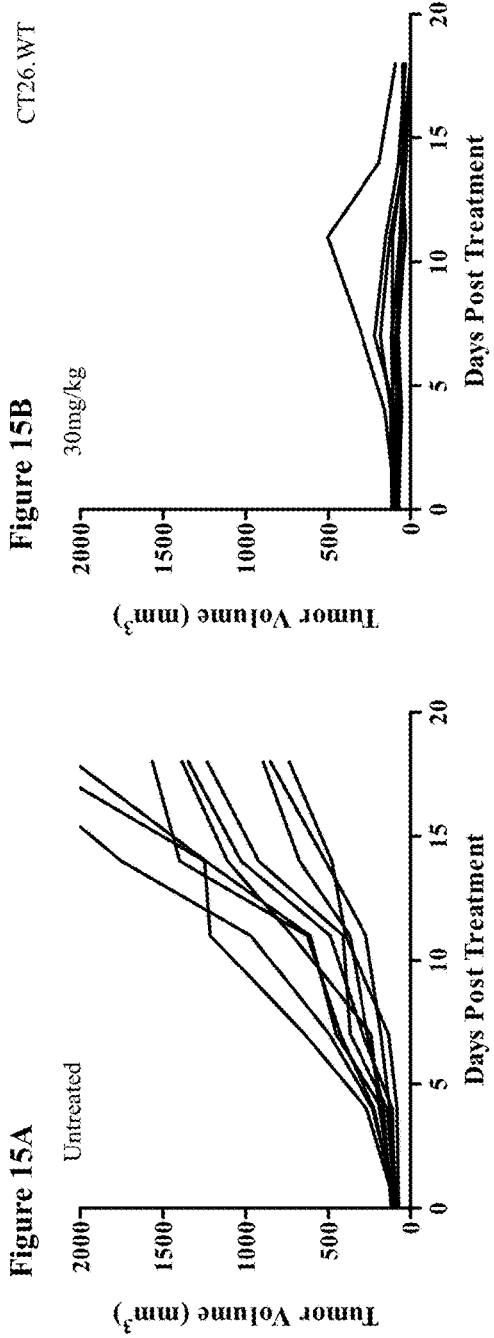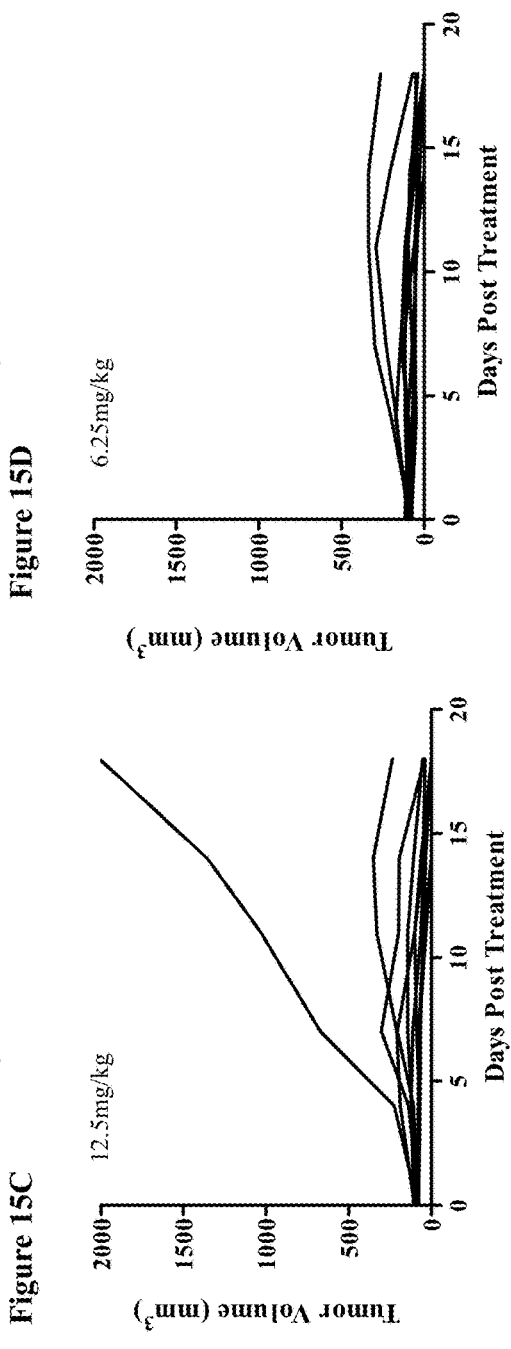

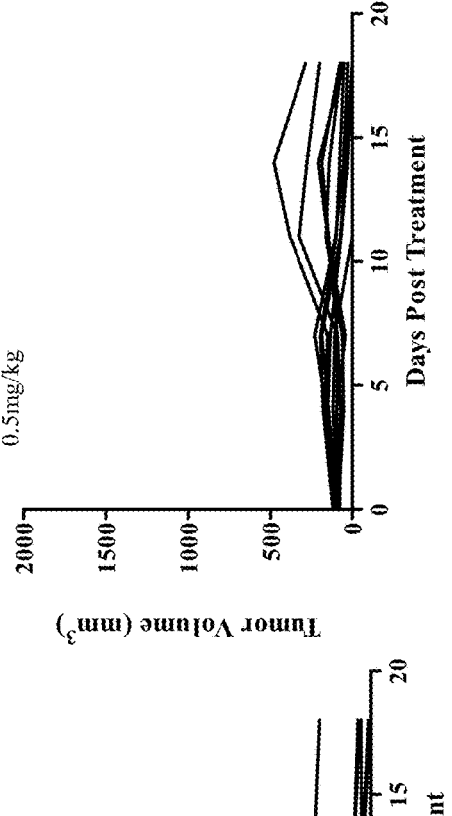
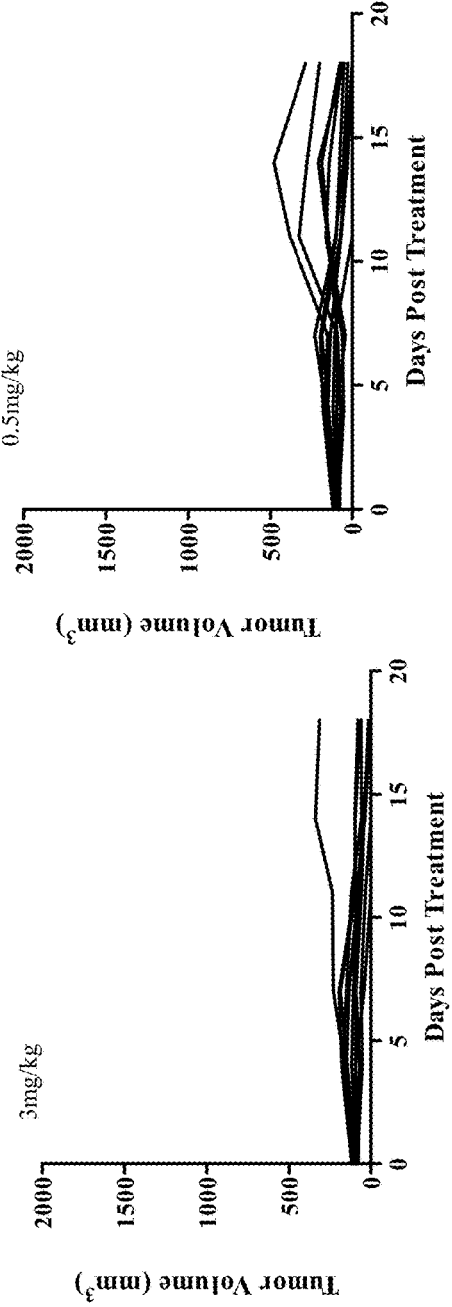
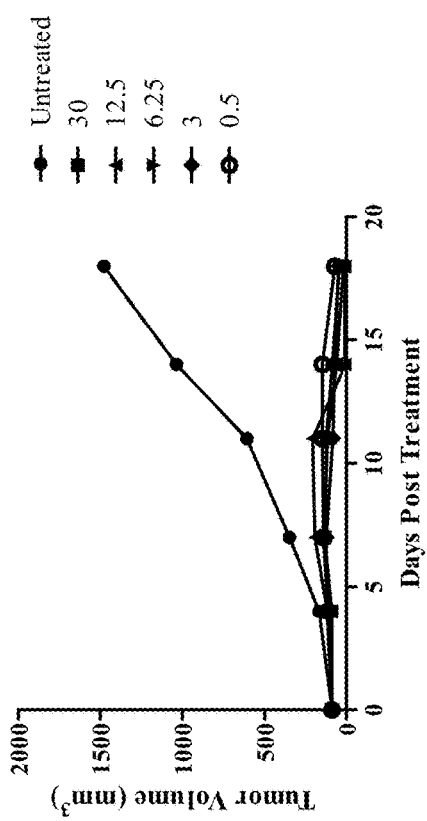

SEQUENCE LISTING

<160> NUMBER OF SEQ ID NOS: 106

<210> SEQ ID NO 1
<211> LENGTH: 199
<212> TYPE: PRT
<213> ORGANISM: Artificial Sequence
<220> FEATURE:
<223> OTHER INFORMATION: Human GITRL (TNFSF18) amino acid sequence

<400> SEQUENCE: 1

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
            20                  25                  30

Leu Ser His Ser Arg Thr Gln Gly Ala Gln Arg Ser Ser Trp Lys Leu
        35                  40                  45

Trp Leu Phe Cys Ser Ile Val Met Leu Leu Phe Leu Cys Ser Phe Ser
    50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
    130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195

```
<210> SEQ ID NO 2
<211> LENGTH: 149
<212> TYPE: PRT
<213> ORGANISM: Artificial Sequence
<220> FEATURE:
<223> OTHER INFORMATION: Human GITRL signal/anchor region and
      extracellular domain amino acid sequence

<400> SEQUENCE: 2

Phe Cys Ser Ile Val Met Leu Leu Phe Leu Cys Ser Phe Ser Trp Leu
1               5                   10                  15

Ile Phe Ile Phe Leu Gln Leu Glu Thr Ala Lys Glu Pro Cys Met Ala
            20                  25                  30

Lys Phe Gly Pro Leu Pro Ser Lys Trp Gln Met Ala Ser Ser Glu Pro
        35                  40                  45

Pro Cys Val Asn Lys Val Ser Asp Trp Lys Leu Glu Ile Leu Gln Asn
    50                  55                  60

Gly Leu Tyr Leu Ile Tyr Gly Gln Val Ala Pro Asn Ala Asn Tyr Asn
65                  70                  75                  80

Asp Val Ala Pro Phe Glu Val Arg Leu Tyr Lys Asn Lys Asp Met Ile
                85                  90                  95

Gln Thr Leu Thr Asn Lys Ser Lys Ile Gln Asn Val Gly Gly Thr Tyr
            100                 105                 110

Glu Leu His Val Gly Asp Thr Ile Asp Leu Ile Phe Asn Ser Glu His
        115                 120                 125

Gln Val Leu Lys Asn Asn Thr Tyr Trp Gly Ile Ile Leu Leu Ala Asn
    130                 135                 140

Pro Gln Phe Ile Ser
145

<210> SEQ ID NO 3
<211> LENGTH: 129
<212> TYPE: PRT
<213> ORGANISM: Artificial Sequence
<220> FEATURE:
<223> OTHER INFORMATION: Human GITRL extracellular domain amino acid
      sequence

<400> SEQUENCE: 3

Leu Gln Leu Glu Thr Ala Lys Glu Pro Cys Met Ala Lys Phe Gly Pro
1               5                   10                  15

Leu Pro Ser Lys Trp Gln Met Ala Ser Ser Glu Pro Pro Cys Val Asn
            20                  25                  30

Lys Val Ser Asp Trp Lys Leu Glu Ile Leu Gln Asn Gly Leu Tyr Leu
        35                  40                  45

Ile Tyr Gly Gln Val Ala Pro Asn Ala Asn Tyr Asn Asp Val Ala Pro
    50                  55                  60

Phe Glu Val Arg Leu Tyr Lys Asn Lys Asp Met Ile Gln Thr Leu Thr
65                  70                  75                  80

Asn Lys Ser Lys Ile Gln Asn Val Gly Gly Thr Tyr Glu Leu His Val
                85                  90                  95

Gly Asp Thr Ile Asp Leu Ile Phe Asn Ser Glu His Gln Val Leu Lys
            100                 105                 110

Asn Asn Thr Tyr Trp Gly Ile Ile Leu Leu Ala Asn Pro Gln Phe Ile
        115                 120                 125

Ser

<210> SEQ ID NO 4
```

```
<211> LENGTH: 414
<212> TYPE: PRT
<213> ORGANISM: Artificial Sequence
<220> FEATURE:
<223> OTHER INFORMATION: Human single chain GITRL trimer amino acid
      sequence
<220> FEATURE:
<221> NAME/KEY: SIGNAL
<222> LOCATION: (1)..(27)

<400> SEQUENCE: 4
```

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Leu Gln Leu Glu Thr
            20                  25                  30

Ala Lys Glu Pro Cys Met Ala Lys Phe Gly Pro Leu Pro Ser Lys Trp
        35                  40                  45

Gln Met Ala Ser Ser Glu Pro Pro Cys Val Asn Lys Val Ser Asp Trp
    50                  55                  60

Lys Leu Glu Ile Leu Gln Asn Gly Leu Tyr Leu Ile Tyr Gly Gln Val
65                  70                  75                  80

Ala Pro Asn Ala Asn Tyr Asn Asp Val Ala Pro Phe Glu Val Arg Leu
                85                  90                  95

Tyr Lys Asn Lys Asp Met Ile Gln Thr Leu Thr Asn Lys Ser Lys Ile
            100                 105                 110

Gln Asn Val Gly Gly Thr Tyr Glu Leu His Val Gly Asp Thr Ile Asp
        115                 120                 125

Leu Ile Phe Asn Ser Glu His Gln Val Leu Lys Asn Asn Thr Tyr Trp
130                 135                 140

Gly Ile Ile Leu Leu Ala Asn Pro Gln Phe Ile Ser Leu Gln Leu Glu
145                 150                 155                 160

Thr Ala Lys Glu Pro Cys Met Ala Lys Phe Gly Pro Leu Pro Ser Lys
                165                 170                 175

Trp Gln Met Ala Ser Ser Glu Pro Pro Cys Val Asn Lys Val Ser Asp
            180                 185                 190

Trp Lys Leu Glu Ile Leu Gln Asn Gly Leu Tyr Leu Ile Tyr Gly Gln
        195                 200                 205

Val Ala Pro Asn Ala Asn Tyr Asn Asp Val Ala Pro Phe Glu Val Arg
    210                 215                 220

Leu Tyr Lys Asn Lys Asp Met Ile Gln Thr Leu Thr Asn Lys Ser Lys
225                 230                 235                 240

Ile Gln Asn Val Gly Gly Thr Tyr Glu Leu His Val Gly Asp Thr Ile
                245                 250                 255

Asp Leu Ile Phe Asn Ser Glu His Gln Val Leu Lys Asn Asn Thr Tyr
            260                 265                 270

Trp Gly Ile Ile Leu Leu Ala Asn Pro Gln Phe Ile Ser Leu Gln Leu
        275                 280                 285

Glu Thr Ala Lys Glu Pro Cys Met Ala Lys Phe Gly Pro Leu Pro Ser
    290                 295                 300

Lys Trp Gln Met Ala Ser Ser Glu Pro Pro Cys Val Asn Lys Val Ser
305                 310                 315                 320

Asp Trp Lys Leu Glu Ile Leu Gln Asn Gly Leu Tyr Leu Ile Tyr Gly
                325                 330                 335

Gln Val Ala Pro Asn Ala Asn Tyr Asn Asp Val Ala Pro Phe Glu Val
            340                 345                 350

Arg Leu Tyr Lys Asn Lys Asp Met Ile Gln Thr Leu Thr Asn Lys Ser 355                 360                 365
Lys Ile Gln Asn Val Gly Gly Thr Tyr Glu Leu His Val Gly Asp Thr
    370                 375                 380

Ile Asp Leu Ile Phe Asn Ser Glu His Gln Val Leu Lys Asn Asn Thr
385                 390                 395                 400

Tyr Trp Gly Ile Ile Leu Leu Ala Asn Pro Gln Phe Ile Ser
                405                 410

<210> SEQ ID NO 5
<211> LENGTH: 387
<212> TYPE: PRT
<213> ORGANISM: Artificial Sequence
<220> FEATURE:
<223> OTHER INFORMATION: Human single chain GITRL trimer amino acid
      sequence

<400> SEQUENCE: 5

Leu Gln Leu Glu Thr Ala Lys Glu Pro Cys Met Ala Lys Phe Gly Pro
1               5                   10                  15

Leu Pro Ser Lys Trp Gln Met Ala Ser Ser Glu Pro Pro Cys Val Asn
                20                  25                  30

Lys Val Ser Asp Trp Lys Leu Glu Ile Leu Gln Asn Gly Leu Tyr Leu
            35                  40                  45

Ile Tyr Gly Gln Val Ala Pro Asn Ala Asn Tyr Asn Asp Val Ala Pro
        50                  55                  60

Phe Glu Val Arg Leu Tyr Lys Asn Lys Asp Met Ile Gln Thr Leu Thr
65                  70                  75                  80

Asn Lys Ser Lys Ile Gln Asn Val Gly Gly Thr Tyr Glu Leu His Val
                85                  90                  95

Gly Asp Thr Ile Asp Leu Ile Phe Asn Ser Glu His Gln Val Leu Lys
            100                 105                 110

Asn Asn Thr Tyr Trp Gly Ile Ile Leu Leu Ala Asn Pro Gln Phe Ile
        115                 120                 125

Ser Leu Gln Leu Glu Thr Ala Lys Glu Pro Cys Met Ala Lys Phe Gly
    130                 135                 140

Pro Leu Pro Ser Lys Trp Gln Met Ala Ser Ser Glu Pro Pro Cys Val
145                 150                 155                 160

Asn Lys Val Ser Asp Trp Lys Leu Glu Ile Leu Gln Asn Gly Leu Tyr
                165                 170                 175

Leu Ile Tyr Gly Gln Val Ala Pro Asn Ala Asn Tyr Asn Asp Val Ala
            180                 185                 190

Pro Phe Glu Val Arg Leu Tyr Lys Asn Lys Asp Met Ile Gln Thr Leu
        195                 200                 205

Thr Asn Lys Ser Lys Ile Gln Asn Val Gly Gly Thr Tyr Glu Leu His
    210                 215                 220

Val Gly Asp Thr Ile Asp Leu Ile Phe Asn Ser Glu His Gln Val Leu
225                 230                 235                 240

Lys Asn Asn Thr Tyr Trp Gly Ile Ile Leu Leu Ala Asn Pro Gln Phe
                245                 250                 255

Ile Ser Leu Gln Leu Glu Thr Ala Lys Glu Pro Cys Met Ala Lys Phe
            260                 265                 270

Gly Pro Leu Pro Ser Lys Trp Gln Met Ala Ser Ser Glu Pro Pro Cys
        275                 280                 285

Val Asn Lys Val Ser Asp Trp Lys Leu Glu Ile Leu Gln Asn Gly Leu
    290                 295                 300

-continued

```
Tyr Leu Ile Tyr Gly Gln Val Ala Pro Asn Ala Asn Tyr Asn Asp Val
305                 310                 315                 320

Ala Pro Phe Glu Val Arg Leu Tyr Lys Asn Lys Asp Met Ile Gln Thr
                325                 330                 335

Leu Thr Asn Lys Ser Lys Ile Gln Asn Val Gly Gly Thr Tyr Glu Leu
            340                 345                 350

His Val Gly Asp Thr Ile Asp Leu Ile Phe Asn Ser Glu His Gln Val
        355                 360                 365

Leu Lys Asn Asn Thr Tyr Trp Gly Ile Ile Leu Leu Ala Asn Pro Gln
    370                 375                 380

Phe Ile Ser
385

<210> SEQ ID NO 6
<211> LENGTH: 641
<212> TYPE: PRT
<213> ORGANISM: Artificial Sequence
<220> FEATURE:
<223> OTHER INFORMATION: 336B11 Human single chain GITRL trimer-Fc
      (IgG1) amino acid sequence
<220> FEATURE:
<221> NAME/KEY: SIGNAL
<222> LOCATION: (1)..(27)

<400> SEQUENCE: 6

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Leu Gln Leu Glu Thr
                20                  25                  30

Ala Lys Glu Pro Cys Met Ala Lys Phe Gly Pro Leu Pro Ser Lys Trp
            35                  40                  45

Gln Met Ala Ser Ser Glu Pro Pro Cys Val Asn Lys Val Ser Asp Trp
        50                  55                  60

Lys Leu Glu Ile Leu Gln Asn Gly Leu Tyr Leu Ile Tyr Gly Gln Val
65                  70                  75                  80

Ala Pro Asn Ala Asn Tyr Asn Asp Val Ala Pro Phe Glu Val Arg Leu
                85                  90                  95

Tyr Lys Asn Lys Asp Met Ile Gln Thr Leu Thr Asn Lys Ser Lys Ile
            100                 105                 110

Gln Asn Val Gly Gly Thr Tyr Glu Leu His Val Gly Asp Thr Ile Asp
        115                 120                 125

Leu Ile Phe Asn Ser Glu His Gln Val Leu Lys Asn Asn Thr Tyr Trp
    130                 135                 140

Gly Ile Ile Leu Leu Ala Asn Pro Gln Phe Ile Ser Leu Gln Leu Glu
145                 150                 155                 160

Thr Ala Lys Glu Pro Cys Met Ala Lys Phe Gly Pro Leu Pro Ser Lys
                165                 170                 175

Trp Gln Met Ala Ser Ser Glu Pro Pro Cys Val Asn Lys Val Ser Asp
            180                 185                 190

Trp Lys Leu Glu Ile Leu Gln Asn Gly Leu Tyr Leu Ile Tyr Gly Gln
        195                 200                 205

Val Ala Pro Asn Ala Asn Tyr Asn Asp Val Ala Pro Phe Glu Val Arg
    210                 215                 220

Leu Tyr Lys Asn Lys Asp Met Ile Gln Thr Leu Thr Asn Lys Ser Lys
225                 230                 235                 240

Ile Gln Asn Val Gly Gly Thr Tyr Glu Leu His Val Gly Asp Thr Ile
                245                 250                 255
```

Asp Leu Ile Phe Asn Ser Glu His Gln Val Leu Lys Asn Asn Thr Tyr
            260                 265                 270

Trp Gly Ile Ile Leu Leu Ala Asn Pro Gln Phe Ile Ser Leu Gln Leu
        275                 280                 285

Glu Thr Ala Lys Glu Pro Cys Met Ala Lys Phe Gly Pro Leu Pro Ser
290                 295                 300

Lys Trp Gln Met Ala Ser Ser Glu Pro Pro Cys Val Asn Lys Val Ser
305                 310                 315                 320

Asp Trp Lys Leu Glu Ile Leu Gln Asn Gly Leu Tyr Leu Ile Tyr Gly
            325                 330                 335

Gln Val Ala Pro Asn Ala Asn Tyr Asn Asp Val Ala Pro Phe Glu Val
            340                 345                 350

Arg Leu Tyr Lys Asn Lys Asp Met Ile Gln Thr Leu Thr Asn Lys Ser
            355                 360                 365

Lys Ile Gln Asn Val Gly Gly Thr Tyr Glu Leu His Val Gly Asp Thr
370                 375                 380

Ile Asp Leu Ile Phe Asn Ser Glu His Gln Val Leu Lys Asn Asn Thr
385                 390                 395                 400

Tyr Trp Gly Ile Ile Leu Leu Ala Asn Pro Gln Phe Ile Ser Asp Lys
            405                 410                 415

Thr His Thr Cys Pro Pro Cys Pro Ala Pro Glu Leu Leu Gly Gly Pro
            420                 425                 430

Ser Val Phe Leu Phe Pro Pro Lys Pro Lys Asp Thr Leu Met Ile Ser
            435                 440                 445

Arg Thr Pro Glu Val Thr Cys Val Val Val Asp Val Ser His Glu Asp
450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
            485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Pro Ile Glu Lys
            515                 520                 525

Thr Ile Ser Lys Ala Lys Gly Gln Pro Arg Glu Pro Gln Val Tyr Thr
530                 535                 540

Leu Pro Pro Ser Arg Glu Glu Met Thr Lys Asn Gln Val Ser Leu Thr
545                 550                 555                 560

Cys Leu Val Lys Gly Phe Tyr Pro Ser Asp Ile Ala Val Glu Trp Glu
            565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Tyr Ser Lys Leu Thr Val Asp Lys
            595                 600                 605

Ser Arg Trp Gln Gln Gly Asn Val Phe Ser Cys Ser Val Met His Glu
            610                 615                 620

Ala Leu His Asn His Tyr Thr Gln Lys Ser Leu Ser Leu Ser Pro Gly
625                 630                 635                 640

Lys

<210> SEQ ID NO 7
<211> LENGTH: 614
<212> TYPE: PRT

<213> ORGANISM: Artificial Sequence
<220> FEATURE:
<223> OTHER INFORMATION: 336B11 Human single chain GITRL trimer-Fc
      (IgG1) amino acid sequence

<400> SEQUENCE: 7

```
Leu Gln Leu Glu Thr Ala Lys Glu Pro Cys Met Ala Lys Phe Gly Pro
1               5                   10                  15
Leu Pro Ser Lys Trp Gln Met Ala Ser Ser Glu Pro Pro Cys Val Asn
            20                  25                  30
Lys Val Ser Asp Trp Lys Leu Glu Ile Leu Gln Asn Gly Leu Tyr Leu
        35                  40                  45
Ile Tyr Gly Gln Val Ala Pro Asn Ala Asn Tyr Asn Asp Val Ala Pro
50                  55                  60
Phe Glu Val Arg Leu Tyr Lys Asn Lys Asp Met Ile Gln Thr Leu Thr
65                  70                  75                  80
Asn Lys Ser Lys Ile Gln Asn Val Gly Gly Thr Tyr Glu Leu His Val
                85                  90                  95
Gly Asp Thr Ile Asp Leu Ile Phe Asn Ser Glu His Gln Val Leu Lys
            100                 105                 110
Asn Asn Thr Tyr Trp Gly Ile Ile Leu Leu Ala Asn Pro Gln Phe Ile
        115                 120                 125
Ser Leu Gln Leu Glu Thr Ala Lys Glu Pro Cys Met Ala Lys Phe Gly
130                 135                 140
Pro Leu Pro Ser Lys Trp Gln Met Ala Ser Ser Glu Pro Pro Cys Val
145                 150                 155                 160
Asn Lys Val Ser Asp Trp Lys Leu Glu Ile Leu Gln Asn Gly Leu Tyr
                165                 170                 175
Leu Ile Tyr Gly Gln Val Ala Pro Asn Ala Asn Tyr Asn Asp Val Ala
            180                 185                 190
Pro Phe Glu Val Arg Leu Tyr Lys Asn Lys Asp Met Ile Gln Thr Leu
        195                 200                 205
Thr Asn Lys Ser Lys Ile Gln Asn Val Gly Gly Thr Tyr Glu Leu His
210                 215                 220
Val Gly Asp Thr Ile Asp Leu Ile Phe Asn Ser Glu His Gln Val Leu
225                 230                 235                 240
Lys Asn Asn Thr Tyr Trp Gly Ile Ile Leu Leu Ala Asn Pro Gln Phe
                245                 250                 255
Ile Ser Leu Gln Leu Glu Thr Ala Lys Glu Pro Cys Met Ala Lys Phe
            260                 265                 270
Gly Pro Leu Pro Ser Lys Trp Gln Met Ala Ser Ser Glu Pro Pro Cys
        275                 280                 285
Val Asn Lys Val Ser Asp Trp Lys Leu Glu Ile Leu Gln Asn Gly Leu
290                 295                 300
Tyr Leu Ile Tyr Gly Gln Val Ala Pro Asn Ala Asn Tyr Asn Asp Val
305                 310                 315                 320
Ala Pro Phe Glu Val Arg Leu Tyr Lys Asn Lys Asp Met Ile Gln Thr
                325                 330                 335
Leu Thr Asn Lys Ser Lys Ile Gln Asn Val Gly Gly Thr Tyr Glu Leu
            340                 345                 350
His Val Gly Asp Thr Ile Asp Leu Ile Phe Asn Ser Glu His Gln Val
        355                 360                 365
Leu Lys Asn Asn Thr Tyr Trp Gly Ile Ile Leu Leu Ala Asn Pro Gln
370                 375                 380
```

Phe Ile Ser Asp Lys Thr His Thr Cys Pro Pro Cys Pro Ala Pro Glu
385                 390                 395                 400

Leu Leu Gly Gly Pro Ser Val Phe Leu Phe Pro Pro Lys Pro Lys Asp
            405                 410                 415

Thr Leu Met Ile Ser Arg Thr Pro Glu Val Thr Cys Val Val Val Asp
        420                 425                 430

Val Ser His Glu Asp Pro Glu Val Lys Phe Asn Trp Tyr Val Asp Gly
    435                 440                 445

Val Glu Val His Asn Ala Lys Thr Lys Pro Arg Glu Glu Gln Tyr Asn
450                 455                 460

Ser Thr Tyr Arg Val Val Ser Val Leu Thr Val Leu His Gln Asp Trp
465                 470                 475                 480

Leu Asn Gly Lys Glu Tyr Lys Cys Lys Val Ser Asn Lys Ala Leu Pro
            485                 490                 495

Ala Pro Ile Glu Lys Thr Ile Ser Lys Ala Lys Gly Gln Pro Arg Glu
        500                 505                 510

Pro Gln Val Tyr Thr Leu Pro Pro Ser Arg Glu Glu Met Thr Lys Asn
    515                 520                 525

Gln Val Ser Leu Thr Cys Leu Val Lys Gly Phe Tyr Pro Ser Asp Ile
530                 535                 540

Ala Val Glu Trp Glu Ser Asn Gly Gln Pro Glu Asn Asn Tyr Lys Thr
545                 550                 555                 560

Thr Pro Pro Val Leu Asp Ser Asp Gly Ser Phe Phe Leu Tyr Ser Lys
            565                 570                 575

Leu Thr Val Asp Lys Ser Arg Trp Gln Gln Gly Asn Val Phe Ser Cys
        580                 585                 590

Ser Val Met His Glu Ala Leu His Asn His Tyr Thr Gln Lys Ser Leu
    595                 600                 605

Ser Leu Ser Pro Gly Lys
    610

<210> SEQ ID NO 8
<211> LENGTH: 643
<212> TYPE: PRT
<213> ORGANISM: Artificial Sequence
<220> FEATURE:
<223> OTHER INFORMATION: 336B14 Human single chain GITRL trimer-Fc
      (IgG2) amino acid sequence
<220> FEATURE:
<221> NAME/KEY: SIGNAL
<222> LOCATION: (1)..(27)

<400> SEQUENCE: 8

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Leu Gln Leu Glu Thr
            20                  25                  30

Ala Lys Glu Pro Cys Met Ala Lys Phe Gly Pro Leu Pro Ser Lys Trp
        35                  40                  45

Gln Met Ala Ser Ser Glu Pro Pro Cys Val Asn Lys Val Ser Asp Trp
    50                  55                  60

Lys Leu Glu Ile Leu Gln Asn Gly Leu Tyr Leu Ile Tyr Gly Gln Val
65                  70                  75                  80

Ala Pro Asn Ala Asn Tyr Asn Asp Val Ala Pro Phe Glu Val Arg Leu
            85                  90                  95

Tyr Lys Asn Lys Asp Met Ile Gln Thr Leu Thr Asn Lys Ser Lys Ile
        100                 105                 110

```
Gln Asn Val Gly Gly Thr Tyr Glu Leu His Val Gly Asp Thr Ile Asp
            115                 120                 125

Leu Ile Phe Asn Ser Glu His Gln Val Leu Lys Asn Asn Thr Tyr Trp
130                 135                 140

Gly Ile Ile Leu Leu Ala Asn Pro Gln Phe Ile Ser Leu Gln Leu Glu
145                 150                 155                 160

Thr Ala Lys Glu Pro Cys Met Ala Lys Phe Gly Pro Leu Pro Ser Lys
                165                 170                 175

Trp Gln Met Ala Ser Ser Glu Pro Pro Cys Val Asn Lys Val Ser Asp
                180                 185                 190

Trp Lys Leu Glu Ile Leu Gln Asn Gly Leu Tyr Leu Ile Tyr Gly Gln
            195                 200                 205

Val Ala Pro Asn Ala Asn Tyr Asn Asp Val Ala Pro Phe Glu Val Arg
        210                 215                 220

Leu Tyr Lys Asn Lys Asp Met Ile Gln Thr Leu Thr Asn Lys Ser Lys
225                 230                 235                 240

Ile Gln Asn Val Gly Gly Thr Tyr Glu Leu His Val Gly Asp Thr Ile
                    245                 250                 255

Asp Leu Ile Phe Asn Ser Glu His Gln Val Leu Lys Asn Asn Thr Tyr
            260                 265                 270

Trp Gly Ile Ile Leu Leu Ala Asn Pro Gln Phe Ile Ser Leu Gln Leu
        275                 280                 285

Glu Thr Ala Lys Glu Pro Cys Met Ala Lys Phe Gly Pro Leu Pro Ser
290                 295                 300

Lys Trp Gln Met Ala Ser Ser Glu Pro Pro Cys Val Asn Lys Val Ser
305                 310                 315                 320

Asp Trp Lys Leu Glu Ile Leu Gln Asn Gly Leu Tyr Leu Ile Tyr Gly
                325                 330                 335

Gln Val Ala Pro Asn Ala Asn Tyr Asn Asp Val Ala Pro Phe Glu Val
            340                 345                 350

Arg Leu Tyr Lys Asn Lys Asp Met Ile Gln Thr Leu Thr Asn Lys Ser
        355                 360                 365

Lys Ile Gln Asn Val Gly Gly Thr Tyr Glu Leu His Val Gly Asp Thr
370                 375                 380

Ile Asp Leu Ile Phe Asn Ser Glu His Gln Val Leu Lys Asn Asn Thr
385                 390                 395                 400

Tyr Trp Gly Ile Ile Leu Leu Ala Asn Pro Gln Phe Ile Ser Val Glu
                405                 410                 415

Arg Lys Ser Cys Val Glu Cys Pro Pro Cys Pro Ala Pro Pro Val Ala
            420                 425                 430

Gly Pro Ser Val Phe Leu Phe Pro Pro Lys Pro Lys Asp Thr Leu Met
        435                 440                 445

Ile Ser Arg Thr Pro Glu Val Thr Cys Val Val Val Asp Val Ser His
450                 455                 460

Glu Asp Pro Glu Val Gln Phe Asn Trp Tyr Val Asp Gly Val Glu Val
465                 470                 475                 480

His Asn Ala Lys Thr Lys Pro Arg Glu Glu Gln Phe Asn Ser Thr Phe
                485                 490                 495

Arg Val Val Ser Val Leu Thr Val Val His Gln Asp Trp Leu Asn Gly
            500                 505                 510

Lys Glu Tyr Lys Cys Lys Val Ser Asn Lys Gly Leu Pro Ala Pro Ile
        515                 520                 525
```

```
Glu Lys Thr Ile Ser Lys Thr Lys Gly Gln Pro Arg Glu Pro Gln Val
            530                 535                 540

Tyr Thr Leu Pro Pro Ser Arg Glu Glu Met Thr Lys Asn Gln Val Ser
545                 550                 555                 560

Leu Thr Cys Leu Val Lys Gly Phe Tyr Pro Ser Asp Ile Ala Val Glu
                565                 570                 575

Trp Glu Ser Asn Gly Gln Pro Glu Asn Asn Tyr Lys Thr Thr Pro Pro
                580                 585                 590

Met Leu Asp Ser Asp Gly Ser Phe Phe Leu Tyr Ser Lys Leu Thr Val
            595                 600                 605

Asp Lys Ser Arg Trp Gln Gln Gly Asn Val Phe Ser Cys Ser Val Met
610                 615                 620

His Glu Ala Leu His Asn His Tyr Thr Gln Lys Ser Leu Ser Leu Ser
625                 630                 635                 640

Pro Gly Lys

<210> SEQ ID NO 9
<211> LENGTH: 616
<212> TYPE: PRT
<213> ORGANISM: Artificial Sequence
<220> FEATURE:
<223> OTHER INFORMATION: 336B14 Human single chain GITRL trimer-Fc
      (IgG2) amino acid sequence

<400> SEQUENCE: 9

Leu Gln Leu Glu Thr Ala Lys Glu Pro Cys Met Ala Lys Phe Gly Pro
1               5                   10                  15

Leu Pro Ser Lys Trp Gln Met Ala Ser Ser Glu Pro Pro Cys Val Asn
            20                  25                  30

Lys Val Ser Asp Trp Lys Leu Glu Ile Leu Gln Asn Gly Leu Tyr Leu
        35                  40                  45

Ile Tyr Gly Gln Val Ala Pro Asn Ala Asn Tyr Asn Asp Val Ala Pro
50                  55                  60

Phe Glu Val Arg Leu Tyr Lys Asn Lys Asp Met Ile Gln Thr Leu Thr
65                  70                  75                  80

Asn Lys Ser Lys Ile Gln Asn Val Gly Gly Thr Tyr Glu Leu His Val
                85                  90                  95

Gly Asp Thr Ile Asp Leu Ile Phe Asn Ser Glu His Gln Val Leu Lys
            100                 105                 110

Asn Asn Thr Tyr Trp Gly Ile Ile Leu Leu Ala Asn Pro Gln Phe Ile
        115                 120                 125

Ser Leu Gln Leu Glu Thr Ala Lys Glu Pro Cys Met Ala Lys Phe Gly
130                 135                 140

Pro Leu Pro Ser Lys Trp Gln Met Ala Ser Ser Glu Pro Pro Cys Val
145                 150                 155                 160

Asn Lys Val Ser Asp Trp Lys Leu Glu Ile Leu Gln Asn Gly Leu Tyr
                165                 170                 175

Leu Ile Tyr Gly Gln Val Ala Pro Asn Ala Asn Tyr Asn Asp Val Ala
            180                 185                 190

Pro Phe Glu Val Arg Leu Tyr Lys Asn Lys Asp Met Ile Gln Thr Leu
        195                 200                 205

Thr Asn Lys Ser Lys Ile Gln Asn Val Gly Gly Thr Tyr Glu Leu His
210                 215                 220

Val Gly Asp Thr Ile Asp Leu Ile Phe Asn Ser Glu His Gln Val Leu
225                 230                 235                 240
```

```
Lys Asn Asn Thr Tyr Trp Gly Ile Ile Leu Ala Asn Pro Gln Phe
            245                 250                 255

Ile Ser Leu Gln Leu Glu Thr Ala Lys Glu Pro Cys Met Ala Lys Phe
        260                 265                 270

Gly Pro Leu Pro Ser Lys Trp Gln Met Ala Ser Ser Glu Pro Pro Cys
            275                 280                 285

Val Asn Lys Val Ser Asp Trp Lys Leu Glu Ile Leu Gln Asn Gly Leu
        290                 295                 300

Tyr Leu Ile Tyr Gly Gln Val Ala Pro Asn Ala Asn Tyr Asn Asp Val
305                 310                 315                 320

Ala Pro Phe Glu Val Arg Leu Tyr Lys Asn Lys Asp Met Ile Gln Thr
            325                 330                 335

Leu Thr Asn Lys Ser Lys Ile Gln Asn Val Gly Gly Thr Tyr Glu Leu
            340                 345                 350

His Val Gly Asp Thr Ile Asp Leu Ile Phe Asn Ser Glu His Gln Val
            355                 360                 365

Leu Lys Asn Asn Thr Tyr Trp Gly Ile Ile Leu Ala Asn Pro Gln
            370                 375                 380

Phe Ile Ser Val Glu Arg Lys Ser Cys Val Glu Cys Pro Pro Cys Pro
385                 390                 395                 400

Ala Pro Pro Val Ala Gly Pro Ser Val Phe Leu Phe Pro Pro Lys Pro
            405                 410                 415

Lys Asp Thr Leu Met Ile Ser Arg Thr Pro Glu Val Thr Cys Val Val
            420                 425                 430

Val Asp Val Ser His Glu Asp Pro Glu Val Gln Phe Asn Trp Tyr Val
            435                 440                 445

Asp Gly Val Glu Val His Asn Ala Lys Thr Lys Pro Arg Glu Glu Gln
450                 455                 460

Phe Asn Ser Thr Phe Arg Val Val Ser Val Leu Thr Val Val His Gln
465                 470                 475                 480

Asp Trp Leu Asn Gly Lys Glu Tyr Lys Cys Lys Val Ser Asn Lys Gly
            485                 490                 495

Leu Pro Ala Pro Ile Glu Lys Thr Ile Ser Lys Thr Lys Gly Gln Pro
            500                 505                 510

Arg Glu Pro Gln Val Tyr Thr Leu Pro Pro Ser Arg Glu Glu Met Thr
            515                 520                 525

Lys Asn Gln Val Ser Leu Thr Cys Leu Val Lys Gly Phe Tyr Pro Ser
            530                 535                 540

Asp Ile Ala Val Glu Trp Glu Ser Asn Gly Gln Pro Glu Asn Asn Tyr
545                 550                 555                 560

Lys Thr Thr Pro Pro Met Leu Asp Ser Asp Gly Ser Phe Phe Leu Tyr
            565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
            595                 600                 605

Ser Leu Ser Leu Ser Pro Gly Lys
        610                 615

<210> SEQ ID NO 10
<211> LENGTH: 227
<212> TYPE: PRT
<213> ORGANISM: Artificial Sequence
<220> FEATURE:
<223> OTHER INFORMATION: Human IgG1 Fc region
```

<400> SEQUENCE: 10

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 11
<211> LENGTH: 230
<212> TYPE: PRT
<213> ORGANISM: Artificial Sequence
<220> FEATURE:
<223> OTHER INFORMATION: Human IgG1 Fc region

<400> SEQUENCE: 11

```
Lys Ser Ser Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110
```

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
            165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
            195                 200                 205

Ser Val Met His Glu Ala Leu His Asn His Tyr Thr Gln Lys Ser Leu
            210                 215                 220

Ser Leu Ser Pro Gly Lys
225                 230

<210> SEQ ID NO 12
<211> LENGTH: 232
<212> TYPE: PRT
<213> ORGANISM: Artificial Sequence
<220> FEATURE:
<223> OTHER INFORMATION: Human IgG1 Fc region

<400> SEQUENCE: 12

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
        100                 105                 110

Leu Pro Ala Pro Ile Glu Lys Thr Ile Ser Lys Ala Lys Gly Gln Pro
    115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 13
<211> LENGTH: 224
<212> TYPE: PRT
<213> ORGANISM: Artificial Sequence
<220> FEATURE:
<223> OTHER INFORMATION: Human IgG2 Fc region

<400> SEQUENCE: 13

```
Cys Val Glu Cys Pro Pro Cys Pro Ala Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220
```

<210> SEQ ID NO 14
<211> LENGTH: 229
<212> TYPE: PRT
<213> ORGANISM: Artificial Sequence
<220> FEATURE:
<223> OTHER INFORMATION: Human IgG2 Fc region

<400> SEQUENCE: 14

```
Val Glu Arg Lys Ser Cys Val Glu Cys Pro Pro Cys Pro Ala Pro Pro
1               5                   10                  15

Val Ala Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Phe Arg Val Val Ser Val Leu Thr Val Val His Gln Asp Trp Leu
                85                  90                  95
```

Asn Gly Lys Glu Tyr Lys Cys Lys Val Ser Asn Lys Gly Leu Pro Ala
                100                 105                 110

Pro Ile Glu Lys Thr Ile Ser Lys Thr Lys Gly Gln Pro Arg Glu Pro
            115                 120                 125

Gln Val Tyr Thr Leu Pro Pro Ser Arg Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Met Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 15
<211> LENGTH: 330
<212> TYPE: PRT
<213> ORGANISM: Artificial Sequence
<220> FEATURE:
<223> OTHER INFORMATION: Human IgG1 Heavy chain constant region

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 16
<211> LENGTH: 326
<212> TYPE: PRT
<213> ORGANISM: Artificial Sequence
<220> FEATURE:
<223> OTHER INFORMATION: Human IgG2 Heavy chain constant region

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 17
<211> LENGTH: 377
<212> TYPE: PRT
<213> ORGANISM: Artificial Sequence
<220> FEATURE:
<223> OTHER INFORMATION: Human IgG3 Heavy chain constant region

<400> SEQUENCE: 17

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285
```

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 18
<211> LENGTH: 327
<212> TYPE: PRT
<213> ORGANISM: Artificial Sequence
<220> FEATURE:
<223> OTHER INFORMATION: Human IgG4 Heavy chain constant region

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 19
<211> LENGTH: 600
<212> TYPE: DNA
<213> ORGANISM: Artificial Sequence
<220> FEATURE:
<223> OTHER INFORMATION: Human GITRL nucleotide sequence

<400> SEQUENCE: 19

```
atgacattgc atccttcacc catcacttgt gaatttttgt tttccacagc tctcatttct    60
ccaaaaatgt gtttgagcca cttggaaaat atgcctttaa gccattcaag aactcaagga   120
gctcagagat catcctggaa gctgtggctc ttttgctcaa tagttatgtt gctatttctt   180
tgctccttca gttggctaat ctttattttt ctccaattag agactgctaa ggagccctgt   240
atggctaagt ttggaccatt accctcaaaa tggcaaatgg catcttctga acctccttgc   300
gtgaataagg tgtctgactg gaagctggag atacttcaga atggcttata tttaatttat   360
ggccaagtgg ctcccaatgc aaactacaat gatgtagctc cttttgaggt gcggctgtat   420
aaaaacaaag acatgataca aactctaaca acaaatcta aaatccaaaa tgtaggaggg   480
acttatgaat tgcatgttgg ggacaccata gacttgatat tcaactctga gcatcaggtt   540
ctaaaaaata atacatactg gggtatcatt ttactagcaa atccccaatt catctcctag   600
```

<210> SEQ ID NO 20
<211> LENGTH: 450
<212> TYPE: DNA
<213> ORGANISM: Artificial Sequence
<220> FEATURE:
<223> OTHER INFORMATION: Human GITRL signal/anchor region and
    extracellular domain nucleotide sequence

<400> SEQUENCE: 20

```
ttttgctcaa tagttatgtt gctatttctt tgctccttca gttggctaat ctttattttt    60
ctccaattag agactgctaa ggagccctgt atggctaagt ttggaccatt accctcaaaa   120
tggcaaatgg catcttctga acctccttgc gtgaataagg tgtctgactg gaagctggag   180
atacttcaga atggcttata tttaatttat ggccaagtgg ctcccaatgc aaactacaat   240
gatgtagctc cttttgaggt gcggctgtat aaaaacaaag acatgataca aactctaaca   300
aacaaatcta aaatccaaaa tgtaggaggg acttatgaat tgcatgttgg ggacaccata   360
gacttgatat tcaactctga gcatcaggtt ctaaaaaata atacatactg gggtatcatt   420
ttactagcaa atccccaatt catctcctag                                    450
```

<210> SEQ ID NO 21
<211> LENGTH: 390
<212> TYPE: DNA
<213> ORGANISM: Artificial Sequence
<220> FEATURE:
<223> OTHER INFORMATION: Human GITRL extracellular domain nucleotide
    sequence

<400> SEQUENCE: 21

```
ctccaattag agactgctaa ggagccctgt atggctaagt ttggaccatt accctcaaaa      60
tggcaaatgg catcttctga acctccttgc gtgaataagg tgtctgactg gaagctggag     120
atacttcaga atggcttata tttaatttat ggccaagtgg ctcccaatgc aaactacaat     180
gatgtagctc cttttgaggt gcggctgtat aaaaacaaag acatgataca aactctaaca     240
aacaaatcta aatccaaaa tgtaggaggg acttatgaat tgcatgttgg ggacaccata      300
gacttgatat tcaactctga gcatcaggtt ctaaaaaata atacatactg gggtatcatt     360
ttactagcaa atccccaatt catctcctag                                      390
```

<210> SEQ ID NO 22
<211> LENGTH: 1161
<212> TYPE: DNA
<213> ORGANISM: Artificial Sequence
<220> FEATURE:
<223> OTHER INFORMATION: Human single chain GITRL trimer

<400> SEQUENCE: 22

```
ctgcaactgg aaaccgctaa ggagccctgt atggctaagt tcggcccact gccttccaaa      60
tggcagatgg catctagtga gccacccgt gttaataaag ttagcgattg gaaactggag      120
atcctgcaaa acgggctcta cctgatttac ggacaagttg ctcctaatgc taactacaat     180
gatgtggctc cttttgaagt taggctgtat aaaaacaaag acatgatcca aactctcact     240
aacaaaagca aaatccaaaa tgtcggtggg acttatgagc tccatgttgg ggacaccatc     300
gacctgattt tcaactctga gcatcaggtt ctcaaaaata atacatactg gggaatcatt     360
ctcctcgcga atccacaatt catctctctc caactggaaa ccgctaaaga accttgcatg     420
gccaaatttg gacctctccc aagcaaatgg caaatggctt cttctgaacc tccttgcgtg     480
aataaggtgt ctgactggaa gctggagatt ctgcagaatg gcctctatct gatttatggg     540
caagttgcac ctaacgctaa ttataacgac gtcgcaccat cgaagttcg cctctacaaa      600
aataaggaca tgattcaaac actgactaat aaaatccaaa ttcaaaacgt tgggggcaca     660
tacgaactgc acgtcggcga tactattgat ctcatcttta attccgaaca ccaggtcctc     720
aaaaacaata cctatggggg gatcatcctc ctggctaacc cacaatttat atctctccaa     780
ctcgaaacag ccaaggaacc atgtatggca agtttggtc ccctcccatc caagtggcaa      840
atggccagtt ctgaaccccc atgcgttaat aaggtttccg actggaaact ggagatcctg     900
caaaatggtc tgtacctcat ctatggtcaa gttgcaccaa acgccaatta caatgatgtt     960
gcaccatttg aagttcgcct gtacaaaaac aaagatatga tccaaaccct cactaacaaa    1020
tctaaaatcc aaaatgttgg tggtacttac gaactgcatg tgggtgacac catcgacctc    1080
atcttcaatt ccgagcatca ggtgctcaaa acaatacat attggggcat aattctgctc     1140
gcaaatccac aattcatctc t                                              1161
```

<210> SEQ ID NO 23
<211> LENGTH: 1242
<212> TYPE: DNA
<213> ORGANISM: Artificial Sequence
<220> FEATURE:
<223> OTHER INFORMATION: Human single chain GITRL trimer with signal
      sequence nucleotide sequence

<400> SEQUENCE: 23

```
atggagtggg gttatctgct cgaagtgacc tccctgctgg ccgccctgct cctgctgcaa      60
```

-continued

| | |
|---|---|
| cgctctccta tcgtgcacgc cctgcaactg gaaaccgcta aggagccctg tatggctaag | 120 |
| ttcggcccac tgccttccaa atggcagatg gcatctagtg agccaccctg tgttaataaa | 180 |
| gttagcgatt ggaaactgga gatcctgcaa acgggctct acctgattta cggacaagtt | 240 |
| gctcctaatg ctaactacaa tgatgtggct ccttttgaag ttaggctgta taaaaacaaa | 300 |
| gacatgatcc aaactctcac taacaaaagc aaaatccaaa atgtcggtgg gacttatgag | 360 |
| ctccatgttg gggacaccat cgacctgatt ttcaactctg agcatcaggt tctcaaaaat | 420 |
| aatacatact ggggaatcat tctcctcgcg aatccacaat tcatctctct ccaactggaa | 480 |
| accgctaaag aaccttgcat ggccaaattt ggacctctcc caagcaaatg gcaaatggct | 540 |
| tcttctgaac ctccttgcgt gaataaggtg tctgactgga agctggagat tctgcagaat | 600 |
| ggcctctatc tgatttatgg gcaagttgca cctaacgcta attataacga cgtcgcacca | 660 |
| ttcgaagttc gcctctacaa aaataaggac atgattcaaa cactgactaa taaatccaaa | 720 |
| attcaaaacg ttgggggcac atacgaactg cacgtcggcg atactattga tctcatcttt | 780 |
| aattccgaac caggtcct caaaaacaat acctattggg ggatcatcct cctggctaac | 840 |
| ccacaattta tatctctcca actcgaaaca gccaaggaac catgtatggc aaagtttggt | 900 |
| cccctcccat ccagtggca atggccagt tctgaaccc catgcgttaa taaggtttcc | 960 |
| gactggaaac tggagatcct gcaaaatggt ctgtacctca tctatggtca agttgcacca | 1020 |
| aacgccaatt acaatgatgt tgcaccattt gaagttcgcc tgtacaaaaa caagatatg | 1080 |
| atccaaaccc tcactaacaa atctaaaatc caaaatgttg gtggtactta cgaactgcat | 1140 |
| gtgggtgaca ccatcgacct catcttcaat tccgagcatc aggtgctcaa aaacaataca | 1200 |
| tattggggca taattctgct cgcaaatcca caattcatct ct | 1242 |

<210> SEQ ID NO 24
<211> LENGTH: 1926
<212> TYPE: DNA
<213> ORGANISM: Artificial Sequence
<220> FEATURE:
<223> OTHER INFORMATION: 336B11 Human single chain GITRL trimer-Fc
(IgG1) nucleotide sequence

<400> SEQUENCE: 24

| | |
|---|---|
| atggagtggg gttatctgct cgaagtgacc tccctgctgg ccgccctgct cctgctgcaa | 60 |
| cgctctccta tcgtgcacgc cctgcaactg gaaaccgcta aggagccctg tatggctaag | 120 |
| ttcggcccac tgccttccaa atggcagatg gcatctagtg agccaccctg tgttaataaa | 180 |
| gttagcgatt ggaaactgga gatcctgcaa acgggctct acctgattta cggacaagtt | 240 |
| gctcctaatg ctaactacaa tgatgtggct ccttttgaag ttaggctgta taaaaacaaa | 300 |
| gacatgatcc aaactctcac taacaaaagc aaaatccaaa atgtcggtgg gacttatgag | 360 |
| ctccatgttg gggacaccat cgacctgatt ttcaactctg agcatcaggt tctcaaaaat | 420 |
| aatacatact ggggaatcat tctcctcgcg aatccacaat tcatctctct ccaactggaa | 480 |
| accgctaaag aaccttgcat ggccaaattt ggacctctcc caagcaaatg gcaaatggct | 540 |
| tcttctgaac ctccttgcgt gaataaggtg tctgactgga agctggagat tctgcagaat | 600 |
| ggcctctatc tgatttatgg gcaagttgca cctaacgcta attataacga cgtcgcacca | 660 |
| ttcgaagttc gcctctacaa aaataaggac atgattcaaa cactgactaa taaatccaaa | 720 |
| attcaaaacg ttgggggcac atacgaactg cacgtcggcg atactattga tctcatcttt | 780 |
| aattccgaac caggtcct caaaaacaat acctattggg ggatcatcct cctggctaac | 840 |

```
ccacaattta tatctctcca actcgaaaca gccaaggaac catgtatggc aaagtttggt      900
cccctcccat ccaagtggca aatggccagt tctgaacccc catgcgttaa taaggtttcc      960
gactggaaac tggagatcct gcaaaatggt ctgtacctca tctatggtca agttgcacca     1020
aacgccaatt acaatgatgt tgcaccattt gaagttcgcc tgtacaaaaa caaagatatg     1080
atccaaaccc tcactaacaa atctaaaatc aaaatgttg gtggtactta cgaactgcat      1140
gtgggtgaca ccatcgacct catcttcaat tccgagcatc aggtgctcaa aacaataca      1200 tattggggca taattctgct cgcaaatcca caattcatct ctgacaagac ccacacctgc     1260
cctccctgcc ctgcccctga gctgctgggc ggaccttccg tgttcctgtt ccctcctaag     1320
cctaaggaca ccctgatgat ctcccggacc cctgaagtga catgcgtggt ggtggacgtg     1380
tcccacgagg accctgaggt gaagttcaac tggtatgtgg acggcgtgga ggtgcacaac     1440
gctaagacca agcctaggga ggagcagtac aactccacct accgggtggt gtctgtgctg     1500
accgtgctgc accaggactg gctgaacggc aagaataca agtgcaaggt ctccaacaag      1560
gccctgcccg ctcccatcga gaaaaccatc agcaaggcaa agggccagcc tcgcgagcct     1620
caggtgtaca ccctgccacc cagccgggag gagatgacca gaaccaggt gtccctgacc      1680 tgtctggtga agggctttta cccttccgat attgccgtgg agtgggagtc taacggccag     1740
cccgagaaca actacaagac caccctcct gtgctggact ccgacggctc cttcttcctg      1800
tactccaagc tgaccgtgga caagtcccgg tggcagcagg gcaacgtgtt ctcctgctcc     1860
gtgatgcacg aggccctgca caaccactac acccagaaga gcctgtctct gtctcctggc     1920
aagtga                                                               1926

<210> SEQ ID NO 25
<211> LENGTH: 1932
<212> TYPE: DNA
<213> ORGANISM: Artificial Sequence
<220> FEATURE:
<223> OTHER INFORMATION: 336B14 Human single chain GITRL trimer-Fc
      (IgG2) nucleotide sequence

<400> SEQUENCE: 25
atggagtggg gttatctgct cgaagtgacc tccctgctgg ccgccctgct cctgctgcaa       60
cgctctccta tcgtgcacgc cctgcaactg gaaaccgcta aggagccctg tatggctaag      120
ttcggcccac tgccttccaa atggcagatg gcatctagtg agccaccctg tgttaataaa      180
gttagcgatt ggaaactgga gatcctgcaa aacgggctct acctgattta cggacaagtt      240
gctcctaatg ctaactacaa tgatgtggct ccttttgaag ttaggctgta taaaaacaaa      300
gacatgatcc aaactctcac taacaaaagc aaaatccaaa atgtcggtgg acttatgag      360 ctccatgttg ggacaccat cgacctgatt ttcaactctg agcatcaggt tctcaaaaat       420
aatacatact ggggaatcat tctcctcgcg aatccacaat tcatctctct ccaactggaa      480
accgctaaag aaccttgcat ggccaaattt ggacctctcc caagcaaatg gcaaatggct     540
tcttctgaac ctccttgcgt gaataaggtg tctgactgga agctggagat tctgcagaat     600
ggcctctatc tgatttatgg gcaagttgca cctaacgcta attataacga cgtcgcacca     660
ttcgaagttc gcctctacaa aaataaggac atgattcaaa cactgactaa taatccaaa      720 attcaaaacg ttgggggcac atacgaactg cacgtcggcg atactattga tctcatcttt     780
aattccgaac caggtcct caaaaacaat acctattggg ggatcatcct cctggctaac      840
ccacaattta tatctctcca actcgaaaca gccaaggaac catgtatggc aaagtttggt     900
```

```
cccctcccat ccaagtggca aatggccagt tctgaacccc catgcgttaa taaggtttcc    960
gactggaaac tggagatcct gcaaaatggt ctgtacctca tctatggtca agttgcacca   1020
aacgccaatt acaatgatgt tgcaccattt gaagttcgcc tgtacaaaaa caagatatg    1080 atccaaaccc tcactaacaa atctaaaatc caaaatgttg gtggtactta cgaactgcat   1140
gtgggtgaca ccatcgacct catcttcaat tccgagcatc aggtgctcaa aacaataca    1200 tattgggca taattctgct cgcaaatcca caattcatct ctgttgagcg caaatcttgt    1260
gtcgagtgcc caccttgccc agcaccacct gtggcaggac cttcagtctt cctcttcccc   1320
ccaaaaccca aggacaccct catgatctcc cggacccctg aggtcacatg cgtggtggtg   1380
gacgtgagcc acgaagaccc cgaggtccag tttaattggt atgtcgacgg cgtggaggtg   1440
cataatgcca agacaaagcc acgggaggag cagttcaaca gcacattcag ggtggtcagc   1500
gtcctcaccg ttgtgcacca ggactggctg aacggcaagg agtacaagtg caaggtgtcc   1560
aacaaaggcc tcccagcccc catcgagaaa accatctcca aaaccaaagg gcagcccaga   1620
gaaccacagg tgtacaccct gccccatcc cgggaggaga tgaccaagaa ccaggtcagc    1680
ctgacctgcc tggtgaaggg attttatcct tccgacatcg ccgtggagtg ggagagcaat   1740
gggcagcctg agaacaacta caagaccaca cctcccatgc tggactccga cggctccttc   1800
ttcctgtatt ccaaactcac cgtggacaag agcaggtggc agcagggaa cgtcttctca    1860 tgctccgtga tgcatgaggc tctgcacaac cactacacac agaagagcct ctccctgtcc   1920
cctggaaagt ga                                                        1932
```

<210> SEQ ID NO 26
<211> LENGTH: 224
<212> TYPE: PRT
<213> ORGANISM: Artificial Sequence
<220> FEATURE:
<223> OTHER INFORMATION: Human IgG2 Fc region (13A Version)

<400> SEQUENCE: 26

```
Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Lys Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Lys
                165                 170                 175
```

```
Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 27
<211> LENGTH: 224
<212> TYPE: PRT
<213> ORGANISM: Artificial Sequence
<220> FEATURE:
<223> OTHER INFORMATION: Human IgG2 Fc region (13B Version)

<400> SEQUENCE: 27

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Glu Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Glu Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 28
<211> LENGTH: 235
<212> TYPE: PRT
<213> ORGANISM: Artificial Sequence
<220> FEATURE:
<223> OTHER INFORMATION: Human IgG2 Fc region (13A Version)

<400> SEQUENCE: 28

Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45
```

```
Cys Val Val Asp Val Ser His Glu Asp Pro Glu Val Gln Phe Asn
 50                  55                  60

Trp Tyr Val Asp Gly Val Glu Val His Asn Ala Lys Thr Lys Pro Arg
 65                  70                  75                  80

Glu Glu Gln Phe Asn Ser Thr Phe Arg Val Val Ser Val Leu Thr Val
                 85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
        115                 120                 125

Gly Gln Pro Arg Glu Pro Gln Val Tyr Thr Leu Pro Pro Ser Arg Glu
    130                 135                 140

Lys Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Lys Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 29
<211> LENGTH: 235
<212> TYPE: PRT
<213> ORGANISM: Artificial Sequence
<220> FEATURE:
<223> OTHER INFORMATION: Human IgG2 Fc region (13A Version )

<400> SEQUENCE: 29

Thr Lys Val Asp Lys Thr Val Glu Arg Lys Ser Cys Val Glu Cys Pro
1               5                  10                  15

Pro Cys Pro Ala Pro Pro Val Ala Gly Pro Ser Val Phe Leu Phe Pro
                20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
 50                  55                  60

Trp Tyr Val Asp Gly Val Glu Val His Asn Ala Lys Thr Lys Pro Arg
 65                  70                  75                  80

Glu Glu Gln Phe Asn Ser Thr Phe Arg Val Val Ser Val Leu Thr Val
                 85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
        115                 120                 125

Gly Gln Pro Arg Glu Pro Gln Val Tyr Thr Leu Pro Pro Ser Arg Glu
    130                 135                 140

Lys Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175
```

```
Asn Asn Tyr Lys Thr Thr Pro Pro Met Leu Lys Ser Asp Gly Ser Phe
            180                 185                 190

Phe Leu Tyr Ser Lys Leu Thr Val Asp Lys Ser Arg Trp Gln Gln Gly
            195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

<210> SEQ ID NO 30
<211> LENGTH: 235
<212> TYPE: PRT
<213> ORGANISM: Artificial Sequence
<220> FEATURE:
<223> OTHER INFORMATION: Human IgG2 Fc region (13B Version)

<400> SEQUENCE: 30

Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65              70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
            115                 120                 125

Gly Gln Pro Arg Glu Pro Gln Val Tyr Thr Leu Pro Pro Ser Arg Glu
            130                 135                 140

Glu Met Thr Lys Asn Gln Val Ser Leu Thr Cys Leu Val Glu Gly Phe
145                 150                 155                 160

Tyr Pro Ser Asp Ile Ala Val Glu Trp Glu Ser Asn Gly Gln Pro Glu
            165                 170                 175

Asn Asn Tyr Lys Thr Thr Pro Pro Met Leu Asp Ser Asp Gly Ser Phe
            180                 185                 190

Phe Leu Tyr Ser Glu Leu Thr Val Asp Lys Ser Arg Trp Gln Gln Gly
            195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
225                 230                 235

<210> SEQ ID NO 31
<211> LENGTH: 235
<212> TYPE: PRT
<213> ORGANISM: Artificial Sequence
<220> FEATURE:
<223> OTHER INFORMATION: Human IgG2 Fc region (13B Version)

<400> SEQUENCE: 31

Thr Lys Val Asp Lys Thr Val Glu Arg Lys Ser Cys Val Glu Cys Pro
```

```
                1               5                  10                 15
        Pro Cys Pro Ala Pro Val Ala Gly Pro Ser Val Phe Leu Phe Pro
                         20                  25                 30

Pro Lys Pro Lys Asp Thr Leu Met Ile Ser Arg Thr Pro Glu Val Thr
                         35                  40                 45

Cys Val Val Asp Val Ser His Glu Asp Pro Glu Val Gln Phe Asn
            50                  55                  60

Trp Tyr Val Asp Gly Val Glu Val His Asn Ala Lys Thr Lys Pro Arg
         65                  70                  75                  80

Glu Glu Gln Phe Asn Ser Thr Phe Arg Val Val Ser Val Leu Thr Val
                             85                  90                  95

Val His Gln Asp Trp Leu Asn Gly Lys Glu Tyr Lys Cys Lys Val Ser
                         100                 105                 110

Asn Lys Gly Leu Pro Ala Pro Ile Glu Lys Thr Ile Ser Lys Thr Lys
                         115                 120                 125

Gly Gln Pro Arg Glu Pro Gln Val Tyr Thr Leu Pro Pro Ser Arg Glu
            130                 135                 140

Glu Met Thr Lys Asn Gln Val Ser Leu Thr Cys Leu Val Glu Gly Phe
        145                 150                 155                 160

Tyr Pro Ser Asp Ile Ala Val Glu Trp Glu Ser Asn Gly Gln Pro Glu
                         165                 170                 175

Asn Asn Tyr Lys Thr Thr Pro Pro Met Leu Asp Ser Asp Gly Ser Phe
                         180                 185                 190

Phe Leu Tyr Ser Glu Leu Thr Val Asp Lys Ser Arg Trp Gln Gln Gly
                         195                 200                 205

Asn Val Phe Ser Cys Ser Val Met His Glu Ala Leu His Asn His Tyr
            210                 215                 220

Thr Gln Lys Ser Leu Ser Leu Ser Pro Gly Lys
        225                 230                 235

<210> SEQ ID NO 32
<211> LENGTH: 7
<212> TYPE: PRT
<213> ORGANISM: Artificial Sequence
<220> FEATURE:
<223> OTHER INFORMATION: Human GITRL Stalk Region

<400> SEQUENCE: 32

Leu Gln Leu Glu Thr Ala Lys
1               5

<210> SEQ ID NO 33
<211> LENGTH: 103
<212> TYPE: PRT
<213> ORGANISM: Artificial Sequence
<220> FEATURE:
<223> OTHER INFORMATION: Human GITRL TNF Homology Domain

<400> SEQUENCE: 33

Lys Trp Gln Met Ala Ser Ser Glu Pro Pro Cys Val Asn Lys Val Ser
1               5                  10                  15

Asp Trp Lys Leu Glu Ile Leu Gln Asn Gly Leu Tyr Leu Ile Tyr Gly
                 20                  25                  30

Gln Val Ala Pro Asn Ala Asn Tyr Asn Asp Val Ala Pro Phe Glu Val
             35                  40                  45

Arg Leu Tyr Lys Asn Lys Asp Met Ile Gln Thr Leu Thr Asn Lys Ser
         50                  55                  60
```

```
Lys Ile Gln Asn Val Gly Gly Thr Tyr Glu Leu His Val Gly Asp Thr
 65                  70                  75                  80

Ile Asp Leu Ile Phe Asn Ser Glu His Gln Val Leu Lys Asn Asn Thr
                 85                  90                  95

Tyr Trp Gly Ile Ile Leu Leu
            100

<210> SEQ ID NO 34
<211> LENGTH: 8
<212> TYPE: PRT
<213> ORGANISM: Artificial Sequence
<220> FEATURE:
<223> OTHER INFORMATION: Linker

<400> SEQUENCE: 34

Glu Ser Gly Gly Gly Gly Val Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Linker

<400> SEQUENCE: 35

Leu Glu Ser Gly Gly Gly Gly Val Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Linker

<400> SEQUENCE: 36

Gly Arg Ala Gln Val Thr
1               5

<210> SEQ ID NO 37
<211> LENGTH: 6
<212> TYPE: PRT
<213> ORGANISM: Artificial Sequence
<220> FEATURE:
<223> OTHER INFORMATION: Linker

<400> SEQUENCE: 37

Trp Arg Ala Gln Val Thr
1               5

<210> SEQ ID NO 38
<211> LENGTH: 12
<212> TYPE: PRT
<213> ORGANISM: Artificial Sequence
<220> FEATURE:
<223> OTHER INFORMATION: Linker

<400> SEQUENCE: 38

Ala Arg Gly Arg Ala Gln Val Thr Phe Leu Ala Gly
1               5                   10

<210> SEQ ID NO 39
<211> LENGTH: 8
<212> TYPE: PRT
<213> ORGANISM: Artificial Sequence
```

<220> FEATURE:
<223> OTHER INFORMATION: FLAG Tag

<400> SEQUENCE: 39

Asp Tyr Lys Asp Asp Asp Asp Lys
1               5

<210> SEQ ID NO 40
<211> LENGTH: 183
<212> TYPE: PRT
<213> ORGANISM: Artificial Sequence
<220> FEATURE:
<223> OTHER INFORMATION: Human OX40L (TNFSF4) amino acid sequence

<400> SEQUENCE: 40

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 41
<211> LENGTH: 160
<212> TYPE: PRT
<213> ORGANISM: Artificial Sequence
<220> FEATURE:
<223> OTHER INFORMATION: Human OX40L transmembrane and extracellular
      domain amino acid sequence

<400> SEQUENCE: 41

Leu Leu Leu Val Ala Ser Val Ile Gln Gly Leu Gly Leu Leu Leu Cys
1               5                   10                  15

Phe Thr Tyr Ile Cys Leu His Phe Ser Ala Leu Gln Val Ser His Arg
            20                  25                  30

Tyr Pro Arg Ile Gln Ser Ile Lys Val Gln Phe Thr Glu Tyr Lys Lys
        35                  40                  45

Glu Lys Gly Phe Ile Leu Thr Ser Gln Lys Glu Asp Glu Ile Met Lys
    50                  55                  60

Val Gln Asn Asn Ser Val Ile Ile Asn Cys Asp Gly Phe Tyr Leu Ile
65                  70                  75                  80

Ser Leu Lys Gly Tyr Phe Ser Gln Glu Val Asn Ile Ser Leu His Tyr
                85                  90                  95

Gln Lys Asp Glu Glu Pro Leu Phe Gln Leu Lys Lys Val Arg Ser Val
            100                 105                 110

Asn Ser Leu Met Val Ala Ser Leu Thr Tyr Lys Asp Lys Val Tyr Leu
        115                 120                 125

Asn Val Thr Thr Asp Asn Thr Ser Leu Asp Asp Phe His Val Asn Gly
    130                 135                 140

Gly Glu Leu Ile Leu Ile His Gln Asn Pro Gly Glu Phe Cys Val Leu
145                 150                 155                 160

<210> SEQ ID NO 42
<211> LENGTH: 133
<212> TYPE: PRT
<213> ORGANISM: Artificial Sequence
<220> FEATURE:
<223> OTHER INFORMATION: Human OX40L extracellular domain amino acid
      sequence

<400> SEQUENCE: 42

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 43
<211> LENGTH: 426
<212> TYPE: PRT
<213> ORGANISM: Artificial Sequence
<220> FEATURE:
<223> OTHER INFORMATION: Human single chain OX40L trimer amino acid
      sequence
<220> FEATURE:
<221> NAME/KEY: SIGNAL
<222> LOCATION: (1)..(27)

<400> SEQUENCE: 43

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Gln Val Ser His Arg
            20                  25                  30

Tyr Pro Arg Ile Gln Ser Ile Lys Val Gln Phe Thr Glu Tyr Lys Lys
        35                  40                  45

Glu Lys Gly Phe Ile Leu Thr Ser Gln Lys Glu Asp Glu Ile Met Lys
    50                  55                  60

```
Val Gln Asn Asn Ser Val Ile Ile Asn Cys Asp Gly Phe Tyr Leu Ile
 65                  70                  75                  80

Ser Leu Lys Gly Tyr Phe Ser Gln Glu Val Asn Ile Ser Leu His Tyr
             85                  90                  95

Gln Lys Asp Glu Glu Pro Leu Phe Gln Leu Lys Lys Val Arg Ser Val
            100                 105                 110

Asn Ser Leu Met Val Ala Ser Leu Thr Tyr Lys Asp Lys Val Tyr Leu
            115                 120                 125

Asn Val Thr Thr Asp Asn Thr Ser Leu Asp Asp Phe His Val Asn Gly
            130                 135                 140

Gly Glu Leu Ile Leu Ile His Gln Asn Pro Gly Glu Phe Cys Val Leu
145                 150                 155                 160

Gln Val Ser His Arg Tyr Pro Arg Ile Gln Ser Ile Lys Val Gln Phe
                165                 170                 175

Thr Glu Tyr Lys Lys Glu Lys Gly Phe Ile Leu Thr Ser Gln Lys Glu
            180                 185                 190

Asp Glu Ile Met Lys Val Gln Asn Asn Ser Val Ile Ile Asn Cys Asp
            195                 200                 205

Gly Phe Tyr Leu Ile Ser Leu Lys Gly Tyr Phe Ser Gln Glu Val Asn
210                 215                 220

Ile Ser Leu His Tyr Gln Lys Asp Glu Glu Pro Leu Phe Gln Leu Lys
225                 230                 235                 240

Lys Val Arg Ser Val Asn Ser Leu Met Val Ala Ser Leu Thr Tyr Lys
                245                 250                 255

Asp Lys Val Tyr Leu Asn Val Thr Thr Asp Asn Thr Ser Leu Asp Asp
            260                 265                 270

Phe His Val Asn Gly Gly Glu Leu Ile Leu Ile His Gln Asn Pro Gly
            275                 280                 285

Glu Phe Cys Val Leu Gln Val Ser His Arg Tyr Pro Arg Ile Gln Ser
290                 295                 300

Ile Lys Val Gln Phe Thr Glu Tyr Lys Lys Glu Lys Gly Phe Ile Leu
305                 310                 315                 320

Thr Ser Gln Lys Glu Asp Glu Ile Met Lys Val Gln Asn Asn Ser Val
                325                 330                 335

Ile Ile Asn Cys Asp Gly Phe Tyr Leu Ile Ser Leu Lys Gly Tyr Phe
            340                 345                 350

Ser Gln Glu Val Asn Ile Ser Leu His Tyr Gln Lys Asp Glu Glu Pro
            355                 360                 365

Leu Phe Gln Leu Lys Lys Val Arg Ser Val Asn Ser Leu Met Val Ala
            370                 375                 380

Ser Leu Thr Tyr Lys Asp Lys Val Tyr Leu Asn Val Thr Thr Asp Asn
385                 390                 395                 400

Thr Ser Leu Asp Asp Phe His Val Asn Gly Gly Glu Leu Ile Leu Ile
                405                 410                 415

His Gln Asn Pro Gly Glu Phe Cys Val Leu
            420                 425

<210> SEQ ID NO 44
<211> LENGTH: 399
<212> TYPE: PRT
<213> ORGANISM: Artificial Sequence
<220> FEATURE:
<223> OTHER INFORMATION: Human single chain OX40L trimer amino acid
      sequence
```

```
<400> SEQUENCE: 44

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Gln Val Ser His Arg Tyr Pro Arg Ile Gln Ser
130                 135                 140

Ile Lys Val Gln Phe Thr Glu Tyr Lys Lys Glu Lys Gly Phe Ile Leu
145                 150                 155                 160

Thr Ser Gln Lys Glu Asp Glu Ile Met Lys Val Gln Asn Asn Ser Val
                165                 170                 175

Ile Ile Asn Cys Asp Gly Phe Tyr Leu Ile Ser Leu Lys Gly Tyr Phe
            180                 185                 190

Ser Gln Glu Val Asn Ile Ser Leu His Tyr Gln Lys Asp Glu Glu Pro
        195                 200                 205

Leu Phe Gln Leu Lys Lys Val Arg Ser Val Asn Ser Leu Met Val Ala
    210                 215                 220

Ser Leu Thr Tyr Lys Asp Lys Val Tyr Leu Asn Val Thr Thr Asp Asn
225                 230                 235                 240

Thr Ser Leu Asp Asp Phe His Val Asn Gly Gly Glu Leu Ile Leu Ile
                245                 250                 255

His Gln Asn Pro Gly Glu Phe Cys Val Leu Gln Val Ser His Arg Tyr
            260                 265                 270

Pro Arg Ile Gln Ser Ile Lys Val Gln Phe Thr Glu Tyr Lys Lys Glu
        275                 280                 285

Lys Gly Phe Ile Leu Thr Ser Gln Lys Glu Asp Glu Ile Met Lys Val
    290                 295                 300

Gln Asn Asn Ser Val Ile Ile Asn Cys Asp Gly Phe Tyr Leu Ile Ser
305                 310                 315                 320

Leu Lys Gly Tyr Phe Ser Gln Glu Val Asn Ile Ser Leu His Tyr Gln
                325                 330                 335

Lys Asp Glu Glu Pro Leu Phe Gln Leu Lys Lys Val Arg Ser Val Asn
            340                 345                 350

Ser Leu Met Val Ala Ser Leu Thr Tyr Lys Asp Lys Val Tyr Leu Asn
        355                 360                 365

Val Thr Thr Asp Asn Thr Ser Leu Asp Asp Phe His Val Asn Gly Gly
    370                 375                 380

Glu Leu Ile Leu Ile His Gln Asn Pro Gly Glu Phe Cys Val Leu
385                 390                 395

<210> SEQ ID NO 45
```

```
<211> LENGTH: 653
<212> TYPE: PRT
<213> ORGANISM: Artificial Sequence
<220> FEATURE:
<223> OTHER INFORMATION: 338F3 Human single chain OX40L trimer-Fc (IgG1)
      amino acid sequence
<220> FEATURE:
<221> NAME/KEY: SIGNAL
<222> LOCATION: (1)..(27)

<400> SEQUENCE: 45

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Gln Val Ser His Arg
            20                  25                  30

Tyr Pro Arg Ile Gln Ser Ile Lys Val Gln Phe Thr Glu Tyr Lys Lys
        35                  40                  45

Glu Lys Gly Phe Ile Leu Thr Ser Gln Lys Glu Asp Glu Ile Met Lys
    50                  55                  60

Val Gln Asn Asn Ser Val Ile Ile Asn Cys Asp Gly Phe Tyr Leu Ile
65                  70                  75                  80

Ser Leu Lys Gly Tyr Phe Ser Gln Glu Val Asn Ile Ser Leu His Tyr
                85                  90                  95

Gln Lys Asp Glu Glu Pro Leu Phe Gln Leu Lys Lys Val Arg Ser Val
            100                 105                 110

Asn Ser Leu Met Val Ala Ser Leu Thr Tyr Lys Asp Lys Val Tyr Leu
        115                 120                 125

Asn Val Thr Thr Asp Asn Thr Ser Leu Asp Asp Phe His Val Asn Gly
    130                 135                 140

Gly Glu Leu Ile Leu Ile His Gln Asn Pro Gly Glu Phe Cys Val Leu
145                 150                 155                 160

Gln Val Ser His Arg Tyr Pro Arg Ile Gln Ser Ile Lys Val Gln Phe
                165                 170                 175

Thr Glu Tyr Lys Lys Glu Lys Gly Phe Ile Leu Thr Ser Gln Lys Glu
            180                 185                 190

Asp Glu Ile Met Lys Val Gln Asn Asn Ser Val Ile Ile Asn Cys Asp
        195                 200                 205

Gly Phe Tyr Leu Ile Ser Leu Lys Gly Tyr Phe Ser Gln Glu Val Asn
    210                 215                 220

Ile Ser Leu His Tyr Gln Lys Asp Glu Glu Pro Leu Phe Gln Leu Lys
225                 230                 235                 240

Lys Val Arg Ser Val Asn Ser Leu Met Val Ala Ser Leu Thr Tyr Lys
                245                 250                 255

Asp Lys Val Tyr Leu Asn Val Thr Thr Asp Asn Thr Ser Leu Asp Asp
            260                 265                 270

Phe His Val Asn Gly Gly Glu Leu Ile Leu Ile His Gln Asn Pro Gly
        275                 280                 285

Glu Phe Cys Val Leu Gln Val Ser His Arg Tyr Pro Arg Ile Gln Ser
    290                 295                 300

Ile Lys Val Gln Phe Thr Glu Tyr Lys Lys Glu Lys Gly Phe Ile Leu
305                 310                 315                 320

Thr Ser Gln Lys Glu Asp Glu Ile Met Lys Val Gln Asn Asn Ser Val
                325                 330                 335

Ile Ile Asn Cys Asp Gly Phe Tyr Leu Ile Ser Leu Lys Gly Tyr Phe
            340                 345                 350

Ser Gln Glu Val Asn Ile Ser Leu His Tyr Gln Lys Asp Glu Glu Pro
```

```
                355                 360                 365
Leu Phe Gln Leu Lys Lys Val Arg Ser Val Asn Ser Leu Met Val Ala
            370                 375                 380

Ser Leu Thr Tyr Lys Asp Lys Val Tyr Leu Asn Val Thr Thr Asp Asn
385                 390                 395                 400

Thr Ser Leu Asp Asp Phe His Val Asn Gly Gly Glu Leu Ile Leu Ile
                405                 410                 415

His Gln Asn Pro Gly Glu Phe Cys Val Leu Asp Lys Thr His Thr Cys
            420                 425                 430

Pro Pro Cys Pro Ala Pro Glu Leu Leu Gly Gly Pro Ser Val Phe Leu
        435                 440                 445

Phe Pro Pro Lys Pro Lys Asp Thr Leu Met Ile Ser Arg Thr Pro Glu
    450                 455                 460

Val Thr Cys Val Val Val Asp Val Ser His Glu Asp Pro Glu Val Lys
465                 470                 475                 480

Phe Asn Trp Tyr Val Asp Gly Val Glu Val His Asn Ala Lys Thr Lys
                485                 490                 495

Pro Arg Glu Glu Gln Tyr Asn Ser Thr Tyr Arg Val Val Ser Val Leu
            500                 505                 510

Thr Val Leu His Gln Asp Trp Leu Asn Gly Lys Glu Tyr Lys Cys Lys
        515                 520                 525

Val Ser Asn Lys Ala Leu Pro Ala Pro Ile Glu Lys Thr Ile Ser Lys
    530                 535                 540

Ala Lys Gly Gln Pro Arg Glu Pro Gln Val Tyr Thr Leu Pro Pro Ser
545                 550                 555                 560

Arg Glu Glu Met Thr Lys Asn Gln Val Ser Leu Thr Cys Leu Val Lys
                565                 570                 575

Gly Phe Tyr Pro Ser Asp Ile Ala Val Glu Trp Glu Ser Asn Gly Gln
            580                 585                 590

Pro Glu Asn Asn Tyr Lys Thr Thr Pro Pro Val Leu Asp Ser Asp Gly
        595                 600                 605

Ser Phe Phe Leu Tyr Ser Lys Leu Thr Val Asp Lys Ser Arg Trp Gln
    610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys
                645                 650

<210> SEQ ID NO 46
<211> LENGTH: 626
<212> TYPE: PRT
<213> ORGANISM: Artificial Sequence
<220> FEATURE:
<223> OTHER INFORMATION: 338F3 Human single chain OX40L trimer-Fc (IgG1)
      amino acid sequence

<400> SEQUENCE: 46

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60
```

```
Ile Ser Leu His Tyr Gln Lys Asp Glu Glu Pro Leu Phe Gln Leu Lys
 65                  70                  75                  80

Lys Val Arg Ser Val Asn Ser Leu Met Val Ala Ser Leu Thr Tyr Lys
                 85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Gln Val Ser His Arg Tyr Pro Arg Ile Gln Ser
    130                 135                 140

Ile Lys Val Gln Phe Thr Glu Tyr Lys Lys Glu Lys Gly Phe Ile Leu
145                 150                 155                 160

Thr Ser Gln Lys Glu Asp Glu Ile Met Lys Val Gln Asn Asn Ser Val
                165                 170                 175

Ile Ile Asn Cys Asp Gly Phe Tyr Leu Ile Ser Leu Lys Gly Tyr Phe
            180                 185                 190

Ser Gln Glu Val Asn Ile Ser Leu His Tyr Gln Lys Asp Glu Glu Pro
        195                 200                 205

Leu Phe Gln Leu Lys Lys Val Arg Ser Val Asn Ser Leu Met Val Ala
    210                 215                 220

Ser Leu Thr Tyr Lys Asp Lys Val Tyr Leu Asn Val Thr Thr Asp Asn
225                 230                 235                 240

Thr Ser Leu Asp Asp Phe His Val Asn Gly Gly Glu Leu Ile Leu Ile
                245                 250                 255

His Gln Asn Pro Gly Glu Phe Cys Val Leu Gln Val Ser His Arg Tyr
            260                 265                 270

Pro Arg Ile Gln Ser Ile Lys Val Gln Phe Thr Glu Tyr Lys Lys Glu
        275                 280                 285

Lys Gly Phe Ile Leu Thr Ser Gln Lys Glu Asp Glu Ile Met Lys Val
    290                 295                 300

Gln Asn Asn Ser Val Ile Ile Asn Cys Asp Gly Phe Tyr Leu Ile Ser
305                 310                 315                 320

Leu Lys Gly Tyr Phe Ser Gln Glu Val Asn Ile Ser Leu His Tyr Gln
                325                 330                 335

Lys Asp Glu Glu Pro Leu Phe Gln Leu Lys Lys Val Arg Ser Val Asn
            340                 345                 350

Ser Leu Met Val Ala Ser Leu Thr Tyr Lys Asp Lys Val Tyr Leu Asn
        355                 360                 365

Val Thr Thr Asp Asn Thr Ser Leu Asp Asp Phe His Val Asn Gly Gly
    370                 375                 380

Glu Leu Ile Leu Ile His Gln Asn Pro Gly Glu Phe Cys Val Leu Asp
385                 390                 395                 400

Lys Thr His Thr Cys Pro Pro Cys Pro Ala Pro Glu Leu Leu Gly Gly
                405                 410                 415

Pro Ser Val Phe Leu Phe Pro Pro Lys Pro Lys Asp Thr Leu Met Ile
            420                 425                 430

Ser Arg Thr Pro Glu Val Thr Cys Val Val Val Asp Val Ser His Glu
        435                 440                 445

Asp Pro Glu Val Lys Phe Asn Trp Tyr Val Asp Gly Val Glu Val His
    450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
```

```
                    485             490             495
Glu Tyr Lys Cys Lys Val Ser Asn Lys Ala Leu Pro Ala Pro Ile Glu
            500                 505                 510

Lys Thr Ile Ser Lys Ala Lys Gly Gln Pro Arg Glu Pro Gln Val Tyr
            515                 520                 525

Thr Leu Pro Pro Ser Arg Glu Glu Met Thr Lys Asn Gln Val Ser Leu
            530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
            565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
            610                 615                 620

Gly Lys
625

<210> SEQ ID NO 47
<211> LENGTH: 655
<212> TYPE: PRT
<213> ORGANISM: Artificial Sequence
<220> FEATURE:
<223> OTHER INFORMATION: Human single chain OX40L trimer-Fc (IgG2) amino
      acid sequence
<220> FEATURE:
<221> NAME/KEY: SIGNAL
<222> LOCATION: (1)..(27)

<400> SEQUENCE: 47

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Gln Val Ser His Arg
            20                  25                  30

Tyr Pro Arg Ile Gln Ser Ile Lys Val Gln Phe Thr Glu Tyr Lys Lys
        35                  40                  45

Glu Lys Gly Phe Ile Leu Thr Ser Gln Lys Glu Asp Glu Ile Met Lys
    50                  55                  60

Val Gln Asn Asn Ser Val Ile Ile Asn Cys Asp Gly Phe Tyr Leu Ile
65                  70                  75                  80

Ser Leu Lys Gly Tyr Phe Ser Gln Glu Val Asn Ile Ser Leu His Tyr
                85                  90                  95

Gln Lys Asp Glu Glu Pro Leu Phe Gln Leu Lys Lys Val Arg Ser Val
            100                 105                 110

Asn Ser Leu Met Val Ala Ser Leu Thr Tyr Lys Asp Lys Val Tyr Leu
        115                 120                 125

Asn Val Thr Thr Asp Asn Thr Ser Leu Asp Asp Phe His Val Asn Gly
    130                 135                 140

Gly Glu Leu Ile Leu Ile His Gln Asn Pro Gly Glu Phe Cys Val Leu
145                 150                 155                 160

Gln Val Ser His Arg Tyr Pro Arg Ile Gln Ser Ile Lys Val Gln Phe
                165                 170                 175

Thr Glu Tyr Lys Lys Glu Lys Gly Phe Ile Leu Thr Ser Gln Lys Glu
            180                 185                 190
```

```
Asp Glu Ile Met Lys Val Gln Asn Asn Ser Val Ile Asn Cys Asp
        195                 200                 205
Gly Phe Tyr Leu Ile Ser Leu Lys Gly Tyr Phe Ser Gln Glu Val Asn
210                 215                 220
Ile Ser Leu His Tyr Gln Lys Asp Glu Glu Pro Leu Phe Gln Leu Lys
225                 230                 235                 240
Lys Val Arg Ser Val Asn Ser Leu Met Val Ala Ser Leu Thr Tyr Lys
                245                 250                 255
Asp Lys Val Tyr Leu Asn Val Thr Thr Asp Asn Thr Ser Leu Asp Asp
                260                 265                 270
Phe His Val Asn Gly Gly Glu Leu Ile Leu Ile His Gln Asn Pro Gly
                275                 280                 285
Glu Phe Cys Val Leu Gln Val Ser His Arg Tyr Pro Arg Ile Gln Ser
        290                 295                 300
Ile Lys Val Gln Phe Thr Glu Tyr Lys Lys Glu Lys Gly Phe Ile Leu
305                 310                 315                 320
Thr Ser Gln Lys Glu Asp Glu Ile Met Lys Val Gln Asn Asn Ser Val
                325                 330                 335
Ile Ile Asn Cys Asp Gly Phe Tyr Leu Ile Ser Leu Lys Gly Tyr Phe
                340                 345                 350
Ser Gln Glu Val Asn Ile Ser Leu His Tyr Gln Lys Asp Glu Glu Pro
                355                 360                 365
Leu Phe Gln Leu Lys Lys Val Arg Ser Val Asn Ser Leu Met Val Ala
        370                 375                 380
Ser Leu Thr Tyr Lys Asp Lys Val Tyr Leu Asn Val Thr Thr Asp Asn
385                 390                 395                 400
Thr Ser Leu Asp Asp Phe His Val Asn Gly Gly Glu Leu Ile Leu Ile
                405                 410                 415
His Gln Asn Pro Gly Glu Phe Cys Val Leu Glu Arg Lys Ser Cys
                420                 425                 430
Val Glu Cys Pro Pro Cys Pro Ala Pro Pro Val Ala Gly Pro Ser Val
        435                 440                 445
Phe Leu Phe Pro Pro Lys Pro Lys Asp Thr Leu Met Ile Ser Arg Thr
450                 455                 460
Pro Glu Val Thr Cys Val Val Asp Val Ser His Glu Asp Pro Glu
465                 470                 475                 480
Val Gln Phe Asn Trp Tyr Val Asp Gly Val Glu Val His Asn Ala Lys
                485                 490                 495
Thr Lys Pro Arg Glu Glu Gln Phe Asn Ser Thr Phe Arg Val Val Ser
                500                 505                 510
Val Leu Thr Val Val His Gln Asp Trp Leu Asn Gly Lys Glu Tyr Lys
        515                 520                 525
Cys Lys Val Ser Asn Lys Gly Leu Pro Ala Pro Ile Glu Lys Thr Ile
530                 535                 540
Ser Lys Thr Lys Gly Gln Pro Arg Glu Pro Gln Val Tyr Thr Leu Pro
545                 550                 555                 560
Pro Ser Arg Glu Glu Met Thr Lys Asn Gln Val Ser Leu Thr Cys Leu
                565                 570                 575
Val Lys Gly Phe Tyr Pro Ser Asp Ile Ala Val Glu Trp Glu Ser Asn
                580                 585                 590
Gly Gln Pro Glu Asn Asn Tyr Lys Thr Thr Pro Pro Met Leu Asp Ser
        595                 600                 605
Asp Gly Ser Phe Phe Leu Tyr Ser Lys Leu Thr Val Asp Lys Ser Arg
```

```
          610                 615                 620
Trp Gln Gln Gly Asn Val Phe Ser Cys Ser Val Met His Glu Ala Leu
625                 630                 635                 640

His Asn His Tyr Thr Gln Lys Ser Leu Ser Leu Ser Pro Gly Lys
                    645                 650                 655

<210> SEQ ID NO 48
<211> LENGTH: 628
<212> TYPE: PRT
<213> ORGANISM: Artificial Sequence
<220> FEATURE:
<223> OTHER INFORMATION: Human single chain OX40L trimer-Fc (IgG2) amino
      acid sequence

<400> SEQUENCE: 48

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Gln Val Ser His Arg Tyr Pro Arg Ile Gln Ser
130                 135                 140

Ile Lys Val Gln Phe Thr Glu Tyr Lys Lys Glu Lys Gly Phe Ile Leu
145                 150                 155                 160

Thr Ser Gln Lys Glu Asp Glu Ile Met Lys Val Gln Asn Asn Ser Val
                165                 170                 175

Ile Ile Asn Cys Asp Gly Phe Tyr Leu Ile Ser Leu Lys Gly Tyr Phe
            180                 185                 190

Ser Gln Glu Val Asn Ile Ser Leu His Tyr Gln Lys Asp Glu Glu Pro
        195                 200                 205

Leu Phe Gln Leu Lys Lys Val Arg Ser Val Asn Ser Leu Met Val Ala
210                 215                 220

Ser Leu Thr Tyr Lys Asp Lys Val Tyr Leu Asn Val Thr Thr Asp Asn
225                 230                 235                 240

Thr Ser Leu Asp Asp Phe His Val Asn Gly Gly Glu Leu Ile Leu Ile
                245                 250                 255

His Gln Asn Pro Gly Glu Phe Cys Val Leu Gln Val Ser His Arg Tyr
            260                 265                 270

Pro Arg Ile Gln Ser Ile Lys Val Gln Phe Thr Glu Tyr Lys Lys Glu
        275                 280                 285

Lys Gly Phe Ile Leu Thr Ser Gln Lys Glu Asp Glu Ile Met Lys Val
290                 295                 300

Gln Asn Asn Ser Val Ile Ile Asn Cys Asp Gly Phe Tyr Leu Ile Ser
305                 310                 315                 320
```

Leu Lys Gly Tyr Phe Ser Gln Glu Val Asn Ile Ser Leu His Tyr Gln
            325                 330                 335
Lys Asp Glu Glu Pro Leu Phe Gln Leu Lys Lys Val Arg Ser Val Asn
        340                 345                 350
Ser Leu Met Val Ala Ser Leu Thr Tyr Lys Asp Lys Val Tyr Leu Asn
    355                 360                 365
Val Thr Thr Asp Asn Thr Ser Leu Asp Asp Phe His Val Asn Gly Gly
370                 375                 380
Glu Leu Ile Leu Ile His Gln Asn Pro Gly Glu Phe Cys Val Leu Val
385                 390                 395                 400
Glu Arg Lys Ser Cys Val Glu Cys Pro Cys Pro Ala Pro Pro Val
                405                 410                 415
Ala Gly Pro Ser Val Phe Leu Phe Pro Pro Lys Pro Lys Asp Thr Leu
        420                 425                 430
Met Ile Ser Arg Thr Pro Glu Val Thr Cys Val Val Val Asp Val Ser
            435                 440                 445
His Glu Asp Pro Glu Val Gln Phe Asn Trp Tyr Val Asp Gly Val Glu
    450                 455                 460
Val His Asn Ala Lys Thr Lys Pro Arg Glu Glu Gln Phe Asn Ser Thr
465                 470                 475                 480
Phe Arg Val Val Ser Val Leu Thr Val Val His Gln Asp Trp Leu Asn
                485                 490                 495
Gly Lys Glu Tyr Lys Cys Lys Val Ser Asn Lys Gly Leu Pro Ala Pro
        500                 505                 510
Ile Glu Lys Thr Ile Ser Lys Thr Lys Gly Gln Pro Arg Glu Pro Gln
            515                 520                 525
Val Tyr Thr Leu Pro Pro Ser Arg Glu Glu Met Thr Lys Asn Gln Val
    530                 535                 540
Ser Leu Thr Cys Leu Val Lys Gly Phe Tyr Pro Ser Asp Ile Ala Val
545                 550                 555                 560
Glu Trp Glu Ser Asn Gly Gln Pro Glu Asn Asn Tyr Lys Thr Thr Pro
                565                 570                 575
Pro Met Leu Asp Ser Asp Gly Ser Phe Phe Leu Tyr Ser Lys Leu Thr
        580                 585                 590
Val Asp Lys Ser Arg Trp Gln Gln Gly Asn Val Phe Ser Cys Ser Val
            595                 600                 605
Met His Glu Ala Leu His Asn His Tyr Thr Gln Lys Ser Leu Ser Leu
    610                 615                 620
Ser Pro Gly Lys
625

<210> SEQ ID NO 49
<211> LENGTH: 552
<212> TYPE: DNA
<213> ORGANISM: Artificial Sequence
<220> FEATURE:
<223> OTHER INFORMATION: Human OX40L nucleotide sequence

<400> SEQUENCE: 49
atggaaaggg tccaacccct ggaagagaat gtgggaaatg cagccaggcc aagattcgag     60
aggaacaagc tattgctggt ggcctctgta attcagggac tggggctgct cctgtgcttc    120
acctacatct gcctgcactt ctctgctctt caggtatcac atcggtatcc tcgaattcaa    180
agtatcaaag tacaatttac cgaatataag aaggagaaag gtttcatcct cacttcccaa    240
aaggaggatg aaatcatgaa ggtgcagaac aactcagtca tcatcaactg tgatgggttt    300

```
tatctcatct ccctgaaggg ctacttctcc caggaagtca acattagcct tcattaccag    360
aaggatgagg agcccctctt ccaactgaag aaggtcaggt ctgtcaactc cttgatggtg    420
gcctctctga cttacaaaga caaagtctac ttgaatgtga ccactgacaa tacctccctg    480
gatgacttcc atgtgaatgg cggagaactg attcttatcc atcaaaatcc tggtgaattc    540
tgtgtccttt ga                                                       552
```

<210> SEQ ID NO 50
<211> LENGTH: 402
<212> TYPE: DNA
<213> ORGANISM: Artificial Sequence
<220> FEATURE:
<223> OTHER INFORMATION: Human OX40L extracellular domain nucleotide
      sequence

<400> SEQUENCE: 50

```
caggtatcac atcggtatcc tcgaattcaa agtatcaaag tacaatttac cgaatataag    60
aaggagaaag gtttcatcct cacttcccaa aaggaggatg aaatcatgaa ggtgcagaac    120
aactcagtca tcatcaactg tgatgggttt atctcatct ccctgaaggg ctacttctcc    180
caggaagtca acattagcct tcattaccag aaggatgagg agcccctctt ccaactgaag    240
aaggtcaggt ctgtcaactc cttgatggtg gcctctctga cttacaaaga caaagtctac    300
ttgaatgtga ccactgacaa tacctccctg gatgacttcc atgtgaatgg cggagaactg    360
attcttatcc atcaaaatcc tggtgaattc tgtgtccttt ga                      402
```

<210> SEQ ID NO 51
<211> LENGTH: 1278
<212> TYPE: DNA
<213> ORGANISM: Artificial Sequence
<220> FEATURE:
<223> OTHER INFORMATION: Human single chain OX40L trimer with signal
      sequence nucleotide sequence

<400> SEQUENCE: 51

```
atggagtggg gttatctgct cgaagtgacc tccctgctgg ccgccctgct cctgctgcaa    60
cgctctccta tcgtgcacgc ccaggtctct catagatacc cacgcataca atcaatcaaa    120
gtccaattta cagaatataa gaaggaaaaa ggattcattc tcacatctca gaaggaggac    180
gaaatcatga aagtgcaaaa taacagcgtg ataattaatt gcgacggttt ttacctgatc    240
tccctgaagg ggtatttctc ccaggaggtc aatatttctc tccactacca aaaggacgag    300
gaacctctct tccagctcaa gaaagttaga gcgtcaatt ccctgatggt ggcctccctg    360
acttataagg ataaagtgta tctcaatgtt accacagata acacttctct ggatgatttc    420
catgtcaatg gtgagagct catcctcatt caccagaacc ctggggagtt ctgcgtactg    480
caagtctcac accggtaccc gcgcatccaa agcataaaag ttcaattcac cgagtataaa    540
aaagagaagg gtttcatact cacatcacaa aaggaagatg aaattatgaa ggttcaaaac    600
aactctgtta tcattaactg cgatgggttc tatctgattt cactgaaagg ttacttcagc    660
caagaggtga acatatctct gcattatcag aaagatgaag agcccctgtt ccaactgaag    720
aaggtccgct cagtcaactc actgatggtt gcatccctca catataaaga taaggtctat    780
ctgaatgtga caactgacaa tacctcactg gatgactttc atgttaacgg aggcgaactg    840
attctcatac atcagaatcc aggagagttc tgtgtcctcc aagtttccca tcgctatcct    900
cggattcaat ctatcaaggt tcagtttact gagtacaaaa agaaaaggg atttattctg    960
```

| acctctcaaa aagaggatga gataatgaag gtccagaata attccgtcat tataaactgt | 1020 |
| gacggcttct atctcatatc cctcaagggg tacttttcac aagaagttaa tatatcactc | 1080 |
| cattaccaaa aagatgaaga gccactcttt caactgaaaa aagtcagatc cgtcaactct | 1140 |
| ctcatggtcg cttctctcac ctacaaagac aaagtttacc tgaacgttac tacagacaac | 1200 |
| acatccctgg acgacttcca cgtgaatggc ggggaactga tactgatcca ccaaaatccc | 1260 |
| ggcgaatttt gtgtgctc | 1278 |

<210> SEQ ID NO 52
<211> LENGTH: 1197
<212> TYPE: DNA
<213> ORGANISM: Artificial Sequence
<220> FEATURE:
<223> OTHER INFORMATION: Human single chain OX40L trimer without signal
      sequence nucleotide sequence

<400> SEQUENCE: 52

| caggtctctc atagataccc acgcatacaa tcaatcaaag tccaatttac agaatataag | 60 |
| aaggaaaaag gattcattct cacatctcag aaggaggacg aaatcatgaa agtgcaaaat | 120 |
| aacagcgtga taattaattg cgacggtttt tacctgatct ccctgaaggg gtatttctcc | 180 |
| caggaggtca atatttctct ccactaccaa aaggacgagg aacctctctt ccagctcaag | 240 |
| aaagttagaa gcgtcaattc cctgatggtg gcctccctga cttataagga taaagtgtat | 300 |
| ctcaatgtta ccacagataa cacttctctg gatgatttcc atgtcaatgg tggagagctc | 360 |
| atcctcattc accagaaccc tggggagttc tgcgtactgc aagtctcaca ccggtacccg | 420 |
| cgcatccaaa gcataaaagt tcaattcacc gagtataaaa agagaagggg tttcatactc | 480 |
| acatcacaaa aggaagatga aattatgaag gttcaaaaca actctgttat cattaactgc | 540 |
| gatgggttct atctgatttc actgaaaggt tacttcagcc aagaggtgaa catatctctg | 600 |
| cattatcaga aagatgaaga gcccctgttc caactgaaga aggtccgctc agtcaactca | 660 |
| ctgatggttg catccctcac atataaagat aaggtctatc tgaatgtgac aactgacaat | 720 |
| acctcactgg atgactttca tgttaacgga ggcgaactga ttctcataca tcagaatcca | 780 |
| ggagagttct gtgtcctcca gtttcccat cgctatcctc ggattcaatc tatcaaggtt | 840 |
| cagtttactg agtacaaaaa agaaaaggga tttattctga cctctcaaaa agaggatgag | 900 |
| ataatgaagg tccagaataa ttccgtcatt ataaactgtg acggcttcta tctcatatcc | 960 |
| ctcaaggggt acttttcaca agaagttaat atatcactcc attaccaaaa agatgaagag | 1020 |
| ccactctttc aactgaaaaa agtcagatcc gtcaactctc tcatggtcgc ttctctcacc | 1080 |
| tacaaagaca aagtttacct gaacgttact acagacaaca tccctggacg acttccac | 1140 |
| gtgaatggcg ggaactgat actgatccac caaaatcccg cgaattttg tgtgctc | 1197 |

<210> SEQ ID NO 53
<211> LENGTH: 1962
<212> TYPE: DNA
<213> ORGANISM: Artificial Sequence
<220> FEATURE:
<223> OTHER INFORMATION: Human single chain OX40L-Fc (IgG1) trimer
      nucleotide sequence

<400> SEQUENCE: 53

| atggagtggg gttatctgct cgaagtgacc tccctgctgg ccgccctgct cctgctgcaa | 60 |
| cgctctccta tcgtgcacgc ccaggtctct catagataccc acgcatacaa tcaatcaaa | 120 |
| gtccaattta cagaatataa gaaggaaaaa ggattcattc tcacatctca gaaggaggac | 180 |

```
gaaatcatga aagtgcaaaa taacagcgtg ataattaatt gcgacggttt ttacctgatc      240
tccctgaagg ggtatttctc ccaggaggtc aatatttctc tccactacca aaaggacgag      300
gaacctctct tccagctcaa gaaagttaga agcgtcaatt ccctgatggt ggcctccctg      360
acttataagg ataaagtgta tctcaatgtt accacagata acacttctct ggatgatttc      420
catgtcaatg gtggagagct catcctcatt caccagaacc ctggggagtt ctgcgtactg      480
caagtctcac accggtaccc gcgcatccaa agcataaaag ttcaattcac cgagtataaa      540
aaagagaagg gtttcatact cacatcacaa aaggaagatg aaattatgaa ggttcaaaac      600
aactctgtta tcattaactg cgatgggttc tatctgattt cactgaaagg ttacttcagc      660
caagaggtga acatatctct gcattatcag aaagatgaag agcccctgtt ccaactgaag      720
aaggtccgct cagtcaactc actgatggtt gcatccctca catataaaga taaggtctat      780
ctgaatgtga caactgacaa tacctcactg gatgactttc atgttaacgg aggcgaactg      840
attctcatac atcagaatcc aggagagttc tgtgtcctcc aagtttccca tcgctatcct      900
cggattcaat ctatcaaggt tcagtttact gagtacaaaa agaaaaggg atttattctg      960 acctctcaaa aagaggatga gataatgaag gtccagaata attccgtcat tataaactgt     1020
gacggcttct atctcatatc cctcaagggg tacttttcac aagaagttaa tatatcactc     1080
cattaccaaa aagatgaaga gccactcttt caactgaaaa aagtcagatc cgtcaactct     1140
ctcatggtcg cttctctcac ctacaaagac aaagtttacc tgaacgttac tacagacaac     1200
acatccctgg acgacttcca cgtgaatggc ggggaactga tactgatcca ccaaaatccc     1260
ggcgaatttt gtgtgctcga caagacccac acctgccctc cctgccctgc ccctgagctg     1320
ctgggcggac cttccgtgtt cctgttccct cctaagccta aggacaccct gatgatctcc     1380
cggacccctg aagtgacatg cgtggtgtg  acgtgtccc acgaggaccc tgaggtgaag     1440
ttcaactggt atgtggacgg cgtggaggtg cacaacgcta agaccaagcc tagggaggag     1500
cagtacaact ccacctaccg ggtggtgtct gtgctgaccg tgctgcacca ggactggctg     1560
aacggcaaag aatacaagtg caaggtctcc aacaaggccc tgcccgctcc catcgagaaa     1620
accatcagca aggcaaaggg ccagcctcgc gagcctcagg tgtacaccct gccacccagc     1680
cgggaggaga tgaccaagaa ccaggtgtcc ctgacctgtc tggtgaaggg cttttaccct     1740
tccgatattg ccgtggagtg ggagtctaac ggccagcccg agaacaacta caagaccacc     1800
cctcctgtgc tggactccga cggctccttc ttcctgtact ccaagctgac cgtggacaag     1860
tcccggtggc agcagggcaa cgtgttctcc tgctccgtga tgcacgaggc cctgcacaac     1920
cactacaccc agaagagcct gtctctgtct cctggcaagt ga                        1962
```

<210> SEQ ID NO 54
<211> LENGTH: 9
<212> TYPE: PRT
<213> ORGANISM: Artificial Sequence
<220> FEATURE:
<223> OTHER INFORMATION: AH-1 Peptide

<400> SEQUENCE: 54

Ser Pro Ser Tyr Val Tyr His Gln Phe
1               5

<210> SEQ ID NO 55
<211> LENGTH: 7
<212> TYPE: PRT
<213> ORGANISM: Artificial Sequence

```
<220> FEATURE:
<223> OTHER INFORMATION: OX40L Stalk region

<400> SEQUENCE: 55

Gln Val Ser His Arg Tyr Pro
1               5

<210> SEQ ID NO 56
<211> LENGTH: 95
<212> TYPE: PRT
<213> ORGANISM: Artificial Sequence
<220> FEATURE:
<223> OTHER INFORMATION: OX40L TNF homology domain

<400> SEQUENCE: 56

Glu Ile Met Lys Val Gln Asn Asn Ser Val Ile Ile Asn Cys Asp Gly
1               5                   10                  15

Phe Tyr Leu Ile Ser Leu Lys Gly Tyr Phe Ser Gln Glu Val Asn Ile
            20                  25                  30

Ser Leu His Tyr Gln Lys Asp Glu Glu Pro Leu Phe Gln Leu Lys Lys
        35                  40                  45

Val Arg Ser Val Asn Ser Leu Met Val Ala Ser Leu Thr Tyr Lys Asp
    50                  55                  60

Lys Val Tyr Leu Asn Val Thr Thr Asp Asn Thr Ser Leu Asp Asp Phe
65                  70                  75                  80

His Val Asn Gly Gly Glu Leu Ile Leu Ile His Gln Asn Pro Gly
                85                  90                  95

<210> SEQ ID NO 57
<211> LENGTH: 7
<212> TYPE: PRT
<213> ORGANISM: Artificial Sequence
<220> FEATURE:
<223> OTHER INFORMATION: Linker

<400> SEQUENCE: 57

Gly Gly Gly Ser Gly Gly Gly
1               5

<210> SEQ ID NO 58
<211> LENGTH: 227
<212> TYPE: PRT
<213> ORGANISM: Artificial Sequence
<220> FEATURE:
<223> OTHER INFORMATION: Human IgG1 Fc region

<400> SEQUENCE: 58

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110
```

Glu Lys Thr Ile Ser Lys Ala Lys Gly Gln Pro Arg Glu Pro Gln Val
            115                 120                 125

Tyr Thr Leu Pro Pro Ser Arg Asp Lys Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 59
<211> LENGTH: 227
<212> TYPE: PRT
<213> ORGANISM: Artificial Sequence
<220> FEATURE:
<223> OTHER INFORMATION: Human IgG1 Fc region (13B Version)

<400> SEQUENCE: 59

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Glu Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Glu Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 60
<211> LENGTH: 232
<212> TYPE: PRT
<213> ORGANISM: Artificial Sequence
<220> FEATURE:
<223> OTHER INFORMATION: Human IgG1 Fc region (13A Version)

<400> SEQUENCE: 60

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Lys Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Lys Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 61
<211> LENGTH: 232
<212> TYPE: PRT
<213> ORGANISM: Artificial Sequence
<220> FEATURE:
<223> OTHER INFORMATION: Human IgG1 Fc region (13B Version)

<400> SEQUENCE: 61

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
```

```
                65                  70                  75                  80
Tyr Asn Ser Thr Tyr Arg Val Val Ser Val Leu Thr Val Leu His Gln
                    85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
                115                 120                 125
Arg Glu Pro Gln Val Tyr Thr Leu Pro Pro Ser Arg Asp Glu Leu Thr
130                 135                 140
Lys Asn Gln Val Ser Leu Thr Cys Leu Val Glu Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Glu Leu Thr Val Asp Lys Ser Arg Trp Gln Gln Gly Asn Val Phe
                195                 200                 205
Ser Cys Ser Val Met His Glu Ala Leu His Asn His Tyr Thr Gln Lys
                210                 215                 220
Ser Leu Ser Leu Ser Pro Gly Lys
225                 230

<210> SEQ ID NO 62
<211> LENGTH: 641
<212> TYPE: PRT
<213> ORGANISM: Artificial Sequence
<220> FEATURE:
<223> OTHER INFORMATION: 336B13  Human single chain GITRL trimer-Fc
      (IgG1) with linkers
<220> FEATURE:
<221> NAME/KEY: SIGNAL
<222> LOCATION: (1)..(27)

<400> SEQUENCE: 62

Met Glu Trp Gly Tyr Leu Leu Glu Val Thr Ser Leu Leu Ala Ala Leu
1               5                   10                  15
Leu Leu Leu Gln Arg Ser Pro Ile Val His Ala Leu Gln Leu Glu Thr
                20                  25                  30
Ala Lys Glu Pro Cys Met Ala Lys Phe Gly Pro Leu Pro Ser Lys Trp
                35                  40                  45
Gln Met Ala Ser Ser Glu Pro Pro Cys Val Asn Lys Val Ser Asp Trp
                50                  55                  60
Lys Leu Glu Ile Leu Gln Asn Gly Leu Tyr Leu Ile Tyr Gly Gln Val
65                  70                  75                  80
Ala Pro Asn Ala Asn Tyr Asn Asp Val Ala Pro Phe Glu Val Arg Leu
                85                  90                  95
Tyr Lys Asn Lys Asp Met Ile Gln Thr Leu Thr Asn Lys Ser Lys Ile
                100                 105                 110
Gln Asn Val Gly Gly Thr Tyr Glu Leu His Val Gly Asp Thr Ile Asp
                115                 120                 125
Leu Ile Phe Asn Ser Glu His Gln Val Leu Lys Asn Asn Thr Tyr Trp
                130                 135                 140
Gly Ile Ile Leu Leu Ala Asn Pro Gln Phe Ile Ser Gly Gly Gly Ser
145                 150                 155                 160
Gly Gly Gly Glu Pro Cys Met Ala Lys Phe Gly Pro Leu Pro Ser Lys
                165                 170                 175
```

```
Trp Gln Met Ala Ser Ser Glu Pro Pro Cys Val Asn Lys Val Ser Asp
            180                 185                 190

Trp Lys Leu Glu Ile Leu Gln Asn Gly Leu Tyr Leu Ile Tyr Gly Gln
        195                 200                 205

Val Ala Pro Asn Ala Asn Tyr Asn Asp Val Ala Pro Phe Glu Val Arg
    210                 215                 220

Leu Tyr Lys Asn Lys Asp Met Ile Gln Thr Leu Thr Asn Lys Ser Lys
225                 230                 235                 240

Ile Gln Asn Val Gly Gly Thr Tyr Glu Leu His Val Gly Asp Thr Ile
                245                 250                 255

Asp Leu Ile Phe Asn Ser Glu His Gln Val Leu Lys Asn Asn Thr Tyr
            260                 265                 270

Trp Gly Ile Ile Leu Leu Ala Asn Pro Gln Phe Ile Ser Gly Gly Gly
        275                 280                 285

Ser Gly Gly Gly Glu Pro Cys Met Ala Lys Phe Gly Pro Leu Pro Ser
    290                 295                 300

Lys Trp Gln Met Ala Ser Ser Glu Pro Pro Cys Val Asn Lys Val Ser
305                 310                 315                 320

Asp Trp Lys Leu Glu Ile Leu Gln Asn Gly Leu Tyr Leu Ile Tyr Gly
                325                 330                 335

Gln Val Ala Pro Asn Ala Asn Tyr Asn Asp Val Ala Pro Phe Glu Val
            340                 345                 350

Arg Leu Tyr Lys Asn Lys Asp Met Ile Gln Thr Leu Thr Asn Lys Ser
        355                 360                 365

Lys Ile Gln Asn Val Gly Gly Thr Tyr Glu Leu His Val Gly Asp Thr
    370                 375                 380

Ile Asp Leu Ile Phe Asn Ser Glu His Gln Val Leu Lys Asn Asn Thr
385                 390                 395                 400

Tyr Trp Gly Ile Ile Leu Leu Ala Asn Pro Gln Phe Ile Ser Asp Lys
                405                 410                 415

Thr His Thr Cys Pro Pro Cys Pro Ala Pro Glu Leu Leu Gly Gly Pro
            420                 425                 430

Ser Val Phe Leu Phe Pro Pro Lys Pro Lys Asp Thr Leu Met Ile Ser
        435                 440                 445

Arg Thr Pro Glu Val Thr Cys Val Val Val Asp Val Ser His Glu Asp
    450                 455                 460

Pro Glu Val Lys Phe Asn Trp Tyr Val Asp Gly Val Glu Val His Asn
465                 470                 475                 480

Ala Lys Thr Lys Pro Arg Glu Glu Gln Tyr Asn Ser Thr Tyr Arg Val
                485                 490                 495

Val Ser Val Leu Thr Val Leu His Gln Asp Trp Leu Asn Gly Lys Glu
            500                 505                 510

Tyr Lys Cys Lys Val Ser Asn Lys Ala Leu Pro Ala Pro Ile Glu Lys
        515                 520                 525

Thr Ile Ser Lys Ala Lys Gly Gln Pro Arg Glu Pro Gln Val Tyr Thr
    530                 535                 540

Leu Pro Pro Ser Arg Glu Glu Met Thr Lys Asn Gln Val Ser Leu Thr
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Tyr Ser Lys Leu Thr Val Asp Lys
```

Ser Arg Trp Gln Gln Gly Asn Val Phe Ser Cys Ser Val Met His Glu
610                 615                 620

Ala Leu His Asn His Tyr Thr Gln Lys Ser Leu Ser Leu Ser Pro Gly
625                 630                 635                 640

Lys

<210> SEQ ID NO 63
<211> LENGTH: 614
<212> TYPE: PRT
<213> ORGANISM: Artificial Sequence
<220> FEATURE:
<223> OTHER INFORMATION: 336B13 Human single chain GITRL trimer-Fc
      (IgG1) with linkers without signal sequence

<400> SEQUENCE: 63

Leu Gln Leu Glu Thr Ala Lys Glu Pro Cys Met Ala Lys Phe Gly Pro
1               5                   10                  15

Leu Pro Ser Lys Trp Gln Met Ala Ser Ser Glu Pro Pro Cys Val Asn
            20                  25                  30

Lys Val Ser Asp Trp Lys Leu Glu Ile Leu Gln Asn Gly Leu Tyr Leu
        35                  40                  45

Ile Tyr Gly Gln Val Ala Pro Asn Ala Asn Tyr Asn Asp Val Ala Pro
    50                  55                  60

Phe Glu Val Arg Leu Tyr Lys Asn Lys Asp Met Ile Gln Thr Leu Thr
65                  70                  75                  80

Asn Lys Ser Lys Ile Gln Asn Val Gly Gly Thr Tyr Glu Leu His Val
                85                  90                  95

Gly Asp Thr Ile Asp Leu Ile Phe Asn Ser Glu His Gln Val Leu Lys
            100                 105                 110

Asn Asn Thr Tyr Trp Gly Ile Ile Leu Leu Ala Asn Pro Gln Phe Ile
        115                 120                 125

Ser Gly Gly Gly Ser Gly Gly Gly Glu Pro Cys Met Ala Lys Phe Gly
    130                 135                 140

Pro Leu Pro Ser Lys Trp Gln Met Ala Ser Ser Glu Pro Pro Cys Val
145                 150                 155                 160

Asn Lys Val Ser Asp Trp Lys Leu Glu Ile Leu Gln Asn Gly Leu Tyr
                165                 170                 175

Leu Ile Tyr Gly Gln Val Ala Pro Asn Ala Asn Tyr Asn Asp Val Ala
            180                 185                 190

Pro Phe Glu Val Arg Leu Tyr Lys Asn Lys Asp Met Ile Gln Thr Leu
        195                 200                 205

Thr Asn Lys Ser Lys Ile Gln Asn Val Gly Gly Thr Tyr Glu Leu His
    210                 215                 220

Val Gly Asp Thr Ile Asp Leu Ile Phe Asn Ser Glu His Gln Val Leu
225                 230                 235                 240

Lys Asn Asn Thr Tyr Trp Gly Ile Ile Leu Leu Ala Asn Pro Gln Phe
                245                 250                 255

Ile Ser Gly Gly Gly Ser Gly Gly Gly Glu Pro Cys Met Ala Lys Phe
            260                 265                 270

Gly Pro Leu Pro Ser Lys Trp Gln Met Ala Ser Ser Glu Pro Pro Cys
        275                 280                 285

Val Asn Lys Val Ser Asp Trp Lys Leu Glu Ile Leu Gln Asn Gly Leu
    290                 295                 300

Tyr Leu Ile Tyr Gly Gln Val Ala Pro Asn Ala Asn Tyr Asn Asp Val

```
305                 310                 315                 320
Ala Pro Phe Glu Val Arg Leu Tyr Lys Asn Lys Asp Met Ile Gln Thr
                325                 330                 335

Leu Thr Asn Lys Ser Lys Ile Gln Asn Val Gly Gly Thr Tyr Glu Leu
                340                 345                 350

His Val Gly Asp Thr Ile Asp Leu Ile Phe Asn Ser Glu His Gln Val
                355                 360                 365

Leu Lys Asn Asn Thr Tyr Trp Gly Ile Ile Leu Leu Ala Asn Pro Gln
            370                 375                 380

Phe Ile Ser Asp Lys Thr His Thr Cys Pro Pro Cys Pro Ala Pro Glu
385                 390                 395                 400

Leu Leu Gly Gly Pro Ser Val Phe Leu Phe Pro Pro Lys Pro Lys Asp
                405                 410                 415

Thr Leu Met Ile Ser Arg Thr Pro Glu Val Thr Cys Val Val Val Asp
                420                 425                 430

Val Ser His Glu Asp Pro Glu Val Lys Phe Asn Trp Tyr Val Asp Gly
                435                 440                 445

Val Glu Val His Asn Ala Lys Thr Lys Pro Arg Glu Glu Gln Tyr Asn
            450                 455                 460

Ser Thr Tyr Arg Val Val Ser Val Leu Thr Val Leu His Gln Asp Trp
465                 470                 475                 480

Leu Asn Gly Lys Glu Tyr Lys Cys Lys Val Ser Asn Lys Ala Leu Pro
                485                 490                 495

Ala Pro Ile Glu Lys Thr Ile Ser Lys Ala Lys Gly Gln Pro Arg Glu
                500                 505                 510

Pro Gln Val Tyr Thr Leu Pro Pro Ser Arg Glu Glu Met Thr Lys Asn
            515                 520                 525

Gln Val Ser Leu Thr Cys Leu Val Lys Gly Phe Tyr Pro Ser Asp Ile
            530                 535                 540

Ala Val Glu Trp Glu Ser Asn Gly Gln Pro Glu Asn Asn Tyr Lys Thr
545                 550                 555                 560

Thr Pro Pro Val Leu Asp Ser Asp Gly Ser Phe Phe Leu Tyr Ser Lys
                565                 570                 575

Leu Thr Val Asp Lys Ser Arg Trp Gln Gln Gly Asn Val Phe Ser Cys
                580                 585                 590

Ser Val Met His Glu Ala Leu His Asn His Tyr Thr Gln Lys Ser Leu
                595                 600                 605

Ser Leu Ser Pro Gly Lys
            610

<210> SEQ ID NO 64
<211> LENGTH: 122
<212> TYPE: PRT
<213> ORGANISM: Artificial Sequence
<220> FEATURE:
<223> OTHER INFORMATION: Human GITRL extracellular domain without stalk
      region amino acid sequence

<400> SEQUENCE: 64

Glu Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
                20                  25                  30

Glu Ile Leu Gln Asn Gly Leu Tyr Leu Ile Tyr Gly Gln Val Ala Pro
            35                  40                  45
```

Asn Ala Asn Tyr Asn Asp Val Ala Pro Phe Glu Val Arg Leu Tyr Lys
            50                  55                  60

Asn Lys Asp Met Ile Gln Thr Leu Thr Asn Lys Ser Lys Ile Gln Asn
 65                  70                  75                  80

Val Gly Gly Thr Tyr Glu Leu His Val Gly Asp Thr Ile Asp Leu Ile
                    85                  90                  95

Phe Asn Ser Glu His Gln Val Leu Lys Asn Asn Thr Tyr Trp Gly Ile
                100                 105                 110

Ile Leu Leu Ala Asn Pro Gln Phe Ile Ser
            115                 120

<210> SEQ ID NO 65
<211> LENGTH: 407
<212> TYPE: PRT
<213> ORGANISM: Artificial Sequence
<220> FEATURE:
<223> OTHER INFORMATION: Human single chain GITRL trimer (2 stalk
      regions) amino acid sequence
<220> FEATURE:
<221> NAME/KEY: SIGNAL
<222> LOCATION: (1)..(27)

<400> SEQUENCE: 65

Met Glu Trp Gly Tyr Leu Leu Glu Val Thr Ser Leu Leu Ala Ala Leu
 1                   5                  10                  15

Leu Leu Leu Gln Arg Ser Pro Ile Val His Ala Glu Pro Cys Met Ala
                 20                  25                  30

Lys Phe Gly Pro Leu Pro Ser Lys Trp Gln Met Ala Ser Ser Glu Pro
             35                  40                  45

Pro Cys Val Asn Lys Val Ser Asp Trp Lys Leu Glu Ile Leu Gln Asn
 50                  55                  60

Gly Leu Tyr Leu Ile Tyr Gly Gln Val Ala Pro Asn Ala Asn Tyr Asn
 65                  70                  75                  80

Asp Val Ala Pro Phe Glu Val Arg Leu Tyr Lys Asn Lys Asp Met Ile
                 85                  90                  95

Gln Thr Leu Thr Asn Lys Ser Lys Ile Gln Asn Val Gly Gly Thr Tyr
            100                 105                 110

Glu Leu His Val Gly Asp Thr Ile Asp Leu Ile Phe Asn Ser Glu His
        115                 120                 125

Gln Val Leu Lys Asn Asn Thr Tyr Trp Gly Ile Ile Leu Leu Ala Asn
    130                 135                 140

Pro Gln Phe Ile Ser Leu Gln Leu Glu Thr Ala Lys Glu Pro Cys Met
145                 150                 155                 160

Ala Lys Phe Gly Pro Leu Pro Ser Lys Trp Gln Met Ala Ser Ser Glu
                165                 170                 175

Pro Pro Cys Val Asn Lys Val Ser Asp Trp Lys Leu Glu Ile Leu Gln
            180                 185                 190

Asn Gly Leu Tyr Leu Ile Tyr Gly Gln Val Ala Pro Asn Ala Asn Tyr
        195                 200                 205

Asn Asp Val Ala Pro Phe Glu Val Arg Leu Tyr Lys Asn Lys Asp Met
    210                 215                 220

Ile Gln Thr Leu Thr Asn Lys Ser Lys Ile Gln Asn Val Gly Gly Thr
225                 230                 235                 240

Tyr Glu Leu His Val Gly Asp Thr Ile Asp Leu Ile Phe Asn Ser Glu
                245                 250                 255

His Gln Val Leu Lys Asn Asn Thr Tyr Trp Gly Ile Ile Leu Leu Ala
            260                 265                 270

Asn Pro Gln Phe Ile Ser Leu Gln Leu Glu Thr Ala Lys Glu Pro Cys
            275                 280                 285

Met Ala Lys Phe Gly Pro Leu Pro Ser Lys Trp Gln Met Ala Ser Ser
290                 295                 300

Glu Pro Pro Cys Val Asn Lys Val Ser Asp Trp Lys Leu Glu Ile Leu
305                 310                 315                 320

Gln Asn Gly Leu Tyr Leu Ile Tyr Gly Gln Val Ala Pro Asn Ala Asn
            325                 330                 335

Tyr Asn Asp Val Ala Pro Phe Glu Val Arg Leu Tyr Lys Asn Lys Asp
            340                 345                 350

Met Ile Gln Thr Leu Thr Asn Lys Ser Lys Ile Gln Asn Val Gly Gly
            355                 360                 365

Thr Tyr Glu Leu His Val Gly Asp Thr Ile Asp Leu Ile Phe Asn Ser
370                 375                 380

Glu His Gln Val Leu Lys Asn Asn Thr Tyr Trp Gly Ile Ile Leu Leu
385                 390                 395                 400

Ala Asn Pro Gln Phe Ile Ser
            405

<210> SEQ ID NO 66
<211> LENGTH: 380
<212> TYPE: PRT
<213> ORGANISM: Artificial Sequence
<220> FEATURE:
<223> OTHER INFORMATION: Human single chain GITRL trimer (2 stalk
      regions) amino acid sequence

<400> SEQUENCE: 66

Glu Pro Cys Met Ala Lys Phe Gly Pro Leu Pro Ser Lys Trp Gln Met
1               5                   10                  15

Ala Ser Ser Glu Pro Pro Cys Val Asn Lys Val Ser Asp Trp Lys Leu
            20                  25                  30

Glu Ile Leu Gln Asn Gly Leu Tyr Leu Ile Tyr Gly Gln Val Ala Pro
        35                  40                  45

Asn Ala Asn Tyr Asn Asp Val Ala Pro Phe Glu Val Arg Leu Tyr Lys
50                  55                  60

Asn Lys Asp Met Ile Gln Thr Leu Thr Asn Lys Ser Lys Ile Gln Asn
65                  70                  75                  80

Val Gly Gly Thr Tyr Glu Leu His Val Gly Asp Thr Ile Asp Leu Ile
                85                  90                  95

Phe Asn Ser Glu His Gln Val Leu Lys Asn Asn Thr Tyr Trp Gly Ile
            100                 105                 110

Ile Leu Leu Ala Asn Pro Gln Phe Ile Ser Leu Gln Leu Glu Thr Ala
        115                 120                 125

Lys Glu Pro Cys Met Ala Lys Phe Gly Pro Leu Pro Ser Lys Trp Gln
130                 135                 140

Met Ala Ser Ser Glu Pro Pro Cys Val Asn Lys Val Ser Asp Trp Lys
145                 150                 155                 160

Leu Glu Ile Leu Gln Asn Gly Leu Tyr Leu Ile Tyr Gly Gln Val Ala
                165                 170                 175

Pro Asn Ala Asn Tyr Asn Asp Val Ala Pro Phe Glu Val Arg Leu Tyr
            180                 185                 190

Lys Asn Lys Asp Met Ile Gln Thr Leu Thr Asn Lys Ser Lys Ile Gln
        195                 200                 205

Asn Val Gly Gly Thr Tyr Glu Leu His Val Gly Asp Thr Ile Asp Leu

```
Ile Phe Asn Ser Glu His Gln Val Leu Lys Asn Asn Thr Tyr Trp Gly
225                 230                 235                 240

Ile Ile Leu Leu Ala Asn Pro Gln Phe Ile Ser Leu Gln Leu Glu Thr
                245                 250                 255

Ala Lys Glu Pro Cys Met Ala Lys Phe Gly Pro Leu Pro Ser Lys Trp
            260                 265                 270

Gln Met Ala Ser Ser Glu Pro Pro Cys Val Asn Lys Val Ser Asp Trp
        275                 280                 285

Lys Leu Glu Ile Leu Gln Asn Gly Leu Tyr Leu Ile Tyr Gly Gln Val
    290                 295                 300

Ala Pro Asn Ala Asn Tyr Asn Asp Val Ala Pro Phe Glu Val Arg Leu
305                 310                 315                 320

Tyr Lys Asn Lys Asp Met Ile Gln Thr Leu Thr Asn Lys Ser Lys Ile
                325                 330                 335

Gln Asn Val Gly Gly Thr Tyr Glu Leu His Val Gly Asp Thr Ile Asp
            340                 345                 350

Leu Ile Phe Asn Ser Glu His Gln Val Leu Lys Asn Asn Thr Tyr Trp
        355                 360                 365

Gly Ile Ile Leu Leu Ala Asn Pro Gln Phe Ile Ser
    370                 375                 380

<210> SEQ ID NO 67
<211> LENGTH: 126
<212> TYPE: PRT
<213> ORGANISM: Artificial Sequence
<220> FEATURE:
<223> OTHER INFORMATION: Human OX40L extracellular domain without stalk
      region amino acid sequence

<400> SEQUENCE: 67

Arg Ile Gln Ser Ile Lys Val Gln Phe Thr Glu Tyr Lys Lys Glu Lys
1               5                   10                  15

Gly Phe Ile Leu Thr Ser Gln Lys Glu Asp Glu Ile Met Lys Val Gln
            20                  25                  30

Asn Asn Ser Val Ile Ile Asn Cys Asp Gly Phe Tyr Leu Ile Ser Leu
        35                  40                  45

Lys Gly Tyr Phe Ser Gln Glu Val Asn Ile Ser Leu His Tyr Gln Lys
    50                  55                  60

Asp Glu Glu Pro Leu Phe Gln Leu Lys Lys Val Arg Ser Val Asn Ser
65                  70                  75                  80

Leu Met Val Ala Ser Leu Thr Tyr Lys Asp Lys Val Tyr Leu Asn Val
                85                  90                  95

Thr Thr Asp Asn Thr Ser Leu Asp Asp Phe His Val Asn Gly Gly Glu
            100                 105                 110

Leu Ile Leu Ile His Gln Asn Pro Gly Glu Phe Cys Val Leu
        115                 120                 125

<210> SEQ ID NO 68
<211> LENGTH: 419
<212> TYPE: PRT
<213> ORGANISM: Artificial Sequence
<220> FEATURE:
<223> OTHER INFORMATION: Human single chain OX40L trimer (2 stalk
      regions) amino acid sequence
<220> FEATURE:
<221> NAME/KEY: SIGNAL
<222> LOCATION: (1)..(27)
```

```
<400> SEQUENCE: 68

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Arg Ile Gln Ser Ile
            20                  25                  30

Lys Val Gln Phe Thr Glu Tyr Lys Leu Lys Gly Phe Ile Leu Thr
        35                  40                  45

Ser Gln Lys Glu Asp Glu Ile Met Lys Val Gln Asn Asn Ser Val Ile
    50                  55                  60

Ile Asn Cys Asp Gly Phe Tyr Leu Ile Ser Leu Lys Gly Tyr Phe Ser
65                  70                  75                  80

Gln Glu Val Asn Ile Ser Leu His Tyr Gln Lys Asp Glu Glu Pro Leu
                85                  90                  95

Phe Gln Leu Lys Lys Val Arg Ser Val Asn Ser Leu Met Val Ala Ser
            100                 105                 110

Leu Thr Tyr Lys Asp Lys Val Tyr Leu Asn Val Thr Thr Asp Asn Thr
        115                 120                 125

Ser Leu Asp Asp Phe His Val Asn Gly Gly Glu Leu Ile Leu Ile His
    130                 135                 140

Gln Asn Pro Gly Glu Phe Cys Val Leu Gln Val Ser His Arg Tyr Pro
145                 150                 155                 160

Arg Ile Gln Ser Ile Lys Val Gln Phe Thr Glu Tyr Lys Lys Glu Lys
                165                 170                 175

Gly Phe Ile Leu Thr Ser Gln Lys Glu Asp Glu Ile Met Lys Val Gln
            180                 185                 190

Asn Asn Ser Val Ile Ile Asn Cys Asp Gly Phe Tyr Leu Ile Ser Leu
        195                 200                 205

Lys Gly Tyr Phe Ser Gln Glu Val Asn Ile Ser Leu His Tyr Gln Lys
    210                 215                 220

Asp Glu Glu Pro Leu Phe Gln Leu Lys Lys Val Arg Ser Val Asn Ser
225                 230                 235                 240

Leu Met Val Ala Ser Leu Thr Tyr Lys Asp Lys Val Tyr Leu Asn Val
                245                 250                 255

Thr Thr Asp Asn Thr Ser Leu Asp Asp Phe His Val Asn Gly Gly Glu
            260                 265                 270

Leu Ile Leu Ile His Gln Asn Pro Gly Glu Phe Cys Val Leu Gln Val
        275                 280                 285

Ser His Arg Tyr Pro Arg Ile Gln Ser Ile Lys Val Gln Phe Thr Glu
    290                 295                 300

Tyr Lys Lys Glu Lys Gly Phe Ile Leu Thr Ser Gln Lys Glu Asp Glu
305                 310                 315                 320

Ile Met Lys Val Gln Asn Asn Ser Val Ile Ile Asn Cys Asp Gly Phe
                325                 330                 335

Tyr Leu Ile Ser Leu Lys Gly Tyr Phe Ser Gln Glu Val Asn Ile Ser
            340                 345                 350

Leu His Tyr Gln Lys Asp Glu Glu Pro Leu Phe Gln Leu Lys Lys Val
        355                 360                 365

Arg Ser Val Asn Ser Leu Met Val Ala Ser Leu Thr Tyr Lys Asp Lys
    370                 375                 380

Val Tyr Leu Asn Val Thr Thr Asp Asn Thr Ser Leu Asp Asp Phe His
385                 390                 395                 400

Val Asn Gly Gly Glu Leu Ile Leu Ile His Gln Asn Pro Gly Glu Phe
                405                 410                 415
```

Cys Val Leu

<210> SEQ ID NO 69
<211> LENGTH: 392
<212> TYPE: PRT
<213> ORGANISM: Artificial Sequence
<220> FEATURE:
<223> OTHER INFORMATION: Human single chain OX40L trimer (2 stalk regions) amino acid sequence

<400> SEQUENCE: 69

Arg Ile Gln Ser Ile Lys Val Gln Phe Thr Glu Tyr Lys Lys Glu Lys
1               5                   10                  15

Gly Phe Ile Leu Thr Ser Gln Lys Glu Asp Glu Ile Met Lys Val Gln
            20                  25                  30

Asn Asn Ser Val Ile Ile Asn Cys Asp Gly Phe Tyr Leu Ile Ser Leu
        35                  40                  45

Lys Gly Tyr Phe Ser Gln Glu Val Asn Ile Ser Leu His Tyr Gln Lys
50                  55                  60

Asp Glu Glu Pro Leu Phe Gln Leu Lys Lys Val Arg Ser Val Asn Ser
65                  70                  75                  80

Leu Met Val Ala Ser Leu Thr Tyr Lys Asp Lys Val Tyr Leu Asn Val
                85                  90                  95

Thr Thr Asp Asn Thr Ser Leu Asp Asp Phe His Val Asn Gly Gly Glu
            100                 105                 110

Leu Ile Leu Ile His Gln Asn Pro Gly Glu Phe Cys Val Leu Gln Val
        115                 120                 125

Ser His Arg Tyr Pro Arg Ile Gln Ser Ile Lys Val Gln Phe Thr Glu
130                 135                 140

Tyr Lys Lys Glu Lys Gly Phe Ile Leu Thr Ser Gln Lys Glu Asp Glu
145                 150                 155                 160

Ile Met Lys Val Gln Asn Asn Ser Val Ile Ile Asn Cys Asp Gly Phe
                165                 170                 175

Tyr Leu Ile Ser Leu Lys Gly Tyr Phe Ser Gln Glu Val Asn Ile Ser
            180                 185                 190

Leu His Tyr Gln Lys Asp Glu Glu Pro Leu Phe Gln Leu Lys Lys Val
        195                 200                 205

Arg Ser Val Asn Ser Leu Met Val Ala Ser Leu Thr Tyr Lys Asp Lys
210                 215                 220

Val Tyr Leu Asn Val Thr Thr Asp Asn Thr Ser Leu Asp Asp Phe His
225                 230                 235                 240

Val Asn Gly Gly Glu Leu Ile Leu Ile His Gln Asn Pro Gly Glu Phe
                245                 250                 255

Cys Val Leu Gln Val Ser His Arg Tyr Pro Arg Ile Gln Ser Ile Lys
            260                 265                 270

Val Gln Phe Thr Glu Tyr Lys Lys Glu Lys Gly Phe Ile Leu Thr Ser
        275                 280                 285

Gln Lys Glu Asp Glu Ile Met Lys Val Gln Asn Asn Ser Val Ile Ile
290                 295                 300

Asn Cys Asp Gly Phe Tyr Leu Ile Ser Leu Lys Gly Tyr Phe Ser Gln
305                 310                 315                 320

Glu Val Asn Ile Ser Leu His Tyr Gln Lys Asp Glu Glu Pro Leu Phe
                325                 330                 335

Gln Leu Lys Lys Val Arg Ser Val Asn Ser Leu Met Val Ala Ser Leu
            340                 345                 350

Thr Tyr Lys Asp Lys Val Tyr Leu Asn Val Thr Thr Asp Asn Thr Ser
            355                 360                 365

Leu Asp Asp Phe His Val Asn Gly Gly Glu Leu Ile Leu Ile His Gln
370                 375                 380

Asn Pro Gly Glu Phe Cys Val Leu
385                 390

<210> SEQ ID NO 70
<211> LENGTH: 403
<212> TYPE: PRT
<213> ORGANISM: Artificial Sequence
<220> FEATURE:
<223> OTHER INFORMATION: 338F4 Human single chain OX40L trimer amino
      acid sequence

<400> SEQUENCE: 70

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Ala Leu Gln Val Ser His Arg Tyr Pro Arg Ile
    130                 135                 140

Gln Ser Ile Lys Val Gln Phe Thr Glu Tyr Lys Lys Glu Lys Gly Phe
145                 150                 155                 160

Ile Leu Thr Ser Gln Lys Glu Asp Glu Ile Met Lys Val Gln Asn Asn
                165                 170                 175

Ser Val Ile Ile Asn Cys Asp Gly Phe Tyr Leu Ile Ser Leu Lys Gly
            180                 185                 190

Tyr Phe Ser Gln Glu Val Asn Ile Ser Leu His Tyr Gln Lys Asp Glu
        195                 200                 205

Glu Pro Leu Phe Gln Leu Lys Lys Val Arg Ser Val Asn Ser Leu Met
    210                 215                 220

Val Ala Ser Leu Thr Tyr Lys Asp Lys Val Tyr Leu Asn Val Thr Thr
225                 230                 235                 240

Asp Asn Thr Ser Leu Asp Asp Phe His Val Asn Gly Gly Glu Leu Ile
                245                 250                 255

Leu Ile His Gln Asn Pro Gly Glu Phe Cys Val Leu Ala Leu Gln Val
            260                 265                 270

Ser His Arg Tyr Pro Arg Ile Gln Ser Ile Lys Val Gln Phe Thr Glu
        275                 280                 285

Tyr Lys Lys Glu Lys Gly Phe Ile Leu Thr Ser Gln Lys Glu Asp Glu
    290                 295                 300

Ile Met Lys Val Gln Asn Asn Ser Val Ile Ile Asn Cys Asp Gly Phe

```
                    305                 310                 315                 320
Tyr Leu Ile Ser Leu Lys Gly Tyr Phe Ser Gln Glu Val Asn Ile Ser
                325                 330                 335

Leu His Tyr Gln Lys Asp Glu Glu Pro Leu Phe Gln Leu Lys Lys Val
            340                 345                 350

Arg Ser Val Asn Ser Leu Met Val Ala Ser Leu Thr Tyr Lys Asp Lys
        355                 360                 365

Val Tyr Leu Asn Val Thr Thr Asp Asn Thr Ser Leu Asp Asp Phe His
    370                 375                 380

Val Asn Gly Gly Glu Leu Ile Leu Ile His Gln Asn Pro Gly Glu Phe
385                 390                 395                 400

Cys Val Leu

<210> SEQ ID NO 71
<211> LENGTH: 395
<212> TYPE: PRT
<213> ORGANISM: Artificial Sequence
<220> FEATURE:
<223> OTHER INFORMATION: 338F5 Human single chain OX40L trimer amino
      acid sequence

<400> SEQUENCE: 71

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Ser His Arg Tyr Pro Arg Ile Gln Ser Ile Lys
    130                 135                 140

Val Gln Phe Thr Glu Tyr Lys Lys Glu Lys Gly Phe Ile Leu Thr Ser
145                 150                 155                 160

Gln Lys Glu Asp Glu Ile Met Lys Val Gln Asn Asn Ser Val Ile Ile
                165                 170                 175

Asn Cys Asp Gly Phe Tyr Leu Ile Ser Leu Lys Gly Tyr Phe Ser Gln
            180                 185                 190

Glu Val Asn Ile Ser Leu His Tyr Gln Lys Asp Glu Glu Pro Leu Phe
        195                 200                 205

Gln Leu Lys Lys Val Arg Ser Val Asn Ser Leu Met Val Ala Ser Leu
    210                 215                 220

Thr Tyr Lys Asp Lys Val Tyr Leu Asn Val Thr Thr Asp Asn Thr Ser
225                 230                 235                 240

Leu Asp Asp Phe His Val Asn Gly Gly Glu Leu Ile Leu Ile His Gln
                245                 250                 255

Asn Pro Gly Glu Phe Cys Val Leu Ser His Arg Tyr Pro Arg Ile Gln
```

```
                260               265               270
Ser Ile Lys Val Gln Phe Thr Glu Tyr Lys Lys Glu Lys Gly Phe Ile
                275               280               285

Leu Thr Ser Gln Lys Glu Asp Glu Ile Met Lys Val Gln Asn Asn Ser
            290               295               300

Val Ile Ile Asn Cys Asp Gly Phe Tyr Leu Ile Ser Leu Lys Gly Tyr
305               310               315               320

Phe Ser Gln Glu Val Asn Ile Ser Leu His Tyr Gln Lys Asp Glu Glu
                325               330               335

Pro Leu Phe Gln Leu Lys Lys Val Arg Ser Val Asn Ser Leu Met Val
                340               345               350

Ala Ser Leu Thr Tyr Lys Asp Lys Val Tyr Leu Asn Val Thr Thr Asp
            355               360               365

Asn Thr Ser Leu Asp Asp Phe His Val Asn Gly Gly Glu Leu Ile Leu
                370               375               380

Ile His Gln Asn Pro Gly Glu Phe Cys Val Leu
385               390               395

<210> SEQ ID NO 72
<211> LENGTH: 393
<212> TYPE: PRT
<213> ORGANISM: Artificial Sequence
<220> FEATURE:
<223> OTHER INFORMATION: 338F6 Human single chain OX40L trimer amino
      acid sequence

<400> SEQUENCE: 72

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
                20                  25                  30

Asp Glu Ile Met Lys Val Gln Asn Asn Ser Val Ile Ile Asn Cys Asp
            35                  40                  45

Gly Phe Tyr Leu Ile Ser Leu Lys Gly Tyr Phe Ser Gln Glu Val Asn
50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu His Arg Tyr Pro Arg Ile Gln Ser Ile Lys Val
    130                 135                 140

Gln Phe Thr Glu Tyr Lys Lys Glu Lys Gly Phe Ile Leu Thr Ser Gln
145                 150                 155                 160

Lys Glu Asp Glu Ile Met Lys Val Gln Asn Asn Ser Val Ile Ile Asn
                165                 170                 175

Cys Asp Gly Phe Tyr Leu Ile Ser Leu Lys Gly Tyr Phe Ser Gln Glu
            180                 185                 190

Val Asn Ile Ser Leu His Tyr Gln Lys Asp Glu Glu Pro Leu Phe Gln
        195                 200                 205

Leu Lys Lys Val Arg Ser Val Asn Ser Leu Met Val Ala Ser Leu Thr
    210                 215                 220
```

| | | | | | | | | | | | | | | |
|---|---|---|---|---|---|---|---|---|---|---|---|---|---|---|
| Tyr | Lys | Asp | Lys | Val | Tyr | Leu | Asn | Val | Thr | Thr | Asp | Asn | Thr | Ser | Leu |
| 225 | | | | 230 | | | | | 235 | | | | | 240 | |

Asp Asp Phe His Val Asn Gly Gly Glu Leu Ile Leu Ile His Gln Asn
                245                 250                 255

Pro Gly Glu Phe Cys Val Leu His Arg Tyr Pro Arg Ile Gln Ser Ile
            260                 265                 270

Lys Val Gln Phe Thr Glu Tyr Lys Lys Glu Lys Gly Phe Ile Leu Thr
        275                 280                 285

Ser Gln Lys Glu Asp Glu Ile Met Lys Val Gln Asn Asn Ser Val Ile
    290                 295                 300

Ile Asn Cys Asp Gly Phe Tyr Leu Ile Ser Leu Lys Gly Tyr Phe Ser
305                 310                 315                 320

Gln Glu Val Asn Ile Ser Leu His Tyr Gln Lys Asp Glu Glu Pro Leu
                325                 330                 335

Phe Gln Leu Lys Lys Val Arg Ser Val Asn Ser Leu Met Val Ala Ser
            340                 345                 350

Leu Thr Tyr Lys Asp Lys Val Tyr Leu Asn Val Thr Thr Asp Asn Thr
        355                 360                 365

Ser Leu Asp Asp Phe His Val Asn Gly Gly Glu Leu Ile Leu Ile His
    370                 375                 380

Gln Asn Pro Gly Glu Phe Cys Val Leu
385                 390

<210> SEQ ID NO 73
<211> LENGTH: 1188
<212> TYPE: DNA
<213> ORGANISM: Artificial Sequence
<220> FEATURE:
<223> OTHER INFORMATION: 338F5 Human single chain OX40L trimer
      nucleotide sequence

<400> SEQUENCE: 73

| | | |
|---|---|---|
| caggtctctc atagataccc acgcatacaa tcaatcaaag tccaatttac agaatataag | 60 |
| aaggaaaaag gattcattct cacatctcag aaggaggacg aaatcatgaa agtgcaaaat | 120 |
| aacagcgtga taattaattg cgacggtttt tacctgatct ccctgaaggg gtatttctcc | 180 |
| caggaggtca atatttctct ccactaccaa aaggacgagg aacctctctt ccagctcaag | 240 |
| aaagttagaa gcgtcaattc cctgatggtg gcctccctga cttataagga taaagtgtat | 300 |
| ctcaatgtta ccacagataa cacttctctg gatgatttcc atgtcaatgg tggagagctc | 360 |
| atcctcattc accagaaccc tggggagttc tgcgtactgt cacaccggta cccgcgcatc | 420 |
| caaagcataa agttcaatt caccgagtat aaaaaagaga agggtttcat actcacatca | 480 |
| caaaaggaag atgaaattat gaaggttcaa aacaactctg ttatcattaa ctgcgatggg | 540 |
| ttctatctga tttcactgaa aggttacttc agccaagagg tgaacatatc tctgcattat | 600 |
| cagaaagatg aagagcccct gttccaactg aagaaggtcc gctcagtcaa ctcactgatg | 660 |
| gttgcatccc tcacatataa agataaggtc tatctgaatg tgacaactga caatacctca | 720 |
| ctggatgact tcatgttaa cggaggcgaa ctgattctca tacatcagaa tccaggagag | 780 |
| ttctgtgtcc tctcccatcg ctatcctcgg attcaatcta tcaaggttca gtttactgag | 840 |
| tacaaaaaag aaaagggatt tattctgacc tctcaaaaag aggatgagat aatgaaggtc | 900 |
| cagaataatt ccgtcattat aaactgtgac ggcttctatc tcatatccct caagggctac | 960 |
| ttttcacaag aagttaatat atcactccat taccaaaaag atgaagagcc actctttcaa | 1020 |
| ctgaaaaaag tcagatccgt caactctctc atggtcgctt ctctcaccta caagacaaa | 1080 |

```
gtttacctga acgttactac agacaacaca tccctggacg acttccacgt gaatggcggg    1140
gaactgatac tgatccacca aaatcccggc gaattttgtg tgctctga                 1188
```

<210> SEQ ID NO 74
<211> LENGTH: 9
<212> TYPE: PRT
<213> ORGANISM: Artificial Sequence
<220> FEATURE:
<223> OTHER INFORMATION: OX40L Stalk region variant 1

<400> SEQUENCE: 74

Ala Leu Gln Val Ser His Arg Tyr Pro
1               5

<210> SEQ ID NO 75
<211> LENGTH: 5
<212> TYPE: PRT
<213> ORGANISM: Artificial Sequence
<220> FEATURE:
<223> OTHER INFORMATION: OX40L Stalk region variant 2

<400> SEQUENCE: 75

Ser His Arg Tyr Pro
1               5

<210> SEQ ID NO 76
<211> LENGTH: 4
<212> TYPE: PRT
<213> ORGANISM: Artificial Sequence
<220> FEATURE:
<223> OTHER INFORMATION: OX40L Stalk region variant 3

<400> SEQUENCE: 76

His Arg Tyr Pro
1

<210> SEQ ID NO 77
<211> LENGTH: 135
<212> TYPE: PRT
<213> ORGANISM: Artificial Sequence
<220> FEATURE:
<223> OTHER INFORMATION: Human OX40L extracellular domain amino acid
      sequence variant 1

<400> SEQUENCE: 77

Ala Leu Gln Val Ser His Arg Tyr Pro Arg Ile Gln Ser Ile Lys Val
1               5                   10                  15

Gln Phe Thr Glu Tyr Lys Lys Glu Lys Gly Phe Ile Leu Thr Ser Gln
            20                  25                  30

Lys Glu Asp Glu Ile Met Lys Val Gln Asn Asn Ser Val Ile Ile Asn
        35                  40                  45

Cys Asp Gly Phe Tyr Leu Ile Ser Leu Lys Gly Tyr Phe Ser Gln Glu
    50                  55                  60

Val Asn Ile Ser Leu His Tyr Gln Lys Asp Glu Glu Pro Leu Phe Gln
65                  70                  75                  80

Leu Lys Lys Val Arg Ser Val Asn Ser Leu Met Val Ala Ser Leu Thr
                85                  90                  95

Tyr Lys Asp Lys Val Tyr Leu Asn Val Thr Thr Asp Asn Thr Ser Leu
            100                 105                 110

Asp Asp Phe His Val Asn Gly Gly Glu Leu Ile Leu Ile His Gln Asn
        115                 120                 125

```
Pro Gly Glu Phe Cys Val Leu
    130             135

<210> SEQ ID NO 78
<211> LENGTH: 131
<212> TYPE: PRT
<213> ORGANISM: Artificial Sequence
<220> FEATURE:
<223> OTHER INFORMATION: Human OX40L extracellular domain amino acid
      sequence variant 2

<400> SEQUENCE: 78

Ser His Arg Tyr Pro Arg Ile Gln Ser Ile Lys Val Gln Phe Thr Glu
1               5                   10                  15

Tyr Lys Lys Glu Lys Gly Phe Ile Leu Thr Ser Gln Lys Glu Asp Glu
                20                  25                  30

Ile Met Lys Val Gln Asn Asn Ser Val Ile Ile Asn Cys Asp Gly Phe
            35                  40                  45

Tyr Leu Ile Ser Leu Lys Gly Tyr Phe Ser Gln Glu Val Asn Ile Ser
        50                  55                  60

Leu His Tyr Gln Lys Asp Glu Glu Pro Leu Phe Gln Leu Lys Lys Val
65                  70                  75                  80

Arg Ser Val Asn Ser Leu Met Val Ala Ser Leu Thr Tyr Lys Asp Lys
                85                  90                  95

Val Tyr Leu Asn Val Thr Thr Asp Asn Thr Ser Leu Asp Asp Phe His
            100                 105                 110

Val Asn Gly Gly Glu Leu Ile Leu Ile His Gln Asn Pro Gly Glu Phe
        115                 120                 125

Cys Val Leu
    130

<210> SEQ ID NO 79
<211> LENGTH: 130
<212> TYPE: PRT
<213> ORGANISM: Artificial Sequence
<220> FEATURE:
<223> OTHER INFORMATION: Human OX40L extracellular domain amino acid
      sequence variant 3

<400> SEQUENCE: 79

His Arg Tyr Pro Arg Ile Gln Ser Ile Lys Val Gln Phe Thr Glu Tyr
1               5                   10                  15

Lys Lys Glu Lys Gly Phe Ile Leu Thr Ser Gln Lys Glu Asp Glu Ile
                20                  25                  30

Met Lys Val Gln Asn Asn Ser Val Ile Ile Asn Cys Asp Gly Phe Tyr
            35                  40                  45

Leu Ile Ser Leu Lys Gly Tyr Phe Ser Gln Glu Val Asn Ile Ser Leu
        50                  55                  60

His Tyr Gln Lys Asp Glu Glu Pro Leu Phe Gln Leu Lys Lys Val Arg
65                  70                  75                  80

Ser Val Asn Ser Leu Met Val Ala Ser Leu Thr Tyr Lys Asp Lys Val
                85                  90                  95

Tyr Leu Asn Val Thr Thr Asp Asn Thr Ser Leu Asp Asp Phe His Val
            100                 105                 110

Asn Gly Gly Glu Leu Ile Leu Ile His Gln Asn Pro Gly Glu Phe Cys
        115                 120                 125

Val Leu
    130
```

-continued

```
<210> SEQ ID NO 80
<211> LENGTH: 649
<212> TYPE: PRT
<213> ORGANISM: Artificial Sequence
<220> FEATURE:
<223> OTHER INFORMATION: 338F5 Human single chain OX40L trimer-Fc (IgG1)
      amino acid
      sequence
<220> FEATURE:
<221> NAME/KEY: SIGNAL
<222> LOCATION: (1)..(27)

<400> SEQUENCE: 80

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Gln Val Ser His Arg
            20                  25                  30

Tyr Pro Arg Ile Gln Ser Ile Lys Val Gln Phe Thr Glu Tyr Lys Lys
        35                  40                  45

Glu Lys Gly Phe Ile Leu Thr Ser Gln Lys Glu Asp Glu Ile Met Lys
    50                  55                  60

Val Gln Asn Asn Ser Val Ile Ile Asn Cys Asp Gly Phe Tyr Leu Ile
65                  70                  75                  80

Ser Leu Lys Gly Tyr Phe Ser Gln Glu Val Asn Ile Ser Leu His Tyr
                85                  90                  95

Gln Lys Asp Glu Glu Pro Leu Phe Gln Leu Lys Lys Val Arg Ser Val
            100                 105                 110

Asn Ser Leu Met Val Ala Ser Leu Thr Tyr Lys Asp Lys Val Tyr Leu
        115                 120                 125

Asn Val Thr Thr Asp Asn Thr Ser Leu Asp Asp Phe His Val Asn Gly
    130                 135                 140

Gly Glu Leu Ile Leu Ile His Gln Asn Pro Gly Glu Phe Cys Val Leu
145                 150                 155                 160

Ser His Arg Tyr Pro Arg Ile Gln Ser Ile Lys Val Gln Phe Thr Glu
                165                 170                 175

Tyr Lys Lys Glu Lys Gly Phe Ile Leu Thr Ser Gln Lys Glu Asp Glu
            180                 185                 190

Ile Met Lys Val Gln Asn Asn Ser Val Ile Ile Asn Cys Asp Gly Phe
        195                 200                 205

Tyr Leu Ile Ser Leu Lys Gly Tyr Phe Ser Gln Glu Val Asn Ile Ser
    210                 215                 220

Leu His Tyr Gln Lys Asp Glu Glu Pro Leu Phe Gln Leu Lys Lys Val
225                 230                 235                 240

Arg Ser Val Asn Ser Leu Met Val Ala Ser Leu Thr Tyr Lys Asp Lys
                245                 250                 255

Val Tyr Leu Asn Val Thr Thr Asp Asn Thr Ser Leu Asp Asp Phe His
            260                 265                 270

Val Asn Gly Gly Glu Leu Ile Leu Ile His Gln Asn Pro Gly Glu Phe
        275                 280                 285

Cys Val Leu Ser His Arg Tyr Pro Arg Ile Gln Ser Ile Lys Val Gln
    290                 295                 300

Phe Thr Glu Tyr Lys Lys Glu Lys Gly Phe Ile Leu Thr Ser Gln Lys
305                 310                 315                 320

Glu Asp Glu Ile Met Lys Val Gln Asn Asn Ser Val Ile Ile Asn Cys
                325                 330                 335

Asp Gly Phe Tyr Leu Ile Ser Leu Lys Gly Tyr Phe Ser Gln Glu Val
```

```
                340                 345                 350
Asn Ile Ser Leu His Tyr Gln Lys Asp Glu Pro Leu Phe Gln Leu
                355                 360                 365

Lys Lys Val Arg Ser Val Asn Ser Leu Met Val Ala Ser Leu Thr Tyr
370                 375                 380

Lys Asp Lys Val Tyr Leu Asn Val Thr Thr Asp Asn Thr Ser Leu Asp
385                 390                 395                 400

Asp Phe His Val Asn Gly Gly Glu Leu Ile Leu Ile His Gln Asn Pro
                405                 410                 415

Gly Glu Phe Cys Val Leu Asp Lys Thr His Thr Cys Pro Pro Cys Pro
                420                 425                 430

Ala Pro Glu Leu Leu Gly Gly Pro Ser Val Phe Leu Phe Pro Pro Lys
                435                 440                 445

Pro Lys Asp Thr Leu Met Ile Ser Arg Thr Pro Glu Val Thr Cys Val
450                 455                 460

Val Val Asp Val Ser His Glu Asp Pro Glu Val Lys Phe Asn Trp Tyr
465                 470                 475                 480

Val Asp Gly Val Glu Val His Asn Ala Lys Thr Lys Pro Arg Glu Glu
                485                 490                 495

Gln Tyr Asn Ser Thr Tyr Arg Val Val Ser Val Leu Thr Val Leu His
                500                 505                 510

Gln Asp Trp Leu Asn Gly Lys Glu Tyr Lys Cys Lys Val Ser Asn Lys
                515                 520                 525

Ala Leu Pro Ala Pro Ile Glu Lys Thr Ile Ser Lys Ala Lys Gly Gln
                530                 535                 540

Pro Arg Glu Pro Gln Val Tyr Thr Leu Pro Pro Ser Arg Glu Glu Met
545                 550                 555                 560

Thr Lys Asn Gln Val Ser Leu Thr Cys Leu Val Lys Gly Phe Tyr Pro
                565                 570                 575

Ser Asp Ile Ala Val Glu Trp Glu Ser Asn Gly Gln Pro Glu Asn Asn
                580                 585                 590

Tyr Lys Thr Thr Pro Pro Val Leu Asp Ser Asp Gly Ser Phe Phe Leu
                595                 600                 605

Tyr Ser Lys Leu Thr Val Asp Lys Ser Arg Trp Gln Gln Gly Asn Val
                610                 615                 620

Phe Ser Cys Ser Val Met His Glu Ala Leu His Asn His Tyr Thr Gln
625                 630                 635                 640

Lys Ser Leu Ser Leu Ser Pro Gly Lys
                645

<210> SEQ ID NO 81
<211> LENGTH: 622
<212> TYPE: PRT
<213> ORGANISM: Artificial Sequence
<220> FEATURE:
<223> OTHER INFORMATION: 338F5 Human single chain OX40L trimer-Fc (IgG1)
      amino acid sequence

<400> SEQUENCE: 81

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
                20                  25                  30

Asp Glu Ile Met Lys Val Gln Asn Asn Ser Val Ile Ile Asn Cys Asp
                35                  40                  45
```

```
Gly Phe Tyr Leu Ile Ser Leu Lys Gly Tyr Phe Ser Gln Glu Val Asn
    50              55                  60

Ile Ser Leu His Tyr Gln Lys Asp Glu Pro Leu Phe Gln Leu Lys
65              70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
            115                 120                 125

Glu Phe Cys Val Leu Ser His Arg Tyr Pro Arg Ile Gln Ser Ile Lys
    130                 135                 140

Val Gln Phe Thr Glu Tyr Lys Lys Glu Lys Gly Phe Ile Leu Thr Ser
145             150                 155                 160

Gln Lys Glu Asp Glu Ile Met Lys Val Gln Asn Asn Ser Val Ile Ile
                165                 170                 175

Asn Cys Asp Gly Phe Tyr Leu Ile Ser Leu Lys Gly Tyr Phe Ser Gln
            180                 185                 190

Glu Val Asn Ile Ser Leu His Tyr Gln Lys Asp Glu Pro Leu Phe
    195                 200                 205

Gln Leu Lys Lys Val Arg Ser Val Asn Ser Leu Met Val Ala Ser Leu
    210                 215                 220

Thr Tyr Lys Asp Lys Val Tyr Leu Asn Val Thr Thr Asp Asn Thr Ser
225                 230                 235                 240

Leu Asp Asp Phe His Val Asn Gly Gly Glu Leu Ile Leu Ile His Gln
                245                 250                 255

Asn Pro Gly Glu Phe Cys Val Leu Ser His Arg Tyr Pro Arg Ile Gln
            260                 265                 270

Ser Ile Lys Val Gln Phe Thr Glu Tyr Lys Lys Glu Lys Gly Phe Ile
    275                 280                 285

Leu Thr Ser Gln Lys Glu Asp Glu Ile Met Lys Val Gln Asn Asn Ser
    290                 295                 300

Val Ile Ile Asn Cys Asp Gly Phe Tyr Leu Ile Ser Leu Lys Gly Tyr
305                 310                 315                 320

Phe Ser Gln Glu Val Asn Ile Ser Leu His Tyr Gln Lys Asp Glu Glu
                325                 330                 335

Pro Leu Phe Gln Leu Lys Lys Val Arg Ser Val Asn Ser Leu Met Val
            340                 345                 350

Ala Ser Leu Thr Tyr Lys Asp Lys Val Tyr Leu Asn Val Thr Thr Asp
            355                 360                 365

Asn Thr Ser Leu Asp Asp Phe His Val Asn Gly Gly Glu Leu Ile Leu
    370                 375                 380

Ile His Gln Asn Pro Gly Glu Phe Cys Val Leu Asp Lys Thr His Thr
385                 390                 395                 400

Cys Pro Pro Cys Pro Ala Pro Glu Leu Leu Gly Gly Pro Ser Val Phe
                405                 410                 415

Leu Phe Pro Pro Lys Pro Lys Asp Thr Leu Met Ile Ser Arg Thr Pro
            420                 425                 430

Glu Val Thr Cys Val Val Val Asp Val Ser His Glu Asp Pro Glu Val
            435                 440                 445

Lys Phe Asn Trp Tyr Val Asp Gly Val Glu Val His Asn Ala Lys Thr
    450                 455                 460

Lys Pro Arg Glu Glu Gln Tyr Asn Ser Thr Tyr Arg Val Val Ser Val
```

```
               465                 470                 475                 480
Leu Thr Val Leu His Gln Asp Trp Leu Asn Gly Lys Glu Tyr Lys Cys
                    485                 490                 495
Lys Val Ser Asn Lys Ala Leu Pro Ala Pro Ile Glu Lys Thr Ile Ser
                500                 505                 510
Lys Ala Lys Gly Gln Pro Arg Glu Pro Gln Val Tyr Thr Leu Pro Pro
                515                 520                 525
Ser Arg Glu Glu Met Thr Lys Asn Gln Val Ser Leu Thr Cys Leu Val
            530                 535                 540
Lys Gly Phe Tyr Pro Ser Asp Ile Ala Val Glu Trp Glu Ser Asn Gly
545                 550                 555                 560
Gln Pro Glu Asn Asn Tyr Lys Thr Thr Pro Pro Val Leu Asp Ser Asp
                    565                 570                 575
Gly Ser Phe Phe Leu Tyr Ser Lys Leu Thr Val Asp Lys Ser Arg Trp
                580                 585                 590
Gln Gln Gly Asn Val Phe Ser Cys Ser Val Met His Glu Ala Leu His
                595                 600                 605
Asn His Tyr Thr Gln Lys Ser Leu Ser Leu Ser Pro Gly Lys
610                 615                 620

<210> SEQ ID NO 82
<211> LENGTH: 261
<212> TYPE: PRT
<213> ORGANISM: Artificial Sequence
<220> FEATURE:
<223> OTHER INFORMATION: Human CD40L (TNFSF5) amino acid sequence

<400> SEQUENCE: 82

Met Ile Glu Thr Tyr Asn Gln Thr Ser Pro Arg Ser Ala Ala Thr Gly
1               5                   10                  15
Leu Pro Ile Ser Met Lys Ile Phe Met Tyr Leu Leu Thr Val Phe Leu
                20                  25                  30
Ile Thr Gln Met Ile Gly Ser Ala Leu Phe Ala Val Tyr Leu His Arg
            35                  40                  45
Arg Leu Asp Lys Ile Glu Asp Glu Arg Asn Leu His Glu Asp Phe Val
        50                  55                  60
Phe Met Lys Thr Ile Gln Arg Cys Asn Thr Gly Glu Arg Ser Leu Ser
65                  70                  75                  80
Leu Leu Asn Cys Glu Glu Ile Lys Ser Gln Phe Glu Gly Phe Val Lys
                85                  90                  95
Asp Ile Met Leu Asn Lys Glu Glu Thr Lys Lys Glu Asn Ser Phe Glu
                100                 105                 110
Met Gln Lys Gly Asp Gln Asn Pro Gln Ile Ala Ala His Val Ile Ser
            115                 120                 125
Glu Ala Ser Ser Lys Thr Thr Ser Val Leu Gln Trp Ala Glu Lys Gly
        130                 135                 140
Tyr Tyr Thr Met Ser Asn Asn Leu Val Thr Leu Glu Asn Gly Lys Gln
145                 150                 155                 160
Leu Thr Val Lys Arg Gln Gly Leu Tyr Tyr Ile Tyr Ala Gln Val Thr
                165                 170                 175
Phe Cys Ser Asn Arg Glu Ala Ser Ser Gln Ala Pro Phe Ile Ala Ser
                180                 185                 190
Leu Cys Leu Lys Ser Pro Gly Arg Phe Glu Arg Ile Leu Leu Arg Ala
            195                 200                 205
Ala Asn Thr His Ser Ser Ala Lys Pro Cys Gly Gln Gln Ser Ile His
```

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
            245                 250                 255

Gly Leu Leu Lys Leu
        260

<210> SEQ ID NO 83
<211> LENGTH: 215
<212> TYPE: PRT
<213> ORGANISM: Artificial Sequence
<220> FEATURE:
<223> OTHER INFORMATION: Human CD40L extracellular domain amino acid
      sequence

<400> SEQUENCE: 83

His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
                20                  25                  30

Leu Ser Leu Leu Asn Cys Glu Glu Ile Lys Ser Gln Phe Glu Gly Phe
            35                  40                  45

Val Lys Asp Ile Met Leu Asn Lys Glu Glu Thr Lys Lys Glu Asn Ser
50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
                100                 105                 110

Lys Gln Leu Thr Val Lys Arg Gln Gly Leu Tyr Tyr Ile Tyr Ala Gln
            115                 120                 125

Val Thr Phe Cys Ser Asn Arg Glu Ala Ser Ser Gln Ala Pro Phe Ile
130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
            195                 200                 205

Ser Phe Gly Leu Leu Lys Leu
    210                 215

<210> SEQ ID NO 84
<211> LENGTH: 149
<212> TYPE: PRT
<213> ORGANISM: Artificial Sequence
<220> FEATURE:
<223> OTHER INFORMATION: Human CD40L extracellular domain with stalk
      fragment 1 (aa 113-261)

<400> SEQUENCE: 84

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly

```
                    20                  25                  30

Tyr Tyr Thr Met Ser Asn Asn Leu Val Thr Leu Glu Asn Gly Lys Gln
                35                  40                  45

Leu Thr Val Lys Arg Gln Gly Leu Tyr Tyr Ile Tyr Ala Gln Val Thr
        50                  55                  60

Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
               100                 105                 110

Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
        130                 135                 140

Gly Leu Leu Lys Leu
145

<210> SEQ ID NO 85
<211> LENGTH: 447
<212> TYPE: PRT
<213> ORGANISM: Artificial Sequence
<220> FEATURE:
<223> OTHER INFORMATION: Human single chain CD40L trimer amino acid
      sequence

<400> SEQUENCE: 85

Met Gln Lys Gly Asp Gln Asn Pro Gln Ile Ala Ala His Val Ile Ser
 1               5                  10                  15

Glu Ala Ser Ser Lys Thr Thr Ser Val Leu Gln Trp Ala Glu Lys Gly
                20                  25                  30

Tyr Tyr Thr Met Ser Asn Asn Leu Val Thr Leu Glu Asn Gly Lys Gln
                35                  40                  45

Leu Thr Val Lys Arg Gln Gly Leu Tyr Tyr Ile Tyr Ala Gln Val Thr
        50                  55                  60

Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
               100                 105                 110

Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
        130                 135                 140

Gly Leu Leu Lys Leu Met Gln Lys Gly Asp Gln Asn Pro Gln Ile Ala
145                 150                 155                 160

Ala His Val Ile Ser Glu Ala Ser Ser Lys Thr Thr Ser Val Leu Gln
                165                 170                 175

Trp Ala Glu Lys Gly Tyr Tyr Thr Met Ser Asn Asn Leu Val Thr Leu
            180                 185                 190

Glu Asn Gly Lys Gln Leu Thr Val Lys Arg Gln Gly Leu Tyr Tyr Ile
        195                 200                 205

Tyr Ala Gln Val Thr Phe Cys Ser Asn Arg Glu Ala Ser Ser Gln Ala
    210                 215                 220
```

| | | | | | | | | | | | | | | |
|---|---|---|---|---|---|---|---|---|---|---|---|---|---|---|
|Pro|Phe|Ile|Ala|Ser|Leu|Cys|Leu|Lys|Ser|Pro|Gly|Arg|Phe|Glu|Arg|
|225| | | | |230| | | | |235| | | | |240|

Ile Leu Leu Arg Ala Ala Asn Thr His Ser Ser Ala Lys Pro Cys Gly
                 245                250                255

Gln Gln Ser Ile His Leu Gly Gly Val Phe Glu Leu Gln Pro Gly Ala
        260                265                270

Ser Val Phe Val Asn Val Thr Asp Pro Ser Gln Val Ser His Gly Thr
    275                280                285

Gly Phe Thr Ser Phe Gly Leu Leu Lys Leu Met Gln Lys Gly Asp Gln
290                295                300

Asn Pro Gln Ile Ala Ala His Val Ile Ser Glu Ala Ser Ser Lys Thr
305                310                315                320

Thr Ser Val Leu Gln Trp Ala Glu Lys Gly Tyr Tyr Thr Met Ser Asn
        325                330                335

Asn Leu Val Thr Leu Glu Asn Gly Lys Gln Leu Thr Val Lys Arg Gln
            340              345                350

Gly Leu Tyr Tyr Ile Tyr Ala Gln Val Thr Phe Cys Ser Asn Arg Glu
        355                360                365

Ala Ser Ser Gln Ala Pro Phe Ile Ala Ser Leu Cys Leu Lys Ser Pro
370                375                380

Gly Arg Phe Glu Arg Ile Leu Leu Arg Ala Ala Asn Thr His Ser Ser
385                390                395                400

Ala Lys Pro Cys Gly Gln Gln Ser Ile His Leu Gly Gly Val Phe Glu
            405              410                415

Leu Gln Pro Gly Ala Ser Val Phe Val Asn Val Thr Asp Pro Ser Gln
        420                425                430

Val Ser His Gly Thr Gly Phe Thr Ser Phe Gly Leu Leu Lys Leu
            435              440                445

<210> SEQ ID NO 86
<211> LENGTH: 1347
<212> TYPE: DNA
<213> ORGANISM: Artificial Sequence
<220> FEATURE:
<223> OTHER INFORMATION: Human single chain CD40L trimer nucleotide
     sequence

<400> SEQUENCE: 86

```
atgcaaaaag gggatcagaa tcctcaaatt gcagcacatg tcatatctga ggccagctca      60
aaaacaacat ctgtgctcca gtgggctgaa aaggatacta caccatgag caacaacctc     120 gttaccctgg aaaatgggaa acagctgacc gttaaaagac aaggactcta ttatatctat     180
gcccaagtca ccttctgttc aatcgggaa gcatcttcac aagctccatt tatcgccagc     240
ctctgcctca gtcccccgg tcggttcgag agaatcctcc tcagagctgc aaataccccac     300 tcttccgcca aaccttgcgg gcaacaatcc attcacctcg gaggagtttt tgaactgcaa     360 ccagggggctt ctgtgttgt caatgtgact gatccaagcc aagtgtctca tggaactggc     420
ttcacttcct ttggcctcct caaactcatg cagaaagggg accaaaaccc ccagatagcc     480
gctcacgtta tttccgaagc aagctcaaaa acaacatctg tgctccagtg ggctgaaaaa     540
ggatactaca ccatgagcaa caacctcgtt accctggaga cgaaagca actcactgtg     600 aagcggcagg gctgtacta catatacgca caagtgactt tttgcagcaa cagggaggca     660
tcctctcagg cccctttcat tgccagcctc tgcctgaagt cccccggtag attcgagaga     720
atcctcctca gagctgcaaa tacccactcc tccgcaaaac cctgtggcca gcagagcatc     780
```

-continued

```
catctgggcg gcgtgttcga gctccagcct ggggcctccg tcttcgtgaa cgtcaccgac    840
ccttcccaag tcagccacgg cactggcttc acatcctttg gcctcctcaa actcatgcaa    900
aaaggcgatc agaatcctca aattgctgca catgtcattt ccgaagcctc atccaaaact    960
acctccgtcc tgcaatgggc cgagaagggg tattatacaa tgtcaaataa cctggttact   1020
ctggaaaacg gcaaacagct cactgttaag cgccaaggtc tctactatat atatgcacaa   1080
gttactttct gttcaaatcg cgaagcatca tcacaagcac catttatagc atcactctgt   1140
ctcaagtcac caggtcgctt tgaacgcata ctgctccgcg cagcaaatac tcactcatca   1200
gcaaaaccat gcggtcaaca atcaataaac ctcggtggtg ttttttgagct ccaaccaggc   1260 gcttcagttt ttgttaatgt tactgatcca tcacaagttt cacatggtac aggtttcact   1320
tcatttggtc tgctcaaact ctaatag                                        1347
```

<210> SEQ ID NO 87
<211> LENGTH: 239
<212> TYPE: PRT
<213> ORGANISM: Artificial Sequence
<220> FEATURE:
<223> OTHER INFORMATION: Human CD40L anchor region and extracellular domain amino acid sequence

<400> SEQUENCE: 87

```
Ile Phe Met Tyr Leu Leu Thr Val Phe Leu Ile Thr Gln Met Ile Gly
 1               5                  10                  15

Ser Ala Leu Phe Ala Val Tyr Leu His Arg Arg Leu Asp Lys Ile Glu
            20                  25                  30

Asp Glu Arg Asn Leu His Glu Asp Phe Val Phe Met Lys Thr Ile Gln
        35                  40                  45

Arg Cys Asn Thr Gly Glu Arg Ser Leu Ser Leu Leu Asn Cys Glu Glu
    50                  55                  60

Ile Lys Ser Gln Phe Glu Gly Phe Val Lys Asp Ile Met Leu Asn Lys
65                  70                  75                  80

Glu Glu Thr Lys Lys Glu Asn Ser Phe Glu Met Gln Lys Gly Asp Gln
                85                  90                  95

Asn Pro Gln Ile Ala Ala His Val Ile Ser Glu Ala Ser Ser Lys Thr
           100                 105                 110

Thr Ser Val Leu Gln Trp Ala Glu Lys Gly Tyr Tyr Thr Met Ser Asn
       115                 120                 125

Asn Leu Val Thr Leu Glu Asn Gly Lys Gln Leu Thr Val Lys Arg Gln
   130                 135                 140

Gly Leu Tyr Tyr Ile Tyr Ala Gln Val Thr Phe Cys Ser Asn Arg Glu
145                 150                 155                 160

Ala Ser Ser Gln Ala Pro Phe Ile Ala Ser Leu Cys Leu Lys Ser Pro
               165                 170                 175

Gly Arg Phe Glu Arg Ile Leu Leu Arg Ala Ala Asn Thr His Ser Ser
           180                 185                 190

Ala Lys Pro Cys Gly Gln Gln Ser Ile His Leu Gly Gly Val Phe Glu
       195                 200                 205

Leu Gln Pro Gly Ala Ser Val Phe Val Asn Val Thr Asp Pro Ser Gln
   210                 215                 220

Val Ser His Gly Thr Gly Phe Thr Ser Phe Gly Leu Leu Lys Leu
225                 230                 235
```

<210> SEQ ID NO 88
<211> LENGTH: 474

```
<212> TYPE: PRT
<213> ORGANISM: Artificial Sequence
<220> FEATURE:
<223> OTHER INFORMATION: Human single chain CD40L trimer amino acid
      sequence
<220> FEATURE:
<221> NAME/KEY: SIGNAL
<222> LOCATION: (1)..(27)

<400> SEQUENCE: 88
```

| | | | | | | | | | | | | | | | |
|---|---|---|---|---|---|---|---|---|---|---|---|---|---|---|---|
| Met | Glu | Trp | Gly | Tyr | Leu | Leu | Glu | Val | Thr | Ser | Leu | Leu | Ala | Ala | Leu |
| 1 | | | | 5 | | | | | 10 | | | | | 15 | |
| Leu | Leu | Leu | Gln | Arg | Ser | Pro | Ile | Val | His | Ala | Met | Gln | Lys | Gly | Asp |
| | | | 20 | | | | | 25 | | | | | 30 | | |
| Gln | Asn | Pro | Gln | Ile | Ala | Ala | His | Val | Ile | Ser | Glu | Ala | Ser | Ser | Lys |
| | | 35 | | | | | 40 | | | | | 45 | | | |
| Thr | Thr | Ser | Val | Leu | Gln | Trp | Ala | Glu | Lys | Gly | Tyr | Tyr | Thr | Met | Ser |
| 50 | | | | | 55 | | | | | 60 | | | | | |
| Asn | Asn | Leu | Val | Thr | Leu | Glu | Asn | Gly | Lys | Gln | Leu | Thr | Val | Lys | Arg |
| 65 | | | | | 70 | | | | | 75 | | | | | 80 |
| Gln | Gly | Leu | Tyr | Tyr | Ile | Tyr | Ala | Gln | Val | Thr | Phe | Cys | Ser | Asn | Arg |
| | | | | 85 | | | | | 90 | | | | | 95 | |
| Glu | Ala | Ser | Ser | Gln | Ala | Pro | Phe | Ile | Ala | Ser | Leu | Cys | Leu | Lys | Ser |
| | | | 100 | | | | | 105 | | | | | 110 | | |
| Pro | Gly | Arg | Phe | Glu | Arg | Ile | Leu | Leu | Arg | Ala | Ala | Asn | Thr | His | Ser |
| | | 115 | | | | | 120 | | | | | 125 | | | |
| Ser | Ala | Lys | Pro | Cys | Gly | Gln | Gln | Ser | Ile | His | Leu | Gly | Gly | Val | Phe |
| 130 | | | | | 135 | | | | | 140 | | | | | |
| Glu | Leu | Gln | Pro | Gly | Ala | Ser | Val | Phe | Val | Asn | Val | Thr | Asp | Pro | Ser |
| 145 | | | | | 150 | | | | | 155 | | | | | 160 |
| Gln | Val | Ser | His | Gly | Thr | Gly | Phe | Thr | Ser | Phe | Gly | Leu | Leu | Lys | Leu |
| | | | | 165 | | | | | 170 | | | | | 175 | |
| Met | Gln | Lys | Gly | Asp | Gln | Asn | Pro | Gln | Ile | Ala | Ala | His | Val | Ile | Ser |
| | | | 180 | | | | | 185 | | | | | 190 | | |
| Glu | Ala | Ser | Ser | Lys | Thr | Thr | Ser | Val | Leu | Gln | Trp | Ala | Glu | Lys | Gly |
| | | 195 | | | | | 200 | | | | | 205 | | | |
| Tyr | Tyr | Thr | Met | Ser | Asn | Asn | Leu | Val | Thr | Leu | Glu | Asn | Gly | Lys | Gln |
| 210 | | | | | 215 | | | | | 220 | | | | | |
| Leu | Thr | Val | Lys | Arg | Gln | Gly | Leu | Tyr | Tyr | Ile | Tyr | Ala | Gln | Val | Thr |
| 225 | | | | | 230 | | | | | 235 | | | | | 240 |
| Phe | Cys | Ser | Asn | Arg | Glu | Ala | Ser | Ser | Gln | Ala | Pro | Phe | Ile | Ala | Ser |
| | | | 245 | | | | | 250 | | | | | 255 | | |
| Leu | Cys | Leu | Lys | Ser | Pro | Gly | Arg | Phe | Glu | Arg | Ile | Leu | Leu | Arg | Ala |
| | | 260 | | | | | 265 | | | | | 270 | | | |
| Ala | Asn | Thr | His | Ser | Ser | Ala | Lys | Pro | Cys | Gly | Gln | Gln | Ser | Ile | His |
| | | 275 | | | | | 280 | | | | | 285 | | | |
| Leu | Gly | Gly | Val | Phe | Glu | Leu | Gln | Pro | Gly | Ala | Ser | Val | Phe | Val | Asn |
| | | 290 | | | | | 295 | | | | | 300 | | | |
| Val | Thr | Asp | Pro | Ser | Gln | Val | Ser | His | Gly | Thr | Gly | Phe | Thr | Ser | Phe |
| 305 | | | | | 310 | | | | | 315 | | | | | 320 |
| Gly | Leu | Leu | Lys | Leu | Met | Gln | Lys | Gly | Asp | Gln | Asn | Pro | Gln | Ile | Ala |
| | | | | 325 | | | | | 330 | | | | | 335 | |
| Ala | His | Val | Ile | Ser | Glu | Ala | Ser | Ser | Lys | Thr | Thr | Ser | Val | Leu | Gln |
| | | | 340 | | | | | 345 | | | | | 350 | | |
| Trp | Ala | Glu | Lys | Gly | Tyr | Tyr | Thr | Met | Ser | Asn | Asn | Leu | Val | Thr | Leu |
| | | 355 | | | | | 360 | | | | | 365 | | | |

```
Glu Asn Gly Lys Gln Leu Thr Val Lys Arg Gln Gly Leu Tyr Tyr Ile
        370                 375                 380

Tyr Ala Gln Val Thr Phe Cys Ser Asn Arg Glu Ala Ser Ser Gln Ala
385                 390                 395                 400

Pro Phe Ile Ala Ser Leu Cys Leu Lys Ser Pro Gly Arg Phe Glu Arg
                405                 410                 415

Ile Leu Leu Arg Ala Ala Asn Thr His Ser Ser Ala Lys Pro Cys Gly
                420                 425                 430

Gln Gln Ser Ile His Leu Gly Gly Val Phe Glu Leu Gln Pro Gly Ala
            435                 440                 445

Ser Val Phe Val Asn Val Thr Asp Pro Ser Gln Val Ser His Gly Thr
        450                 455                 460

Gly Phe Thr Ser Phe Gly Leu Leu Lys Leu
465                 470
```

<210> SEQ ID NO 89
<211> LENGTH: 701
<212> TYPE: PRT
<213> ORGANISM: Artificial Sequence
<220> FEATURE:
<223> OTHER INFORMATION: Human single chain CD40L trimer-Fc (IgG1) amino
      acid sequence
<220> FEATURE:
<221> NAME/KEY: SIGNAL
<222> LOCATION: (1)..(27)

<400> SEQUENCE: 89

```
Met Glu Trp Gly Tyr Leu Leu Glu Val Thr Ser Leu Leu Ala Ala Leu
1               5                   10                  15

Leu Leu Leu Gln Arg Ser Pro Ile Val His Ala Met Gln Lys Gly Asp
                20                  25                  30

Gln Asn Pro Gln Ile Ala Ala His Val Ile Ser Glu Ala Ser Ser Lys
            35                  40                  45

Thr Thr Ser Val Leu Gln Trp Ala Glu Lys Gly Tyr Tyr Thr Met Ser
    50                  55                  60

Asn Asn Leu Val Thr Leu Glu Asn Gly Lys Gln Leu Thr Val Lys Arg
65                  70                  75                  80

Gln Gly Leu Tyr Tyr Ile Tyr Ala Gln Val Thr Phe Cys Ser Asn Arg
                85                  90                  95

Glu Ala Ser Ser Gln Ala Pro Phe Ile Ala Ser Leu Cys Leu Lys Ser
                100                 105                 110

Pro Gly Arg Phe Glu Arg Ile Leu Leu Arg Ala Ala Asn Thr His Ser
            115                 120                 125

Ser Ala Lys Pro Cys Gly Gln Gln Ser Ile His Leu Gly Gly Val Phe
    130                 135                 140

Glu Leu Gln Pro Gly Ala Ser Val Phe Val Asn Val Thr Asp Pro Ser
145                 150                 155                 160

Gln Val Ser His Gly Thr Gly Phe Thr Ser Phe Gly Leu Leu Lys Leu
                165                 170                 175

Met Gln Lys Gly Asp Gln Asn Pro Gln Ile Ala Ala His Val Ile Ser
                180                 185                 190

Glu Ala Ser Ser Lys Thr Thr Ser Val Leu Gln Trp Ala Glu Lys Gly
            195                 200                 205

Tyr Tyr Thr Met Ser Asn Asn Leu Val Thr Leu Glu Asn Gly Lys Gln
    210                 215                 220

Leu Thr Val Lys Arg Gln Gly Leu Tyr Tyr Ile Tyr Ala Gln Val Thr
```

```
                225                 230                 235                 240
        Phe Cys Ser Asn Arg Glu Ala Ser Ser Gln Ala Pro Phe Ile Ala Ser
                            245                 250                 255
        Leu Cys Leu Lys Ser Pro Gly Arg Phe Glu Arg Ile Leu Leu Arg Ala
                        260                 265                 270
        Ala Asn Thr His Ser Ser Ala Lys Pro Cys Gly Gln Ser Ile His
                    275                 280                 285
        Leu Gly Gly Val Phe Glu Leu Gln Pro Gly Ala Ser Val Phe Val Asn
                290                 295                 300
        Val Thr Asp Pro Ser Gln Val Ser His Gly Thr Gly Phe Thr Ser Phe
        305                 310                 315                 320
        Gly Leu Leu Lys Leu Met Gln Lys Gly Asp Gln Asn Pro Gln Ile Ala
                            325                 330                 335
        Ala His Val Ile Ser Glu Ala Ser Ser Lys Thr Thr Ser Val Leu Gln
                        340                 345                 350
        Trp Ala Glu Lys Gly Tyr Tyr Thr Met Ser Asn Asn Leu Val Thr Leu
                    355                 360                 365
        Glu Asn Gly Lys Gln Leu Thr Val Lys Arg Gln Gly Leu Tyr Tyr Ile
                370                 375                 380
        Tyr Ala Gln Val Thr Phe Cys Ser Asn Arg Glu Ala Ser Ser Gln Ala
        385                 390                 395                 400
        Pro Phe Ile Ala Ser Leu Cys Leu Lys Ser Pro Gly Arg Phe Glu Arg
                            405                 410                 415
        Ile Leu Leu Arg Ala Ala Asn Thr His Ser Ser Ala Lys Pro Cys Gly
                        420                 425                 430
        Gln Gln Ser Ile His Leu Gly Gly Val Phe Glu Leu Gln Pro Gly Ala
                    435                 440                 445
        Ser Val Phe Val Asn Val Thr Asp Pro Ser Gln Val Ser His Gly Thr
                450                 455                 460
        Gly Phe Thr Ser Phe Gly Leu Leu Lys Leu Asp Lys Thr His Thr Cys
        465                 470                 475                 480
        Pro Pro Cys Pro Ala Pro Glu Leu Leu Gly Gly Pro Ser Val Phe Leu
                            485                 490                 495
        Phe Pro Pro Lys Pro Lys Asp Thr Leu Met Ile Ser Arg Thr Pro Glu
                        500                 505                 510
        Val Thr Cys Val Val Val Asp Val Ser His Glu Asp Pro Glu Val Lys
                    515                 520                 525
        Phe Asn Trp Tyr Val Asp Gly Val Glu Val His Asn Ala Lys Thr Lys
                530                 535                 540
        Pro Arg Glu Glu Gln Tyr Asn Ser Thr Tyr Arg Val Val Ser Val Leu
        545                 550                 555                 560
        Thr Val Leu His Gln Asp Trp Leu Asn Gly Lys Glu Tyr Lys Cys Lys
                            565                 570                 575
        Val Ser Asn Lys Ala Leu Pro Ala Pro Ile Glu Lys Thr Ile Ser Lys
                        580                 585                 590
        Ala Lys Gly Gln Pro Arg Glu Pro Gln Val Tyr Thr Leu Pro Pro Ser
                    595                 600                 605
        Arg Glu Glu Met Thr Lys Asn Gln Val Ser Leu Thr Cys Leu Val Lys
                610                 615                 620
        Gly Phe Tyr Pro Ser Asp Ile Ala Val Glu Trp Glu Ser Asn Gly Gln
        625                 630                 635                 640
        Pro Glu Asn Asn Tyr Lys Thr Thr Pro Pro Val Leu Asp Ser Asp Gly
                            645                 650                 655
```

```
Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys
        690                 695                 700

<210> SEQ ID NO 90
<211> LENGTH: 674
<212> TYPE: PRT
<213> ORGANISM: Artificial Sequence
<220> FEATURE:
<223> OTHER INFORMATION: Human single chain CD40L trimer-Fc (IgG1) amino
      acid sequence

<400> SEQUENCE: 90

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu Met Gln Lys Gly Asp Gln Asn Pro Gln Ile Ala
145                 150                 155                 160

Ala His Val Ile Ser Glu Ala Ser Ser Lys Thr Thr Ser Val Leu Gln
                165                 170                 175

Trp Ala Glu Lys Gly Tyr Tyr Thr Met Ser Asn Asn Leu Val Thr Leu
            180                 185                 190

Glu Asn Gly Lys Gln Leu Thr Val Lys Arg Gln Gly Leu Tyr Tyr Ile
        195                 200                 205

Tyr Ala Gln Val Thr Phe Cys Ser Asn Arg Glu Ala Ser Ser Gln Ala
    210                 215                 220

Pro Phe Ile Ala Ser Leu Cys Leu Lys Ser Pro Gly Arg Phe Glu Arg
225                 230                 235                 240

Ile Leu Leu Arg Ala Ala Asn Thr His Ser Ser Ala Lys Pro Cys Gly
                245                 250                 255

Gln Gln Ser Ile His Leu Gly Gly Val Phe Glu Leu Gln Pro Gly Ala
            260                 265                 270

Ser Val Phe Val Asn Val Thr Asp Pro Ser Gln Val Ser His Gly Thr
        275                 280                 285

Gly Phe Thr Ser Phe Gly Leu Leu Lys Leu Met Gln Lys Gly Asp Gln
    290                 295                 300

Asn Pro Gln Ile Ala Ala His Val Ile Ser Glu Ala Ser Ser Lys Thr
```

```
            305                 310                 315                 320
            Thr Ser Val Leu Gln Trp Ala Glu Lys Gly Tyr Tyr Thr Met Ser Asn
                        325                 330                 335
            Asn Leu Val Thr Leu Glu Asn Gly Lys Gln Leu Thr Val Lys Arg Gln
                        340                 345                 350
            Gly Leu Tyr Tyr Ile Tyr Ala Gln Val Thr Phe Cys Ser Asn Arg Glu
                        355                 360                 365
            Ala Ser Ser Gln Ala Pro Phe Ile Ala Ser Leu Cys Leu Lys Ser Pro
                        370                 375                 380
            Gly Arg Phe Glu Arg Ile Leu Leu Arg Ala Ala Asn Thr His Ser Ser
            385                 390                 395                 400
            Ala Lys Pro Cys Gly Gln Gln Ser Ile His Leu Gly Gly Val Phe Glu
                        405                 410                 415
            Leu Gln Pro Gly Ala Ser Val Phe Val Asn Val Thr Asp Pro Ser Gln
                        420                 425                 430
            Val Ser His Gly Thr Gly Phe Thr Ser Phe Gly Leu Leu Lys Leu Asp
                        435                 440                 445
            Lys Thr His Thr Cys Pro Pro Cys Pro Ala Pro Glu Leu Leu Gly Gly
            450                 455                 460
            Pro Ser Val Phe Leu Phe Pro Pro Lys Pro Lys Asp Thr Leu Met Ile
            465                 470                 475                 480
            Ser Arg Thr Pro Glu Val Thr Cys Val Val Val Asp Val Ser His Glu
                        485                 490                 495
            Asp Pro Glu Val Lys Phe Asn Trp Tyr Val Asp Gly Val Glu Val His
                        500                 505                 510
            Asn Ala Lys Thr Lys Pro Arg Glu Glu Gln Tyr Asn Ser Thr Tyr Arg
                        515                 520                 525
            Val Val Ser Val Leu Thr Val Leu His Gln Asp Trp Leu Asn Gly Lys
                        530                 535                 540
            Glu Tyr Lys Cys Lys Val Ser Asn Lys Ala Leu Pro Ala Pro Ile Glu
            545                 550                 555                 560
            Lys Thr Ile Ser Lys Ala Lys Gly Gln Pro Arg Glu Pro Gln Val Tyr
                        565                 570                 575
            Thr Leu Pro Pro Ser Arg Glu Glu Met Thr Lys Asn Gln Val Ser Leu
                        580                 585                 590
            Thr Cys Leu Val Lys Gly Phe Tyr Pro Ser Asp Ile Ala Val Glu Trp
                        595                 600                 605
            Glu Ser Asn Gly Gln Pro Glu Asn Asn Tyr Lys Thr Thr Pro Pro Val
            610                 615                 620
            Leu Asp Ser Asp Gly Ser Phe Phe Leu Tyr Ser Lys Leu Thr Val Asp
            625                 630                 635                 640
            Lys Ser Arg Trp Gln Gln Gly Asn Val Phe Ser Cys Ser Val Met His
                        645                 650                 655
            Glu Ala Leu His Asn His Tyr Thr Gln Lys Ser Leu Ser Leu Ser Pro
                        660                 665                 670
            Gly Lys

<210> SEQ ID NO 91
<211> LENGTH: 703
<212> TYPE: PRT
<213> ORGANISM: Artificial Sequence
<220> FEATURE:
<223> OTHER INFORMATION: Human single chain CD40L trimer-Fc (IgG2) amino
      acid sequence
<220> FEATURE:
```

```
<221> NAME/KEY: SIGNAL
<222> LOCATION: (1)..(27)

<400> SEQUENCE: 91
```

| | | | | | | | | | | | | | | |
|---|---|---|---|---|---|---|---|---|---|---|---|---|---|---|
| Met | Glu | Trp | Gly | Tyr | Leu | Leu | Glu | Val | Thr | Ser | Leu | Ala | Ala | Leu |
| 1 | | | | 5 | | | | | 10 | | | | | 15 |
| Leu | Leu | Leu | Gln | Arg | Ser | Pro | Ile | Val | His | Ala | Met | Gln | Lys | Gly | Asp |
| | | | 20 | | | | | 25 | | | | | 30 | | |
| Gln | Asn | Pro | Gln | Ile | Ala | Ala | His | Val | Ile | Ser | Glu | Ala | Ser | Ser | Lys |
| | | 35 | | | | | 40 | | | | | 45 | | | |
| Thr | Thr | Ser | Val | Leu | Gln | Trp | Ala | Glu | Lys | Gly | Tyr | Tyr | Thr | Met | Ser |
| | 50 | | | | | 55 | | | | | 60 | | | | |
| Asn | Asn | Leu | Val | Thr | Leu | Glu | Asn | Gly | Lys | Gln | Leu | Thr | Val | Lys | Arg |
| 65 | | | | | 70 | | | | | 75 | | | | | 80 |
| Gln | Gly | Leu | Tyr | Tyr | Ile | Tyr | Ala | Gln | Val | Thr | Phe | Cys | Ser | Asn | Arg |
| | | | | 85 | | | | | 90 | | | | | 95 | |
| Glu | Ala | Ser | Ser | Gln | Ala | Pro | Phe | Ile | Ala | Ser | Leu | Cys | Leu | Lys | Ser |
| | | | 100 | | | | | 105 | | | | | 110 | | |
| Pro | Gly | Arg | Phe | Glu | Arg | Ile | Leu | Leu | Arg | Ala | Ala | Asn | Thr | His | Ser |
| | | 115 | | | | | 120 | | | | | 125 | | | |
| Ser | Ala | Lys | Pro | Cys | Gly | Gln | Gln | Ser | Ile | His | Leu | Gly | Gly | Val | Phe |
| | 130 | | | | | 135 | | | | | 140 | | | | |
| Glu | Leu | Gln | Pro | Gly | Ala | Ser | Val | Phe | Val | Asn | Val | Thr | Asp | Pro | Ser |
| 145 | | | | | 150 | | | | | 155 | | | | | 160 |
| Gln | Val | Ser | His | Gly | Thr | Gly | Phe | Thr | Ser | Phe | Gly | Leu | Leu | Lys | Leu |
| | | | | 165 | | | | | 170 | | | | | 175 | |
| Met | Gln | Lys | Gly | Asp | Gln | Asn | Pro | Gln | Ile | Ala | Ala | His | Val | Ile | Ser |
| | | | 180 | | | | | 185 | | | | | 190 | | |
| Glu | Ala | Ser | Ser | Lys | Thr | Thr | Ser | Val | Leu | Gln | Trp | Ala | Glu | Lys | Gly |
| | | | 195 | | | | | 200 | | | | | 205 | | |
| Tyr | Tyr | Thr | Met | Ser | Asn | Asn | Leu | Val | Thr | Leu | Glu | Asn | Gly | Lys | Gln |
| | | 210 | | | | | 215 | | | | | 220 | | | |
| Leu | Thr | Val | Lys | Arg | Gln | Gly | Leu | Tyr | Tyr | Ile | Tyr | Ala | Gln | Val | Thr |
| 225 | | | | | 230 | | | | | 235 | | | | | 240 |
| Phe | Cys | Ser | Asn | Arg | Glu | Ala | Ser | Ser | Gln | Ala | Pro | Phe | Ile | Ala | Ser |
| | | | | 245 | | | | | 250 | | | | | 255 | |
| Leu | Cys | Leu | Lys | Ser | Pro | Gly | Arg | Phe | Glu | Arg | Ile | Leu | Leu | Arg | Ala |
| | | | 260 | | | | | 265 | | | | | 270 | | |
| Ala | Asn | Thr | His | Ser | Ser | Ala | Lys | Pro | Cys | Gly | Gln | Gln | Ser | Ile | His |
| | | 275 | | | | | 280 | | | | | 285 | | | |
| Leu | Gly | Gly | Val | Phe | Glu | Leu | Gln | Pro | Gly | Ala | Ser | Val | Phe | Val | Asn |
| | 290 | | | | | 295 | | | | | 300 | | | | |
| Val | Thr | Asp | Pro | Ser | Gln | Val | Ser | His | Gly | Thr | Gly | Phe | Thr | Ser | Phe |
| 305 | | | | | 310 | | | | | 315 | | | | | 320 |
| Gly | Leu | Leu | Lys | Leu | Met | Gln | Lys | Gly | Asp | Gln | Asn | Pro | Gln | Ile | Ala |
| | | | | 325 | | | | | 330 | | | | | 335 | |
| Ala | His | Val | Ile | Ser | Glu | Ala | Ser | Ser | Lys | Thr | Thr | Ser | Val | Leu | Gln |
| | | | 340 | | | | | 345 | | | | | 350 | | |
| Trp | Ala | Glu | Lys | Gly | Tyr | Tyr | Thr | Met | Ser | Asn | Asn | Leu | Val | Thr | Leu |
| | | | 355 | | | | | 360 | | | | | 365 | | |
| Glu | Asn | Gly | Lys | Gln | Leu | Thr | Val | Lys | Arg | Gln | Gly | Leu | Tyr | Tyr | Ile |
| | | 370 | | | | | 375 | | | | | 380 | | | |
| Tyr | Ala | Gln | Val | Thr | Phe | Cys | Ser | Asn | Arg | Glu | Ala | Ser | Ser | Gln | Ala |
| 385 | | | | | 390 | | | | | 395 | | | | | 400 |

Pro Phe Ile Ala Ser Leu Cys Leu Lys Ser Pro Gly Arg Phe Glu Arg
                405                 410                 415

Ile Leu Leu Arg Ala Ala Asn Thr His Ser Ser Ala Lys Pro Cys Gly
            420                 425                 430

Gln Gln Ser Ile His Leu Gly Gly Val Phe Glu Leu Gln Pro Gly Ala
        435                 440                 445

Ser Val Phe Val Asn Val Thr Asp Pro Ser Gln Val Ser His Gly Thr
    450                 455                 460

Gly Phe Thr Ser Phe Gly Leu Leu Lys Leu Val Glu Arg Lys Ser Cys
465                 470                 475                 480

Val Glu Cys Pro Pro Cys Pro Ala Pro Pro Val Ala Gly Pro Ser Val
                485                 490                 495

Phe Leu Phe Pro Pro Lys Pro Lys Asp Thr Leu Met Ile Ser Arg Thr
                500                 505                 510

Pro Glu Val Thr Cys Val Val Val Asp Val Ser His Glu Asp Pro Glu
            515                 520                 525

Val Gln Phe Asn Trp Tyr Val Asp Gly Val Glu Val His Asn Ala Lys
        530                 535                 540

Thr Lys Pro Arg Glu Glu Gln Phe Asn Ser Thr Phe Arg Val Val Ser
545                 550                 555                 560

Val Leu Thr Val Val His Gln Asp Trp Leu Asn Gly Lys Glu Tyr Lys
                565                 570                 575

Cys Lys Val Ser Asn Lys Gly Leu Pro Ala Pro Ile Glu Lys Thr Ile
                580                 585                 590

Ser Lys Thr Lys Gly Gln Pro Arg Glu Pro Gln Val Tyr Thr Leu Pro
            595                 600                 605

Pro Ser Arg Glu Glu Met Thr Lys Asn Gln Val Ser Leu Thr Cys Leu
        610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Met Leu Asp Ser
                645                 650                 655

Asp Gly Ser Phe Phe Leu Tyr Ser Lys Leu Thr Val Asp Lys Ser Arg
                660                 665                 670

Trp Gln Gln Gly Asn Val Phe Ser Cys Ser Val Met His Glu Ala Leu
            675                 680                 685

His Asn His Tyr Thr Gln Lys Ser Leu Ser Leu Ser Pro Gly Lys
        690                 695                 700

<210> SEQ ID NO 92
<211> LENGTH: 676
<212> TYPE: PRT
<213> ORGANISM: Artificial Sequence
<220> FEATURE:
<223> OTHER INFORMATION: Human single chain CD40L trimer-Fc (IgG2) amino
      acid sequence

<400> SEQUENCE: 92

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr

```
                50                    55                    60
    Phe Cys Ser Asn Arg Glu Ala Ser Ser Gln Ala Pro Phe Ile Ala Ser
    65                      70                      75                      80

Leu Cys Leu Lys Ser Pro Gly Arg Phe Glu Arg Ile Leu Leu Arg Ala
                            85                      90                      95

Ala Asn Thr His Ser Ser Ala Lys Pro Cys Gly Gln Gln Ser Ile His
                            100                     105                     110

Leu Gly Gly Val Phe Glu Leu Gln Pro Gly Ala Ser Val Phe Val Asn
                            115                     120                     125

Val Thr Asp Pro Ser Gln Val Ser His Gly Thr Gly Phe Thr Ser Phe
                            130                     135                     140

Gly Leu Leu Lys Leu Met Gln Lys Gly Asp Gln Asn Pro Gln Ile Ala
    145                     150                     155                     160

Ala His Val Ile Ser Glu Ala Ser Ser Lys Thr Thr Ser Val Leu Gln
                            165                     170                     175

Trp Ala Glu Lys Gly Tyr Tyr Thr Met Ser Asn Asn Leu Val Thr Leu
                            180                     185                     190

Glu Asn Gly Lys Gln Leu Thr Val Lys Arg Gln Gly Leu Tyr Tyr Ile
                            195                     200                     205

Tyr Ala Gln Val Thr Phe Cys Ser Asn Arg Glu Ala Ser Ser Gln Ala
                            210                     215                     220

Pro Phe Ile Ala Ser Leu Cys Leu Lys Ser Pro Gly Arg Phe Glu Arg
    225                     230                     235                     240

Ile Leu Leu Arg Ala Ala Asn Thr His Ser Ser Ala Lys Pro Cys Gly
                            245                     250                     255

Gln Gln Ser Ile His Leu Gly Gly Val Phe Glu Leu Gln Pro Gly Ala
                            260                     265                     270

Ser Val Phe Val Asn Val Thr Asp Pro Ser Gln Val Ser His Gly Thr
                            275                     280                     285

Gly Phe Thr Ser Phe Gly Leu Leu Lys Leu Met Gln Lys Gly Asp Gln
                            290                     295                     300

Asn Pro Gln Ile Ala Ala His Val Ile Ser Glu Ala Ser Ser Lys Thr
    305                     310                     315                     320

Thr Ser Val Leu Gln Trp Ala Glu Lys Gly Tyr Tyr Thr Met Ser Asn
                            325                     330                     335

Asn Leu Val Thr Leu Glu Asn Gly Lys Gln Leu Thr Val Lys Arg Gln
                            340                     345                     350

Gly Leu Tyr Tyr Ile Tyr Ala Gln Val Thr Phe Cys Ser Asn Arg Glu
                            355                     360                     365

Ala Ser Ser Gln Ala Pro Phe Ile Ala Ser Leu Cys Leu Lys Ser Pro
                            370                     375                     380

Gly Arg Phe Glu Arg Ile Leu Leu Arg Ala Ala Asn Thr His Ser Ser
    385                     390                     395                     400

Ala Lys Pro Cys Gly Gln Gln Ser Ile His Leu Gly Gly Val Phe Glu
                            405                     410                     415

Leu Gln Pro Gly Ala Ser Val Phe Val Asn Val Thr Asp Pro Ser Gln
                            420                     425                     430

Val Ser His Gly Thr Gly Phe Thr Ser Phe Gly Leu Leu Lys Leu Val
                            435                     440                     445

Glu Arg Lys Ser Cys Val Glu Cys Pro Pro Cys Pro Ala Pro Pro Val
    450                     455                     460

Ala Gly Pro Ser Val Phe Leu Phe Pro Pro Lys Pro Lys Asp Thr Leu
    465                     470                     475                     480
```

```
Met Ile Ser Arg Thr Pro Glu Val Thr Cys Val Val Asp Val Ser
                485                 490                 495

His Glu Asp Pro Glu Val Gln Phe Asn Trp Tyr Val Asp Gly Val Glu
                500                 505                 510

Val His Asn Ala Lys Thr Lys Pro Arg Glu Glu Gln Phe Asn Ser Thr
            515                 520                 525

Phe Arg Val Val Ser Val Leu Thr Val His Gln Asp Trp Leu Asn
    530                 535                 540

Gly Lys Glu Tyr Lys Cys Lys Val Ser Asn Lys Gly Leu Pro Ala Pro
545                 550                 555                 560

Ile Glu Lys Thr Ile Ser Lys Thr Lys Gly Gln Pro Arg Glu Pro Gln
                565                 570                 575

Val Tyr Thr Leu Pro Pro Ser Arg Glu Glu Met Thr Lys Asn Gln Val
            580                 585                 590

Ser Leu Thr Cys Leu Val Lys Gly Phe Tyr Pro Ser Asp Ile Ala Val
            595                 600                 605

Glu Trp Glu Ser Asn Gly Gln Pro Glu Asn Asn Tyr Lys Thr Thr Pro
    610                 615                 620

Pro Met Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro Gly Lys
            675

<210> SEQ ID NO 93
<211> LENGTH: 72
<212> TYPE: PRT
<213> ORGANISM: Artificial Sequence
<220> FEATURE:
<223> OTHER INFORMATION: Human CD40L Stalk Region

<400> SEQUENCE: 93

His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
                20                  25                  30

Leu Ser Leu Leu Asn Cys Glu Glu Ile Lys Ser Gln Phe Glu Gly Phe
            35                  40                  45

Val Lys Asp Ile Met Leu Asn Lys Glu Glu Thr Lys Lys Glu Asn Ser
    50                  55                  60

Phe Glu Met Gln Lys Gly Asp Gln
65                  70

<210> SEQ ID NO 94
<211> LENGTH: 140
<212> TYPE: PRT
<213> ORGANISM: Artificial Sequence
<220> FEATURE:
<223> OTHER INFORMATION: Human CD40L TNF homology domain

<400> SEQUENCE: 94

Ile Ala Ala His Val Ile Ser Glu Ala Ser Ser Lys Thr Thr Ser Val
1               5                   10                  15

Leu Gln Trp Ala Glu Lys Gly Tyr Tyr Thr Met Ser Asn Asn Leu Val
```

```
                  20                  25                  30

Thr Leu Glu Asn Gly Lys Gln Leu Thr Val Lys Arg Gln Gly Leu Tyr
            35                  40                  45

Tyr Ile Tyr Ala Gln Val Thr Phe Cys Ser Asn Arg Glu Ala Ser Ser
    50                  55                  60

Gln Ala Pro Phe Ile Ala Ser Leu Cys Leu Lys Ser Pro Gly Arg Phe
65                  70                  75                  80

Glu Arg Ile Leu Leu Arg Ala Ala Asn Thr His Ser Ser Ala Lys Pro
                85                  90                  95

Cys Gly Gln Gln Ser Ile His Leu Gly Gly Val Phe Glu Leu Gln Pro
            100                 105                 110

Gly Ala Ser Val Phe Val Asn Val Thr Asp Pro Ser Gln Val Ser His
        115                 120                 125

Gly Thr Gly Phe Thr Ser Phe Gly Leu Leu Lys Leu
    130                 135                 140

<210> SEQ ID NO 95
<211> LENGTH: 143
<212> TYPE: PRT
<213> ORGANISM: Artificial Sequence
<220> FEATURE:
<223> OTHER INFORMATION: Human CD40L extracellular domain without stalk
      region amino acid sequence

<400> SEQUENCE: 95

Asn Pro Gln Ile Ala Ala His Val Ile Ser Glu Ala Ser Ser Lys Thr
1               5                   10                  15

Thr Ser Val Leu Gln Trp Ala Glu Lys Gly Tyr Tyr Thr Met Ser Asn
            20                  25                  30

Asn Leu Val Thr Leu Glu Asn Gly Lys Gln Leu Thr Val Lys Arg Gln
        35                  40                  45

Gly Leu Tyr Tyr Ile Tyr Ala Gln Val Thr Phe Cys Ser Asn Arg Glu
    50                  55                  60

Ala Ser Ser Gln Ala Pro Phe Ile Ala Ser Leu Cys Leu Lys Ser Pro
65                  70                  75                  80

Gly Arg Phe Glu Arg Ile Leu Leu Arg Ala Ala Asn Thr His Ser Ser
                85                  90                  95

Ala Lys Pro Cys Gly Gln Gln Ser Ile His Leu Gly Gly Val Phe Glu
            100                 105                 110

Leu Gln Pro Gly Ala Ser Val Phe Val Asn Val Thr Asp Pro Ser Gln
        115                 120                 125

Val Ser His Gly Thr Gly Phe Thr Ser Phe Gly Leu Leu Lys Leu
    130                 135                 140

<210> SEQ ID NO 96
<211> LENGTH: 468
<212> TYPE: PRT
<213> ORGANISM: Artificial Sequence
<220> FEATURE:
<223> OTHER INFORMATION: Human single chain CD40L trimer (2 stalks
      regions) amino acid sequence
<220> FEATURE:
<221> NAME/KEY: SIGNAL
<222> LOCATION: (1)..(27)

<400> SEQUENCE: 96

Met Glu Trp Gly Tyr Leu Leu Glu Val Thr Ser Leu Leu Ala Ala Leu
1               5                   10                  15

Leu Leu Leu Gln Arg Ser Pro Ile Val His Ala Asn Pro Gln Ile Ala
```

```
                20                  25                  30
Ala His Val Ile Ser Glu Ala Ser Ser Lys Thr Thr Ser Val Leu Gln
             35                  40                  45

Trp Ala Glu Lys Gly Tyr Tyr Thr Met Ser Asn Asn Leu Val Thr Leu
 50                  55                  60

Glu Asn Gly Lys Gln Leu Thr Val Lys Arg Gln Gly Leu Tyr Tyr Ile
 65                  70                  75                  80

Tyr Ala Gln Val Thr Phe Cys Ser Asn Arg Glu Ala Ser Ser Gln Ala
                 85                  90                  95

Pro Phe Ile Ala Ser Leu Cys Leu Lys Ser Pro Gly Arg Phe Glu Arg
            100                 105                 110

Ile Leu Leu Arg Ala Ala Asn Thr His Ser Ser Ala Lys Pro Cys Gly
            115                 120                 125

Gln Gln Ser Ile His Leu Gly Gly Val Phe Glu Leu Gln Pro Gly Ala
        130                 135                 140

Ser Val Phe Val Asn Val Thr Asp Pro Ser Gln Val Ser His Gly Thr
145                 150                 155                 160

Gly Phe Thr Ser Phe Gly Leu Leu Lys Leu Met Gln Lys Gly Asp Gln
                165                 170                 175

Asn Pro Gln Ile Ala Ala His Val Ile Ser Glu Ala Ser Ser Lys Thr
            180                 185                 190

Thr Ser Val Leu Gln Trp Ala Glu Lys Gly Tyr Tyr Thr Met Ser Asn
        195                 200                 205

Asn Leu Val Thr Leu Glu Asn Gly Lys Gln Leu Thr Val Lys Arg Gln
        210                 215                 220

Gly Leu Tyr Tyr Ile Tyr Ala Gln Val Thr Phe Cys Ser Asn Arg Glu
225                 230                 235                 240

Ala Ser Ser Gln Ala Pro Phe Ile Ala Ser Leu Cys Leu Lys Ser Pro
                245                 250                 255

Gly Arg Phe Glu Arg Ile Leu Leu Arg Ala Ala Asn Thr His Ser Ser
            260                 265                 270

Ala Lys Pro Cys Gly Gln Gln Ser Ile His Leu Gly Gly Val Phe Glu
        275                 280                 285

Leu Gln Pro Gly Ala Ser Val Phe Val Asn Val Thr Asp Pro Ser Gln
        290                 295                 300

Val Ser His Gly Thr Gly Phe Thr Ser Phe Gly Leu Leu Lys Leu Met
305                 310                 315                 320

Gln Lys Gly Asp Gln Asn Pro Gln Ile Ala Ala His Val Ile Ser Glu
                325                 330                 335

Ala Ser Ser Lys Thr Thr Ser Val Leu Gln Trp Ala Glu Lys Gly Tyr
            340                 345                 350

Tyr Thr Met Ser Asn Asn Leu Val Thr Leu Glu Asn Gly Lys Gln Leu
        355                 360                 365

Thr Val Lys Arg Gln Gly Leu Tyr Tyr Ile Tyr Ala Gln Val Thr Phe
        370                 375                 380

Cys Ser Asn Arg Glu Ala Ser Ser Gln Ala Pro Phe Ile Ala Ser Leu
385                 390                 395                 400

Cys Leu Lys Ser Pro Gly Arg Phe Glu Arg Ile Leu Leu Arg Ala Ala
                405                 410                 415

Asn Thr His Ser Ser Ala Lys Pro Cys Gly Gln Gln Ser Ile His Leu
            420                 425                 430

Gly Gly Val Phe Glu Leu Gln Pro Gly Ala Ser Val Phe Val Asn Val
        435                 440                 445
```

Thr Asp Pro Ser Gln Val Ser His Gly Thr Gly Phe Thr Ser Phe Gly
    450                 455                 460

Leu Leu Lys Leu
465

<210> SEQ ID NO 97
<211> LENGTH: 441
<212> TYPE: PRT
<213> ORGANISM: Artificial Sequence
<220> FEATURE:
<223> OTHER INFORMATION: Human single chain CD40L trimer (2 stalks
      regions) amino acid sequence

<400> SEQUENCE: 97

Asn Pro Gln Ile Ala Ala His Val Ile Ser Glu Ala Ser Ser Lys Thr
1               5                   10                  15

Thr Ser Val Leu Gln Trp Ala Glu Lys Gly Tyr Tyr Thr Met Ser Asn
            20                  25                  30

Asn Leu Val Thr Leu Glu Asn Gly Lys Gln Leu Thr Val Lys Arg Gln
        35                  40                  45

Gly Leu Tyr Tyr Ile Tyr Ala Gln Val Thr Phe Cys Ser Asn Arg Glu
    50                  55                  60

Ala Ser Ser Gln Ala Pro Phe Ile Ala Ser Leu Cys Leu Lys Ser Pro
65                  70                  75                  80

Gly Arg Phe Glu Arg Ile Leu Leu Arg Ala Ala Asn Thr His Ser Ser
                85                  90                  95

Ala Lys Pro Cys Gly Gln Gln Ser Ile His Leu Gly Gly Val Phe Glu
            100                 105                 110

Leu Gln Pro Gly Ala Ser Val Phe Val Asn Val Thr Asp Pro Ser Gln
        115                 120                 125

Val Ser His Gly Thr Gly Phe Thr Ser Phe Gly Leu Leu Lys Leu Met
    130                 135                 140

Gln Lys Gly Asp Gln Asn Pro Gln Ile Ala Ala His Val Ile Ser Glu
145                 150                 155                 160

Ala Ser Ser Lys Thr Thr Ser Val Leu Gln Trp Ala Glu Lys Gly Tyr
                165                 170                 175

Tyr Thr Met Ser Asn Asn Leu Val Thr Leu Glu Asn Gly Lys Gln Leu
            180                 185                 190

Thr Val Lys Arg Gln Gly Leu Tyr Tyr Ile Tyr Ala Gln Val Thr Phe
        195                 200                 205

Cys Ser Asn Arg Glu Ala Ser Ser Gln Ala Pro Phe Ile Ala Ser Leu
    210                 215                 220

Cys Leu Lys Ser Pro Gly Arg Phe Glu Arg Ile Leu Leu Arg Ala Ala
225                 230                 235                 240

Asn Thr His Ser Ser Ala Lys Pro Cys Gly Gln Gln Ser Ile His Leu
                245                 250                 255

Gly Gly Val Phe Glu Leu Gln Pro Gly Ala Ser Val Phe Val Asn Val
            260                 265                 270

Thr Asp Pro Ser Gln Val Ser His Gly Thr Gly Phe Thr Ser Phe Gly
        275                 280                 285

Leu Leu Lys Leu Met Gln Lys Gly Asp Gln Asn Pro Gln Ile Ala Ala
    290                 295                 300

His Val Ile Ser Glu Ala Ser Ser Lys Thr Thr Ser Val Leu Gln Trp
305                 310                 315                 320

Ala Glu Lys Gly Tyr Tyr Thr Met Ser Asn Asn Leu Val Thr Leu Glu

```
                        325                 330                 335
Asn Gly Lys Gln Leu Thr Val Lys Arg Gln Gly Leu Tyr Tyr Ile Tyr
                340                 345                 350

Ala Gln Val Thr Phe Cys Ser Asn Arg Glu Ala Ser Ser Gln Ala Pro
            355                 360                 365

Phe Ile Ala Ser Leu Cys Leu Lys Ser Pro Gly Arg Phe Glu Arg Ile
        370                 375                 380

Leu Leu Arg Ala Ala Asn Thr His Ser Ser Ala Lys Pro Cys Gly Gln
385                 390                 395                 400

Gln Ser Ile His Leu Gly Gly Val Phe Glu Leu Gln Pro Gly Ala Ser
                405                 410                 415

Val Phe Val Asn Val Thr Asp Pro Ser Gln Val Ser His Gly Thr Gly
            420                 425                 430

Phe Thr Ser Phe Gly Leu Leu Lys Leu
        435                 440

<210> SEQ ID NO 98
<211> LENGTH: 6
<212> TYPE: PRT
<213> ORGANISM: Artificial Sequence
<220> FEATURE:
<223> OTHER INFORMATION: Human CD40L Stalk Region - fragment 1

<400> SEQUENCE: 98

Met Gln Lys Gly Asp Gln
1               5

<210> SEQ ID NO 99
<211> LENGTH: 8
<212> TYPE: PRT
<213> ORGANISM: Artificial Sequence
<220> FEATURE:
<223> OTHER INFORMATION: Human CD40L Stalk Region - fragment 2

<400> SEQUENCE: 99

Phe Glu Met Gln Lys Gly Asp Gln
1               5

<210> SEQ ID NO 100
<211> LENGTH: 7
<212> TYPE: PRT
<213> ORGANISM: Artificial Sequence
<220> FEATURE:
<223> OTHER INFORMATION: Human CD40L Stalk Region - fragment 3

<400> SEQUENCE: 100

Glu Met Gln Lys Gly Asp Gln
1               5

<210> SEQ ID NO 101
<211> LENGTH: 5
<212> TYPE: PRT
<213> ORGANISM: Artificial Sequence
<220> FEATURE:
<223> OTHER INFORMATION: Human CD40L Stalk Region - fragment 4

<400> SEQUENCE: 101

Gln Lys Gly Asp Gln
1               5

<210> SEQ ID NO 102
<211> LENGTH: 4
<212> TYPE: PRT
```

<213> ORGANISM: Artificial Sequence
<220> FEATURE:
<223> OTHER INFORMATION: Human CD40L Stalk Region - fragment 5

<400> SEQUENCE: 102

Lys Gly Asp Gln
1

<210> SEQ ID NO 103
<211> LENGTH: 151
<212> TYPE: PRT
<213> ORGANISM: Artificial Sequence
<220> FEATURE:
<223> OTHER INFORMATION: Human CD40L extracellular domain with stalk
      fragment 2 (aa 111-261)

<400> SEQUENCE: 103

Phe Glu Met Gln Lys Gly Asp Gln Asn Pro Gln Ile Ala Ala His Val
1               5                   10                  15

Ile Ser Glu Ala Ser Ser Lys Thr Thr Ser Val Leu Gln Trp Ala Glu
            20                  25                  30

Lys Gly Tyr Tyr Thr Met Ser Asn Asn Leu Val Thr Leu Glu Asn Gly
        35                  40                  45

Lys Gln Leu Thr Val Lys Arg Gln Gly Leu Tyr Tyr Ile Tyr Ala Gln
    50                  55                  60

Val Thr Phe Cys Ser Asn Arg Glu Ala Ser Ser Gln Ala Pro Phe Ile
65                  70                  75                  80

Ala Ser Leu Cys Leu Lys Ser Pro Gly Arg Phe Glu Arg Ile Leu Leu
                85                  90                  95

Arg Ala Ala Asn Thr His Ser Ser Ala Lys Pro Cys Gly Gln Gln Ser
            100                 105                 110

Ile His Leu Gly Gly Val Phe Glu Leu Gln Pro Gly Ala Ser Val Phe
        115                 120                 125

Val Asn Val Thr Asp Pro Ser Gln Val Ser His Gly Thr Gly Phe Thr
    130                 135                 140

Ser Phe Gly Leu Leu Lys Leu
145                 150

<210> SEQ ID NO 104
<211> LENGTH: 150
<212> TYPE: PRT
<213> ORGANISM: Artificial Sequence
<220> FEATURE:
<223> OTHER INFORMATION: Human CD40L extracellular domain with stalk
      fragment 3 (aa 112-261)

<400> SEQUENCE: 104

Glu Met Gln Lys Gly Asp Gln Asn Pro Gln Ile Ala Ala His Val Ile
1               5                   10                  15

Ser Glu Ala Ser Ser Lys Thr Thr Ser Val Leu Gln Trp Ala Glu Lys
            20                  25                  30

Gly Tyr Tyr Thr Met Ser Asn Asn Leu Val Thr Leu Glu Asn Gly Lys
        35                  40                  45

Gln Leu Thr Val Lys Arg Gln Gly Leu Tyr Tyr Ile Tyr Ala Gln Val
    50                  55                  60

Thr Phe Cys Ser Asn Arg Glu Ala Ser Ser Gln Ala Pro Phe Ile Ala
65                  70                  75                  80

Ser Leu Cys Leu Lys Ser Pro Gly Arg Phe Glu Arg Ile Leu Leu Arg
                85                  90                  95

Ala Ala Asn Thr His Ser Ser Ala Lys Pro Cys Gly Gln Gln Ser Ile
            100                 105                 110

His Leu Gly Gly Val Phe Glu Leu Gln Pro Gly Ala Ser Val Phe Val
        115                 120                 125

Asn Val Thr Asp Pro Ser Gln Val Ser His Gly Thr Gly Phe Thr Ser
    130                 135                 140

Phe Gly Leu Leu Lys Leu
145             150

<210> SEQ ID NO 105
<211> LENGTH: 148
<212> TYPE: PRT
<213> ORGANISM: Artificial Sequence
<220> FEATURE:
<223> OTHER INFORMATION: Human CD40L extracellular domain with stalk
      fragment 4 (aa 114-261)

<400> SEQUENCE: 105

Gln Lys Gly Asp Gln Asn Pro Gln Ile Ala Ala His Val Ile Ser Glu
1               5                   10                  15

Ala Ser Ser Lys Thr Thr Ser Val Leu Gln Trp Ala Glu Lys Gly Tyr
            20                  25                  30

Tyr Thr Met Ser Asn Asn Leu Val Thr Leu Glu Asn Gly Lys Gln Leu
        35                  40                  45

Thr Val Lys Arg Gln Gly Leu Tyr Tyr Ile Tyr Ala Gln Val Thr Phe
    50                  55                  60

Cys Ser Asn Arg Glu Ala Ser Ser Gln Ala Pro Phe Ile Ala Ser Leu
65                  70                  75                  80

Cys Leu Lys Ser Pro Gly Arg Phe Glu Arg Ile Leu Leu Arg Ala Ala
                85                  90                  95

Asn Thr His Ser Ser Ala Lys Pro Cys Gly Gln Gln Ser Ile His Leu
            100                 105                 110

Gly Gly Val Phe Glu Leu Gln Pro Gly Ala Ser Val Phe Val Asn Val
        115                 120                 125

Thr Asp Pro Ser Gln Val Ser His Gly Thr Gly Phe Thr Ser Phe Gly
    130                 135                 140

Leu Leu Lys Leu
145

<210> SEQ ID NO 106
<211> LENGTH: 147
<212> TYPE: PRT
<213> ORGANISM: Artificial Sequence
<220> FEATURE:
<223> OTHER INFORMATION: Human CD40L extracellular domain with stalk
      fragment 5 (aa 115-261)

<400> SEQUENCE: 106

Lys Gly Asp Gln Asn Pro Gln Ile Ala Ala His Val Ile Ser Glu Ala
1               5                   10                  15

Ser Ser Lys Thr Thr Ser Val Leu Gln Trp Ala Glu Lys Gly Tyr Tyr
            20                  25                  30

Thr Met Ser Asn Asn Leu Val Thr Leu Glu Asn Gly Lys Gln Leu Thr
        35                  40                  45

Val Lys Arg Gln Gly Leu Tyr Tyr Ile Tyr Ala Gln Val Thr Phe Cys
    50                  55                  60

Ser Asn Arg Glu Ala Ser Ser Gln Ala Pro Phe Ile Ala Ser Leu Cys
65                  70                  75                  80

-continued

```
Leu Lys Ser Pro Gly Arg Phe Glu Arg Ile Leu Leu Arg Ala Ala Asn
            85                  90                  95

Thr His Ser Ser Ala Lys Pro Cys Gly Gln Gln Ser Ile His Leu Gly
            100                 105                 110

Gly Val Phe Glu Leu Gln Pro Gly Ala Ser Val Phe Val Asn Val Thr
            115                 120                 125

Asp Pro Ser Gln Val Ser His Gly Thr Gly Phe Thr Ser Phe Gly Leu
    130                 135                 140

Leu Lys Leu
145
```

METHOD OF TREATING CANCER BY ADMINISTERING TUMOR NECROSIS FACTOR RECEPTOR LIGAND SUPERFAMILY (TNFRSF) SINGLE-CHAIN POLYPEPTIDES

CROSS-REFERENCE TO RELATED APPLICATIONS

This application is a divisional application of U.S. Application Ser. No. 15/014,134, filed Feb. 3, 2016, now U.S. Pat. No. 9,724,390, which claims the priority benefit of U.S. Provisional Application No. 62/111,404, filed Feb. 3, 2015, U.S. Provisional Application No. 62/153,272, filed Apr. 27, 2015, U.S. Provisional Application No. 62/154,008, filed Apr. 28, 2015, U.S. Provisional Application No. 62/218,956, filed Sept. 15, 2015, and U.S. Provisional Application No. 62/259,129, filed Nov. 24, 2015 each of which is hereby incorporated by reference herein in its entirety.

REFERENCE TO SEQUENCE LISTING SUBMITTED ELECTRONICALLY VIA EFS-WEB

The content of the electronically submitted sequence listing (Name: 2293_1360006_SeqListing_ST25.txt; Size: 251,506 bytes; and Date of Creation: Jun. 12, 2017) is herein incorporated by reference in its entirety.

FIELD OF THE INVENTION

The present invention generally relates to agents that bind tumor necrosis factor receptor superfamily members, particularly agents comprising the extracellular domain of GITRL, OX40L, or CD40L. The invention also relates to methods of using the agents for the modulation of immune responses and/or the treatment of diseases such as cancer.

BACKGROUND OF THE INVENTION

The basis for immunotherapy is the manipulation and/or modulation of the immune system, including both innate immune responses and adaptive immune responses. The general aim of immunotherapy is to treat diseases by controlling the immune response to a "foreign agent", for example a pathogen or a tumor cell. However, in some instances immunotherapy is used to treat autoimmune diseases which may arise from an abnormal immune response against proteins, molecules, and/or tissues normally present in the body. Immunotherapy may include methods to induce or enhance specific immune responses or to inhibit or reduce specific immune responses.

The immune system is a highly complex system made up of a great number of cell types, including but not limited to, T-cells, B-cells, natural killer cells, antigen-presenting cells, dendritic cells, monocytes, and macrophages. These cells possess complex and subtle systems for controlling their interactions and responses. The cells utilize both activating and inhibitory mechanisms and feedback loops to keep responses in check and not allow negative consequences of an uncontrolled immune response (e.g., autoimmune diseases or a cytokine storm).

The concept of cancer immunosurveillance is based on the theory that the immune system can recognize tumor cells, mount an immune response, and suppress the development and/or progression of a tumor. However, it is clear that many cancerous cells have developed mechanisms to evade the immune system which can allow for uninhibited growth of tumors. Cancer/tumor immunotherapy (immuno-oncology) focuses on the development of new and novel agents that can activate and/or boost the immune system to achieve a more effective attack against tumor cells resulting in increased killing of tumor cells and/or inhibition of tumor growth.

BRIEF SUMMARY OF THE INVENTION

Proteins belonging to the tumor necrosis factor receptor superfamily (TNFRSF) and their ligands (TNFSF) are intimately involved in the activation, differentiation, and survival of cells of the immune system. TNFRSF members include, but may not be limited to, 4-1BB, BAFF, BCMA, CD27, CD30, CD40, DcR3, DcTRAIL R1, DcTRAIL R2, DR3, DR6, EDA2R, EDAR, Fas (CD95), GITR, HVEM, lymphotoxin beta R, NGFR, osteoprotegerin, OX40, RANK, RELT, TACI, TNFRH3, TNF R1, TNF R2, TRAIL R1, TRAIL R2, TRAIL R3, TRAIL R4, TROY, and TWEAK R. Receptors for TNF family ligands are oligomeric, type I or type III transmembrane proteins that contain multiple extracellular cysteine-rich domains. Several of these receptors also contain intracellular death domains (DDs) that recruit caspase-interacting proteins following ligand binding to initiate the extrinsic pathway of caspase activation. Other TNF superfamily receptors that lack death domains bind TNF receptor-associated factors and activate intracellular signaling pathways that can lead to proliferation or differentiation. These receptors can also initiate apoptosis, but they do so via indirect mechanisms. In addition to regulating apoptosis, several TNF superfamily receptors are involved in regulating immune cell functions such as B-cell homeostasis and activation, natural killer cell activation, and T-cell co-stimulation. Several others regulate cell type-specific responses such as hair follicle development and osteoclast development.

TNFSF members include, but may not be limited to, 4-1BB ligand, APRIL, BAFF, CD27 ligand, CD30 ligand, CD40 ligand (CD40L), EDA, EDA-A1, EDA-A2, Fas ligand (CD95L), GITR ligand (GITRL), LIGHT, lymphotoxin, lymphotoxin beta, lymphotoxin-alpha, OX40 ligand (OX40L), TL1A, TNF-alpha, TRAIL, TRANCE, and TWEAK. Most TNF ligands are type II transmembrane proteins whose extracellular domains can be cleaved by specific metalloproteinases to generate soluble cytokines. Cleaved and non-cleaved ligands are active as non-covalent homotrimers except for lymphotoxin beta (which forms heterotrimers with TNF-beta) and BAFF (which forms heterotrimers with APRIL). TNF family ligands are characterized by a stalk of varying length connecting the transmembrane domain to the core region, which contains the hallmark structure of TNF family ligands, the TNF homology domain (THD) or TNF domain. The TNF domain is an anti-parallel beta-pleated sheet sandwich with a "jelly-roll" topology. Conserved residues within the beta-strands provide specific inter-subunit contacts, which stabilize the trimeric structure. Sequences in the loops connecting adjacent beta-strands are family member-specific and are important for conferring receptor specificity. Interestingly, GITRL (glucocorticoid-induced TNF-related ligand; TNFSF18) appears to be relatively loosely associated as a trimer as compared to other TNF family members, and has been shown to also exist in dimeric states. Further, there is evidence that GITRL trimers can themselves associate to form "superclusters" (Zhou et al., 2008, *PNAS*, 105:5465-5470). Crosslinking of GITRL to stabilize the trimer formation resulted in enhanced activity (Wyzgol et al., 2009, *J. Immunol.*, 183:1851-1861). These results have led to the suggestion that GITRL may exist in a range of oligomeric states ranging from dimers to trimers, to superclusters of trimers, and that these states may result in a range of GITR activity from weak to robust, respectively.

Because agonist antibodies targeting members of the TNFR superfamily are generally dimeric molecules with each arm of the antibody binding one subunit of a TNFR, the inventors hypothesized that they may not be able to fully recapitulate the signaling impact of the native trimeric TNF family member. In light of the data suggesting that GITRL may achieve distinct signaling levels through variation of the oligomerization status of GITRL, it was hypothesized that a therapeutic agent that presents the GITRL in a stable trimeric form could be more active than an agonist GITR antibody at eliciting signaling, and that such a trimeric GITRL form might therefore be a superior immunotherapeutic agent. Further, it was hypothesized that a therapeutic agent that provided two or more GITRL trimers might achieve the impact of a GITRL "supercluster" and be more effective than an agonist GITR antibody. It is believed that this theory would be true for most, if not all, of the TNFR ligands in comparison to TNFR agonist antibodies.

As GITRL has a relatively loose association as a trimer, the means of achieving effective production of a stable therapeutic GITRL trimer is not clear. One strategy to stabilize the GITRL trimer is to express the three subunits of the trimer as a single polypeptide. It has previously been shown that TNF family members can be expressed as a single chain trimer (US Application Publication Nos. 2007/0286843 and 2011/0162095). However, a major drawback of previous single chain TNF family member trimer variants has been the introduction of exogenous linker sequences interconnecting the three subunits of the trimer. Such linkers may introduce potential instability and lability to the trimer, and/or provide a source of potential immunogenicity as the linkers are foreign sequences.

The crystal structure of a human GITRL trimer was examined by the inventors and it was observed that the N-terminal amino acid residues from one monomer and the C-terminal amino acid residues from a second monomer were in close proximity to each other. This suggested that a very short span of amino acid residues, for example only 3-7 residues, might be sufficient to bridge the distance between each monomer and thereby enable a single chain GITRL trimer to be produced without a long peptide linker. Upon further analysis of GITRL it was recognized that there exists a "stalk" of several amino acids between the transmembrane domain and the TNF homology domain of the protein. It was hypothesized that it could be possible to utilize this short stalk region to bridge the distance from the C-terminus of a GITRL monomer to the N-terminus of an adjacent GITRL monomer and in this fashion construct a single chain GITRL trimer that was devoid of exogenous peptide linker sequences.

Other ligands of the TNF superfamily have similar structures, however the size and the amino acid composition of the stalk region varies with each ligand. Furthermore, the native trimer structure of each TNFSF ligand is slightly unique and the amount of the stalk region required for proper folding of each single chain trimeric fusion protein may be different for each TNFSF ligand. For some TNFSF ligands, particularly where the stalk region is very long, only a fragment of the stalk region may be used to generate a single chain trimer.

The present invention provides a variety of polypeptides and agents that bind human tumor necrosis factor receptor superfamily (TNFRSF) members. As used herein, the term "agent" includes, but is not limited to, polypeptides, fusion proteins, homodimeric molecules, and heterodimeric molecules. In some embodiments, a polypeptide or agent binds human glucocorticoid-induced tumor necrosis factor-related protein (GITR). In certain embodiments, the polypeptide or agent is a GITR agonist. In some embodiments, the polypeptide or agent that binds GITR is a soluble GITR ligand (GITRL). In some embodiments, a polypeptide or agent binds human OX40. In certain embodiments, the polypeptide or agent is an OX40 agonist. In some embodiments, the polypeptide or agent that binds OX40 is a soluble OX40 ligand (OX40L). In some embodiments, a polypeptide or agent binds human CD40. In certain embodiments, the polypeptide or agent is a CD40 agonist. In some embodiments, the polypeptide or agent that binds CD40 is a soluble CD40 ligand (CD40L). The invention provides methods of using the polypeptides and agents described herein. In some embodiments, the invention provides methods of using the polypeptides and agents for cancer immunotherapy or immuno-oncology. In some embodiments, the polypeptides and agents are used in methods of inducing, activating, promoting, increasing, enhancing, or prolonging an immune response. In some embodiments, the polypeptides and agents are used in methods of inducing, activating, promoting, increasing, enhancing, or prolonging an immune response to cancer, a tumor, and/or tumor cells. In some embodiments, the polypeptides and agents are used in methods of inhibiting the growth of a tumor or tumor cells. In some embodiments, the polypeptides and agents are used in methods for the treatment of cancer. In some embodiments, the methods comprise inhibiting the growth of cancer cells. The invention also provides compositions comprising the agents described herein. In some embodiments, the compositions are pharmaceutical compositions comprising the polypeptides and agents described herein. Polynucleotides encoding the polypeptides and agents and methods of making the agents are also provided.

In one aspect, the invention provides a polypeptide that comprises a first, second, and third copy of the extracellular domain of a human tumor necrosis factor receptor ligand superfamily (TNFSF) protein or a fragment thereof capable of binding a receptor of the TNFSF protein. In some embodiments, a polypeptide comprises a first, second, and third copy of the extracellular domain of a human tumor necrosis factor receptor ligand superfamily (TNFSF) protein or a fragment thereof capable of binding a receptor of the TNFSF protein, wherein at least one of the first, second, or third copies of the extracellular domain or fragment thereof comprises the stalk region of the TNFSF protein. In some embodiments, the the TNFSF protein is selected from the group consisting of: GITRL, OX40L, 4-1BB ligand, APRIL, BAFF, CD27 ligand, CD30 ligand, CD40 ligand, EDA, EDA-A1, EDA-A2, Fas ligand, LIGHT, lymphotoxin, lymphotoxin beta, lymphotoxin-alpha, TL1A, TNF-alpha, TRAIL, TRANCE, and TWEAK. In some embodiments, the TNFSF protein is GITRL and any copies of fragments of the extracellular domain are GITR-binding fragments. In certain alternative embodiments, the TNFSF protein is OX40L and any copies of fragments of the extracellular domain are OX40-binding fragments. In certain alternative embodiments, the TNFSF protein is CD40L and any copies of fragments of the extracellular domain are CD40-binding fragments. In some embodiments, at least one, at least two, or all three of the copies of the extracellular domains or fragments thereof comprise the stalk region of the extracellular domain. In some embodiments, the polypeptide further comprises an Fc region. Polypeptides and agents, including without limitation homodimeric agents, heterodimeric agents, and bispecific agents, comprising or consisting of the polypeptides described herein are provided.

In some embodiments, a polypeptide comprises a first, second, and third copy of the extracellular domain of a human tumor necrosis factor receptor ligand superfamily (TNFSF) protein or a fragment thereof capable of binding a receptor of the TNFSF protein, wherein at least one of the first, second, or third copies of the extracellular domain or fragment thereof comprises the stalk region of the TNFSF protein. In some embodiments, extracellular domain of the TNFSF protein comprises the stalk region or a fragment of the stalk region. In some embodiments, the extracellular domain comprises only a short fragment of the stalk region. In some embodiments, the stalk region is about 4-20 amino acids. In some embodiments, the stalk region is about 4, 5, 6, 7, 8, 9, or 10 amino acids. In some embodiments, the extracellular domain comprises a stalk region (e.g., 4-10 amino acids) directly upstream from the TNF homology domain. In some embodiments, the extracellular domain comprises a stalk region (e.g., 4-10 amino acids) adjacent to the TNF homology domain.

In another aspect, the present invention provides polypeptides and agents that bind GITR (TNFRSF18). In some embodiments, the polypeptide or agent binds human GITR. In some embodiments, the polypeptide or agent binds mouse GITR. In some embodiments, the polypeptide or agent is a soluble protein. In some embodiments, the polypeptide or agent is a soluble protein that binds human GITR. In some embodiments, the polypeptide or agent is a fusion polypeptide. In some embodiments, the polypeptide or agent comprises at least one copy of the extracellular domain, or a fragment thereof, of GITRL. As used herein, a "copy" of the extracellular domain, or a fragment thereof, of a protein generally refers to a monomer of the extracellular domain of the protein or fragment thereof. For instance, a copy of the extracellular domain, or a fragment thereof, of GITRL generally refers to a monomer of the extracellular domain of the protein, or a fragment thereof, of GITRL. Therefore, multiple "copies" of the extracellular domain generally refers to a dimer (2 copies) of the extracellular domain or a trimer (3 copies) of the extracellular domain of GITRL. In some embodiments, the copies are polypeptides that are exact replicates of the known sequence (e.g., have 100% sequence identity to the native extracellular domain). In certain alternative embodiments, one or more of the copies comprise mutations, such as conservative substitutions, as long as the polypeptide or fusion polypeptide retains the ability to bind to the receptor, i.e., GITR. For example, in certain embodiments, the copies may be polypeptides that have at least about 98%, at least 99%, or 100% sequence identity to the native extracellular domain, or a fragment thereof. In some embodiments, the polypeptide or agent comprises at least one copy of the extracellular domain, or a fragment thereof, of human GITRL. In some embodiments, the polypeptide or agent comprises at least one copy of the extracellular domain, or a fragment thereof, of mouse GITRL. In some embodiments, the polypeptide or agent is a single chain fusion polypeptide comprising at least a first, second, and third copy of the extracellular domain of human GITRL. In some embodiments, the polypeptide or agent is a single chain fusion polypeptide comprising a first, second, and third copy of the extracellular domain of human GITRL or a GITR-binding fragment thereof. In some embodiments, the polypeptide or agent is a single chain fusion polypeptide comprising at least a first, second, and third copy of the extracellular domain of human GITRL, wherein at least one of the extracellular domains comprises the "stalk region" of GITRL. In some embodiments, the stalk region of GITRL is LQLETAK (SEQ ID NO:32). In some embodiments, the polypeptide or agent is a single chain fusion polypeptide comprising at least a first, second, and third copy of the extracellular domain of human GITRL, wherein each extracellular domain comprises the "stalk region" of GITRL. In some embodiments, the polypeptide or agent is a single chain fusion polypeptide comprising at least a first, second, and third copy of the extracellular domain of human GITRL, wherein only the second and third extracellular domains include the "stalk region" of GITRL. In some embodiments, the polypeptide or agent is a single chain fusion polypeptide comprising at least a first, second, and third copy of the extracellular domain of human GITRL or a fragment thereof, wherein the polypeptide does not comprise any peptide linkers. In some embodiments, the polypeptide or agent is a single chain fusion polypeptide comprising a first, second, and third copy of the extracellular domain of human GITRL or a fragment thereof, wherein the polypeptide does not comprise an exogenous peptide linker between any of the copies of the extracellular domain or a fragment thereof. In some embodiments, the polypeptide or agent is a single chain fusion polypeptide comprising a first, second, and third copy of the extracellular domain of human GITRL or a fragment thereof, wherein the polypeptide does not comprise an exogenous peptide linker between the first copy and the second copy of the extracellular domain of human GITRL or a fragment thereof. In some embodiments, the polypeptide or agent is a single chain fusion polypeptide comprising a first, second, and third copy of the extracellular domain of human GITRL or a fragment thereof, wherein the polypeptide does not comprise an exogenous peptide linker between the second copy and the third copy of the extracellular domain of human GITRL or a fragment thereof.

In some embodiments, the agent (e.g., polypeptide) comprises approximately amino acids 71 to 199 of human GITRL. In some embodiments, the polypeptide or agent comprises approximately amino acids 71 to 199 of human GITRL, wherein the sequence of human GITRL is UniProt No. Q9UNG2. In some embodiments, the agent (e.g., polypeptide) comprises at least one copy of SEQ ID NO:3 or a fragment thereof. In some embodiments, the agent (e.g., polypeptide) comprises at least two copies of SEQ ID NO:3 or a fragment thereof. In some embodiments, the agent (e.g., polypeptide) comprises three copies of SEQ ID NO:3. In some embodiments, the agent (e.g., polypeptide) comprises at least one copy of SEQ ID NO:64. In some embodiments, the agent (e.g., polypeptide) comprises at least two copies of SEQ ID NO:64. In some embodiments, the agent (e.g., polypeptide) comprises three copies of SEQ ID NO:64. In some embodiments, the agent (e.g., polypeptide) comprises SEQ ID NO:5. In some embodiments, the agent (e.g., polypeptide) comprises SEQ ID NO:66. In some embodiments, the agent is a fusion polypeptide or fusion protein. In some embodiments, the fusion protein comprises a non-GITRL polypeptide (i.e., a heterologous protein). In some embodiments, the fusion polypeptide comprises a Fc region. In some embodiments, the non-GITRL polypeptide comprises a Fc region. In some embodiments, the Fc region is from an IgG1, IgG2, IgG3, or IgG4 immunoglobulin. In some embodiments, the Fc region is selected from the group consisting of SEQ ID NO:10, SEQ ID NO:11, SEQ ID NO:12, SEQ ID NO:13, and SEQ ID NO:14. In some embodiments, the non-GITRL polypeptide comprises an immunoglobulin heavy chain. In some embodiments, the immunoglobulin heavy chain is associated with an immunoglobulin light chain. In some embodiments, the immunoglobulin heavy chain and light chain form an antigen-binding site. In some embodiments, the non-GITRL polypeptide comprises a single chain antibody or a Fab.

In some embodiments, the agent or polypeptide comprises SEQ ID NO:6 or SEQ ID NO:7. In some embodiments, the agent comprises a polypeptide encoded by the hGITRL-hIgG1 plasmid deposited with ATCC and assigned designation number PTA-122112. In some embodiments, the agent or polypeptide comprises SEQ ID NO:8 or SEQ ID NO:9.

In an additional aspect, the invention provides a polypeptide having at least about 90% sequence identity to SEQ ID NO:5 or SEQ ID NO:66, as well as polypeptides or agents comprising such a polypeptide. In some embodiments, the polypeptides or agents comprise a polypeptide consisting of SEQ ID NO:5 or SEQ ID NO:66.

In a further aspect, the present invention provides polypeptides and agents that bind OX40 (TNFRSF4). In some embodiments, the polypeptide or agent binds human OX40. In some embodiments, the polypeptide or agent binds mouse OX40. In some embodiments, the agent is a polypeptide. In some embodiments, the polypeptide or agent is a soluble protein. In some embodiments, the polypeptide or agent is a soluble protein that binds human OX40. In some embodiments, the polypeptide or agent is a fusion polypeptide. In some embodiments, the agent (e.g., polypeptide) comprises at least one copy of the extracellular domain, or an OX40-binding fragment thereof, of OX40L (TNFSF4). In some embodiments, the agent (e.g., polypeptide) comprises at least one copy of the extracellular domain, or a fragment thereof, of human OX40L. In some embodiments, the polypeptide or agent comprises at least one copy of the extracellular domain, or a fragment thereof, of mouse OX40L. In some embodiments, the polypeptide or agent is a single chain fusion polypeptide comprising at least a first, second, and third copy of the extracellular domain of human OX40L. In some embodiments, the polypeptide or agent is a single chain fusion polypeptide comprising at least a first, second, and third copy of the extracellular domain of human OX40L, wherein at least one of the extracellular domains comprises the "stalk region" of OX40L. In some embodiments, the stalk region of OX40L is QVSHRYP (SEQ ID NO:55). In some embodiments, the stalk region of OX40L is a variant including but not limited to, ALQVSHRYP (SEQ ID NO:74), SHRYP (SEQ ID NO:75), or HRYP (SEQ ID NO:76). As used herein, the variant stalk regions consist of amino acid sequences of OX40L, i.e., these variant stalk regions do not comprise any exogenous amino acids, such as an exogenous linker. In some embodiments, the polypeptide or agent is a single chain fusion polypeptide comprising a first, second, and third copy of the extracellular domain of human OX40L, wherein each extracellular domain comprises the "stalk region" of OX40L or a variant stalk region. In some embodiments, the polypeptide or agent is a single chain fusion polypeptide comprising a first, second, and third copy of the extracellular domain of human OX40L, wherein the second and third extracellular domains include the "stalk region" of OX40L or a variant stalk region. In some embodiments, the polypeptide or agent is a single chain fusion polypeptide comprising at least a first, second, and third copy of the extracellular domain of human OX40L or an OX40-binding fragment thereof, wherein the polypeptide does not comprise any peptide linkers. In some embodiments, the polypeptide or agent is a single chain fusion polypeptide comprising a first, second, and third copy of the extracellular domain of human OX40L or an OX-40-binding fragment thereof, wherein the polypeptide does not comprise an exogenous peptide linker between the first copy and the second copy of the extracellular domain of human OX40L or an OX40-binding fragment thereof. In some embodiments, the polypeptide or agent is a single chain fusion polypeptide comprising a first, second, and third copy of the extracellular domain of human OX40L or an OX40-binding fragment thereof, wherein the polypeptide does not comprise an exogenous peptide linker between the second copy and the third copy of the extracellular domain of human OX40L or an OX40-binding fragment thereof.

In some embodiments, the agent (e.g., a polypeptide) comprises approximately amino acids 50 to 183 of human OX40L. In some embodiments, the agent (e.g., a polypeptide) comprises approximately amino acids 51 to 183 of human OX40L. In some embodiments, the agent (e.g., a polypeptide) comprises approximately amino acids 53 to 183 of human OX40L. In some embodiments, the polypeptide or agent comprises approximately amino acids 50 to 183, 51 to 183, or 53 to 183 of human OX40L, wherein the sequence of human OX40L is UniProt No. P23510. In some embodiments, the polypeptide or agent comprises at least one copy of SEQ ID NO:42 or a fragment thereof. In some embodiments, the polypeptide or agent comprises at least two copies of SEQ ID NO:42 or a fragment thereof. In some embodiments, the polypeptide or agent comprises three copies of SEQ ID NO:42. In some embodiments, the polypeptide or agent comprises at least one copy of SEQ ID NO:67 or a fragment thereof. In some embodiments, the polypeptide or agent comprises at least two copies of SEQ ID NO:67 or a fragment thereof. In some embodiments, the polypeptide or agent comprises three copies of SEQ ID NO:67. In some embodiments, the polypeptide or agent comprises at least one copy of SEQ ID NO:78 or a fragment thereof. In some embodiments, the polypeptide or agent comprises at least two copies of SEQ ID NO:78 or a fragment thereof. In some embodiments, the polypeptide or agent comprises three copies of SEQ ID NO:78. In some embodiments, the polypeptide or agent comprises at least one copy of SEQ ID NO:77 or a fragment thereof. In some embodiments, the polypeptide or agent comprises at least two copies of SEQ ID NO:77 or a fragment thereof. In some embodiments, the polypeptide or agent comprises three copies of SEQ ID NO:77. In some embodiments, the polypeptide or agent comprises at least one copy of SEQ ID NO:79 or a fragment thereof. In some embodiments, the polypeptide or agent comprises at least two copies of SEQ ID NO:79 or a fragment thereof. In some embodiments, the polypeptide or agent comprises three copies of SEQ ID NO:79. In some embodiments, the polypeptide or agent comprises SEQ ID NO:44. In some embodiments, the polypeptide or agent comprises SEQ ID NO:69. In some embodiments, the polypeptide or agent comprises SEQ ID NO:70. In some embodiments, the polypeptide or agent comprises SEQ ID NO:71. In some embodiments, the polypeptide or agent comprises SEQ ID NO:72. In some embodiments, the polypeptide or agent is a fusion polypeptide or fusion protein. In some embodiments, the fusion protein comprises a non-OX40L polypeptide (i.e., a heterologous protein). In some embodiments, the fusion polypeptide comprises a Fc region. In some embodiments, the non-OX40L polypeptide comprises a Fc region. In some embodiments, the Fc region is from an IgG1, IgG2, IgG3, or IgG4 immunoglobulin. In some embodiments, the Fc region is selected from the group consisting of SEQ ID NO:10, SEQ ID NO:11, SEQ ID NO:12, SEQ ID NO:13, and SEQ ID NO:14. In some embodiments, the non-OX40L polypeptide comprises an immunoglobulin heavy chain. In some embodiments, the immunoglobulin heavy chain is associated with an immunoglobulin light chain. In some embodiments, the immunoglobulin heavy chain and light chain form an antigen-binding site. In some embodiments, the non-OX40L polypeptide comprises a single chain antibody or a Fab.

In some embodiments, the agent or polypeptide comprises SEQ ID NO:45 or SEQ ID NO:46. In some embodiments, the agent or polypeptide comprises SEQ ID NO:47 or SEQ ID NO:48. In some embodiments, the agent or polypeptide comprises SEQ ID NO:80 or SEQ ID NO:81.

In an additional aspect, the invention provides a polypeptide having at least about 90% sequence identity to SEQ ID NO:44, SEQ ID NO:69, SEQ ID NO:70, SEQ ID NO:71, or SEQ ID NO:72, as well as polypeptides or agents comprising such a polypeptide. In some embodiments, the polypeptides or agents comprise a polypeptide consisting of SEQ ID NO:44, SEQ ID NO:69, SEQ ID NO:70, SEQ ID NO:71, or SEQ ID NO:72.

In a further aspect, the present invention provides polypeptides and agents that bind CD40 (TNFRSF5). In some embodiments, the polypeptide or agent binds human CD40. In some embodiments, the polypeptide or agent binds mouse CD40. In some embodiments, the agent is a polypeptide. In some embodiments, the polypeptide or agent is a soluble protein. In some embodiments, the polypeptide or agent is a soluble protein that binds human CD40. In some embodiments, the polypeptide or agent is a fusion polypeptide. In some embodiments, the agent (e.g., polypeptide) comprises at least one copy of the extracellular domain, or a CD40-binding fragment thereof, of CD40L (TNFSF5). In some embodiments, the agent (e.g., polypeptide) comprises at least one copy of the extracellular domain, or a fragment thereof, of human CD40L. In some embodiments, the polypeptide or agent comprises at least one copy of the extracellular domain, or a fragment thereof, of mouse CD40L. In some embodiments, the polypeptide or agent is a single chain fusion polypeptide comprising at least a first, second, and third copy of the extracellular domain of human CD40L. In some embodiments, the polypeptide or agent is a single chain fusion polypeptide comprising at least a first, second, and third copy of the extracellular domain of human CD40L, wherein at least one of the extracellular domains comprises the "stalk region" of CD40L. The stalk region of CD40L is very long in comparison to some of the other TNFSF members (i.e., GITRL and OX40L), therefore in some embodiments the extracellular domain(s) of human CD40L comprise only a short fragment of the stalk region. In some embodiments, the stalk region comprises about 4-20 amino acids. In some embodiments, the stalk region comprises about 4-10 amino acids. In some embodiments, the stalk region comprises the amino acids (e.g., 4-10 amino acids) upstream from the TNF homology domain. In some embodiments, the stalk region comprises the amino acids (e.g., 4-10 amino acids) adjacent to the TNF homology domain. In some embodiments, the fragment of the stalk region of CD40L is MQKGDQ (SEQ ID NO:98). In some embodiments, the fragment of the stalk region of CD40L is FEMQKGDQ (SEQ ID NO:99), EMQKGDQ (SEQ ID NO:100), QKGDQ (SEQ ID NO:101), or KGDQ (SEQ ID NO:102). As used herein, the stalk regions consist of amino acid sequences of CD40L, i.e., these stalk regions do not comprise any exogenous amino acids, such as an exogenous linker. In some embodiments, the polypeptide or agent is a single chain fusion polypeptide comprising a first, second, and third copy of the extracellular domain of human CD40L, wherein each extracellular domain comprises a fragment of the stalk region of CD40L. In some embodiments, the polypeptide or agent is a single chain fusion polypeptide comprising a first, second, and third copy of the extracellular domain of human CD40L, wherein the second and third extracellular domains include a fragment of the stalk region of CD40L. In some embodiments, the polypeptide or agent is a single chain fusion polypeptide comprising at least a first, second, and third copy of the extracellular domain of human CD40L or a CD40-binding fragment thereof, wherein the polypeptide does not comprise any peptide linkers. In some embodiments, the polypeptide or agent is a single chain fusion polypeptide comprising a first, second, and third copy of the extracellular domain of human CD40L or a CD40-binding fragment thereof, wherein the polypeptide does not comprise an exogenous peptide linker between the first copy and the second copy of the extracellular domain of human CD40L or a CD40-binding fragment thereof. In some embodiments, the polypeptide or agent is a single chain fusion polypeptide comprising a first, second, and third copy of the extracellular domain of human CD40L or a CD40-binding fragment thereof, wherein the polypeptide does not comprise an exogenous peptide linker between the second copy and the third copy of the extracellular domain of human CD40L or a CD40-binding fragment thereof.

In some embodiments, the agent (e.g., a polypeptide) comprises approximately amino acids 113 to 261 of human CD40L. In some embodiments, the agent (e.g., a polypeptide) comprises approximately amino acids 111 to 261 of human CD40L. In some embodiments, the agent (e.g., a polypeptide) comprises approximately amino acids 112 to 261 of human CD40L. In some embodiments, the agent (e.g., a polypeptide) comprises approximately amino acids 114 to 261 of human CD40L. In some embodiments, the agent (e.g., a polypeptide) comprises approximately amino acids 115 to 261 of human CD40L. In some embodiments, the polypeptide or agent comprises approximately amino acids 113 to 261, 111 to 261, 112 to 261, 114 to 261, or 115 to 261 of human CD40L, wherein the sequence of human CD40L is UniProt No. P29965. In some embodiments, the polypeptide or agent comprises at least one copy of SEQ ID NO:84 or a fragment thereof. In some embodiments, the polypeptide or agent comprises at least two copies of SEQ ID NO:84 or a fragment thereof. In some embodiments, the polypeptide or agent comprises three copies of SEQ ID NO:84. In some embodiments, the polypeptide or agent comprises at least one copy of SEQ ID NO:103 or a fragment thereof. In some embodiments, the polypeptide or agent comprises at least two copies of SEQ ID NO:103 or a fragment thereof. In some embodiments, the polypeptide or agent comprises three copies of SEQ ID NO:103. In some embodiments, the polypeptide or agent comprises at least one copy of SEQ ID NO:104 or a fragment thereof. In some embodiments, the polypeptide or agent comprises at least two copies of SEQ ID NO:104 or a fragment thereof. In some embodiments, the polypeptide or agent comprises three copies of SEQ ID NO:104. In some embodiments, the polypeptide or agent comprises at least one copy of SEQ ID NO:105 or a fragment thereof. In some embodiments, the polypeptide or agent comprises at least two copies of SEQ ID NO:105 or a fragment thereof. In some embodiments, the polypeptide or agent comprises three copies of SEQ ID NO:105. In some embodiments, the polypeptide or agent comprises at least one copy of SEQ ID NO:106 or a fragment thereof. In some embodiments, the polypeptide or agent comprises at least two copies of SEQ ID NO:106 or a fragment thereof. In some embodiments, the polypeptide or agent comprises three copies of SEQ ID NO:106. In some embodiments, the polypeptide or agent comprises SEQ ID NO:85. In some embodiments, the polypeptide or agent comprises SEQ ID NO:97. In some embodiments, the polypeptide or agent is a fusion polypeptide or fusion protein. In some embodiments, the fusion protein comprises a non-CD40L polypeptide (i.e., a heterologous protein). In some embodiments, the fusion polypeptide comprises a Fc region. In some embodiments, the non-CD40L polypeptide comprises a Fc region. In some embodiments, the Fc region is from an IgG1, IgG2, IgG3, or IgG4 immunoglobulin. In some embodiments, the Fc region is selected from the group consisting of SEQ ID NO:10, SEQ ID NO:11, SEQ ID NO:12, SEQ ID NO:13, and SEQ ID NO:14. In some embodiments, the non-CD40L polypeptide comprises an immunoglobulin heavy chain. In some embodiments, the immunoglobulin heavy chain is associated with an immunoglobulin light chain. In some embodiments, the immunoglobulin heavy chain and light chain form an antigen-binding site. In some embodiments, the non-CD40L polypeptide comprises a single chain antibody or a Fab.

In some embodiments, the agent or polypeptide comprises SEQ ID NO:89 or SEQ ID NO:90. In some embodiments, the agent or polypeptide comprises SEQ ID NO:91 or SEQ ID NO:92.

In an additional aspect, the invention provides a polypeptide having at least about 90% sequence identity to SEQ ID NO:85 or SEQ ID NO:97, as well as polypeptides or agents comprising such a polypeptide. In some embodiments, the polypeptides or agents comprise a polypeptide consisting of SEQ ID NO:85 or SEQ ID NO:97.

In some embodiments of each of the aforementioned aspects and embodiments, as well as other aspects and embodiments described herein, the agent or polypeptide is monovalent. In some embodiments, the agent is bivalent. In some embodiments, the agent or polypeptide is monospecific. In some embodiments, the agent or polypeptide is bispecific.

In some embodiments of each of the aforementioned aspects and embodiments, as well as other aspects and embodiments described herein, the agent or polypeptide is a bispecific agent. In some embodiments, the bispecific agent is a homodimeric protein. In some embodiments, the homodimer bispecific agent comprises a polypeptide comprising a heavy chain immunoglobulin and a TNFSF trimer. In some embodiments, the heavy chain immunoglobulin is associated with a light chain to form an antigen-binding site. In some embodiments, the homodimeric bispecific agent comprises a polypeptide comprising an antibody and a single chain TNFSF trimer. In some embodiments, the homodimeric bispecific agent comprises a polypeptide comprising an antibody and a single chain GITRL trimer. In some embodiments, the homodimeric bispecific agent comprises a polypeptide comprising an antibody and a single chain OX40L trimer. In some embodiments, the homodimeric bispecific agent comprises a polypeptide comprising an antibody and a single chain CD40L trimer. In some embodiments, the homodimeric bispecific agent comprises an antibody that specifically binds a tumor antigen. In some embodiments, the homodimeric bispecific agent comprises an antibody that specifically binds PD-1, PD-L1, CTLA-4, LAG-3, TIGIT, or TIM3. In some embodiments, the homodimeric bispecific agent binds GITR and PD-1. In some embodiments, the homodimeric bispecific agent binds GITR and PD-L1. In some embodiments, the homodimeric bispecific agent binds OX40 and PD-1. In some embodiments, the homodimeric bispecific agent binds OX40 and PD-L1. In some embodiments, the homodimeric bispecific agent binds CD40 and PD-1. In some embodiments, the homodimeric bispecific agent binds CD40 and PD-L1.

In some embodiments of each of the aforementioned aspects and embodiments, as well as other aspects and embodiments described herein, the agent or polypeptide is a heterodimeric bispecific agent. In some embodiments, the bispecific agent comprises a first arm which binds a member of the TNFR superfamily and a second arm which binds a second target. In some embodiments, the bispecific agent comprises a first arm which binds GITR and a second arm which binds a second target. In some embodiments, the bispecific agent comprises a first arm which binds OX40 and a second arm which binds a second target. In some embodiments, the bispecific agent comprises a first arm which binds CD40 and a second arm which binds a second target. In some embodiments, the bispecific agent comprises a first arm which binds GITR and a second arm which comprises an antigen-binding site from an antibody. In some embodiments, the bispecific agent comprises a first arm which binds OX40 and a second arm which comprises an antigen-binding site from an antibody. In some embodiments, the bispecific agent comprises a first arm which binds CD40 and a second arm which comprises an antigen-binding site from an antibody. In some embodiments, the bispecific agent comprises a second arm wherein the antigen-binding site specifically binds a tumor antigen. In some embodiments, the bispecific agent comprises a second arm wherein the antigen-binding site specifically binds PD-1, PD-L1, CTLA-4, LAG-3, TIGIT, or TIM3. In some embodiments, the bispecific agent comprises a first arm which binds GITR and a second arm which comprises an immune response stimulating agent. In some embodiments, the bispecific agent comprises a first arm which binds OX40 and a second arm which comprises an immune response stimulating agent. In some embodiments, the bispecific agent comprises a first arm which binds CD40 and a second arm which comprises an immune response stimulating agent. In some embodiments, the immune response stimulating agent may be an agonist of a target. In some embodiments, the immune response stimulating agent may be an antagonist of a target. In some embodiments, the immune response stimulating agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, anti-CD3 antibody, anti-CTLA-4 antibody, anti-TIGIT antibody, anti-PD1 antibody, anti-PD-L 1 antibody, anti-LAG-3 antibody, and anti-TIM-3 antibody.

In some embodiments, the bispecific agent comprises two arms, wherein each arm comprises a human CH3 domain, wherein each CH3 domain is modified to promote formation of heterodimers. In some embodiments, the first and second CH3 domains are modified using a knobs-into-holes technique. In some embodiments, the first and second CD3 domains are modified based upon electrostatic effects. In some embodiments, the bispecific agent comprises two arms, wherein the first arm comprises a first human IgG1 constant region with amino acids substitutions at positions corresponding to positions 253 and 292 of SEQ ID NO:15, wherein the amino acids are replaced with glutamate or aspartate, and the second arm comprises a second human IgG1 constant region with amino acid substitutions at positions corresponding to positions 240 and 282 of SEQ ID NO:15, wherein the amino acids are replaced with lysine. In some embodiments, the two arms comprise a Fc region selected from the group consisting of SEQ ID NO:58, SEQ ID NO:59, SEQ ID NO:60, and SEQ ID NO:61. In some embodiments, the bispecific agent comprises two arms, wherein the first arm comprises a first human IgG2 constant region with amino acids substitutions at positions corresponding to positions 249 and 288 of SEQ ID NO:16, wherein the amino acids are replaced with glutamate or aspartate, and the second arm comprises a second human IgG2 constant region with amino acid substitutions at positions corresponding to positions 236 and 278 of SEQ ID NO:16, wherein the amino acids are replaced with lysine. In some embodiments, the two arms comprise a Fc region selected from the group consisting of SEQ ID NO:26, SEQ ID NO:27, SEQ ID NO:28, SEQ ID NO:29, SEQ ID NO:30, and SEQ ID NO:31.

In some embodiments of each of the aforementioned aspects and embodiments, as well as other aspects and embodiments described herein, the agent or polypeptide induces, activates, promotes, increases, enhances, and/or prolongs an immune response. In some embodiments, the agent increases Th1-type immune responses. In some embodiments, the agent or polypeptide increases cell-mediated immunity. In some embodiments, the agent or polypeptide increases T-cell activity. In some embodiments, the agent or polypeptide increases cytolytic T-cell (CTL) activity. In some embodiments, the agent or polypeptide increases natural killer (NK) cell activity. In some embodiments, the agent or polypeptide decreases regulatory T-cell (Treg) activity. In some embodiments, the agent or polypeptide decreases myeloid-derived suppressor cell (MDSC) activity. In some embodiments, the agent or polypeptide increases the number or the percentage of memory T-cells. In some embodiments, the agent or polypeptide increases or enhances an effective immune response without causing substantial side effects and/or immune-based toxicities. In some embodiments, the agent or polypeptide increases or enhances an effective immune response without causing cytokine release syndrome (CRS) or a cytokine storm. In some embodiments, the agent or polypeptide is an agonist of GITRL-mediated signaling. In some embodiments, the agent or polypeptide is an agonist of GITR signaling. In some embodiments, the agent or polypeptide is an agonist of OX40L-mediated signaling. In some embodiments, the agent or polypeptide is an agonist of OX40 signaling. In some embodiments, the agent or polypeptide is an agonist of CD40L-mediated signaling. In some embodiments, the agent or polypeptide is an agonist of CD40 signaling.

In another aspect, the invention provides compositions comprising a polypeptide or agent described herein. Methods of using a composition comprising a polypeptide or agent described herein are also provided.

In another aspect, the invention provides pharmaceutical compositions comprising a polypeptide or agent described herein and a pharmaceutically acceptable carrier. Methods of treating cancer and/or inhibiting tumor growth in a subject (e.g., a human) comprising administering to the subject an effective amount of a composition comprising a polypeptide or agent described herein are also provided. Methods of treating a viral infection in a subject (e.g., a human) comprising administering to the subject an effective amount of a composition comprising a polypeptide or agent described herein are also provided.

In certain embodiments of each of the aforementioned aspects, as well as other aspects and/or embodiments described elsewhere herein, the agent or polypeptide is isolated. In certain embodiments, the agent or polypeptide is substantially pure.

In another aspect, the invention provides polynucleotides comprising a polynucleotide that encodes a polypeptide or agent described herein. In some embodiments, the polynucleotide is isolated. In some embodiments, the invention provides vectors that comprise the polynucleotides, as well as cells that comprise the vectors and/or the polynucleotides. In some embodiments, the invention also provides cells comprising or producing a polypeptide or agent described herein. In some embodiments, the cell is a monoclonal cell line.

In another aspect, the invention provides methods of modulating the immune response of a subject. In some embodiments, the invention provides a method of inducing an immune response in a subject comprising administering a polypeptide or agent described herein. In some embodiments, the invention provides a method of activating an immune response in a subject comprising administering a polypeptide or agent described herein. In some embodiments, the invention provides a method of promoting an immune response in a subject comprising administering a polypeptide or agent described herein. In some embodiments, the invention provides a method of increasing an immune response in a subject comprising administering a polypeptide or agent described herein. In some embodiments, the invention provides a method of enhancing an immune response in a subject comprising administering a polypeptide or agent described herein. In some embodiments, the invention provides a method of prolonging an immune response in a subject comprising administering a polypeptide or agent described herein. In some embodiments, the immune response is to an antigenic stimulation. In some embodiments, the antigenic stimulation is a tumor or a tumor cell. In some embodiments, the antigenic stimulation is a pathogen. In some embodiments, the antigenic stimulation is a virus. In some embodiments, the antigenic stimulation is a virally-infected cell.

In some embodiments, the invention provides a method of increasing the activity of immune cells. In some embodiments, the invention provides a method of increasing the activity of immune cells comprising contacting the cells with an effective amount of a polypeptide or agent described herein. In some embodiments, the immune cells are T-cells, NK cells, monocytes, macrophages, antigen-presenting cells (APCs), and/or B-cells. In some embodiments, the invention provides a method of increasing the activity of NK cells in a subject comprising administering to the subject a therapeutically effective amount of a polypeptide or agent described herein. In some embodiments, the invention provides a method of increasing the activity of T-cells in a subject comprising administering to the subject a therapeutically effective amount of a polypeptide or agent described herein. In some embodiments, the invention provides a method of increasing the activity of CD4+ and/or CD8+ T-cells in a subject comprising administering to the subject a therapeutically effective amount of a polypeptide or agent described herein. In some embodiments, the invention provides a method of increasing the activity of CTLs in a subject comprising administering to the subject a therapeutically effective amount of a polypeptide or agent described herein. In some embodiments, the invention provides a method of increasing the activation of T-cells, CTLs, and/or NK cells in a subject comprising administering to the subject a therapeutically effective amount of a polypeptide or agent described herein. In some embodiments, the invention provides a method of increasing the T-cell response in a subject comprising administering to the subject a therapeutically effective amount of a polypeptide or agent described herein. In some embodiments, the invention provides a method of inhibiting the activity of Tregs in a subject comprising administering to the subject a therapeutically effective amount of a polypeptide or agent described herein. In some embodiments, the invention provides a method of inhibiting the suppressive activity of Tregs in a subject comprising administering to the subject a therapeutically effective amount of a polypeptide or agent described herein. In some embodiments, the invention provides a method of inhibiting the activity of MDSCs in a subject comprising administering to the subject a therapeutically effective amount of a polypeptide or agent described herein. In some embodiments, the invention provides a method of inhibiting the suppressive activity of MDSCs in a subject comprising administering to the subject a therapeutically effective amount of a polypeptide or agent described herein. In some embodiments, the invention provides a method of inducing an immune response in a subject without causing substantial side effects and/or immune-based toxicities comprising administering to the subject a therapeutically effective amount of a polypeptide or agent described herein. In some embodiments, the invention provides a method of inducing an immune response in a subject without causing cytokine release syndrome or a cytokine storm comprising administering to the subject a therapeutically effective amount of a polypeptide or agent described herein.

In another aspect, the invention provides methods of inducing, activating, promoting, increasing, enhancing, or prolonging an immune response in a subject. In some embodiments, the invention provides methods of inducing, activating, promoting, increasing, enhancing, or prolonging an immune response in a subject, comprising administering to the subject a therapeutically effective amount of a polypeptide or agent described herein. In some embodiments, the invention provides methods of inducing, activating, promoting, increasing, enhancing, or prolonging an immune response in a subject, comprising administering to the subject a therapeutically effective amount of a polypeptide or agent that binds human GITR. In some embodiments, the invention provides methods of inducing, activating, promoting, increasing, enhancing, or prolonging an immune response in a subject, comprising administering to the subject a therapeutically effective amount of a polypeptide or agent that activates or enhances GITR signaling. In some embodiments, the invention provides methods of inducing, activating, promoting, increasing, enhancing, or prolonging an immune response in a subject, comprising administering to the subject a therapeutically effective amount of a polypeptide or agent that binds human OX40. In some embodiments, the invention provides methods of inducing, activating, promoting, increasing, enhancing, or prolonging an immune response in a subject, comprising administering to the subject a therapeutically effective amount of a polypeptide or agent that activates or enhances OX40 signaling. In some embodiments, the invention provides methods of inducing, activating, promoting, increasing, enhancing, or prolonging an immune response in a subject, comprising administering to the subject a therapeutically effective amount of a polypeptide or agent that binds human CD40. In some embodiments, the invention provides methods of inducing, activating, promoting, increasing, enhancing, or prolonging an immune response in a subject, comprising administering to the subject a therapeutically effective amount of a polypeptide or agent that activates or enhances CD40 signaling. In some embodiments, the immune response is against a tumor cell, a tumor or cancer. In some embodiments, the immune response is against a viral infection, a viral antigen, or a virally-infected cell.

In some embodiments, the invention provides a method of increasing T-cell activity in a subject, comprising administering to the subject a therapeutically effective amount of a polypeptide comprising a first, second, and third copy of the extracellular domain of a human tumor necrosis factor receptor ligand superfamily (TNFSF) protein or a fragment thereof capable of binding a receptor of the TNFSF protein. In some embodiments, the invention provides a method of increasing CTL activity in a subject, comprising administering to the subject a therapeutically effective amount of a polypeptide comprising a first, second, and third copy of the extracellular domain of a human TNFSF protein or a fragment thereof capable of binding a receptor of the TNFSF protein. In some embodiments, the invention provides a method of increasing NK activity in a subject, comprising administering to the subject a therapeutically effective amount of a polypeptide comprising a first, second, and third copy of the extracellular domain of a human TNFSF protein or a fragment thereof capable of binding a receptor of the TNFSF protein. In some embodiments, the invention provides a method of decreasing or inhibiting Treg activity in a subject, comprising administering to the subject a therapeutically effective amount of a polypeptide comprising a first, second, and third copy of the extracellular domain of a human TNFSF protein or a fragment thereof capable of binding a receptor of the TNFSF protein. In some embodiments, the invention provides a method of decreasing or inhibiting MDSC activity in a subject, comprising administering to the subject a therapeutically effective amount of a polypeptide comprising a first, second, and third copy of the extracellular domain of a human TNFSF protein or a fragment thereof capable of binding a receptor of the TNFSF protein. In some embodiments, the TNFSF protein is GITRL. In some embodiments, the TNFSF protein is OX40L. In some embodiments, the TNFSF protein is CD40L. In some embodiments of the methods described herein, the subject has cancer.

In some embodiments, the invention provides a method of increasing T-cell activity in a subject, comprising administering to the subject a therapeutically effective amount of any of the polypeptides, agents, and/or bispecific agents described herein. In some embodiments, the invention provides a method of increasing CTL activity in a subject, comprising administering to the subject a therapeutically effective amount of the polypeptide of any of the polypeptides, agents, and/or bispecific agents described herein. In some embodiments, the invention provides a method of increasing NK activity in a subject, comprising administering to the subject a therapeutically effective amount of the polypeptide of any of the polypeptides, agents, and/or bispecific agents described herein. In some embodiments, the invention provides a method of decreasing or inhibiting Treg activity in a subject, comprising administering to the subject a therapeutically effective amount of any of the polypeptides, agents, and/or bispecific agents described herein. In some embodiments, the invention provides a method of decreasing or inhibiting MDSC activity in a subject, comprising administering to the subject a therapeutically effective amount of the polypeptide of any of the polypeptides, agents, and/or bispecific agents described herein. In some embodiments of the methods described herein, the subject has cancer.

In another aspect, the invention provides a method of enhancing the antigen-specific memory response to a tumor. In some embodiments, a method of enhancing the antigen-specific memory response to a tumor comprises administering to a subject a therapeutically effective amount of any of the polypeptides, agents, and/or bispecific agents described herein. In some embodiments, a method of enhancing the antigen-specific memory response to a tumor comprises administering to a subject a therapeutically effective amount of a polypeptide comprising a first, second, and third copy of the extracellular domain of a human TNFSF protein or a fragment thereof capable of binding a receptor of the TNFSF protein. In some embodiments, the TNFSF protein is GITRL. In some embodiments, the TNFSF protein is OX40L. In some embodiments, the TNFSF protein is CD40L.

In another aspect, the invention provides a method of activating or enhancing a persistent or long-term immune response to a tumor. In some embodiments, a method of activating or enhancing a persistent immune response to a tumor comprises administering to a subject a therapeutically effective amount of any of the polypeptides, agents, and/or bispecific agents described herein. In some embodiments, a method of activating or enhancing a persistent immune response to a tumor comprises administering to a subject a therapeutically effective amount of a polypeptide comprising a first, second, and third copy of the extracellular domain of a human TNFSF protein or a fragment thereof capable of binding a receptor of the TNFSF protein. In some embodiments, the TNFSF protein is GITRL. In some embodiments, the TNFSF protein is OX40L. In some embodiments, the TNFSF protein is CD40L.

In another aspect, the invention provides a method of inducing a persistent or long-term immunity which inhibits tumor relapse or tumor regrowth. In some embodiments, a method of inducing a persistent immunity which inhibits tumor relapse or tumor regrowth comprises administering to a subject a therapeutically effective amount of any of the polypeptides, agents, and/or bispecific agents described herein. In some embodiments, a method of inducing a persistent immunity which inhibits tumor relapse or tumor regrowth comprises administering to a subject a therapeutically effective amount of a polypeptide comprising a first, second, and third copy of the extracellular domain of a human TNFSF protein or a fragment thereof capable of binding a receptor of the TNFSF protein. In some embodiments, the TNFSF protein is GITRL. In some embodiments, the TNFSF protein is OX40L. In some embodiments, the TNFSF protein is CD40L.

In another aspect, the invention provides methods of inhibiting tumor growth comprising contacting a tumor or tumor cell with an effective amount of a polypeptide or agent described herein. In some embodiments, a method of inhibiting growth of a tumor comprises contacting a tumor or tumor cell with an effective amount of a polypeptide or agent that binds human GITR. In some embodiments, a method of inhibiting growth of a tumor comprises contacting a tumor or tumor cell with an effective amount of a polypeptide or agent that binds human OX40. In some embodiments, a method of inhibiting growth of a tumor comprises contacting a tumor or tumor cell with an effective amount of a polypeptide or agent that binds human CD40. In some embodiments, a method of inhibiting growth of a tumor comprises contacting a tumor microenvironment with an effective amount of a polypeptide or agent that binds human GITR. In some embodiments, a method of inhibiting growth of a tumor comprises contacting a tumor microenvironment with an effective amount of a polypeptide or agent that binds human OX40. In some embodiments, a method of inhibiting growth of a tumor comprises contacting a tumor microenvironment with an effective amount of a polypeptide or agent that binds human CD40.

In another aspect, the invention provides methods of inhibiting tumor growth in a subject comprising administering to the subject a therapeutically effective amount of a polypeptide or agent described herein. In some embodiments, a method of inhibiting growth of a tumor in a subject comprises administering to the subject a therapeutically effective amount of a polypeptide or agent that binds human GITR. In some embodiments, a method of inhibiting growth of a tumor in a subject comprises administering to the subject a therapeutically effective amount of a polypeptide or agent that binds human OX40. In some embodiments, a method of inhibiting growth of a tumor in a subject comprises administering to the subject a therapeutically effective amount of a polypeptide or agent that binds human CD40.

In another aspect, the invention provides methods of treating cancer in a subject comprising administering to the subject a therapeutically effective amount of a polypeptide or agent described herein. In some embodiments, a method of treating cancer in a subject comprises administering to the subject a therapeutically effective amount of a polypeptide or agent that binds GITR. In some embodiments, a method of treating cancer in a subject comprises administering to the subject a therapeutically effective amount of a polypeptide or agent that binds OX40. In some embodiments, a method of treating cancer in a subject comprises administering to the subject a therapeutically effective amount of a polypeptide or agent that binds CD40.

In another aspect, the invention provides methods of stimulating a protective response in a subject comprising administering to the subject a therapeutically effective amount of a polypeptide or agent described herein in combination with an antigen of interest. In some embodiments, the antigen of interest is a tumor antigen or tumor-associated antigen (TAA). In some embodiments, the antigen of interest is a cancer cell biomarker. In some embodiments, the antigen of interest is a cancer stem cell marker.

In some embodiments of each of the aforementioned aspects and embodiments, as well as other aspects and embodiments described herein, the methods further comprise administering to the subject at least one additional therapeutic agent. In some embodiments, the at least one additional therapeutic agent is a chemotherapeutic agent. In some embodiments, the at least one additional therapeutic agent is a second immune response stimulating agent. In some embodiments, the at least one additional therapeutic agent is a checkpoint inhibitor. In some embodiments, the immune response stimulating agent is selected from the group consisting of GM-CSF, M-CSF, G-CSF, IL-3, IL-12, IL-1, IL-2, B7-1 (CD80), B7-2 (CD86), 4-1BB ligand, anti-CD3 antibody, anti-CTLA-4 antibody, anti-TIGIT antibody, anti-PD-1 antibody, anti-PD-L1 antibody, anti-LAG-3 antibody, and anti-TIM-3 antibody. In some embodiments, the additional therapeutic agent is an anti-PD-1 antibody. In some embodiments, the additional therapeutic agent is an anti-PD-L1 antibody.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE FIGURES

(FIG. 1A) Shown is a representative drawing depicting the membrane anchored trimer topology of human GITRL. (FIG. 1B) The amino acid sequence of human GITRL is shown (SEQ ID NO:1). The cytoplasmic region, signal-anchor region, and the extracellular domain are marked. The "stalk region" within the extracellular domain is underlined. (FIG. 1C) A schematic depiction of native GITRL. (FIG. 1D) A schematic depiction of a membrane bound single chain GITRL trimer comprising the signal-anchor region of GITRL and three copies of the extracellular domain of GITRL. (FIG. 1E) A schematic depiction of a soluble single chain GITRL trimer comprising three copies of the extracellular domain of GITRL. (FIG. 1F) A schematic depiction of a soluble single chain GITRL trimer-Fc fusion polypeptide comprising three copies of the extracellular domain of GITRL linked to a Fc region.

FIGS. 8A and 8B. Inhibition of tumor growth by single chain GITRL trimer-Fc fusion polypeptide. The murine colon tumor line CT26.WT was implanted subcutaneously into Balb/c mice (n=10 mice/group). Mice were injected on days 7, 10, 14, and 17 with 0.25 mg/mouse of single chain mGITRL trimer-Fc fusion protein 336B3, anti-mGITR antibody DTA-1, or a control antibody. Tumor growth was monitored and tumor volumes were measured with electronic calipers at the indicated time points. Data is shown as tumor volume ($mm^3$) over days post injection. (FIG. 8A) The mean values±SEM for each group. (FIG. 8B) The tumor volumes of each individual mouse from the group treated with 336B3 and the group treated with DTA-1.

(FIG. 9A) The number of cells producing IFN-gamma is shown. (FIG. 9B) The number of cells producing IL-10 is shown.

(FIG. 14A) Natural killer cell activity. Cells were harvested from the spleens of Renca-tumor bearing mice treated with anti-mGITR antibody DTA-1, mGITRL trimer-Fc 336B3, or a control. YAC-1 target cells were labeled with 10 μM calcein AM mixed with the splenocytes at an E:T ratio of 25:1 and 50:1. Supernatants were harvested and calcein release was quantified on a fluorometer at an excitation of 485 nm and an emission of 535 nm. (FIG. 14B) T-cell cytotoxicity assay. Cells were harvested from the spleens of Renca-tumor bearing mice treated with anti-mGITR antibody DTA-1, mGITRL trimer-Fc 336B3, or a control. Renca target cells were labeled with 10 μM calcein AM mixed with the splenocytes at an E:T ratio of 25:1. Supernatants were harvested and calcein release was quantified on a fluorometer at an excitation of 485 nm and an emission of 535 nm.

FIGS. 15A-15G. Inhibition of tumor growth by single chain GITRL trimer-Fc fusion polypeptide—a dose study. The murine colon tumor line CT26.WT was implanted subcutaneously into Balb/c mice (n=10 mice/group). Mice were treated with 30, 12.5, 6.25, 3, or 0.5 mg/kg of mGITRL trimer-Fc 336B3 or were untreated. Mice were dosed by intraperitoneal injection twice a week for a total of 6 doses. Tumor growth was monitored and tumor volumes were measured with electronic calipers at the indicated time points. (FIG. 15A-15F) The tumor volumes of individual mice within each treatment group. (FIG. 15G) The average tumor volume of each treatment group.

(FIG. 16A-16F) The tumor volumes of individual mice within each treatment group. (FIG. 16G) The average tumor volume of each treatment group.

(FIG. 17A-17E) The tumor volumes of individual mice within each treatment group. (FIG. 17F) The average tumor volume of each treatment group.

(FIG. 18A-18D) The tumor volumes of individual mice within each treatment group.

FIG. 19A-19D. The tumor volumes of individual mice within each treatment group. FIG. 19E. Tumor growth after re-challenge with CT26.WT cells.

(FIG. 20A-20D) The tumor volumes of individual mice within each treatment group. (FIG. 20E) The average tumor volume of each treatment group.

FIG. 21A. The tumor volumes of each individual mouse from the group treated with control antibody. FIG. 21B. The tumor volumes of each individual mouse from the group treated with mOX40L-Fc. FIG. 21C. The tumor volumes of each individual mouse from the group treated with agonist anti-OX40 antibody. FIG. 21D. Average tumor volume of three groups of mice. FIG. 21E. Average tumor volume of five groups of mice. Data is shown as tumor volume (mm$^3$) over days post injection.

FIG. 23A. IL-2. FIG. 23B. IL-4. FIG. 23C. IL-5. FIG. 23D. IL-6. FIG. 23E. IL-10. FIG. 23F. IL-13. FIG. 23G. MIP-1b. FIG. 23H. FasL—The cytokine levels for the control, OX40L-Fc and gITRL-Fc were below the limits of the assay. FIG. 23I. GM-CSF. FIG. 23J. sCD137. FIG. 23K. IFN-gamma. FIG. 23L. Granzyme B.

FIG. 24A. The tumor volumes of each individual mouse from the group treated with control antibody. FIG. 24B. The tumor volumes of each individual mouse from the group treated with mGITRL-Fc. FIG. 24C. The tumor volumes of each individual mouse from the group treated with agonist anti-GITR antibody DTA-1. FIG. 24D. Survival curve of all treated groups.

DETAILED DESCRIPTION OF THE INVENTION

Figures 1A, 1B:
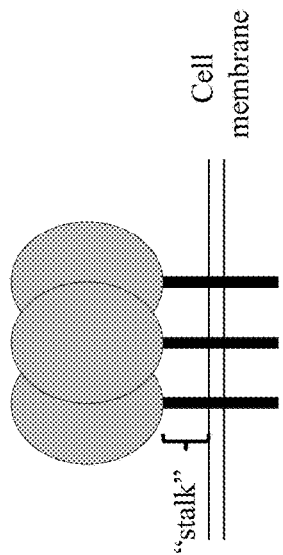
FIGS. 1A-1F.
Figure 1C:
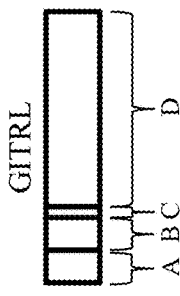

The present invention provides novel agents, including, but not limited to, polypeptides, soluble proteins, fusion proteins, homodimeric bispecific molecules, and heterodimeric bispecific molecules that modulate the immune response. The agents include agonists and antagonists of receptors and ligands that are members of the TNF superfamily involved in cell interactions and immune response signaling. Related polypeptides and polynucleotides, compositions comprising the agents, and methods of making the agents are also provided. Methods of screening for agents that modulate the immune response are provided. Methods of using the novel agents, such as methods of activating an immune response, methods of stimulating an immune response, methods of promoting an immune response, methods of increasing an immune response, methods of activating NK cells, methods of activating T-cells, including CTLs, methods of increasing the activity of NK cells, methods of increasing the activity of T-cells, including CTLs, methods of promoting the activity of NK cells, methods of promoting the activity of T-cells, including CTLs, methods of inhibiting the activity of Tregs, methods of inhibiting the activity of MDSCs, methods of inhibiting tumor growth, methods of treating cancer, and/or methods of treating viral diseases are provided. Methods of inhibiting an immune response, methods of suppressing an immune response, methods of decreasing activity of T-cells, and/or methods of treating autoimmune diseases are further provided.

I. Definitions

To facilitate an understanding of the present invention, a number of terms and phrases are defined below.

The terms "agonist" and "agonistic" as used herein refer to or describe a polypeptide or agent that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the activity of a protein or other target of interest.

The terms "antagonist" and "antagonistic" as used herein refer to or describe a polypeptide or agent that is capable of, directly or indirectly, partially or fully blocking, inhibiting, reducing, or neutralizing a biological activity of a target and/or pathway. The term "antagonist" is used herein to include any agent that partially or fully blocks, inhibits, reduces, or neutralizes the activity of a protein or other target of interest.

The terms "modulation" and "modulate" as used herein refer to a change or an alteration in a biological activity. Modulation includes, but is not limited to, stimulating an activity or inhibiting an activity. Modulation may be an increase in activity or a decrease in activity, a change in binding characteristics, or any other change in the biological, functional, or immunological properties associated with the activity of a protein, a pathway, a system, or other biological targets of interest.

The term "soluble protein" as used herein refers to a protein or a fragment thereof that can be secreted from a cell in soluble form.

The term "fusion protein" or "fusion polypeptide" as used herein refers to a hybrid protein expressed by a nucleic acid molecule comprising nucleotide sequences of at least two genes.

The term "linker" or "linker region" as used herein refers to a linker inserted between a first polypeptide (e.g., copies of a GITRL extracellular domain or fragments thereof) and a second polypeptide (e.g., a Fc region). In some embodiments, the linker is a peptide linker. Linkers should not adversely affect the expression, secretion, or bioactivity of the polypeptides. Preferably, linkers are not antigenic and do not elicit an immune response.

The term "antibody" as used herein refers to an immunoglobulin molecule that recognizes and specifically binds a target, such as a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) antibodies, multispecific antibodies, bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen-binding site as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain, or the variable region of an antibody heavy chain, either alone or in combination. Generally, the variable region of heavy and light chains each consist of four framework regions (FR) and three complementarity determining regions (CDRs), also known as "hypervariable regions". The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability (i.e., Kabat et al., 1991, *Sequences of Proteins of Immunological Interest, 5th Edition*, National Institutes of Health, Bethesda Md.), and (2) an approach based on crystallographic studies of antigen-antibody complexes (Al Lazikani et al., 1997, *J. Mol. Biol.,* 273:927-948). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability. In some instances, the Fv framework region residues of a human immunoglobulin are replaced with the corresponding residues in an antibody from a non-human species. The humanized antibody can be further modified by the substitution of additional residues either in the Fv framework region and/or within the replaced non-human residues to refine and optimize antibody specificity, affinity, and/or binding capability. The humanized antibody may comprise variable domains containing all or substantially all of the CDRs that correspond to the non-human immunoglobulin whereas all or substantially all of the framework regions are those of a human immunoglobulin sequence. In some embodiments, the variable domains comprise the framework regions of a human immunoglobulin sequence. In some embodiments, the variable domains comprise the framework regions of a human immunoglobulin consensus sequence. The humanized antibody can also comprise at least a portion of an immunoglobulin constant region or domain (Fc), typically that of a human immunoglobulin. A humanized antibody is usually considered distinct from a chimeric antibody.

The term "human antibody" as used herein refers to an antibody produced by a human or an antibody having an amino acid sequence corresponding to an antibody produced by a human made using any of the techniques known in the art.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions are homologous to the sequences in antibodies derived from another species (usually human) to avoid eliciting an immune response in that species.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation.

The terms "selectively binds" or "specifically binds" mean that a polypeptide or agent interacts more frequently, more rapidly, with greater duration, with greater affinity, or with some combination of the above to the epitope, protein, or target molecule than with alternative substances, including related and unrelated proteins. In certain embodiments "specifically binds" means, for instance, that a polypeptide or agent binds a protein or target with a $K_D$ of about 0.1 mM or less, but more usually less than about 1 µM. In certain embodiments, "specifically binds" means that a polypeptide or agent binds a target with a $K_D$ of at least about 0.1 µM or less, at least about 0.01 µM or less, or at least about 1 nM or less. Because of the sequence identity between homologous proteins in different species, specific binding can include a polypeptide or agent that recognizes a protein or target in more than one species. Likewise, because of homology within certain regions of polypeptide sequences of different proteins, specific binding can include a polypeptide or agent that recognizes more than one protein or target. It is understood that, in certain embodiments, a polypeptide or agent that specifically binds a first target may or may not specifically bind a second target. As such, "specific binding" does not necessarily require (although it can include) exclusive binding, i.e. binding to a single target. Thus, a polypeptide or agent may, in certain embodiments, specifically bind more than one target. In certain embodiments, multiple targets may be bound by the same antigen-binding site on the polypeptide or agent. For example, an antibody may, in certain instances, comprise two identical antigen-binding sites, each of which specifically binds the same epitope on two or more proteins. In certain alternative embodiments, an antibody may be bispecific and comprise at least two antigen-binding sites with differing specificities. Generally, but not necessarily, reference to "binding" means "specific binding".

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies or other members of the immunoglobulin superfamily, in certain embodiments, the polypeptides can occur as single chains or as associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

A "conservative amino acid substitution" is one in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the invention do not abrogate the binding of the polypeptide, soluble protein, or antibody containing the amino acid sequence, to the target binding site. Methods of identifying amino acid conservative substitutions which do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, soluble protein, antibody, polynucleotide, vector, cell, or composition which is "isolated" is a polypeptide, soluble protein, antibody, polynucleotide, vector, cell, or composition which is in a form not found in nature. Isolated polypeptides, soluble proteins, antibodies, polynucleotides, vectors, cells, or compositions include those which have been purified to a degree that they are no longer in a form in which they are found in nature. In some embodiments, a polypeptide, soluble protein, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The term "immune response" as used herein includes responses from both the innate immune system and the adaptive immune system. It includes both cell-mediated and/or humoral immune responses. It includes both T-cell and B-cell responses, as well as responses from other cells of the immune system such as natural killer (NK) cells, monocytes, macrophages, etc.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an appropriate host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into appropriate hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a substance approved or approvable by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one agent of the present disclosure, and which does not destroy the pharmacological activity thereof and is nontoxic when administered in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of a polypeptide or agent described herein (e.g., a fusion protein, a soluble receptor, an antibody, a polypeptide, a polynucleotide, a small organic molecule, or other drug) effective to "treat" a disease or disorder in a subject such as, a mammal. In the case of cancer or a tumor, the therapeutically effective amount of a polypeptide or agent (e.g., polypeptide, soluble protein, or antibody) has a therapeutic effect and as such can boost the immune response, boost the anti-tumor response, increase cytolytic activity of immune cells, increase killing of tumor cells by immune cells, reduce the number of tumor cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented. In the case of cancer or a tumor, a subject is successfully "treated" according to the methods of the present invention if the patient shows one or more of the following: an increased immune response, an increased anti-tumor response, increased cytolytic activity of immune cells, increased killing of tumor cells by immune cells, a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. TNF Receptor Superfamily Binding Agents

The present invention provides agents that bind members of the TNF receptor superfamily (TNFRSF). TNFRSF members include, but may not be limited to, 4-1BB, BAFF, BCMA, CD27, CD30, CD40, DcR3, DcTRAIL R1, DcTRAIL R2, DR3, DR6, EDA2R, EDAR, Fas (CD95), GITR, HVEM, lymphotoxin beta R, NGFR, osteoprotegerin, OX40, RANK, RELT, TACI, TNFRH3, TNF R1, TNF R2, TRAIL R1, TRAIL R2, TRAIL R3, TRAIL R4, TROY, and TWEAK R. In some embodiments, the polypeptide or agent binds glucocorticoid-induced tumor necrosis factor receptor-related protein (GITR). These agents may be referred to herein as "GITR-binding agents". In certain embodiments, the polypeptide or agent is a GITR agonist. In certain embodiments, the polypeptide or agent induces, activates, enhances, increases, and/or prolongs GITR signaling. In some embodiments, the polypeptide or agent binds OX40. These polypeptides or agents may be referred to herein as "OX40-binding agents". In certain embodiments, the polypeptide or agent is an OX40 agonist. In certain embodiments, the polypeptide or agent induces, activates, enhances, increases, and/or prolongs OX40 signaling In some embodiments, the polypeptide or agent binds CD40. These polypeptides or agents may be referred to herein as "CD40-binding agents". In certain embodiments, the polypeptide or agent is a CD40 agonist. In certain embodiments, the polypeptide or agent induces, activates, enhances, increases, and/or prolongs CD40 signaling.

In certain embodiments, the agent is a polypeptide. In certain embodiments, the agent is a soluble protein. In some embodiments, the agent is a fusion polypeptide. In some embodiments, the agent is a soluble ligand or soluble "co-receptor". In some embodiments, the polypeptide or agent comprises a fragment of human GITRL. In some embodiments, the polypeptide or agent comprises a fragment of human OX40L. In some embodiments, the polypeptide or agent comprises a fragment of human CD40L. In some embodiments, a fragment of the extracellular domain of human GITRL, OX40L, or CD40L can demonstrate altered biological activity (e.g., increased protein half-life) compared to a soluble agent comprising the entire extracellular domain.

In some embodiments, a polypeptide or agent comprises a first, second, and third copy of the extracellular domain of a human tumor necrosis factor receptor ligand superfamily (TNFSF) protein or a fragment thereof capable of binding a receptor of the TNFSF protein. In some embodiments, a polypeptide or agent comprises a first, second, and third copy of the extracellular domain of a human tumor necrosis factor receptor ligand superfamily (TNFSF) protein or a fragment thereof capable of binding a receptor of the TNFSF protein, wherein at least one of the first, second, or third copies of the extracellular domain or a fragment thereof comprises the stalk region of the TNFSF protein. In some embodiments, the TNFSF protein is selected from the group consisting of: GITRL, OX40L, 4-1BB ligand, APRIL, BAFF, CD27 ligand, CD30 ligand, CD40 ligand (CD40L), EDA, EDA-A1, EDA-A2, Fas ligand (CD95L), LIGHT, lymphotoxin, lymphotoxin-beta, lymphotoxin-alpha, TL1A, TNF-alpha, TRAIL, TRANCE, and TWEAK.

The full-length amino acid (aa) sequence of human GITRL is known in the art (UniProt No. Q9UNG2) and is provided herein as SEQ ID NO:1. In some embodiments, a polypeptide or agent comprises at least one copy of the extracellular domain of GITRL or a GITR-binding fragment thereof. In certain embodiments, the "extracellular domain" of GITRL is approximately amino acids 71-199 of SEQ ID NO:1. Those of skill in the art may differ in their understanding of the exact amino acids corresponding to the extracellular domain of GITRL. Thus, the N-terminus and/or C-terminus of the extracellular domain described herein may extend or be shortened by 1, 2, 3, 4, 5, 6, 7, 8, 9, 10 or more amino acids. As used herein, the extracellular domain of GITRL generally comprises the "stalk region" and the "TNF family domain". Thus, in some embodiments, the copy of the extracellular domain of GITRL in the polypeptides or agents described herein comprises the "stalk region" of GITRL. The "stalk region" of GITRL is approximately amino acids 71-77 of SEQ ID NO:1. The stalk region comprises approximately amino acids LQLETAK (SEQ ID NO:32). The "TNF homology domain" or "TNF family domain" of GITRL is approximately amino acids 89-192 of SEQ ID NO:1. The TNF homology domain of GITRL comprises SEQ ID NO:33. In certain embodiments, a polypeptide or agent comprises a first, second, and third copy of the extracellular domain of GITRL or a GITR-binding fragment thereof. In some embodiments, a polypeptide or agent comprises at least one copy of SEQ ID NO:3. In some embodiments, a polypeptide or agent comprises at least two copies of SEQ ID NO:3. In some embodiments, a polypeptide or agent comprises three copies of SEQ ID NO:3. In some embodiments, a polypeptide or agent comprises at least one copy of SEQ ID NO:64. In some embodiments, a polypeptide or agent comprises at least two copies of SEQ ID NO:64. In some embodiments, a polypeptide or agent comprises three copies of SEQ ID NO:64. In certain embodiments, a polypeptide or agent comprises at least a first, second, and third copy of the extracellular domain of GITRL or a GITR-binding fragment thereof as a single chain polypeptide. In certain embodiments, a polypeptide or agent comprises SEQ ID NO:5. In certain embodiments, a polypeptide or agent comprises a polypeptide having at least about 90% sequence identity to SEQ ID NO:5. In certain embodiments, a polypeptide or agent comprises a polypeptide having at least about 95% sequence identity to SEQ ID NO:5. In certain embodiments, a polypeptide or agent comprises a polypeptide having at least 96%, 97%, 98%, 99% sequence identity to SEQ ID NO:5. In some embodiments, a polypeptide or agent comprises a polypeptide consisting essentially of SEQ ID NO:5. In some embodiments, a polypeptide or agent comprises a polypeptide consisting of SEQ ID NO:5. In some embodiments, a polypeptide or agent comprises SEQ ID NO:66. In certain embodiments, a polypeptide or agent comprises a polypeptide having at least about 90% sequence identity to SEQ ID NO:66. In certain embodiments, a polypeptide or agent comprises a polypeptide having at least about 95% sequence identity to SEQ ID NO:66. In certain embodiments, a polypeptide or agent comprises a polypeptide having at least about 96%, 97%, 98%, 99% sequence identity to SEQ ID NO:66. In some embodiments, a polypeptide or agent comprises a polypeptide consisting essentially of SEQ ID NO:66. In some embodiments, a polypeptide or agent comprises a polypeptide consisting of SEQ ID NO:66. In certain embodiments, a polypeptide or agent comprises at least a first, second, and third copy of a fragment of the extracellular domain of GITRL. In some embodiments, the copies of the extracellular domain of GITRL consist of the same amino acid sequence. In some embodiments, the copies of the extracellular domain of GITRL are not identical. In some embodiments, the copies of the extracellular domain of GITRL comprise substitutions, deletions, and/or additions to the amino acid sequence of human GITRL as compared to the wild-type sequence.

In some embodiments, a polypeptide or agent is a single chain fusion polypeptide comprising a first, second, and third copy of the extracellular domain of human GITRL or a fragment thereof. In some embodiments, a polypeptide or agent is a single chain fusion polypeptide comprising a first, second, and third copy of the extracellular domain of human GITRL or a fragment thereof, wherein at least one of the extracellular domains comprises the stalk region of GITRL. In some embodiments, a polypeptide or agent is a single chain fusion polypeptide comprising a first, second, and third copy of the extracellular domain of human GITRL or a fragment thereof, wherein at least two of the extracellular domains comprise the stalk region of GITRL. In some embodiments, a polypeptide or agent is a single chain fusion polypeptide comprising a first, second, and third copy of the extracellular domain of human GITRL or a fragment thereof, wherein each extracellular domain comprises the stalk region of GITRL. In some embodiments, a polypeptide or agent is a single chain fusion polypeptide comprising a first, second, and third copy of the extracellular domain of human GITRL, wherein the polypeptide does not comprise any peptide linkers (i.e., exogenous peptide linkers). In some embodiments, a polypeptide or agent is a single chain fusion polypeptide comprising a first, second, and third copy of the extracellular domain of human GITRL, wherein the polypeptide does not comprise an exogenous peptide linker between any of the copies of the extracellular domain or a fragment thereof. In some embodiments, a polypeptide or agent is a single chain fusion polypeptide comprising a first, second, and third copy of the extracellular domain of human GITRL, wherein each extracellular domain comprises the stalk region and the polypeptide does not comprise any peptide linkers (i.e., exogenous peptide linkers). In some embodiments, a polypeptide or agent is a single chain fusion polypeptide comprising a first, second, and third copy of the extracellular domain of human GITRL or a GITR-binding fragment thereof, wherein the second and third copies of the extracellular domain comprise a stalk. In some embodiments, a polypeptide or extracellular domain of GITRL comprises a polypeptide having at least 96%, 97%, 98%, comprises amino acids 71-199 of SEQ ID NO:1. In some embodiments, the extracellular domain of GITRL comprises SEQ ID NO:3. In some embodiments, the extracellular domain of GITRL comprises SEQ ID NO:64. In some embodiments, the single chain fusion polypeptide comprises SEQ ID NO:5. In some embodiments, the single chain fusion polypeptide consists of SEQ ID NO:5. In some embodiments, the single chain fusion polypeptide comprises SEQ ID NO:66. In some embodiments, the single chain fusion polypeptide consists of SEQ ID NO:66.

The full-length amino acid (aa) sequence of human OX40L is known in the art (UniProt No. P23510) and is provided herein as SEQ ID NO:40. In some embodiments, the polypeptide or agent comprises at least one copy of the extracellular domain of OX40L or a fragment thereof. In certain embodiments, the "extracellular domain" of OX40L is approximately amino acids 51-183 of SEQ ID NO:40. Those of skill in the art may differ in their understanding of the exact amino acids corresponding to the extracellular domain of OX40L. Thus, the N-terminus and/or C-terminus of the extracellular domain described herein may extend or be shortened by 1, 2, 3, 4, 5, 6, 7, 8, 9, 10 or more amino acids. As used herein, the extracellular domain of OX40L generally comprises the "stalk region" and the "TNF family domain". Thus, in some embodiments, a copy of the extracellular domain of OX40L in the polypeptides or agents described herein comprises the "stalk region" of OX40L. The "stalk region" of OX40L is approximately amino acids 51-57 of SEQ ID NO:40. The stalk region comprises approximately amino acids QVSHRYP (SEQ ID NO:55). In some embodiments, the stalk region comprises about 4-20 amino acids. In some embodiments, the stalk region comprises about 4-10 amino acids. In some embodiments, the stalk region comprises the amino acids (e.g., 4-10 amino acids) upstream from the TNF homology domain. In some embodiments, the stalk region comprises a fragment of the stalk region. In some embodiments, the stalk region comprises additional amino acids. In some embodiments, the stalk region comprises amino acids ALQVSHRYP (variant 1; SEQ ID NO:74). In some embodiments, the stalk region comprises amino acids SHRYP (variant 2; SEQ ID NO:75). In some embodiments, the stalk region comprises amino acids HRYP (variant 3; SEQ ID NO:76). The "TNF homology domain" or "TNF family domain" of OX40L is approximately amino acids 84-178 of SEQ ID NO:40. The TNF homology domain comprises SEQ ID NO:56. In some embodiments, a polypeptide or agent comprises at least one copy of SEQ ID NO:42. In some embodiments, a polypeptide or agent comprises at least two copies of SEQ ID NO:42. In some embodiments, a polypeptide or agent comprises three copies of SEQ ID NO:42. In some embodiments, a polypeptide or agent comprises at least one copy of SEQ ID NO:67. In some embodiments, a polypeptide or agent comprises at least two copies of SEQ ID NO:67. In some embodiments, a polypeptide or agent comprises three copies of SEQ ID NO:67. In some embodiments, a polypeptide or agent comprises at least one copy of SEQ ID NO:77. In some embodiments, a polypeptide or agent comprises at least two copies of SEQ ID NO:77. In some embodiments, a polypeptide or agent comprises three copies of SEQ ID NO:77. In some embodiments, a polypeptide or agent comprises at least one copy of SEQ ID NO:78. In some embodiments, a polypeptide or agent comprises at least two copies of SEQ ID NO:78. In some embodiments, a polypeptide or agent comprises three copies of SEQ ID NO:78. In some embodiments, the polypeptide or agent comprises at least one copy of SEQ ID NO:79. In some embodiments, a polypeptide or agent comprises at least two copies of SEQ ID NO:79. In some embodiments, a polypeptide or agent comprises three copies of SEQ ID NO:79. In certain embodiments, a polypeptide or agent comprises a first, second, and third copy of the extracellular domain of OX40L or an OX40-binding fragment thereof. In certain embodiments, a polypeptide or agent comprises a first, second, and third copy of the extracellular domain of OX40L or a fragment thereof as a single chain polypeptide. In certain embodiments, a polypeptide or agent comprises SEQ ID NO:44. In certain embodiments, a polypeptide or agent comprises a polypeptide having at least about 90% sequence identity to SEQ ID NO:44. In certain embodiments, a polypeptide or agent comprises a polypeptide having at least about 95% sequence identity to SEQ ID NO:44. In certain embodiments, a polypeptide or agent comprises a polypeptide having at least 96%, 97%, 98%, 99% sequence identity to SEQ ID NO:44. In some embodiments, a polypeptide or agent comprises a polypeptide consisting essentially of SEQ ID NO:44. In some embodiments, a polypeptide or agent comprises a polypeptide consisting of SEQ ID NO:44. In certain embodiments, the polypeptide or agent comprises SEQ ID NO:69. In certain embodiments, a polypeptide or agent comprises a polypeptide having at least about 90% sequence identity to SEQ ID NO:69. In certain embodiments, a polypeptide or agent comprises a polypeptide having at least about 95% sequence identity to SEQ ID NO:69. In certain embodiments, a polypeptide or agent comprises a polypeptide having at least 96%, 97%, 98%, 99% sequence identity to SEQ ID NO:69. In some embodiments, a polypeptide or agent comprises a polypeptide consisting essentially of SEQ ID NO:69. In some embodiments, a polypeptide or agent comprises a polypeptide consisting of SEQ ID NO:69. In certain embodiments, a polypeptide or agent comprises SEQ ID NO:71. In certain embodiments, a polypeptide or agent comprises a polypeptide having at least about 90% sequence identity to SEQ ID NO:71. In certain embodiments, a polypeptide or agent comprises a polypeptide having at least about 95% sequence identity to SEQ ID NO:71. In certain embodiments, a polypeptide or agent comprises a polypeptide having at least 96%, 97%, 98%, 99% sequence identity to SEQ ID NO:71. In some embodiments, a polypeptide or agent comprises a polypeptide consisting essentially of SEQ ID NO:71. In some embodiments, a polypeptide or agent comprises a polypeptide consisting of SEQ ID NO:71. In certain embodiments, a polypeptide or agent comprises at least a first, second, and third copy of a fragment of the extracellular domain of OX40L. In some embodiments, the copies of the extracellular domain of OX40L consist of the same amino acid sequence. In some embodiments, the copies of the extracellular domain of OX40L are not identical. In some embodiments, the copies of the extracellular domain of OX40L comprise substitutions, deletions, and/or additions to the amino acid sequence of human OX40L as compared to the wild-type sequence.

In some embodiments, a polypeptide or agent is a single chain fusion polypeptide comprising at least a first, second, and third copy of the extracellular domain of human OX40L or a fragment thereof. In some embodiments, a polypeptide or agent is a single chain fusion polypeptide comprising at least a first, second, and third copy of the extracellular domain of human OX40L or a fragment thereof, wherein at least one of the extracellular domains comprises the stalk region. In some embodiments, a polypeptide or agent is a single chain fusion polypeptide comprising at least a first, second, and third copy of the extracellular domain of human OX40L or a fragment thereof, wherein each extracellular domain comprises the stalk region. In some embodiments, a polypeptide or agent is a single chain fusion polypeptide comprising at least a first, second, and third copy of the extracellular domain of human OX40L, wherein the polypeptide does not comprise any peptide linkers (i.e., exogenous peptide linkers). In some embodiments, a polypeptide or agent is a single chain fusion polypeptide comprising at least a first, second, and third copy of the extracellular domain of human OX40L, wherein each extracellular domain comprises the stalk region and the polypeptide does not comprise any peptide linkers (i.e., exogenous peptide linkers). In some embodiments, the extracellular domain of OX40L comprises amino acids 51-183 of SEQ ID NO:40. In some embodiments, the extracellular domain of OX40L comprises SEQ ID NO:42. In some embodiments, the extracellular domain of OX40L consists of SEQ ID NO:42. In some embodiments, the single chain fusion polypeptide comprises SEQ ID NO:44. In some embodiments, the single chain fusion polypeptide consists of SEQ ID NO:44. In some embodiments, the single chain fusion polypeptide comprises SEQ ID NO:69. In some embodiments, the single chain fusion polypeptide consists of SEQ ID NO:69.

The full-length amino acid (aa) sequence of human CD40L is known in the art (UniProt No. P29965) and is provided herein as SEQ ID NO:82. In some embodiments, the polypeptide or agent comprises at least one copy of the extracellular domain of CD40L or a fragment thereof. In certain embodiments, the "extracellular domain" of CD40L is approximately amino acids 47-261 of SEQ ID NO:82. Those of skill in the art may differ in their understanding of the exact amino acids corresponding to the extracellular domain of CD40L. Thus, the N-terminus and/or C-terminus of the extracellular domain described herein may extend or be shortened by 1, 2, 3, 4, 5, 6, 7, 8, 9, 10 or more amino acids. As used herein, the extracellular domain of CD40L generally comprises the "stalk region" or a fragment of the stalk region and the "TNF family domain". The stalk region of CD40L is approximately 72 amino acids, much longer than the stalk regions of GITRL and CD40L. In some embodiments, to allow for proper folding and conformation of a single chain CD40L trimer, the stalk region comprises a fragment of the CD40L stalk region more equivalent in length to the stalk regions of GITRL or OX40L. Thus, in some embodiments, a copy of the extracellular domain of CD40L in the polypeptides or agents described herein comprises a fragment of the stalk region of CD40L. In some embodiments, the stalk region comprises about 4-20 amino acids. In some embodiments, the stalk region comprises about 4-10 amino acids. In some embodiments, the stalk region comprises the amino acids (e.g., 4-10 amino acids) upstream from the TNF homology domain. The stalk region of CD40L is approximately amino acids 47-112 of SEQ ID NO:82. In some embodiments, the stalk region comprises a fragment of the CD40L stalk region. In some embodiments, fragments of the CD40L stalk region comprise MQKGDQ (SEQ ID NO:98; fragment 1); FEMQKGDQ (SEQ ID NO:99; fragment 2); EMQKGDQ (SEQ ID NO:100; fragment 3); QKGDQ (SEQ ID NO:101; fragment 4); or KGDQ (SEQ ID NO:102; fragment 5). The "TNF homology domain" or "TNF family domain" of CD40L is approximately amino acids 122-261 of SEQ ID NO:82. The TNF homology domain comprises SEQ ID NO:94. In some embodiments, a polypeptide or agent comprises at least one copy of SEQ ID NO:84. In some embodiments, a polypeptide or agent comprises at least two copies of SEQ ID NO:84. In some embodiments, a polypeptide or agent comprises three copies of SEQ ID NO:84. In some embodiments, a polypeptide or agent comprises at least one copy of SEQ ID NO:95. In some embodiments, a polypeptide or agent comprises at least two copies of SEQ ID NO:95. In some embodiments, a polypeptide or agent comprises three copies of SEQ ID NO:95. In some embodiments, a polypeptide or agent comprises at least one copy of SEQ ID NO:103. In some embodiments, a polypeptide or agent comprises at least two copies of SEQ ID NO:103. In some embodiments, a polypeptide or agent comprises three copies of SEQ ID NO:103. In some embodiments, a polypeptide or agent comprises at least one copy of SEQ ID NO:104. In some embodiments, a polypeptide or agent comprises at least two copies of SEQ ID NO:104. In some embodiments, a polypeptide or agent comprises three copies of SEQ ID NO:104. In some embodiments, the polypeptide or agent comprises at least one copy of SEQ ID NO:105. In some embodiments, a polypeptide or agent comprises at least two copies of SEQ ID NO:105. In some embodiments, a polypeptide or agent comprises three copies of SEQ ID NO:105. In some embodiments, the polypeptide or agent comprises at least one copy of SEQ ID NO:106. In some embodiments, a polypeptide or agent comprises at least two copies of SEQ ID NO:106. In some embodiments, a polypeptide or agent comprises three copies of SEQ ID NO:106. In certain embodiments, a polypeptide or agent comprises a first, second, and third copy of the extracellular domain of CD40L or an CD40-binding fragment thereof. In certain embodiments, a polypeptide or agent comprises a first, second, and third copy of the extracellular domain of CD40L or a fragment thereof as a single chain polypeptide. In certain embodiments, a polypeptide or agent comprises SEQ ID NO:85. In certain embodiments, a polypeptide or agent comprises a polypeptide having at least about 90% sequence identity to SEQ ID NO:85. In certain embodiments, a polypeptide or agent comprises a polypeptide having at least about 95% sequence identity to SEQ ID NO:85. In certain embodiments, a polypeptide or agent comprises a polypeptide having at least 96%, 97%, 98%, 99% sequence identity to SEQ ID NO:85. In some embodiments, a polypeptide or agent comprises a polypeptide consisting essentially of SEQ ID NO:85. In some embodiments, a polypeptide or agent comprises a polypeptide consisting of SEQ ID NO:85. In certain embodiments, the polypeptide or agent comprises SEQ ID NO:97. In certain embodiments, a polypeptide or agent comprises a polypeptide having at least about 90% sequence identity to SEQ ID NO:97. In certain embodiments, a polypeptide or agent comprises a polypeptide having at least about 95% sequence identity to SEQ ID NO:97. In certain embodiments, a polypeptide or agent comprises a polypeptide having at least 96%, 97%, 98%, 99% sequence identity to SEQ ID NO:97. In some embodiments, a polypeptide or agent comprises a polypeptide consisting essentially of SEQ ID NO:97. In some embodiments, a polypeptide or agent comprises a polypeptide consisting of SEQ ID NO:97. In certain embodiments, a polypeptide or agent comprises at least a first, second, and third copy of a fragment of the extracellular domain of CD40L. In some embodiments, the copies of the extracellular domain of CD40L consist of the same amino acid sequence. In some embodiments, the copies of the extracellular domain of CD40L are not identical. In some embodiments, the copies of the extracellular domain of CD40L comprise substitutions, deletions, and/or additions to the amino acid sequence of human CD40L as compared to the wild-type sequence.

In some embodiments, a polypeptide or agent is a single chain fusion polypeptide comprising at least a first, second, and third copy of the extracellular domain of human CD40L or a fragment thereof. In some embodiments, a polypeptide or agent is a single chain fusion polypeptide comprising at least a first, second, and third copy of the extracellular domain of human CD40L or a fragment thereof, wherein at least one of the extracellular domains comprises the stalk region or a stalk region fragment. In some embodiments, a polypeptide or agent is a single chain fusion polypeptide comprising at least a first, second, and third copy of the extracellular domain of human CD40L or a fragment thereof, wherein each extracellular domain comprises the stalk region or a stalk region fragment. In some embodiments, a polypeptide or agent is a single chain fusion polypeptide comprising at least a first, second, and third copy of the extracellular domain of human CD40L, wherein the polypeptide does not comprise any peptide linkers (i.e., exogenous peptide linkers). In some embodiments, a polypeptide or agent is a single chain fusion polypeptide comprising at least a first, second, and third copy of the extracellular domain of human CD40L, wherein each extracellular domain comprises the stalk region or a stalk region fragment and the polypeptide does not comprise any peptide linkers (i.e., exogenous peptide linkers). In some embodiments, the extracellular domain of CD40L comprises amino acids 113-261 of SEQ ID NO:82. In some embodiments, the extracellular domain of CD40L comprises SEQ ID NO:84. In some embodiments, the extracellular domain of OX40L consists of SEQ ID NO:84. In some embodiments, the extracellular domain of CD40L comprises SEQ ID NO:103. In some embodiments, the extracellular domain of OX40L consists of SEQ ID NO:103. In some embodiments, the extracellular domain of CD40L comprises SEQ ID NO:104. In some embodiments, the extracellular domain of OX40L consists of SEQ ID NO:104. In some embodiments, the extracellular domain of CD40L comprises SEQ ID NO:105. In some embodiments, the extracellular domain of OX40L consists of SEQ ID NO:105. In some embodiments, the extracellular domain of CD40L comprises SEQ ID NO:106. In some embodiments, the extracellular domain of OX40L consists of SEQ ID NO:106. In some embodiments, the single chain fusion polypeptide comprises SEQ ID NO:85. In some embodiments, the single chain fusion polypeptide consists of SEQ ID NO:85. In some embodiments, the single chain fusion polypeptide comprises SEQ ID NO:97. In some embodiments, the single chain fusion polypeptide consists of SEQ ID NO:97.

In certain embodiments, a polypeptide or agent comprises a variant of the extracellular domain GITRL amino acid sequence or a fragment thereof that comprises one or more (e.g., one, two, three, four, five, six, seven, eight, nine, ten, etc.) conservative substitutions and is capable of binding GITR. In certain embodiments, a polypeptide or agent comprises a variant of the extracellular domain OX40L amino acid sequence or a fragment thereof that comprises one or more (e.g., one, two, three, four, five, six, seven, eight, nine, ten, etc.) conservative substitutions and is capable of binding OX40. In certain embodiments, a polypeptide or agent comprises a variant of the extracellular domain CD40L amino acid sequence or a fragment thereof that comprises one or more (e.g., one, two, three, four, five, six, seven, eight, nine, ten, etc.) conservative substitutions and is capable of binding CD40.

In some embodiments, the agent is a polypeptide. In some embodiments, the polypeptide is a fusion protein. In certain embodiments, the fusion protein comprises at least one copy of the extracellular domain of a member of the human TNFSF or a fragment thereof, and further comprises a non-TNFSF polypeptide. In certain embodiments, the fusion protein comprises at least one copy of the extracellular domain of human GITRL or a fragment thereof, and further comprises a non-GITRL polypeptide. In certain embodiments, the fusion protein comprises at least one copy of the extracellular domain of human OX40L or a fragment thereof, and further comprises a non-OX40L polypeptide. In certain embodiments, the fusion protein comprises at least one copy of the extracellular domain of human CD40L or a fragment thereof, and further comprises a non-CD40L polypeptide. In some embodiments, the fusion protein may include an extracellular domain or fragment thereof linked to a heterologous functional and structural polypeptide including, but not limited to, a human Fc region, one or more protein tags (e.g., myc, FLAG, GST), other endogenous proteins or protein fragments, or any other useful protein sequence including any peptide sequence between the extracellular domain and the non-TNFSF polypeptide (e.g., a non-GITRL polypeptide or a non-OX40L polypeptide). In certain embodiments, the non-TNFSF polypeptide comprises a human Fc region. In certain embodiments, the non-GITRL polypeptide comprises a human Fc region. In certain embodiments, the non-OX40L polypeptide comprises a human Fc region. In certain embodiments, the non-CD40L polypeptide comprises a human Fc region. The Fc region can be obtained from any of the classes of immunoglobulin, IgG, IgA, IgM, IgD and IgE. In some embodiments, the Fc region is a human IgG1 Fc region. In some embodiments, the Fc region is a human IgG2 Fc region. In some embodiments, the Fc region is a wild-type Fc region. In some embodiments, the Fc region is a natural variant of a wild-type Fc region. In some embodiments, the Fc region is a mutated Fc region. In some embodiments, the Fc region is truncated at the N-terminal end by 1, 2, 3, 4, 5, 6, 7, 8, 9, or 10 amino acids, (e.g., in the hinge domain). In some embodiments, the Fc region is truncated at the C-terminal end (e.g., lysine is absent). In some embodiments, an amino acid in the hinge domain is changed to hinder undesirable disulfide bond formation. In some embodiments, a cysteine is replaced with a different amino acid to hinder undesirable disulfide bond formation. In some embodiments, a cysteine is replaced with a serine to hinder undesirable disulfide bond formation. In some embodiments, the Fc region comprises SEQ ID NO:10, SEQ ID NO:11, SEQ ID NO:12, SEQ ID NO:13, or SEQ ID NO:14. In some embodiments, the Fc region comprise SEQ ID NO:10. In some embodiments, the Fc region comprises SEQ ID NO:14.

In some embodiments, the polypeptide or agent is a single chain GITRL trimer-Fc protein. In some embodiments, the polypeptide or agent is a single chain GITRL trimer-IgG1 Fc protein. In some embodiments, the polypeptide or agent comprises SEQ ID NO:6 or SEQ ID NO:7. In some embodiments, the polypeptide or agent comprises SEQ ID NO:6. In some embodiments, the polypeptide or agent comprises SEQ ID NO:7. In some embodiments, the polypeptide or agent consists essentially of SEQ ID NO:6 or SEQ ID NO:7. In some embodiments, the polypeptide or agent consists of SEQ ID NO:6. In some embodiments, the polypeptide or agent consists of SEQ ID NO:7. In some embodiments, the polypeptide or agent comprises a polypeptide encoded by the "hGITRL-hIgG1" plasmid deposited with ATCC and assigned designation number PTA-122112. In some embodiments, the polypeptide or agent is a single chain GITRL trimer-IgG2 Fc protein. In some embodiments, the polypeptide or agent comprises SEQ ID NO:8 or SEQ ID NO:9. In some embodiments, the polypeptide or agent comprises SEQ ID NO:8. In some embodiments, the polypeptide or agent comprises SEQ ID NO:9. In some embodiments, the polypeptide or agent consists essentially of SEQ ID NO:8 or SEQ ID NO:9. In some embodiments, the polypeptide or agent consists of SEQ ID NO:8. In some embodiments, the polypeptide or agent consists of SEQ ID NO:9.

In some embodiments, the polypeptide or agent is a single chain OX40L trimer-Fc protein. In some embodiments, the polypeptide or agent is a single chain OX40L trimer-IgG1 Fc protein. In some embodiments, the polypeptide or agent comprises SEQ ID NO:45 or SEQ ID NO:46. In some embodiments, the polypeptide or agent comprises SEQ ID NO:45. In some embodiments, the polypeptide or agent comprises SEQ ID NO:46. In some embodiments, the polypeptide or agent consists essentially of SEQ ID NO:45 or SEQ ID NO:46. In some embodiments, the polypeptide or agent consists of SEQ ID NO:45. In some embodiments, the polypeptide or agent consists of SEQ ID NO:46. In some embodiments, the polypeptide or agent is a single chain OX40L trimer-IgG2 Fc protein. In some embodiments, the polypeptide or agent comprises SEQ ID NO:47 or SEQ ID NO:48. In some embodiments, the polypeptide or agent comprises SEQ ID NO:47. In some embodiments, the polypeptide or agent comprises SEQ ID NO:48. In some embodiments, the polypeptide or agent consists essentially of SEQ ID NO:47 or SEQ ID NO:48. In some embodiments, the polypeptide or agent consists of SEQ ID NO:47. In some embodiments, the polypeptide or agent consists of SEQ ID NO:48.

In some alternative embodiments, the polypeptide or agent is a single chain OX40L trimer-IgG1 Fc protein. In some embodiments, the polypeptide or agent comprises SEQ ID NO:80 or SEQ ID NO:81. In some embodiments, the polypeptide or agent comprises SEQ ID NO:80. In some embodiments, the polypeptide or agent comprises SEQ ID NO:81. In some embodiments, the polypeptide or agent consists essentially of SEQ ID NO:80 or SEQ ID NO:81. In some embodiments, the polypeptide or agent consists of SEQ ID NO:80. In some embodiments, the polypeptide or agent consists of SEQ ID NO:81.

In some embodiments, the polypeptide or agent is a single chain CD40L trimer-Fc protein. In some embodiments, the polypeptide or agent is a single chain CD40L trimer-IgG1 Fc protein. In some embodiments, the polypeptide or agent comprises SEQ ID NO:89 or SEQ ID NO:90. In some embodiments, the polypeptide or agent comprises SEQ ID NO:89. In some embodiments, the polypeptide or agent comprises SEQ ID NO:90. In some embodiments, the polypeptide or agent consists essentially of SEQ ID NO:89 or SEQ ID NO:90. In some embodiments, the polypeptide or agent consists of SEQ ID NO:89. In some embodiments, the polypeptide or agent consists of SEQ ID NO:90. In some embodiments, the polypeptide or agent is a single chain CD40L trimer-IgG2 Fc protein. In some embodiments, the polypeptide or agent comprises SEQ ID NO:91 or SEQ ID NO:92. In some embodiments, the polypeptide or agent comprises SEQ ID NO:91. In some embodiments, the polypeptide or agent comprises SEQ ID NO:92. In some embodiments, the polypeptide or agent consists essentially of SEQ ID NO:91 or SEQ ID NO:92. In some embodiments, the polypeptide or agent consists of SEQ ID NO:91. In some embodiments, the polypeptide or agent consists of SEQ ID NO:92.

In certain embodiments, the non-TNFSF polypeptide (e.g., non-GITRL polypeptide, non-OX40L polypeptide, or non-CD40L polypeptide) comprises SEQ ID NO:10, SEQ ID NO:11, SEQ ID NO:12, SEQ ID NO:13, or SEQ ID NO:14. In certain embodiments, the non-TNFSF polypeptide (e.g., non-GITRL polypeptide, non-OX40L polypeptide, or non-CD40L polypeptide) consists essentially of SEQ ID NO:10, SEQ ID NO:11, SEQ ID NO:12, SEQ ID NO:13, or SEQ ID NO:14. In certain embodiments, the non-TNFSF polypeptide (e.g., non-GITRL polypeptide, non-OX40L polypeptide, or non-CD40L polypeptide) consists of SEQ ID NO:10, SEQ ID NO:11, SEQ ID NO:12, SEQ ID NO:13, or SEQ ID NO:14.

In certain embodiments, the non-GITRL polypeptide or the non-OX40L polypeptide comprises an immunoglobulin heavy chain. In certain embodiments, the non-CD40L polypeptide comprises an immunoglobulin heavy chain. In certain embodiments, the immunoglobulin heavy chain is associated with an immunoglobulin light chain. In some embodiments, the immunoglobulin heavy chain and the immunoglobulin light chain form an antigen-binding site. In certain embodiments, the non-GITRL polypeptide or the non-OX40L polypeptide comprises an antibody. In certain embodiments, the non-CD40L polypeptide comprises an antibody. In certain embodiments, the non-GITRL polypeptide or the non-OX40L polypeptide comprises a single chain antibody or Fab. In certain embodiments, the non-CD40L polypeptide comprises a single chain antibody or Fab.

In certain embodiments, a fusion protein comprises a first, second, and third copy of the extracellular domain of human GITRL or a fragment thereof and a non-GITRL polypeptide, wherein the C-terminal end of the non-GITRL polypeptide is linked to the extracellular domain(s) of GITRL. In certain embodiments, a fusion protein comprises a first, second, and third copy of the extracellular domain of human GITRL or a fragment thereof and a non-GITRL polypeptide, wherein the N-terminal end of the non-GITRL polypeptide is linked to the extracellular domain(s) of GITRL. In some embodiments, the first copy of the extracellular domain of GITRL is linked to the C-terminal end of the non-GITRL polypeptide. In some embodiments, the third copy of the extracellular domain of GITRL is linked to the N-terminal end of the non-GITRL polypeptide. In some embodiments, the extracellular domain(s) of GITRL is linked to the C-terminal end of a Fc region. In some embodiments, the extracellular domain(s) of GITRL is linked to the N-terminal end of a Fc region. In some embodiments, the extracellular domain(s) of GITRL is directly linked to the Fc region (i.e. without an intervening peptide linker). In some embodiments, the extracellular domain(s) of GITRL is linked to the Fc region via a peptide linker.

In certain embodiments, a fusion protein comprises at least a first, second, and third copy of the extracellular domain of human OX40L or a fragment thereof and a non-OX40L polypeptide, wherein the C-terminal end of the non-OX40L polypeptide is linked to the extracellular domain(s) of OX40L. In certain embodiments, a fusion protein comprises at least a first, second, and third copy of the extracellular domain of human OX40L or a fragment thereof and a non-OX40L polypeptide, wherein the N-terminal end of the non-OX40L polypeptide is linked to the extracellular domain(s) of OX40L. In some embodiments, the first copy of the extracellular domain of OX40L is linked to the C-terminal end of the non-OX40L polypeptide. In some embodiments, the third copy of the extracellular domain of OX40L is linked to the N-terminal end of the non-OX40L polypeptide. In some embodiments, the extracellular domain(s) of OX40L is linked to the C-terminal end of a Fc region. In some embodiments, the extracellular domain(s) of OX40L is linked to the N-terminal end of a Fc region. In some embodiments, the extracellular domain(s) of OX40L is directly linked to the Fc region (i.e. without an intervening peptide linker). In some embodiments, the extracellular domain(s) of OX40L is linked to the Fc region via a peptide linker.

In certain embodiments, a fusion protein comprises at least a first, second, and third copy of the extracellular domain of human CD40L or a fragment thereof and a non-CD40L polypeptide, wherein the C-terminal end of the non-CD40L polypeptide is linked to the extracellular domain(s) of CD40L. In certain embodiments, a fusion protein comprises at least a first, second, and third copy of the extracellular domain of human CD40L or a fragment thereof and a non-CD40L polypeptide, wherein the N-terminal end of the non-CD40L polypeptide is linked to the extracellular domain(s) of CD40L. In some embodiments, the first copy of the extracellular domain of CD40L is linked to the C-terminal end of the non-CD40L polypeptide. In some embodiments, the third copy of the extracellular domain of CD40L is linked to the N-terminal end of the non-CD40L polypeptide. In some embodiments, the extracellular domain(s) of CD40L is linked to the C-terminal end of a Fc region. In some embodiments, the extracellular domain(s) of CD40L is linked to the N-terminal end of a Fc region. In some embodiments, the extracellular domain(s) of CD40L is directly linked to the Fc region (i.e. without an intervening peptide linker). In some embodiments, the extracellular domain(s) of CD40L is linked to the Fc region via a peptide linker.

As used herein, the term "linker" refers to a linker inserted between a first polypeptide (e.g., a extracellular domain of TNFSF (e.g., GITRL, OX40L, or CD40L or a fragment thereof) and a second polypeptide (e.g., a Fc region). In some embodiments, the linker is a peptide linker. Linkers should not adversely affect the expression, secretion, or bioactivity of the fusion protein. Linkers should not be antigenic and should not elicit an immune response. Suitable linkers are known to those of skill in the art and often include mixtures of glycine and serine residues and often include amino acids that are sterically unhindered. Other amino acids that can be incorporated into useful linkers include threonine and alanine residues. Linkers can range in length, for example from 1-50 amino acids in length, 1-22 amino acids in length, 1-10 amino acids in length, 1-5 amino acids in length, or 1-3 amino acids in length. Linkers may include, but are not limited to, SerGly, GGSG, GSGS, GGGS, S(GGS)n where n is 1-7, GRA, poly(Gly), poly(Ala), GGGSGGG (SEQ ID NO:57), ESGGGGVT (SEQ ID NO:34), LESGGGGVT (SEQ ID NO:35), GRAQVT (SEQ ID NO:36), WRAQVT (SEQ ID NO:37), and ARGRAQVT (SEQ ID NO:38). In some embodiments, the linker may comprise a cleavage site. In some embodiments, the linker may comprise an enzyme cleavage site, so that the second polypeptide may be separated from the first polypeptide. As used herein, a linker is an intervening peptide sequence that does not include amino acid residues from either the C-terminus of the first polypeptide (e.g., an extracellular domain of GITRL, OX40L, or CD40L) or the N-terminus of the second polypeptide (e.g., the Fc region).

In some embodiments, a polypeptide or agent described herein specifically binds GITR and acts as a GITR agonist. In some embodiments, a polypeptide or agent described herein specifically binds GITR and activates GITR signaling. In some embodiments, a polypeptide or agent described herein specifically binds GITR and induces, activates, promotes, increases, enhances, or prolongs GITR activity. In some embodiments, a polypeptide or agent described herein specifically binds OX40 and acts as an OX40 agonist. In some embodiments, a polypeptide or agent described herein specifically binds OX40 and activates OX40 signaling. In some embodiments, a polypeptide or agent described herein specifically binds OX40 and induces, activates, promotes, increases, enhances, or prolongs OX40 activity. In some embodiments, a polypeptide or agent described herein specifically binds CD40 and acts as an CD40 agonist. In some embodiments, a polypeptide or agent described herein specifically binds CD40 and activates CD40 signaling. In some embodiments, a polypeptide or agent described herein specifically binds CD40 and induces, activates, promotes, increases, enhances, or prolongs CD40 activity.

In some embodiments, a polypeptide or agent described herein specifically binds GITR and modulates an immune response. In some embodiments, a polypeptide or agent described herein specifically binds GITR and induces, augments, increases, and/or prolongs an immune response. In some embodiments, a polypeptide or agent described herein specifically binds OX40 and modulates an immune response. In some embodiments, a polypeptide or agent described herein specifically binds OX40 and induces, augments, increases, and/or prolongs an immune response. In some embodiments, a polypeptide or agent described herein specifically binds CD40 and modulates an immune response. In some embodiments, a polypeptide or agent described herein specifically binds CD40 and induces, augments, increases, and/or prolongs an immune response.

In some embodiments, a polypeptide or agent described herein specifically binds a member of the TNFRSF (e.g., GITR, OX40, or CD40) with a dissociation constant ($K_D$) of about 1 µM or less, about 100 nM or less, about 40 nM or less, about 20 nM or less, about 10 nM or less, about 1 nM or less, or about 0.1 nM or less. In some embodiments, a polypeptide or agent binds a member of the TNFRSF (e.g., GITR, OX40, or CD40) with a $K_D$ of about 1 nM or less. In some embodiments, a polypeptide or agent binds a member of the TNFRSF (e.g., GITR, OX40, or CD40) with a $K_D$ of about 0.1 nM or less. In some embodiments, a polypeptide or agent binds human TNFRSF and/or mouse TNFRSF with a $K_D$ of about 10 nM or less. In some embodiments, a polypeptide or agent binds human TNFRSF with a $K_D$ of about 10 nM or less.

In some embodiments, a polypeptide or agent binds human GITR and/or mouse GITR with a $K_D$ of about 10 nM or less. In some embodiments, a polypeptide or agent binds human GITR and/or mouse GITR with a $K_D$ of about 1 nM or less. In some embodiments, a polypeptide or agent binds human GITR and/or mouse GITR with a $K_D$ of about 0.1 nM or less. In some embodiments, a polypeptide or agent binds human GITR and does not bind mouse GITR. In some embodiments, a polypeptide or agent binds human GITR with a $K_D$ of about 10 nM or less. In some embodiments, a polypeptide or agent binds human GITR with a $K_D$ of about 1 nM or less. In some embodiments, a polypeptide or agent binds human GITR with a $K_D$ of about 0.1 nM or less.

In some embodiments, a polypeptide or agent binds human OX40 and/or mouse OX40 with a $K_D$ of about 10 nM or less. In some embodiments, a polypeptide or agent binds human OX40 and/or mouse OX40 with a $K_D$ of about 1 nM or less. In some embodiments, a polypeptide or agent binds human OX40 and/or mouse OX40 with a $K_D$ of about 0.1 nM or less. In some embodiments, a polypeptide or agent binds human OX40 and does not bind mouse OX40. In some embodiments, a polypeptide or agent binds human OX40 with a $K_D$ of about 10 nM or less. In some embodiments, a polypeptide or agent binds human OX40 with a $K_D$ of about 1 nM or less. In some embodiments, a polypeptide or agent binds human OX40 with a $K_D$ of about 0.1 nM or less.

In some embodiments, a polypeptide or agent binds human CD40 and/or mouse CD40 with a $K_D$ of about 10 nM or less. In some embodiments, a polypeptide or agent binds human CD40 and/or mouse CD40 with a $K_D$ of about 1 nM or less. In some embodiments, a polypeptide or agent binds human CD40 and/or mouse CD40 with a $K_D$ of about 0.1 nM or less. In some embodiments, a polypeptide or agent binds human CD40 and does not bind mouse CD40. In some embodiments, a polypeptide or agent binds human CD40 with a $K_D$ of about 10 nM or less. In some embodiments, a polypeptide or agent binds human CD40 with a $K_D$ of about 1 nM or less. In some embodiments, a polypeptide or agent binds human CD40 with a $K_D$ of about 0.1 nM or less.

In some embodiments, the dissociation constant of the polypeptide or agent to a member of the TNFRSF (e.g., GITR, OX40, or CD40) is the dissociation constant determined using a TNFRSF fusion protein comprising at least a portion of a TNFRSF extracellular domain immobilized on a Biacore chip.

In some embodiments, a polypeptide or agent binds a member of the TNFRSF (e.g., human GITR, OX40, or CD40) with a half maximal effective concentration ($EC_{50}$) of about 1 µM or less, about 100 nM or less, about 40 nM or less, about 20 nM or less, about 10 nM or less, about 1 nM or less, or about 0.1 nM or less.

In certain embodiments, fusion polypeptides are made using recombinant DNA techniques as known to one skilled in the art. In some embodiments, polynucleotides encoding a specific protein or a fragment thereof are isolated from mammalian cells, such as by RT-PCR using oligonucleotide primers that specifically amplify the gene encoding the protein, and the nucleotide sequence is determined using conventional techniques. The isolated polynucleotides encoding the protein may be cloned into suitable expression vectors which produce the polypeptide when transfected into host cells such as *E. coli*, simian COS cells, or Chinese hamster ovary (CHO) cells. In other embodiments, recombinant proteins, or fragments thereof, can be isolated from phage display libraries or using other cell surface display techniques.

The polynucleotide(s) encoding a protein can be modified in a number of different manners using recombinant DNA technology to generate alternative or variant proteins. Site-directed or high-density mutagenesis of a protein can be used to optimize specificity, affinity, stability, etc. of a recombinant protein.

Proteins generally contain a signal sequence that directs the transport of the proteins. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, 5, 6, 7, 8, 9, 10, or more amino acids. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions as compared to the native sequence of the protein. In some embodiments, the signal sequence of the polypeptide comprises amino acid substitutions and/or deletions that allow one cleavage site to be dominant, thereby resulting in a substantially homogeneous polypeptide with one N-terminus. In some embodiments, the signal sequence of a fusion polypeptide is not the native signal sequence of the protein(s) contained within the fusion polypeptide.

In certain embodiments, a polypeptide, agent, or fusion polypeptide described herein comprises the Fc region of an immunoglobulin. Those skilled in the art will appreciate that some of the polypeptides or agents of this invention will comprise fusion proteins in which at least a portion of the Fc region has been deleted or otherwise altered so as to provide desired biochemical characteristics, such as increased cancer cell localization, increased tumor penetration, reduced serum half-life, or increased serum half-life, when compared with a fusion protein of approximately the same immunogenicity comprising a native or unaltered Fc region. Modifications to the Fc region may include additions, deletions, or substitutions of one or more amino acids in one or more domains. The modified fusion proteins disclosed herein may comprise alterations or modifications to one or more of the two heavy chain constant domains (CH2 or CH3) or to the hinge region. In other embodiments, the entire CH2 domain may be removed (ΔCH2 constructs). In some embodiments, the omitted constant region domain is replaced by a short amino acid spacer (e.g., 10 aa residues) that provides some of the molecular flexibility typically imparted by the absent constant region domain.

In some embodiments, the modified fusion proteins are engineered to link the CH3 domain directly to the hinge region or to the first polypeptide. In other embodiments, a peptide spacer or linker is inserted between the hinge region or the first polypeptide and the modified CH2 and/or CH3 domains. For example, constructs may be expressed wherein the CH2 domain has been deleted and the remaining CH3 domain (modified or unmodified) is joined to the hinge region or first polypeptide with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the fusion protein.

In some embodiments, the modified fusion proteins may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete that part of one or more constant region domains that control a specific effector function (e.g., complement C1q binding). Such partial deletions of the constant regions may improve selected characteristics of the polypeptide or agent (e.g., serum half-life) while leaving other desirable functions associated with the subject constant region domain intact. Moreover, as alluded to above, the constant regions of the disclosed fusion proteins may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified fusion protein. In certain embodiments, the modified fusion proteins comprise the addition of one or more amino acids to the constant region to enhance desirable characteristics such as decreasing or increasing effector function, or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors).

In some embodiments, the modified fusion proteins provide for altered effector functions that, in turn, affect the biological profile of the polypeptide or agent. For example, in some embodiments, the deletion or inactivation (through point mutations or other means) of a constant region domain may reduce Fc receptor binding of the circulating modified agent, thereby increasing cancer cell localization and/or tumor penetration. In other embodiments, the constant region modifications increase or reduce the serum half-life of the polypeptide or agent. In some embodiments, the constant region is modified to eliminate disulfide linkages or oligosaccharide moiety attachment sites.

In certain embodiments, a modified fusion protein does not have one or more effector functions normally associated with an Fc region. In some embodiments, the polypeptide or agent has no antibody-dependent cell-mediated cytotoxicity (ADCC) activity, and/or no complement-dependent cytotoxicity (CDC) activity. In certain embodiments, the polypeptide or agent does not bind to the Fc receptor and/or complement factors. In certain embodiments, the polypeptide or agent has no effector function normally associated with an Fc region.

The polypeptides and agents of the present invention can be assayed for specific binding to a target by any method known in the art. The immunoassays which can be used include, but are not limited to, competitive and non-competitive assay systems using techniques such as Biacore analyses, FACS analyses, immunofluorescence, immunocytochemistry, Western blot analyses, radioimmunoassays, ELISAs, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well-known in the art.

For example, the specific binding of a test agent (e.g., a polypeptide) to human GITR may be determined using ELISA. An ELISA assay comprises preparing GITR protein, coating wells of a 96-well microtiter plate with the GITR, adding the test agent conjugated to a detectable compound such as an enzymatic substrate (e.g. horseradish peroxidase or alkaline phosphatase) to the well, incubating for a period of time and detecting the presence of the agent bound to GITR. In some embodiments, the test agent is not conjugated to a detectable compound, but instead a labeled secondary antibody that recognizes the agent is added to the well. In some embodiments, instead of coating the well with GITR, the test agent can be coated to the well, GITR is added, and a second antibody conjugated to a detectable compound that recognizes GITR can be used to detect binding. One of skill in the art would be knowledgeable as to the parameters that can be modified to increase the signal detected as well as other variations of ELISAs known in the art.

In another example, the specific binding of a test agent e.g., a polypeptide) to human GITR may be determined using FACS. A FACS screening assay may comprise generating a cDNA construct that expresses GITR, transfecting the construct into cells, expressing GITR on the surface of the cells, mixing the test agent with the transfected cells, and incubating for a period of time. The cells bound by the test agent may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of a test agent to a target (e.g., human GITR) and the off-rate of an agent-target interaction can be determined by competitive binding assays. One example of a competitive binding assay is a radioimmunoassay comprising the incubation of labeled target (e.g., $^3$H or $^{125}$I-labeled GITR), or fragment or variant thereof, with the agent of interest in the presence of increasing amounts of unlabeled target followed by the detection of the agent bound to the labeled target. The affinity of the agent for a target (e.g., human GITR) and the binding off-rates can be determined from the data by Scatchard plot analysis. In some embodiments, Biacore kinetic analysis is used to determine the binding on and off rates of agents that bind a target (e.g., human GITR). Biacore kinetic analysis comprises analyzing the binding and dissociation of agents from chips with immobilized target (e.g., human GITR) on the chip surface.

This invention also encompasses homodimeric agents and heterodimeric agents/molecules. In some embodiments, the homodimeric agents are polypeptides. In some embodiments, the heterodimeric molecules are polypeptides. Generally the homodimeric molecule comprises two identical polypeptides. Generally the heterodimeric molecule comprises two non-identical polypeptides. In some embodiments, a heterodimeric molecule is capable of binding at least two targets, e.g., a bispecific agent. The targets may be, for example, two different proteins on a single cell or two different proteins on two separate cells. In some embodiments, the bispecific agents are polypeptides. Thus, in some embodiments, one polypeptide of the heterodimeric molecule comprises a polypeptide described herein (e.g., a single chain trimer-Fc protein that binds GITR, OX40, or CD40) and one polypeptide of the heterodimeric molecule is an antibody. The term "arm" may be used herein to describe the structure of a homodimeric agent, a heterodimeric agent, and/or a bispecific agent. As used herein, each "arm" is directed against a target. In some embodiments, one "arm" may comprise an antigen-binding site from an antibody. In some embodiments, one "arm" may comprise a binding portion of a receptor. In some embodiments, a homodimeric agent comprises two identical arms. In some embodiments, a heterodimeric agent comprises two different arms. In some embodiments, a bispecific agent comprises two different arms.

In some embodiments, a bispecific agent comprises the polypeptides or agents described herein. In some embodiments, the bispecific agent is a homodimeric protein (FIG. 3(ii) shows representative depictions). In some embodiments, the homodimer bispecific agent comprises a polypeptide comprising a heavy chain immunoglobulin and a TNFSF trimer. In some embodiments, the heavy chain immunoglobulin is associated with a light chain to form an antigen-binding site. In some embodiments, the homodimeric bispecific agent comprises a polypeptide comprising an antibody and a single chain TNFSF trimer. In some embodiments, the homodimeric bispecific agent comprises a polypeptide comprising a single-chain antibody and a single chain TNFSF trimer. In some embodiments, the homodimeric bispecific agent comprises a polypeptide comprising an antibody and a single chain GITRL trimer. In some embodiments, the homodimeric bispecific agent comprises a polypeptide comprising an antibody and a single chain OX40L trimer. In some embodiments, the homodimeric bispecific agent comprises a polypeptide comprising an antibody and a single chain CD40L trimer. In some embodiments, the homodimeric bispecific agent comprises an antibody that specifically binds a tumor antigen. In some embodiments, the homodimeric bispecific agent comprises an antibody that specifically binds an antigen on an immune cell. In some embodiments, the homodimeric bispecific agent comprises an antibody that specifically binds PD-1, PD-L1, CTLA-4, LAG-3, TIGIT, or TIM3. In some embodiments, the homodimeric bispecific agent binds GITR and PD-1. In some embodiments, the homodimeric bispecific agent binds GITR and PD-L1. In some embodiments, the homodimeric bispecific agent binds OX-40 and PD-1. In some embodiments, the homodimeric bispecific agent binds OX-40 and PD-L1. In some embodiments, the homodimeric bispecific agent binds CD40 and PD-1. In some embodiments, the homodimeric bispecific agent binds CD40 and PD-L1.

Figure 3:
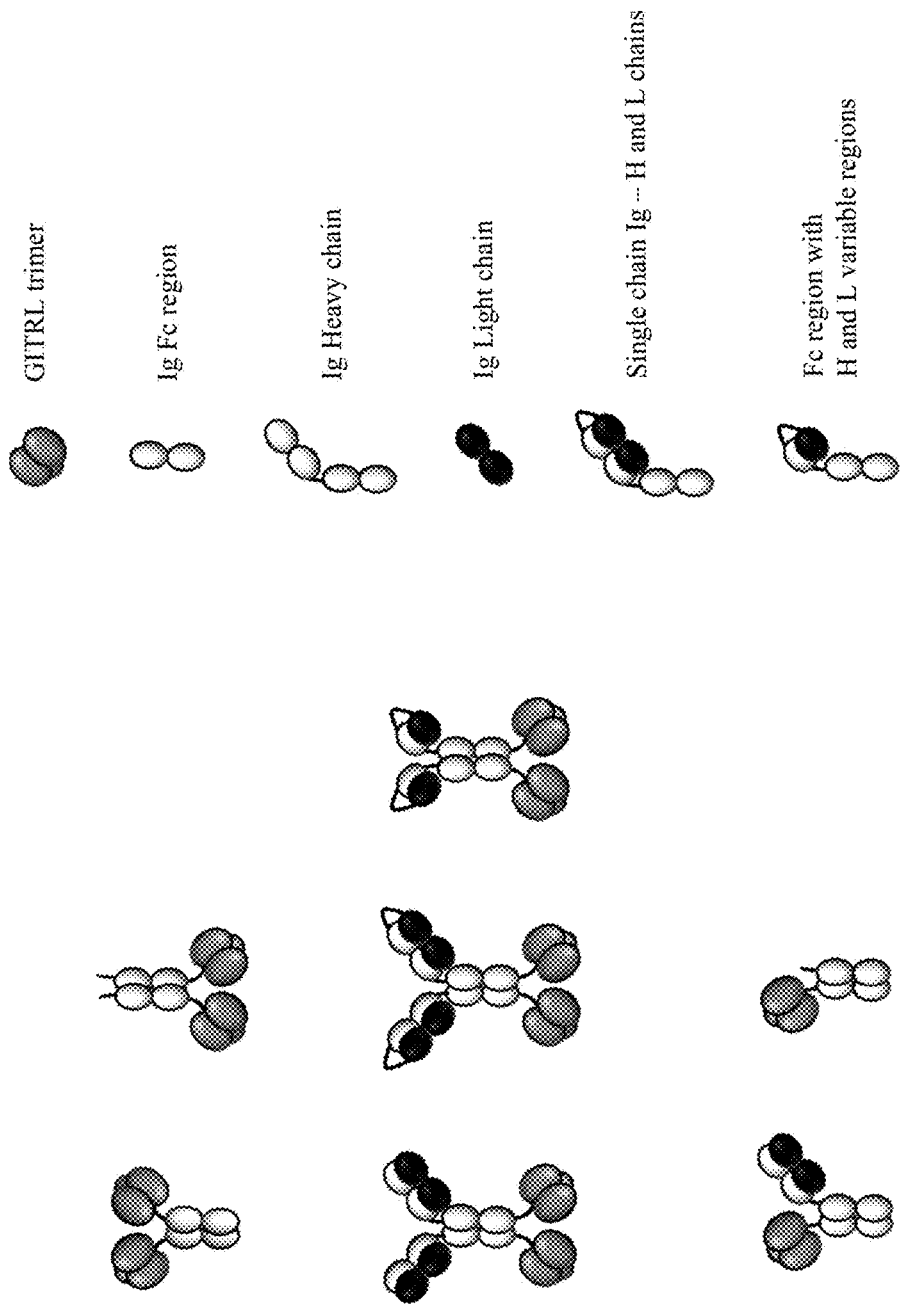
FIG. 3. Schematic depictions of some of the molecules proposed that contain one or more single chain GITRL trimers. These depictions are representative of additional molecules proposed that contain one or more single chain TNFSF ligand trimers.

In some embodiments, the bispecific agent is a heterodimeric protein (FIG. 3(iii) shows a representative depiction). In some embodiments, the heterodimeric bispecific agent comprises an antigen-binding site from an antibody (e.g., an antigen-binding site formed by an immunoglobulin heavy chain and an immunoglobulin light chain) and a TNFSF trimer. In certain embodiments, a bispecific agent comprises an immune response stimulating agent or functional fragment thereof and a TNFSF trimer.

In some embodiments, a heterodimeric bispecific agent is capable of binding one target and also comprises a "non-binding" function. Thus in some embodiments, one polypeptide of the heterodimeric bispecific agent comprises a polypeptide described herein (e.g., binds a TNFRSF such as GITR, OX40, or CD40) and one polypeptide of the heterodimeric agent is an additional immune response stimulating agent. As used herein, the phrase "immune response stimulating agent" is used in the broadest sense and refers to a substance that directly or indirectly stimulates the immune system by inducing activation or increasing activity of any of the immune system's components. For example, immune response stimulating agents may include cytokines, as well as various antigens including tumor antigens, and antigens derived from pathogens. In some embodiments, the immune response stimulating agent includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), an antibody that blocks immunosuppressive functions (e.g., an anti-CTLA-4 antibody, anti-CD28 antibody, anti-PD-1 antibody, anti-PD-L1 antibody), a toll-like receptor (e.g., TLR4, TLR7, TLR9), or a member of the B7 family (e.g., CD80, CD86).

In some embodiments, a heterodimeric bispecific agent comprises a first polypeptide comprising a GITRL trimer and a second polypeptide comprising an antibody that specifically binds a tumor antigen. In some embodiments, a heterodimeric bispecific agent comprises a first polypeptide comprising a OX40L trimer and a second polypeptide comprising an antibody that specifically binds a tumor antigen. In some embodiments, a heterodimeric bispecific agent comprises a first polypeptide comprising a CD40L trimer and a second polypeptide comprising an antibody that specifically binds a tumor antigen. A bispecific agent with a binding specificity for a tumor antigen can be used to direct the GITRL, OX40L, or CD40L trimer polypeptide to a tumor. For example the bispecific agent may be used to direct the GITRL, OX40L, or CD40L trimer polypeptide to a tumor that expresses the tumor antigen or overexpresses the tumor antigen. This may be useful to induce and/or enhance an immune response near or within the tumor microenvironment. In some embodiments, a bispecific agent may be used to induce or enhance the activity of tumor infiltrating immune cells.

In some embodiments, a heterodimeric bispecific agent comprises a first polypeptide comprising a TNFSF trimer and a second polypeptide comprising an antibody that specifically binds an immune response molecule. In some embodiments, a heterodimeric bispecific agent comprises a first polypeptide comprising a GITRL trimer and a second polypeptide comprising an antibody that specifically binds an immune response molecule. In some embodiments, a heterodimeric bispecific agent comprises a first polypeptide comprising a OX40L trimer and a second polypeptide comprising an antibody that specifically binds an immune response molecule. In some embodiments, a heterodimeric bispecific agent comprises a first polypeptide comprising a CD40L trimer and a second polypeptide comprising an antibody that specifically binds an immune response molecule. In some embodiments, a heterodimeric bispecific agent comprises a first polypeptide comprising a GITRL trimer and a second polypeptide comprising an antibody that specifically binds an immune checkpoint protein. In some embodiments, a heterodimeric bispecific agent comprises a first polypeptide comprising an OX40L trimer and a second polypeptide comprising an antibody that specifically binds an immune checkpoint protein. In some embodiments, a heterodimeric bispecific agent comprises a first polypeptide comprising a CD40L trimer and a second polypeptide comprising an antibody that specifically binds an immune checkpoint protein. In some embodiments, a heterodimeric bispecific agent comprises a first polypeptide comprising a GITRL trimer and a second polypeptide comprising an antibody that specifically binds PD-1. In some embodiments, a heterodimeric bispecific agent comprises a first polypeptide comprising a GITRL trimer and a second polypeptide comprising an antibody that specifically binds PD-L1. In some embodiments, a heterodimeric bispecific agent comprises a first polypeptide comprising an OX40L trimer and a second polypeptide comprising an antibody that specifically binds PD-1. In some embodiments, a heterodimeric bispecific agent comprises a first polypeptide comprising an OX40L trimer and a second polypeptide comprising an antibody that specifically binds PD-L1. In some embodiments, a heterodimeric bispecific agent comprises a first polypeptide comprising a CD40L trimer and a second polypeptide comprising an antibody that specifically binds PD-1. In some embodiments, a heterodimeric bispecific agent comprises a first polypeptide comprising a CD40L trimer and a second polypeptide comprising an antibody that specifically binds PD-L1.

In some embodiments, the heterodimeric molecule (e.g., a bispecific agent) can bind a first target, (e.g., GITR, OX40, or CD40) as well as a second target, such as an effector molecule on a leukocyte (e.g., CD2, CD3, CD28, or CD80) or a Fc receptor (e.g., CD64, CD32, or CD16) so as to elicit a stronger cellular immune response.

In some embodiments, a bispecific agent, either heterodimeric or homodimeric, has enhanced potency as compared to an individual agent. It is known to those of skill in the art that any agent (e.g., a soluble protein or a cytokine) may have unique pharmacokinetics (PK) (e.g., circulating half-life). In some embodiments, a bispecific agent has the ability to synchronize the PK of two active agents and/or polypeptides wherein the two individual agents and/or polypeptides have different PK profiles. In some embodiments, a bispecific molecule has the ability to concentrate the actions of two agents and/or polypeptides in a common area (e.g., a tumor and/or tumor microenvironment). In some embodiments, a bispecific molecule has the ability to concentrate the actions of two agents and/or polypeptides to a common target (e.g., a tumor or a tumor cell). In some embodiments, a bispecific agent has the ability to target the actions of two agents and/or polypeptides to more than one biological pathway or more than one aspect of the immune response. In some embodiments, the bispecific agent has decreased toxicity and/or side effects than either of the polypeptides and/or agents alone. In some embodiments, the bispecific agent has decreased toxicity and/or side effects as compared to a mixture of the two individual polypeptides and/or agents. In some embodiments, the bispecific agent has an increased therapeutic index. In some embodiments, the bispecific agent has an increased therapeutic index as compared to a mixture of the two individual polypeptides and/or agents or the polypeptides and/or agents as single agents.

It is believed that a single chain TNFSF molecule may be more active than an anti-TNFSF agonist antibody, because a single chain TNFSF trimer would function, i.e., bind to three TNFRSF molecules, in a very similar manner as three native TNFSF molecules. In contrast, an anti-TNFRSF antibody is able to engage only two TNFRSF molecules, thereby reducing any potential effect. To make a bispecific molecule comprising an antibody, generally involves the antibody being monovalent (i.e., one-armed antibody). This reduces, if not completely eliminates, the effect of an agonist antibody, especially if activation depends upon clustering of the target molecules. A single chain TNFSF (e.g., a GITRL trimer, an OX40L trimer, or a CD40L trimer) is able to bind three TNFRSF molecules, thus as part of a heterodimeric or homodimeric bispecific molecule, it does not lose any functionality or potency.

In some embodiments, a heterodimeric bispecific molecule comprises a first polypeptide comprising a single chain TNFSF trimer and a second polypeptide comprising an antibody. In some embodiments, a heterodimeric bispecific molecule comprises a first polypeptide comprising a single chain TNFSF trimer and a second polypeptide comprising an antagonist antibody. In some embodiments, a heterodimeric bispecific molecule comprises a first polypeptide comprising a single chain GITRL trimer and a second polypeptide comprising an antagonist antibody. In some embodiments, a heterodimeric bispecific molecule comprises a first polypeptide comprising a single chain OX40L trimer and a second polypeptide comprising an antagonist antibody. In some embodiments, a heterodimeric bispecific molecule comprises a first polypeptide comprising a single chain CD40L trimer and a second polypeptide comprising an antagonist antibody.

In some embodiments, a heterodimeric bispecific agent comprises: (a) a first arm comprising a single chain fusion polypeptide comprising a first, second, and third copy of the extracellular domain of GITRL or a GITR-binding fragment thereof, and (b) a second arm comprising an antigen-binding site from an antibody. In some embodiments, a heterodimeric bispecific agent comprises: (a) a first arm comprising a single chain fusion polypeptide comprising a first, second, and third copy of the extracellular domain of GITRL or a GITR-binding fragment thereof, and (b) a second arm comprising an immune response stimulating agent. In some embodiments, at least one copy of the extracellular domain of GITRL of the first arm comprises SEQ ID NO:3 or SEQ ID NO:64. In some embodiments, the heterodimeric bispecific agent comprises a first arm comprising SEQ ID NO:5 or SEQ ID NO:66. In some embodiments, the heterodimeric bispecific agent comprises a first arm which further comprises a non-GITRL polypeptide. In some embodiments, the heterodimeric bispecific agent comprises a single chain fusion GITRL polypeptide described herein which is directly linked to a non-GITRL polypeptide. In some embodiments, the single chain fusion polypeptide is connected to the non-GITRL polypeptide by a linker. In some embodiments, the non-GITRL polypeptide comprises a human Fc region. In some embodiments, the non-GITRL polypeptide comprises SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:60, or SEQ ID NO:61.

In some embodiments, a heterodimeric bispecific agent comprises: (a) a first arm comprising a single chain fusion polypeptide comprising a first, second, and third copy of the extracellular domain of OX40L or an OX40-binding fragment thereof, and (b) a second arm comprising an antigen-binding site from an antibody. In some embodiments, a heterodimeric bispecific agent comprises: (a) a first arm comprising a single chain fusion polypeptide comprising a first, second, and third copy of the extracellular domain of OX40L or an OX40-binding fragment thereof, and (b) a second arm comprising an immune response stimulating agent. In some embodiments, at least one copy of the extracellular domain of OX40L of the first arm comprises SEQ ID NO:42, SEQ ID NO:67, SEQ ID NO:78, or SEQ ID NO:79. In some embodiments, the bispecific agent comprises a first arm comprising SEQ ID NO:44, SEQ ID NO:69, SEQ ID NO:71, or SEQ ID NO:72. In some embodiments, the heterodimeric bispecific agent comprises a first arm which further comprises a non-OX40L polypeptide. In some embodiments, the heterodimeric bispecific agent comprises a single chain fusion OX40L polypeptide described herein which is directly linked to a non-OX40L polypeptide. In some embodiments, the single chain fusion polypeptide is connected to the non-OX40L polypeptide by a linker. In some embodiments, the non-OX40L polypeptide comprises a human Fc region. In some embodiments, the non-OX40L polypeptide comprises SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:60, or SEQ ID NO:61.

In some embodiments, a heterodimeric bispecific agent comprises: (a) a first arm comprising a single chain fusion polypeptide comprising a first, second, and third copy of the extracellular domain of CD40L or an CD40-binding fragment thereof, and (b) a second arm comprising an antigen-binding site from an antibody. In some embodiments, a heterodimeric bispecific agent comprises: (a) a first arm comprising a single chain fusion polypeptide comprising a first, second, and third copy of the extracellular domain of CD40L or an CD40-binding fragment thereof, and (b) a second arm comprising an immune response stimulating agent. In some embodiments, at least one copy of the extracellular domain of CD40L of the first arm comprises SEQ ID NO:84, SEQ ID NO:103, SEQ ID NO:104, SEQ ID NO:105, or SEQ ID NO:106. In some embodiments, the bispecific agent comprises a first arm comprising SEQ ID NO:85 or SEQ ID NO:97. In some embodiments, the heterodimeric bispecific agent comprises a first arm which further comprises a non-CD40L polypeptide. In some embodiments, the heterodimeric bispecific agent comprises a single chain fusion CD40L polypeptide described herein which is directly linked to a non-CD40L polypeptide. In some embodiments, the single chain fusion polypeptide is connected to the non-CD40L polypeptide by a linker. In some embodiments, the non-CD40L polypeptide comprises a human Fc region. In some embodiments, the non-CD40L polypeptide comprises SEQ ID NO:26, SEQ ID NO:27, SEQ ID NO:28, SEQ ID NO:29, SEQ ID NO:30, SEQ ID NO:31, SEQ ID NO:58, SEQ ID NO:59, SEQ ID NO:60, or SEQ ID NO:61.

In some embodiments, a heterodimeric bispecific molecule comprises a first polypeptide comprising a single chain TNFSF trimer and a second polypeptide comprising an immune response stimulating agent. In some embodiments, a heterodimeric bispecific molecule comprises a first polypeptide comprising a single chain GITRL trimer and a second polypeptide comprising an immune response stimulating agent. In some embodiments, a heterodimeric bispecific molecule comprises a first polypeptide comprising a single chain OX40 trimer and a second polypeptide comprising an immune response stimulating agent. In some embodiments, a heterodimeric bispecific molecule comprises a first polypeptide comprising a single chain CD40 trimer and a second polypeptide comprising an immune response stimulating agent.

In some embodiments, the multimeric molecule (e.g., a bispecific agent) comprises a first CH3 domain and a second CH3 domain, each of which is modified to promote formation of heteromultimers or heterodimers. In some embodiments, the first and second CH3 domains are modified using a knobs-into-holes technique. In some embodiments, the first and second CH3 domains comprise changes in amino acids that result in altered electrostatic interactions. In some embodiments, the first and second CH3 domains comprise changes in amino acids that result in altered hydrophobic/hydrophilic interactions (see, for example, U.S. Patent App. Publication No. 2011/0123532).

In some embodiments, the heterodimeric molecule (e.g., a bispecific agent) comprises heavy chain constant regions selected from the group consisting of: (a) a first human IgG1 constant region, wherein the amino acids at positions corresponding to positions 253 and 292 of SEQ ID NO:15 are replaced with glutamate or aspartate, and a second human IgG1 constant region, wherein the amino acids at positions corresponding to 240 and 282 of SEQ ID NO:15 are replaced with lysine; (b) a first human IgG2 constant region, wherein the amino acids at positions corresponding to positions 249 and 288 of SEQ ID NO:16 are replaced with glutamate or aspartate, and a second human IgG2 constant region wherein the amino acids at positions corresponding to positions 236 and 278 of SEQ ID NO:16 are replaced with lysine; (c) a first human IgG3 constant region, wherein the amino acids at positions corresponding to positions 300 and 339 of SEQ ID NO:17 are replaced with glutamate or aspartate, and a second human IgG3 constant region wherein the amino acids at positions corresponding to positions 287 and 329 of SEQ ID NO:17 are replaced with lysine; and (d) a first human IgG4 constant region, wherein the amino acids at positions corresponding to positions 250 and 289 of SEQ ID NO:18 are replaced with glutamate or aspartate, and a second IgG4 constant region wherein the amino acids at positions corresponding to positions 237 and 279 of SEQ ID NO:18 are replaced with lysine.

In some embodiments, the heterodimeric molecule (e.g., a bispecific agent) comprises heavy chain CH2 and CH3 domains selected from the group consisting of: (a) a first human IgG1 CH2 and CH3 domain, wherein the amino acids at positions corresponding to positions 253 and 292 of SEQ ID NO:15 are replaced with glutamate or aspartate, and a second human IgG1 CH2 and CH3 domain, wherein the amino acids at positions corresponding to 240 and 282 of SEQ ID NO:15 are replaced with lysine; (b) a first human IgG2 CH2 and CH3 domain, wherein the amino acids at positions corresponding to positions 249 and 288 of SEQ ID NO:16 are replaced with glutamate or aspartate, and a second human IgG2 CH2 and CH3 domain, wherein the amino acids at positions corresponding to positions 236 and 278 of SEQ ID NO:16 are replaced with lysine; (c) a first human IgG3 CH2 and CH3 domain, wherein the amino acids at positions corresponding to positions 300 and 339 of SEQ ID NO:17 are replaced with glutamate or aspartate, and a second human IgG3 CH2 and CH3 domain, wherein the amino acids at positions corresponding to positions 287 and 329 of SEQ ID NO:17 are replaced with lysine; and (d) a first human IgG4 CH2 and CH3 domain, wherein the amino acids at positions corresponding to positions 250 and 289 of SEQ ID NO:18 are replaced with glutamate or aspartate, and a second IgG4 CH2 and CH3 domain, wherein the amino acids at positions corresponding to positions 237 and 279 of SEQ ID NO:18 are replaced with lysine.

In some embodiments, the heterodimeric molecule comprises two arms, wherein the first arm comprises a first human IgG1 constant region with amino acids substitutions at positions corresponding to positions 253 and 292 of SEQ ID NO:15, wherein the amino acids are replaced with glutamate or aspartate, and the second arm comprises a second human IgG1 constant region with amino acid substitutions at positions corresponding to positions 240 and 282 of SEQ ID NO:15, wherein the amino acids are replaced with lysine. In some embodiments, the two arms comprise a Fc region selected from the group consisting of SEQ ID NO:58, SEQ ID NO:59, SEQ ID NO:60, and SEQ ID NO:61. In some embodiments, the first arm comprises SEQ ID NO:58 and the second arm comprises SEQ ID NO:59. In some embodiments, the first arm comprises SEQ ID NO:60 and the second arm comprises SEQ ID NO:61.

In some embodiments, the heterodimeric molecule comprises two arms, wherein the first arm comprises a first human IgG2 constant region with amino acids substitutions at positions corresponding to positions 249 and 288 of SEQ ID NO:16, wherein the amino acids are replaced with glutamate or aspartate, and the second arm comprises a second human IgG2 constant region with amino acid substitutions at positions corresponding to positions 236 and 278 of SEQ ID NO:16, wherein the amino acids are replaced with lysine. In some embodiments, the two arms comprise a Fc region selected from the group consisting of SEQ ID NO:26, SEQ ID NO:27, SEQ ID NO:28, SEQ ID NO:29, SEQ ID NO:30, and SEQ ID NO:31. In some embodiments, the first arm comprises SEQ ID NO:26 and the second arm comprises SEQ ID NO:27. In some embodiments, the first arm comprises SEQ ID NO:28 and the second arm comprises SEQ ID NO:30. In some embodiments, the first arm comprises SEQ ID NO:29 and the second arm comprises SEQ ID NO:31.

In some embodiments, the polypeptides or agents are monovalent. In some embodiments, the polypeptide or agent is a soluble protein that is monovalent. In some embodiments, the polypeptides or agents described herein are bivalent. In some embodiments, the polypeptides or agents described herein are trivalent. In some embodiments, the polypeptides or agents described herein are monospecific. In some embodiments, the polypeptides or agents described herein are bispecific. In some embodiments, the polypeptides or agents described herein are multispecific. In some embodiments, the agent is a heterodimeric protein that comprises two arms wherein at least one arm is monovalent. In some embodiments, the agent is a heterodimeric protein that comprises two arms wherein at least one arm is bivalent. In some embodiments, the agent is a heterodimeric protein that comprises two arms wherein at least one arm is trivalent (i.e., binds three target molecules).

In some embodiments, the polypeptides or agents comprise polypeptides that are substantially homologous to the fusion proteins and/or polypeptides described herein. These agents can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art and described herein.

In certain embodiments, a polypeptide or agent described herein binds GITR and modulates an immune response. In certain embodiments, a polypeptide or agent described herein binds OX40 and modulates an immune response. In certain embodiments, a polypeptide or agent described herein binds CD40 and modulates an immune response. In some embodiments, a polypeptide or agent described herein activates and/or increases an immune response. In some embodiments, a polypeptide or agent described herein increases, promotes, or enhances cell-mediated immunity. In some embodiments, a polypeptide or agent described herein increases, promotes, or enhances innate cell-mediated immunity. In some embodiments, a polypeptide or agent described herein increases, promotes, or enhances adaptive cell-mediated immunity. In some embodiments, a polypeptide or agent described herein increases, promotes, or enhances T-cell activity. In some embodiments, a polypeptide or agent described herein increases, promotes, or enhances CD4+ T-cell activity. In some embodiments, a polypeptide or agent described herein increases, promotes, or enhances CD8+ T-cell activity. In some embodiments, a polypeptide or agent described herein increases, promotes, or enhances CTL activity. In some embodiments, a polypeptide or agent described herein increases, promotes, or enhances NK cell activity. In some embodiments, a polypeptide or agent described herein increases, promotes, or enhances lymphokine-activated killer cell (LAK) activity. In some embodiments, a polypeptide or agent described herein increases, promotes, or enhances tumor-infiltrating lymphocyte (TIL) activity. In some embodiments, a polypeptide or agent described herein inhibits or decreases Treg cell activity. In some embodiments, a polypeptide or agent described herein inhibits or decreases MDSC cell activity. In some embodiments, a polypeptide or agent described herein increases, promotes, or enhances tumor cell killing. In some embodiments, a polypeptide or agent described herein increases, promotes, or enhances the inhibition of tumor growth. In some embodiments, a polypeptide or agent described herein increases or enhances an effective immune response without causing substantial side effects and/or immune-based toxicities. In some embodiments, a polypeptide or agent described herein increases or enhances an effective immune response without causing cytokine release syndrome (CRS) or a cytokine storm.

In some embodiments, a polypeptide or agent described herein binds GITR and induces, enhances, increases, and/or prolongs GITR signaling. In some embodiments, a polypeptide or agent described herein binds OX40 and induces, enhances, increases, and/or prolongs OX40 signaling. In some embodiments, a polypeptide or agent described herein binds CD40 and induces, enhances, increases, and/or prolongs CD40 signaling.

In certain embodiments, a polypeptide or agent described herein is an agonist (either directly or indirectly) of human GITR. In some embodiments, a polypeptide or agent is an agonist of GITR and activates and/or increases an immune response. In some embodiments, a polypeptide or agent is an agonist of GITR and activates and/or increases activity of NK cells and/or T-cells (e.g., cytolytic activity or cytokine production). In certain embodiments, a polypeptide or agent increases the activity by at least about 10%, at least about 20%, at least about 30%, at least about 50%, at least about 75%, at least about 90%, or about 100%.

In certain embodiments, a polypeptide or agent described herein is an agonist (either directly or indirectly) of human OX40. In some embodiments, a polypeptide or agent is an agonist of OX40 and activates and/or increases an immune response. In some embodiments, a polypeptide or agent is an agonist of OX40 and activates and/or increases activity of NK cells and/or T-cells (e.g., cytolytic activity or cytokine production). In certain embodiments, a polypeptide or agent increases the activity by at least about 10%, at least about 20%, at least about 30%, at least about 50%, at least about 75%, at least about 90%, or about 100%.

In certain embodiments, a polypeptide or agent described herein is an agonist (either directly or indirectly) of human CD40. In some embodiments, a polypeptide or agent is an agonist of CD40 and activates and/or increases an immune response. In some embodiments, a polypeptide or agent is an agonist of CD40 and activates and/or increases activity of NK cells and/or T-cells (e.g., cytolytic activity or cytokine production). In certain embodiments, a polypeptide or agent increases the activity by at least about 10%, at least about 20%, at least about 30%, at least about 50%, at least about 75%, at least about 90%, or about 100%.

In certain embodiments, a polypeptide or agent described herein increases activation of a NK cell. In certain embodiments, a polypeptide or agent increases activation of a T-cell. In certain embodiments, the activation of a NK cell and/or a T-cell by a polypeptide or agent results in an increase in the level of activation of a NK cell and/or a T-cell of at least about 10%, at least about 25%, at least about 50%, at least about 75%, at least about 90%, or at least about 95%.

In certain embodiments, a polypeptide or agent described herein inhibits or decreases the suppressive activity of a Treg cell. In certain embodiments, a polypeptide or agent inhibits activity of a Treg cell. In certain embodiments, the inhibition of suppressive activity of a Treg cell by a polypeptide or agent results in an inhibition of suppressive activity of a Treg cell of at least about 10%, at least about 25%, at least about 50%, at least about 75%, at least about 90%, or at least about 95%.

In certain embodiments, a polypeptide or agent described herein inhibits or decreases the suppressive activity of a MDSC. In certain embodiments, a polypeptide or agent inhibits activity of a MDSC. In certain embodiments, the inhibition of suppressive activity of a MDSC by a polypeptide or agent results in an inhibition of suppressive activity of a MDSC of at least about 10%, at least about 25%, at least about 50%, at least about 75%, at least about 90%, or at least about 95%.

In vivo and in vitro assays for determining whether a polypeptide or agent (or candidate binding agent) modulates an immune response are known in the art or are being developed. In some embodiments, a functional assay that detects T-cell activation can be used. In some embodiments, a functional assay that detects Treg activity can be used. In some embodiments, a functional assay that detects MDSC activity can be used. In some embodiments, a functional assay that detects NK cell activity can be used. In some embodiments, a functional assay that detects cytolytic T-cell activity can be used. In some embodiments, an assay that detects cytokine production can be used. In some embodiments, an assay that detects cytokine-producing cells can be used.

In certain embodiments, a polypeptide or agent described herein is capable of inhibiting tumor growth. In certain embodiments, the polypeptide or agent is capable of inhibiting tumor growth in vivo (e.g., in a mouse model and/or in a human having cancer).

In certain embodiments, a polypeptide or agent described herein is capable of reducing the tumorigenicity of a tumor. In certain embodiments, the polypeptide or agent is capable of reducing the tumorigenicity of a tumor in an animal model, such as a mouse model. In certain embodiments, the polypeptide or agent is capable of reducing the tumorigenicity of a tumor comprising cancer stem cells in an animal model, such as a mouse model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236; U.S. Patent Publication No. 2008/0064049; and U.S. Patent Publication No. 2008/0178305.

In certain embodiments, a polypeptide or agent described herein has one or more of the following effects: inhibits proliferation of tumor cells, inhibits tumor growth, reduces the tumorigenicity of a tumor, reduces the tumorigenicity of a tumor by reducing the frequency of cancer stem cells in the tumor, triggers cell death of tumor cells, increases cell contact-dependent growth inhibition, increases tumor cell apoptosis, reduces epithelial mesenchymal transition (EMT), or decreases survival of tumor cells. In some embodiments, the polypeptide or agent has one or more of the following effects: inhibits viral infection, inhibits chronic viral infection, reduces viral load, triggers cell death of virus-infected cells, or reduces the number or percentage of virus-infected cells.

In certain embodiments, a polypeptide or agent described herein has a circulating half-life in mice, rats, cynomolgus monkeys, or humans of at least about 5 hours, at least about 10 hours, at least about 24 hours, at least about 2 days, at least about 3 days, at least about 1 week, at least about 2 weeks, or at least 3 weeks. In certain embodiments, the polypeptide or agent is an IgG (e.g., IgG1 or IgG2) fusion protein that has a circulating half-life in mice, rats, cynomolgus monkeys, or humans of at least about 5 hours, at least about 10 hours, at least about 24 hours, at least about 3 days, at least about 1 week, at least about 2 weeks, or at least 3 weeks. Methods of increasing (or decreasing) the half-life of agents such as polypeptides and soluble receptors are known in the art. For example, known methods of increasing the circulating half-life of IgG fusion proteins include the introduction of mutations in the Fc region which increase the pH-dependent binding of the antibody to the neonatal Fc receptor (FcRn) at pH 6.0. Known methods of increasing the circulating half-life of soluble receptors lacking a Fc region include such techniques as PEGylation.

In some embodiments of the present invention, the agent is a polypeptide. The polypeptide can be a recombinant polypeptide, a natural polypeptide, or a synthetic polypeptide that binds GITR. The polypeptide can be a recombinant polypeptide, a natural polypeptide, or a synthetic polypeptide that binds OX40. The polypeptide can be a recombinant polypeptide, a natural polypeptide, or a synthetic polypeptide that binds CD40. It will be recognized in the art that some amino acid sequences of the invention can be varied without significant effect of the structure or function of the protein. Thus, the invention further includes variations of the polypeptides which show substantial binding activity to GITR. The invention also includes variations of the polypeptides which show substantial binding activity to OX40. The invention also includes variations of the polypeptides which show substantial binding activity to CD40. In some embodiments, amino acid sequence variations of the polypeptides include deletions, insertions, inversions, repeats, and/or other types of substitutions.

The polypeptides, analogs and variants thereof, can be further modified to contain additional chemical moieties not normally part of the polypeptide. The derivatized moieties can improve the solubility, the biological half-life, and/or absorption of the polypeptide. The moieties can also reduce or eliminate undesirable side effects of the polypeptides and variants. An overview for chemical moieties can be found in *Remington: The Science and Practice of Pharmacy*, 22$^{nd}$ Edition, 2012, Pharmaceutical Press, London.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, a recombinant expression vector is used to amplify and express DNA encoding a polypeptide or agent described herein. For example, a recombinant expression vector can be a replicable DNA construct which has synthetic or cDNA-derived DNA fragments encoding a polypeptide chain of an agent operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9 and their derivatives, and wider host range plasmids, such as M13 and other filamentous single-stranded DNA phages.

Suitable host cells for expression of a polypeptide (or a protein to use as a target) include prokaryotes, yeast cells, insect cells, or higher eukaryotic cells under the control of appropriate promoters. Prokaryotes include gram-negative or gram-positive organisms, for example E. coli or Bacillus. Higher eukaryotic cells include established cell lines of mammalian origin as described below. Cell-free translation systems may also be employed. Appropriate cloning and expression vectors for use with bacterial, fungal, yeast, and mammalian cellular hosts are well known by those skilled in the art.

Various mammalian cell culture systems are used to express recombinant polypeptides. Expression of recombinant proteins in mammalian cells can be preferred because such proteins are generally correctly folded, appropriately modified, and biologically functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), and HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present invention provides cells comprising the polypeptides and agents described herein. In some embodiments, the cells produce the polypeptides and agents described herein. In certain embodiments, the cells produce a fusion protein. In some embodiments, the cells produce a soluble receptor/ligand. In some embodiments, the cells produce an antibody. In some embodiments, the cells produce a bispecific agent. In some embodiments, the cells produce a bispecific antibody. In some embodiments, the cells produce a homodimeric bispecific agent. In some embodiments, the cells produce a heterodimeric bispecific agent.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Isolated proteins can also be physically characterized using such techniques as proteolysis, mass spectrometry (MS), nuclear magnetic resonance (NMR), high performance liquid chromatography (HPLC), and x-ray crystallography.

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a polypeptide or agent. Some or all of the foregoing purification steps, in various combinations, can also be employed to provide a homogeneous recombinant protein.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

In certain embodiments, a polypeptide or agent described herein is a polypeptide that does not comprise an immunoglobulin Fc region. In certain embodiments, the polypeptide comprises a protein scaffold of a type selected from the group consisting of protein A, protein G, a lipocalin, a fibronectin domain, an ankyrin consensus repeat domain, and thioredoxin. A variety of methods for identifying and producing non-antibody polypeptides that bind with high affinity to a protein target are known in the art. In certain embodiments, phage display technology may be used to produce and/or identify a binding polypeptide. In certain embodiments, mammalian cell display technology may be used to produce and/or identify a binding polypeptide.

It can further be desirable to modify a polypeptide in order to increase (or decrease) its serum half-life. This can be achieved, for example, by incorporation of a salvage receptor binding epitope into the polypeptide by mutation of the appropriate region in the polypeptide or by incorporating the epitope into a peptide tag that is then fused to the polypeptide at either end or in the middle (e.g., by DNA or peptide synthesis).

Heteroconjugate molecules are also within the scope of the present invention. Heteroconjugate molecules are composed of two covalently joined polypeptides. Such molecules have, for example, been proposed to target immune cells to unwanted cells, such as tumor cells. It is also contemplated that the heteroconjugate molecules can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

In certain embodiments, a polypeptide or agent described herein can be used in any one of a number of conjugated (i.e. an immunoconjugate or radioconjugate) or non-conjugated forms. In certain embodiments, the polypeptides or agents can be used in a non-conjugated form to harness the subject's natural defense mechanisms including CDC and ADCC to eliminate malignant or cancer cells.

In certain embodiments, an agent described herein is a small molecule. The term "small molecule" generally refers to a low molecular weight organic compound which is by definition not a peptide/protein.

In some embodiments, a polypeptide or agent described herein is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, Aleurites fordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated agent. A variety of radionuclides are available for the production of radioconjugated agents including, but not limited to $^{90}Y$, $^{125}I$, $^{131}I$, $^{123}I$, $^{111}In$, $^{131}In$, $^{105}Rh$, $^{153}Sm$, $^{67}Cu$, $^{67}Ga$, $^{166}Ho$, $^{177}Lu$, $^{186}Re$, $^{188}Re$, and $^{212}Bi$. Conjugates of a polypeptide or agent and one or more small molecule toxins, such as a calicheamicin, maytansinoids, a trichothene, and CC1065, and the derivatives of these toxins that have toxin activity, can also be used. Conjugates of a polypeptide or agent and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

III. Polynucleotides

In certain embodiments, the invention encompasses polynucleotides comprising polynucleotides that encode a polypeptide or agent described herein. The term "polynucleotides that encode a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotide comprises a polynucleotide encoding a polypeptide comprising an amino acid sequence selected from the group consisting of: SEQ ID NO:3, SEQ ID NO:4, SEQ ID NO:5, SEQ ID NO:6, SEQ ID NO:7, SEQ ID NO:8, and SEQ ID NO:9. In certain embodiments, the polynucleotide comprises a polynucleotide encoding a polypeptide comprising an amino acid sequence selected from the group consisting of: SEQ ID NO:42, SEQ ID NO:43, SEQ ID NO:44, SEQ ID NO:45, SEQ ID NO:46, SEQ ID NO:47, SEQ ID NO:48, SEQ ID NO:70, SEQ ID NO:71, SEQ ID NO:72, SEQ ID NO:77, SEQ ID NO:78, SEQ ID NO:79, SEQ ID NO:80, and SEQ ID NO:81. In certain embodiments, the polynucleotide comprises a polynucleotide encoding a polypeptide comprising an amino acid sequence selected from the group consisting of: SEQ ID NO:83, SEQ ID NO:84, SEQ ID NO:85, SEQ ID NO:89, SEQ ID NO:90, SEQ ID NO:91, SEQ ID NO:92, SEQ ID NO:103, SEQ ID NO:104, SEQ ID NO:105, and SEQ ID NO:106. In some embodiments, the polynucleotide comprises a polynucleotide comprising a nucleotide sequence selected from the group consisting of: SEQ ID NO:22, SEQ ID NO:23, SEQ ID NO:24, SEQ ID NO:25, SEQ ID NO:51, SEQ ID NO:52, SEQ ID NO:53, SEQ ID NO:73, and SEQ ID NO:86. In some embodiments, a polynucleotide comprises a polynucleotide that encodes a polypeptide of any of the GITR-binding agents described herein. In some embodiments, the polynucleotide is a plasmid "hGITRL-hIgG1" deposited with ATCC at 10801 University Boulevard, Manassas, Va., USA, under the conditions of the Budapest Treaty on Apr. 21, 2015 and assigned designation number PTA-122112. In some embodiments, a polynucleotide comprises a polynucleotide that encodes a polypeptide of any of the OX40-binding agents described herein. In some embodiments, a polynucleotide comprises a polynucleotide that encodes a polypeptide of any of the CD40-binding agents described herein. In some embodiments, a polynucleotide comprises a polynucleotide that encodes a polypeptide of any of the GITR-binding agents described herein and a signal sequence. In some embodiments, a polynucleotide comprises a polynucleotide that encodes a polypeptide of any of the OX40-binding agents described herein and a signal sequence. In some embodiments, a polynucleotide comprises a polynucleotide that encodes a polypeptide of any of the CD40-binding agents described herein and a signal sequence. In some embodiments, a vector comprises the polynucleotide. In some embodiments, a cell comprises the polynucleotide. In some embodiments, a cell comprises the vector. In some embodiments, the cell is isolated.

In certain embodiments, a polynucleotide comprises a polynucleotide having a nucleotide sequence at least 80% identical, at least 85% identical, at least 90% identical, at least 95% identical, and in some embodiments, at least 96%, 97%, 98% or 99% identical to a polynucleotide encoding an amino acid sequence selected from the group consisting of: SEQ ID NO:3, SEQ ID NO:4, SEQ ID NO:5, SEQ ID NO:6, SEQ ID NO:7, SEQ ID NO:8, and SEQ ID NO:9. In certain embodiments, a polynucleotide comprises a polynucleotide having a nucleotide sequence at least 80% identical, at least 85% identical, at least 90% identical, at least 95% identical, and in some embodiments, at least 96%, 97%, 98% or 99% identical to a polynucleotide encoding an amino acid sequence selected from the group consisting of: SEQ ID NO:43, SEQ ID NO:43, SEQ ID NO:44, SEQ ID NO:45, SEQ ID NO:46, SEQ ID NO:47, SEQ ID NO:48, SEQ ID NO:70, SEQ ID NO:71, SEQ ID NO:72, SEQ ID NO:77, SEQ ID NO:78, SEQ ID NO:79, SEQ ID NO:80, and SEQ ID NO:81. In certain embodiments, a polynucleotide comprises a polynucleotide having a nucleotide sequence at least 80% identical, at least 85% identical, at least 90% identical, at least 95% identical, and in some embodiments, at least 96%, 97%, 98% or 99% identical to a polynucleotide encoding an amino acid sequence selected from the group consisting of: SEQ ID NO:83, SEQ ID NO:84, SEQ ID NO:85, SEQ ID NO:89, SEQ ID NO:90, SEQ ID NO:91, SEQ ID NO:92, SEQ ID NO:103, SEQ ID NO:104, SEQ ID NO:105, and SEQ ID NO:106.

Also provided is a polynucleotide that comprises a polynucleotide that hybridizes to a polynucleotide encoding an amino acid sequence selected from the group consisting of: SEQ ID NO:3, SEQ ID NO:4, SEQ ID NO:5, SEQ ID NO:6, SEQ ID NO:7, SEQ ID NO:8, and SEQ ID NO:9. Also provided is a polynucleotide that comprises a polynucleotide that hybridizes to a polynucleotide encoding an amino acid sequence selected from the group consisting of: SEQ ID NO:42, SEQ ID NO:43, SEQ ID NO:44, SEQ ID NO:45, SEQ ID NO:46, SEQ ID NO:47, SEQ ID NO:48, SEQ ID NO:70, SEQ ID NO:71, SEQ ID NO:72, SEQ ID NO:77, SEQ ID NO:78, SEQ ID NO:79, SEQ ID NO:80, and SEQ ID NO:81. Also provided is a polynucleotide that comprises a polynucleotide that hybridizes to a polynucleotide encoding an amino acid sequence selected from the group consisting of: SEQ ID NO:83, SEQ ID NO:84, SEQ ID NO:85, SEQ ID NO:89, SEQ ID NO:90, SEQ ID NO:91, SEQ ID NO:92, SEQ ID NO:103, SEQ ID NO:104, SEQ ID NO:105, and SEQ ID NO:106. In certain embodiments, the hybridization is under conditions of high stringency. Conditions of high stringency are known to those of skill in the art and may include but are not limited to, (1) employ low ionic strength and high temperature for washing, for example 15 mM sodium chloride/1.5 mM sodium citrate (1×SSC) with 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ 50% formamide, 5×SSC, 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes in 0.2×SSC containing 50% formamide at 55° C., followed by a high-stringency wash consisting of 0.1×SSC containing EDTA at 55° C.

In certain embodiments, a polynucleotide comprises the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide. The polynucleotides can also encode for a pro-protein which is the mature protein plus additional 5' amino acid residues. A mature protein having a pro-sequence is a pro-protein and is an inactive form of the protein. Once the pro-sequence is cleaved an active mature protein remains.

In certain embodiments, a polynucleotide comprises the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:39) which can be used in conjunction with other affinity tags.

The present invention further relates to variants of the hereinabove described polynucleotides encoding, for example, fragments, analogs, and/or derivatives.

In certain embodiments, the present invention provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a polypeptide or agent described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heterodimeric molecule. In some embodiments, at least one polynucleotide variant is produced (without changing the amino acid sequence of the encoded polypeptide) to increase production of a bispecific agent, a bispecific antibody, or a heterodimeric agent.

In certain embodiments, the polynucleotides are isolated. In certain embodiments, the polynucleotides are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

IV. Methods of Use and Pharmaceutical Compositions

The polypeptides or agents of the invention are useful in a variety of applications including, but not limited to, therapeutic treatment methods, such as immunotherapy for cancer. In certain embodiments, a polypeptide or agent described herein is useful for activating, promoting, increasing, and/or enhancing an immune response, inhibiting tumor growth, reducing tumor volume, inducing tumor regression, increasing tumor cell apoptosis, and/or reducing the tumorigenicity of a tumor. In certain embodiments, the polypeptides or agents of the invention are also useful for immunotherapy against pathogens, such as viruses. In certain embodiments, a polypeptide or agent described herein is useful for inhibiting viral infection, reducing viral infection, increasing virally-infected cell apoptosis, and/or increasing killing of virus-infected cells. The methods of use may be in vitro, ex vivo, or in vivo methods.

The present invention provides methods for activating an immune response in a subject using a polypeptide or agent described herein. In some embodiments, the invention provides methods for promoting an immune response in a subject using a polypeptide or agent described herein. In some embodiments, the invention provides methods for increasing an immune response in a subject using a polypeptide or agent described herein. In some embodiments, the invention provides methods for enhancing an immune response in a subject using a polypeptide or agent described herein. In some embodiments, the activating, promoting, increasing, and/or enhancing of an immune response comprises increasing cell-mediated immunity. In some embodiments, the activating, promoting, increasing, and/or enhancing of an immune response comprises increasing Th1-type responses. In some embodiments, the activating, promoting, increasing, and/or enhancing of an immune response comprises increasing T-cell activity. In some embodiments, the activating, promoting, increasing, and/or enhancing of an immune response comprises increasing CD4+ T-cell activity. In some embodiments, the activating, promoting, increasing, and/or enhancing of an immune response comprises increasing CD8+ T-cell activity. In some embodiments, the activating, promoting, increasing, and/or enhancing of an immune response comprises increasing CTL activity. In some embodiments, the activating, promoting, increasing, and/or enhancing of an immune response comprises increasing NK cell activity. In some embodiments, the activating, promoting, increasing, and/or enhancing of an immune response comprises increasing T-cell activity and increasing NK cell activity. In some embodiments, the activating, promoting, increasing, and/or enhancing of an immune response comprises increasing CU activity and increasing NK cell activity. In some embodiments, the activating, promoting, increasing, and/or enhancing of an immune response comprises inhibiting or decreasing the suppressive activity of Treg cells. In some embodiments, the activating, promoting, increasing, and/or enhancing of an immune response comprises inhibiting or decreasing the suppressive activity of MDSCs. In some embodiments, the activating, promoting, increasing, and/or enhancing of an immune response comprises increasing the number of the percentage of memory T-cells. In some embodiments, the activating, promoting, increasing, and/or enhancing of an immune response comprises increasing long-term immune memory function. In some embodiments, the activating, promoting, increasing, and/or enhancing of an immune response comprises increasing long-term memory. In some embodiments, the activating, promoting, increasing, and/or enhancing of an immune response comprises no evidence of substantial side effects and/or immune-based toxicities. In some embodiments, the activating, promoting, increasing, and/or enhancing of an immune response comprises no evidence of cytokine release syndrome (CRS) or a cytokine storm. In some embodiments, the immune response is a result of antigenic stimulation. In some embodiments, the antigenic stimulation is a tumor cell. In some embodiments, the antigenic stimulation is cancer. In some embodiments, the antigenic stimulation is a pathogen. In some embodiments, the antigenic stimulation is a virally-infected cell.

In vivo and in vitro assays for determining whether an agent or polypeptide modulates, activates, or inhibits an immune response are known in the art or are being developed.

In some embodiments, a method of increasing an immune response in a subject comprises administering to the subject a therapeutically effective amount of a polypeptide or agent described herein, wherein the polypeptide or agent binds human GITR. In some embodiments, a method of increasing an immune response in a subject comprises administering to the subject a therapeutically effective amount of a polypeptide or agent described herein, wherein the polypeptide or agent is a single chain fusion polypeptide that specifically binds to GITR. In some embodiments, a method of increasing an immune response in a subject comprises administering to the subject a therapeutically effective amount of a polypeptide or agent described herein, wherein the polypeptide or agent comprises a single chain GITRL trimer.

In some embodiments, a method of increasing an immune response in a subject comprises administering to the subject a therapeutically effective amount of a polypeptide or agent described herein, wherein the polypeptide or agent binds human OX40. In some embodiments, a method of increasing an immune response in a subject comprises administering to the subject a therapeutically effective amount of a polypeptide or agent described herein, wherein the polypeptide or agent is a single chain fusion polypeptide that specifically binds to OX40. In some embodiments, a method of increasing an immune response in a subject comprises administering to the subject a therapeutically effective amount of a polypeptide or agent described herein, wherein the polypeptide or agent comprises a single chain OX40L trimer.

In some embodiments, a method of increasing an immune response in a subject comprises administering to the subject a therapeutically effective amount of a polypeptide or agent described herein, wherein the polypeptide or agent binds human CD40. In some embodiments, a method of increasing an immune response in a subject comprises administering to the subject a therapeutically effective amount of a polypeptide or agent described herein, wherein the polypeptide or agent is a single chain fusion polypeptide that specifically binds to CD40. In some embodiments, a method of increasing an immune response in a subject comprises administering to the subject a therapeutically effective amount of a polypeptide or agent described herein, wherein the polypeptide or agent comprises a single chain CD40L trimer.

In certain embodiments of the methods described herein, a method of activating or enhancing a persistent or long-term immune response to a tumor comprises administering to a subject a therapeutically effective amount of a polypeptide or agent which binds human GITR. In some embodiments, a method of activating or enhancing a persistent immune response to a tumor comprises administering to a subject a therapeutically effective amount of a polypeptide or agent described herein, wherein the polypeptide or agent is a single chain fusion polypeptide that specifically binds to GITR. In some embodiments, a method of activating or enhancing a persistent immune response to a tumor comprises administering to a subject a therapeutically effective amount of a polypeptide or agent described herein, wherein the polypeptide or agent comprises a single chain GITRL trimer. In some embodiments, the polypeptide comprises a single chain GITRL trimer and a Fc region. In some embodiments, the polypeptide is 336B3. In some embodiments, the polypeptide is 336B11.

In certain embodiments of the methods described herein, a method of activating or enhancing a persistent or long-term immune response to a tumor comprises administering to a subject a therapeutically effective amount of a polypeptide or agent which binds human OX40. In some embodiments, a method of activating or enhancing a persistent immune response to a tumor comprises administering to a subject a therapeutically effective amount of a polypeptide or agent described herein, wherein the polypeptide or agent is a single chain fusion polypeptide that specifically binds to OX40. In some embodiments, a method of activating or enhancing a persistent immune response to a tumor comprises administering to a subject a therapeutically effective amount of a polypeptide or agent described herein, wherein the polypeptide or agent comprises a single chain OX40L trimer. In some embodiments, the polypeptide comprises a single chain OX40L trimer and a Fc region.

In certain embodiments of the methods described herein, a method of activating or enhancing a persistent or long-term immune response to a tumor comprises administering to a subject a therapeutically effective amount of a polypeptide or agent which binds human CD40. In some embodiments, a method of activating or enhancing a persistent immune response to a tumor comprises administering to a subject a therapeutically effective amount of a polypeptide or agent described herein, wherein the polypeptide or agent is a single chain fusion polypeptide that specifically binds to CD40. In some embodiments, a method of activating or enhancing a persistent immune response to a tumor comprises administering to a subject a therapeutically effective amount of a polypeptide or agent described herein, wherein the polypeptide or agent comprises a single chain CD40L trimer. In some embodiments, the polypeptide comprises a single chain CD40L trimer and a Fc region.

In certain embodiments of the methods described herein, a method of inducing a persistent or long-term immunity which inhibits tumor relapse or tumor regrowth comprises administering to a subject a therapeutically effective amount of a polypeptide or agent which binds human GITR. In some embodiments, a method of inducing a persistent immunity which inhibits tumor relapse or tumor regrowth comprises administering to a subject a therapeutically effective amount of a polypeptide or agent described herein, wherein the polypeptide or agent is a single chain fusion polypeptide that specifically binds to GITR. In some embodiments, a method of inducing a persistent immunity which inhibits tumor relapse or tumor regrowth comprises administering to a subject a therapeutically effective amount of a polypeptide or agent described herein, wherein the polypeptide or agent comprises a single chain GITRL trimer. In some embodiments, the polypeptide comprises a single chain GITRL trimer and a Fc region. In some embodiments, the polypeptide is 336B3. In some embodiments, the polypeptide is 336B11.

In certain embodiments of the methods described herein, a method of inducing a persistent or long-term immunity which inhibits tumor relapse or tumor regrowth comprises administering to a subject a therapeutically effective amount of a polypeptide or agent which binds human OX40. In some embodiments, a method of inducing a persistent immunity which inhibits tumor relapse or tumor regrowth comprises administering to a subject a therapeutically effective amount of a polypeptide or agent described herein, wherein the polypeptide or agent is a single chain fusion polypeptide that specifically binds to OX40. In some embodiments, a method of inducing a persistent immunity which inhibits tumor relapse or tumor regrowth comprises administering to a subject a therapeutically effective amount of a polypeptide or agent described herein, wherein the polypeptide or agent comprises a single chain OX40L trimer. In some embodiments, the polypeptide comprises a single chain OX40L trimer and a Fc region.

In certain embodiments of the methods described herein, a method of inducing a persistent or long-term immunity which inhibits tumor relapse or tumor regrowth comprises administering to a subject a therapeutically effective amount of a polypeptide or agent which binds human CD40. In some embodiments, a method of inducing a persistent immunity which inhibits tumor relapse or tumor regrowth comprises administering to a subject a therapeutically effective amount of a polypeptide or agent described herein, wherein the polypeptide or agent is a single chain fusion polypeptide that specifically binds to CD40. In some embodiments, a method of inducing a persistent immunity which inhibits tumor relapse or tumor regrowth comprises administering to a subject a therapeutically effective amount of a polypeptide or agent described herein, wherein the polypeptide or agent comprises a single chain CD40L trimer. In some embodiments, the polypeptide comprises a single chain CD40L trimer and a Fc region.

In certain embodiments of the methods described herein, a method of inhibiting tumor relapse or tumor regrowth comprises administering to a subject a therapeutically effective amount of a polypeptide or agent which binds human GITR. In some embodiments, a method of inhibiting tumor relapse or tumor regrowth comprises administering to a subject a therapeutically effective amount of a polypeptide or agent described herein, wherein the polypeptide or agent is a single chain fusion polypeptide that specifically binds to GITR. In some embodiments, a method of inhibiting tumor relapse or tumor regrowth comprises administering to a subject a therapeutically effective amount of a polypeptide or agent described herein, wherein the polypeptide or agent comprises a single chain GITRL trimer. In some embodiments, the polypeptide comprises a single chain GITRL trimer and a Fc region. In some embodiments, the polypeptide is 336B3. In some embodiments, the polypeptide is 336B11.

In certain embodiments of the methods described herein, a method of inhibiting tumor relapse or tumor regrowth comprises administering to a subject a therapeutically effective amount of a polypeptide or agent which binds human OX40. In some embodiments, a method of inhibiting tumor relapse or tumor regrowth comprises administering to a subject a therapeutically effective amount of a polypeptide or agent described herein, wherein the polypeptide or agent is a single chain fusion polypeptide that specifically binds to OX40. In some embodiments, a method of inhibiting tumor relapse or tumor regrowth comprises administering to a subject a therapeutically effective amount of a polypeptide or agent described herein, wherein the polypeptide or agent comprises a single chain OX40L trimer. In some embodiments, the polypeptide comprises a single chain OX40L trimer and a Fc region.

In certain embodiments of the methods described herein, a method of inhibiting tumor relapse or tumor regrowth comprises administering to a subject a therapeutically effective amount of a polypeptide or agent which binds human CD40. In some embodiments, a method of inhibiting tumor relapse or tumor regrowth comprises administering to a subject a therapeutically effective amount of a polypeptide or agent described herein, wherein the polypeptide or agent is a single chain fusion polypeptide that specifically binds to CD40. In some embodiments, a method of inhibiting tumor relapse or tumor regrowth comprises administering to a subject a therapeutically effective amount of a polypeptide or agent described herein, wherein the polypeptide or agent comprises a single chain CD40L trimer. In some embodiments, the polypeptide comprises a single chain CD40L trimer and a Fc region.

The present invention also provides methods for inhibiting growth of a tumor using a polypeptide or agent described herein. In certain embodiments, the method of inhibiting growth of a tumor comprises contacting a cell mixture with a polypeptide or agent in vitro. For example, an immortalized cell line or a cancer cell line mixed with immune cells (e.g., T-cells, cytolytic T-cells, or NK cells) is cultured in medium to which is added a test agent. In some embodiments, tumor cells are isolated from a patient sample such as, for example, a tissue biopsy, pleural effusion, or blood sample, mixed with immune cells (e.g., T-cells, cytolytic T-cell, and/or NK cells), and cultured in medium to which is added a test agent. In some embodiments, the polypeptide or agent increases, promotes, and/or enhances the activity of the immune cells. In some embodiments, the polypeptide or agent inhibits tumor cell growth.

In some embodiments, the method of inhibiting growth of a tumor comprises contacting the tumor or tumor cells with a polypeptide or agent described herein in vivo. In certain embodiments, contacting a tumor or tumor cell with a polypeptide or agent is undertaken in an animal model. For example, a test agent may be administered to mice which have tumors. In some embodiments, the polypeptide or agent increases, promotes, and/or enhances the activity of immune cells in the mice. In some embodiments, the polypeptide or agent inhibits tumor growth. In some embodiments, the polypeptide or agent is administered at the same time or shortly after introduction of tumor cells into the animal to prevent tumor growth ("preventative model"). In some embodiments, the polypeptide or agent is administered as a therapeutic after tumors have grown to a specified size ("therapeutic model").

In certain embodiments, the method of inhibiting growth of a tumor comprises administering to a subject a therapeutically effective amount of a polypeptide or agent described herein. In certain embodiments, the subject is a human. In certain embodiments, the subject has a tumor or the subject had a tumor which was removed.

In addition, the invention provides a method of inhibiting growth of a tumor in a subject, comprising administering to the subject a therapeutically effective amount of a polypeptide or agent described herein. In certain embodiments, the tumor comprises cancer stem cells. In certain embodiments, the frequency of cancer stem cells in the tumor is reduced by administration of the polypeptide or agent. In some embodiments, a method of reducing the frequency of cancer stem cells in a tumor in a subject, comprising administering to the subject a therapeutically effective amount of a polypeptide or agent is provided. In some embodiments, the polypeptide is 336B3. In some embodiments, the polypeptide is 336B11.

In addition, the invention provides a method of reducing the tumorigenicity of a tumor in a subject, comprising administering to the subject a therapeutically effective amount of a polypeptide or agent described herein. In certain embodiments, the tumor comprises cancer stem cells. In some embodiments, the tumorigenicity of a tumor is reduced by reducing the frequency of cancer stem cells in the tumor. In some embodiments, the methods comprise using the polypeptides or agents described herein. In certain embodiments, the frequency of cancer stem cells in the tumor is reduced by administration of a polypeptide or agent.

In some embodiments, the tumor is a solid tumor. In certain embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, and head and neck tumor. In certain embodiments, the tumor is a colorectal tumor. In certain embodiments, the tumor is an ovarian tumor. In some embodiments, the tumor is a lung tumor. In certain embodiments, the tumor is a pancreatic tumor. In certain embodiments, the tumor is a melanoma tumor. In some embodiments, the tumor is a bladder tumor.

In some embodiments, the tumor expresses or overexpresses a tumor antigen targeted by the polypeptide or agent, such as a bispecific agent which comprises an antigen-binding site that specifically binds the tumor antigen.

The present invention further provides methods for treating cancer in a subject comprising administering to the subject a therapeutically effective amount of a polypeptide or agent described herein. In some embodiments, the polypeptide or agent binds GITR and inhibits or reduces growth of the cancer. In some embodiments, the polypeptide or agent binds OX40 and inhibits or reduces growth of the cancer. In some embodiments, the polypeptide or agent binds CD40 and inhibits or reduces growth of the cancer. In some embodiments, the polypeptide is 336B3. In some embodiments, the polypeptide is 336B11.

The present invention provides for methods of treating cancer comprising administering to a subject (e.g., a subject in need of treatment) a therapeutically effective amount of a polypeptide or agent described herein. In certain embodiments, the subject is a human. In certain embodiments, the subject has a cancerous tumor. In certain embodiments, the subject has had a tumor removed.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, brain cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer. In certain embodiments, the cancer is melanoma. In some embodiments, the cancer is bladder cancer.

In some embodiments, the cancer is a hematologic cancer. In some embodiment, the cancer is selected from the group consisting of: acute myelogenous leukemia (AML), Hodgkin lymphoma, multiple myeloma, T-cell acute lymphoblastic leukemia (T-ALL), chronic lymphocytic leukemia (CLL), hairy cell leukemia, chronic myelogenous leukemia (CML), non-Hodgkin lymphoma, diffuse large B-cell lymphoma (DLBCL), mantle cell lymphoma (MCL), and cutaneous T-cell lymphoma (CTCL).

The invention also provides a method of activating or enhancing TNFRSF (e.g., GITR, OX40, or CD40) signaling in a cell comprising contacting the cell with an effective amount of a polypeptide or agent described herein. In some embodiments, a method of activating or enhancing GITR signaling in a cell comprises contacting the cell with an effective amount of a GITR-binding polypeptide or agent described herein. In some embodiments, a method of activating or enhancing OX40 signaling in a cell comprises contacting the cell with an effective amount of an OX40-binding polypeptide or agent described herein. In some embodiments, a method of activating or enhancing CD40 signaling in a cell comprises contacting the cell with an effective amount of a CD40-binding polypeptide or agent described herein. In some embodiments, the polypeptide is 336B3. In some embodiments, the polypeptide is 336B11. In certain embodiments, the cell is a T-cell. In some embodiments, the cell is a cytolytic cell. In some embodiments, the cell is a CTL. In some embodiments, the cell is a NK cell. In certain embodiments, the method is an in vivo method wherein the step of contacting the cell with the polypeptide or agent comprises administering a therapeutically effective amount of the polypeptide or agent to the subject. In some embodiments, the method is an in vitro or ex vivo method.

The present invention provides methods of determining the level of expression of TNFRSF and/or TNFSF. In some embodiments, the level of expression of GITR is determined. In some embodiments, the level of expression of GITRL is determined. In some embodiments, the level of expression of OX40 is determined. In some embodiments, the level of expression of OX40L is determined. In some embodiments, the level of expression of CD40 is determined. In some embodiments, the level of expression of CD40L is determined. Methods for determining the level of nucleic acid expression in a cell, tumor, or cancer are known by those of skill in the art. These methods include, but are not limited to, PCR-based assays, microarray analyses, and nucleotide sequencing (e.g., NextGen sequencing). Methods for determining the level of protein expression in a cell, tumor, or cancer include, but are not limited to, Western blot analyses, protein arrays, ELISAs, immunohistochemistry (IHC), and FACS.

Methods for determining whether a tumor or cancer has an elevated level of expression of a nucleic acid or protein can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a blood sample. In some embodiments, the sample is a plasma sample. In some embodiments, the sample is processed to a cell lysate. In some embodiments, the sample is processed to DNA or RNA.

The present invention provides compositions comprising a polypeptide or agent described herein. The present invention also provides pharmaceutical compositions comprising a polypeptide or agent described herein and a pharmaceutically acceptable vehicle. In some embodiments, the pharmaceutical compositions find use in immunotherapy. In some embodiments, the pharmaceutical compositions find use in immuno-oncology. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining a purified agent of the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

In some embodiments, the polypeptides or agents described herein are formulated in a buffer comprising of 20 mM histidine, 40 mM NaCl, 5% sucrose, and 0.01% polysorbate 20. In some embodiments, the polypeptides or agents described herein are formulated in a buffer comprising of 20 mM histidine, 40 mM NaCl, 5% sucrose, and 0.01% polysorbate 20 at pH 5.5. In some embodiments, the polypeptides or agents described herein are formulated in a buffer comprising of 20 mM histidine, 40 mM NaCl, 5% sucrose, and 0.01% polysorbate 20 at pH 6.0. In some embodiments, the polypeptides or agents described herein are formulated in a buffer comprising of 20 mM histidine, 40 mM NaCl, 5% sucrose, and 0.01% polysorbate 20 at pH 6.5. In some embodiments, the polypeptides or agents described herein are formulated in a buffer comprising of 20 mM histidine, 100 mM NaCl, 150 mM sucrose, and 0.01% polysorbate 20 at pH 6.0. In some embodiments, the polypeptides or agents described herein are formulated in a buffer comprising of 10 mM potassium phosphate and 0.04% polysorbate 20 at pH 7.5.

Thus, in some embodiments the invention provides compositions or pharmaceutical compositions comprising a polypeptide or agent described herein and further comprising about 20 mM histidine, about 40 mM NaCl, about 5% sucrose, and about 0.01% polysorbate 20. In some embodiments the pH of the composition is about pH 5.5, about pH 6.0, or about pH 6.5.

In some embodiments, a polypeptide or agent described herein is lyophilized and/or stored in a lyophilized form. In some embodiments, a formulation comprising a polypeptide or agent described herein is lyophilized.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, 22$^{nd}$ Edition, 2012, Pharmaceutical Press, London.).

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The polypeptides or agents described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy*, 22$^{nd}$ Edition, 2012, Pharmaceutical Press, London.

In certain embodiments, pharmaceutical formulations include a polypeptide or agent of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising the polypeptides or agents described herein can be produced. Suitable examples of sustained-release preparations include semi-permeable matrices of solid hydrophobic polymers containing a polypeptide or agent, where the matrices are in the form of shaped articles (e.g., films or microcapsules). Examples of sustained-release matrices include polyesters, hydrogels such as poly(2-hydroxyethylmethacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering a polypeptide or agent described herein, the method or treatment further comprises administering at least one additional immune response stimulating agent. In some embodiments, the additional immune response stimulating agent includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), a checkpoint inhibitor, an antibody that blocks immunosuppressive functions (e.g., an anti-CTLA-4 antibody, anti-CD28 antibody, anti-CD3 antibody), a toll-like receptor (e.g., TLR4, TLR7, TLR9), or a member of the B7 family (e.g., CD80, CD86). An additional immune response stimulating agent can be administered prior to, concurrently with, and/or subsequently to, administration of the polypeptide or agent. Pharmaceutical compositions comprising a polypeptide or agent and the immune response stimulating agent(s) are also provided. In some embodiments, the immune response stimulating agent comprises 1, 2, 3, or more immune response stimulating agents.

In certain embodiments, in addition to administering a polypeptide or agent described herein, the method or treatment further comprises administering at least one additional therapeutic agent. An additional therapeutic agent can be administered prior to, concurrently with, and/or subsequently to, administration of the polypeptide or agent. Pharmaceutical compositions comprising a polypeptide or agent and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the polypeptide or agent(s). Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments of the methods described herein, the combination of a polypeptide or agent described herein and at least one additional therapeutic agent results in additive or synergistic results. In some embodiments, the combination therapy results in an increase in the therapeutic index of the polypeptide or agent. In some embodiments, the combination therapy results in an increase in the therapeutic index of the additional therapeutic agent(s). In some embodiments, the combination therapy results in a decrease in the toxicity and/or side effects of the polypeptide or agent. In some embodiments, the combination therapy results in a decrease in the toxicity and/or side effects of the additional therapeutic agent(s).

Useful classes of therapeutic agents include, for example, anti-tubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, anti-folates, anti-metabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor.

Therapeutic agents that may be administered in combination with the polypeptides or agents described herein include chemotherapeutic agents. Thus, in some embodiments, the method or treatment involves the administration of a polypeptide or agent of the present invention in combination with a chemotherapeutic agent or in combination with a cocktail of chemotherapeutic agents. Treatment with a polypeptide or agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book, 4th Edition*, 2008, M. C. Perry, Editor, Lippincott, Williams & Wilkins, Philadelphia, Pa.

Chemotherapeutic agents useful in the present invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments of the methods described herein, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments of the methods described herein, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (nab-paclitaxel; ABRAXANE), DHA-paclitaxel, or PG-paclitaxel. In certain alternative embodiments, the antimitotic agent comprises a vinca alkaloid, such as vincristine, vinblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel. In certain embodiments, the additional therapeutic agent is nab-paclitaxel.

In some embodiments of the methods described herein, an additional therapeutic agent comprises an agent such as a small molecule. For example, treatment can involve the combined administration of a polypeptide or agent of the present invention with a small molecule that acts as an inhibitor against tumor-associated antigens including, but not limited to, EGFR, HER2 (ErbB2), and/or VEGF. In some embodiments, a polypeptide or agent of the present invention is administered in combination with a protein kinase inhibitor selected from the group consisting of: gefitinib (IRESSA), erlotinib (TARCEVA), sunitinib (SUTENT), lapatinib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In certain embodiments of the methods described herein, the additional therapeutic agent is a small molecule that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an inhibitor of the Hippo pathway. In some embodiments, the additional therapeutic agent is an inhibitor of the mTOR/AKR pathway. In some embodiments, the additional therapeutic agent is an inhibitor of the RSPO/LGR pathway.

In some embodiments of the methods described herein, an additional therapeutic agent comprises a biological molecule, such as an antibody. For example, treatment can involve the combined administration of a polypeptide or agent of the present invention with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

In some embodiments of the methods described herein, the additional therapeutic agent is an antibody that modulates the immune response. In some embodiments, the additional therapeutic agent is an anti-PD-1 antibody, an anti-PD-L1 antibody, an anti-CTLA-4 antibody, or an anti-TIGIT antibody.

Furthermore, treatment with a polypeptide or agent described herein can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician. In some embodiments, the additional therapeutic agent is an immune response stimulating agent.

In some embodiments of the methods described herein, the polypeptide or agent can be combined with a growth factor selected from the group consisting of: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, P1GF, IL-1, IL-2, IL-3, IL-4, IL-5, IL-6, IL-7, IL-12, IL-15, and IL-18.

In some embodiments of the methods described herein, the additional therapeutic agent is an immune response stimulating agent. In some embodiments, the immune response stimulating agent is selected from the group consisting of granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), B7-1 (CD80), B7-2 (CD86), 4-1BB ligand, anti-CD3 antibody, anti-CTLA-4 antibody, anti-TIGIT antibody, anti-PD-1 antibody, anti-PD-L1 antibody, anti-LAG-3 antibody, and anti-TIM-3 antibody.

In some embodiments of the methods described herein, an immune response stimulating agent is selected from the group consisting of: a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, and an immunostimulatory oligonucleotide.

In some embodiments of the methods described herein, an immune response stimulating agent is selected from the group consisting of: a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, and/or an IDO1 antagonist.

In some embodiments of the methods described herein, the PD-1 antagonist is an antibody that specifically binds PD-1. In some embodiments, the antibody that binds PD-1 is KEYTRUDA (MK-3475), pidilizumab (CT-011), nivolumab (OPDIVO, BMS-936558, MDX-1106), MEDI0680 (AMP-514), REGN2810, BGB-A317, PDR-001, or STI-A1110. In some embodiments, the antibody that binds PD-1 is described in PCT Publication WO 2014/179664, for example, an antibody identified as APE2058, APE1922, APE1923, APE1924, APE 1950, or APE1963, or an antibody containing the CDR regions of any of these antibodies. In other embodiments, the PD-1 antagonist is a fusion protein that includes PD-L2, for example, AMP-224. In other embodiments, the PD-1 antagonist is a peptide inhibitor, for example, AUNP-12.

In some embodiments, the PD-L1 antagonist is an antibody that specifically binds PD-L1. In some embodiments, the antibody that binds PD-L1 is atezolizumab (RG7446, MPDL3280A), MEDI4736, BMS-936559 (MDX-1105), avelumab (MSB0010718C), KD033, the antibody portion of KD033, or STI-A1014. In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies.

In some embodiments, the CTLA-4 antagonist is an antibody that specifically binds CTLA-4. In some embodiments, the antibody that binds CTLA-4 is ipilimumab (YERVOY) or tremelimumab (CP-675,206). In some embodiments, the CTLA-4 antagonist a CTLA-4 fusion protein, for example, KAHR-102.

In some embodiments, the LAG3 antagonist is an antibody that specifically binds LAG3. In some embodiments, the antibody that binds LAG3 is IMP701, IMP731, BMS-986016, LAG525, and GSK2831781. In some embodiments, the LAG3 antagonist includes a soluble LAG3 receptor, for example, IMP321.

In some embodiments, the KIR antagonist is an antibody that specifically binds KIR. In some embodiments, the antibody that binds KIR is lirilumab.

In some embodiments, an immune response stimulating agent is selected from the group consisting of: a CD28 agonist, a 4-1BB agonist, an OX40 agonist, a CD27 agonist, a CD80 agonist, a CD86 agonist, a CD40 agonist, and a GITR agonist. p In some embodiments, the OX40 agonist includes OX40 ligand, or an OX40-binding portion thereof. For example, the OX40 agonist may be MEDI6383. In some embodiments, the OX40 agonist is an antibody that specifically binds OX40. In some embodiments, the antibody that binds OX40 is MEDI6469, MEDI0562, or MOXR0916 (RG7888). In some embodiments, the OX40 agonist is a vector (e.g., an expression vector or virus, such as an adenovirus) capable of expressing OX40 ligand. In some embodiments the OX40-expressing vector is Delta-24-RGDOX or DNX2401.

In some embodiments, the 4-1BB (CD137) agonist is a binding molecule, such as an anticalin. In some embodiments, the anticalin is PRS-343. In some embodiments, the 4-1BB agonist is an antibody that specifically binds 4-1BB. In some embodiments, antibody that binds 4-1BB is PF-2566 (PF-05082566) or urelumab (BMS-663513).

In some embodiments, the CD27 agonist is an antibody that specifically binds CD27. In some embodiments, the antibody that binds CD27 is varlilumab (CDX-1127).

In some embodiments, the GITR agonist comprises GITR ligand or a GITR-binding portion thereof. In some embodiments, the GITR agonist is an antibody that specifically binds GITR. In some embodiments, the antibody that binds GITR is TRX518, MK-4166, or INBRX-110.

In some embodiments, immune response stimulating agents include, but are not limited to, cytokines such as chemokines, interferons, interleukins, lymphokines, and members of the tumor necrosis factor (TNF) family. In some embodiments, immune response stimulating agents include immunostimulatory oligonucleotides, such as CpG dinucleotides.

In some embodiments, an immune response stimulating agent includes, but is not limited to, anti-PD-1 antibodies, anti-PD-L1 antibodies, anti-PD-L2 antibodies, anti-CTLA-4 antibodies, anti-CD28 antibodies, anti-CD80 antibodies, anti-CD86 antibodies, anti-4-1BB antibodies, anti-OX40 antibodies, anti-KIR antibodies, anti-Tim-3 antibodies, anti-LAG3 antibodies, anti-CD27 antibodies, anti-CD40 antibodies, anti-GITR antibodies, anti-TIGIT antibodies, anti-CD20 antibodies, anti-CD96 antibodies, or anti-IDO1 antibodies.

In some embodiments, a method of treating cancer in a subject comprises administering to the subject a therapeutically effective amount of a GITR-binding polypeptide or agent described herein in combination with a checkpoint inhibitor. In some embodiments, the checkpoint inhibitor is an anti-PD-1 antibody. In some embodiments, the checkpoint inhibitor is an anti-PD-1 antibody and the cancer is melanoma. In some embodiments, the checkpoint inhibitor is an anti-PD-1 antibody and the cancer is lung cancer. In some embodiments, the checkpoint inhibitor is an anti-PD-1 antibody and the cancer is bladder cancer. In some embodiments, the checkpoint inhibitor is an anti-PD-1 antibody and the cancer is a hematologic cancer.

In some embodiments, a method of treating cancer in a subject comprises administering to the subject a therapeutically effective amount of a GITR-binding polypeptide or agent described herein in combination with a checkpoint inhibitor. In some embodiments, the checkpoint inhibitor is an anti-PD-L1 antibody. In some embodiments, the checkpoint inhibitor is an anti-PD-L1 antibody and the cancer is melanoma. In some embodiments, the checkpoint inhibitor is an anti-PD-L1 antibody and the cancer is lung cancer. In some embodiments, the checkpoint inhibitor is an anti-PD-L1 antibody and the cancer is bladder cancer. In some embodiments, the checkpoint inhibitor is an anti-PD-L1 antibody and the cancer is breast cancer. In some embodiments, the checkpoint inhibitor is an anti-PD-L1 antibody and the cancer is a hematologic cancer.

In some embodiments, a method of treating cancer in a subject comprises administering to the subject a therapeutically effective amount of an OX40-binding polypeptide or agent described herein in combination with a checkpoint inhibitor. In some embodiments, the checkpoint inhibitor is an anti-PD-1 antibody. In some embodiments, the checkpoint inhibitor is an anti-PD-1 antibody and the cancer is melanoma. In some embodiments, the checkpoint inhibitor is an anti-PD-1 antibody and the cancer is lung cancer. In some embodiments, the checkpoint inhibitor is an anti-PD-1 antibody and the cancer is bladder cancer. In some embodiments, the checkpoint inhibitor is an anti-PD-1 antibody and the cancer is a hematologic cancer. In some embodiments, the checkpoint inhibitor is an anti-PD-L1 antibody. In some embodiments, the checkpoint inhibitor is an anti-PD-L1 antibody and the cancer is melanoma. In some embodiments, the checkpoint inhibitor is an anti-PD-L1 antibody and the cancer is lung cancer. In some embodiments, the checkpoint inhibitor is an anti-PD-L1 antibody and the cancer is bladder cancer. In some embodiments, the checkpoint inhibitor is an anti-PD-L1 antibody and the cancer is breast cancer. In some embodiments, the checkpoint inhibitor is an anti-PD-L1 antibody and the cancer is a hematologic cancer.

In some embodiments, a method of treating cancer in a subject comprises administering to the subject a therapeutically effective amount of a CD40-binding polypeptide or agent described herein in combination with a checkpoint inhibitor. In some embodiments, the checkpoint inhibitor is an anti-PD-1 antibody. In some embodiments, the checkpoint inhibitor is an anti-PD-1 antibody and the cancer is melanoma. In some embodiments, the checkpoint inhibitor is an anti-PD-1 antibody and the cancer is lung cancer. In some embodiments, the checkpoint inhibitor is an anti-PD-1 antibody and the cancer is bladder cancer. In some embodiments, the checkpoint inhibitor is an anti-PD-1 antibody and the cancer is a hematologic cancer. In some embodiments, the checkpoint inhibitor is an anti-PD-L1 antibody. In some embodiments, the checkpoint inhibitor is an anti-PD-L1 antibody and the cancer is melanoma. In some embodiments, the checkpoint inhibitor is an anti-PD-L1 antibody and the cancer is lung cancer. In some embodiments, the checkpoint inhibitor is an anti-PD-L1 antibody and the cancer is bladder cancer. In some embodiments, the checkpoint inhibitor is an anti-PD-L1 antibody and the cancer is breast cancer. In some embodiments, the checkpoint inhibitor is an anti-PD-L1 antibody and the cancer is a hematologic cancer.

In certain embodiments of the methods described herein, the treatment involves the administration of a polypeptide or agent of the present invention in combination with radiation therapy. Treatment with a polypeptide or agent can occur prior to, concurrently with, or subsequent to administration of radiation therapy. Dosing schedules for such radiation therapy can be determined by the skilled medical practitioner.

In certain embodiments of the methods described herein, the treatment involves the administration of a polypeptide or agent of the present invention in combination with anti-viral therapy. Treatment with a polypeptide or agent can occur prior to, concurrently with, or subsequent to administration of antiviral therapy. The anti-viral drug used in combination therapy will depend upon the virus the subject is infected with.

Combined administration can include co-administration, either in a single pharmaceutical formulation or using separate formulations, or consecutive administration in either order but generally within a time period such that all active agents can exert their biological activities simultaneously.

It will be appreciated that the combination of a polypeptide or agent described herein and at least one additional therapeutic agent may be administered in any order or concurrently. In some embodiments, the polypeptide or agent will be administered to patients that have previously undergone treatment with a second therapeutic agent. In certain other embodiments, the polypeptide or agent and a second therapeutic agent will be administered substantially simultaneously or concurrently. For example, a subject may be given a polypeptide or agent while undergoing a course of treatment with a second therapeutic agent (e.g., chemotherapy). In certain embodiments, a polypeptide or agent will be administered within 1 year of the treatment with a second therapeutic agent. In certain alternative embodiments, a polypeptide or agent will be administered within 10, 8, 6, 4, or 2 months of any treatment with a second therapeutic agent. In certain other embodiments, a polypeptide or agent will be administered within 4, 3, 2, or 1 weeks of any treatment with a second therapeutic agent. In some embodiments, a polypeptide or agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of a polypeptide or agent of the present invention depends on the type of disease to be treated, the severity and course of the disease, the responsiveness of the disease, whether the polypeptide or agent is administered for therapeutic or preventative purposes, previous therapy, the patient's clinical history, and so on, all at the discretion of the treating physician. The polypeptide or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual agent. The administering physician can determine optimum dosages, dosing methodologies, and repetition rates. In certain embodiments, dosage is from 0.01 µg to 100 mg/kg of body weight, from 0.1 µg to 100 mg/kg of body weight, from 1 µg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the polypeptide or agent is from about 0.1 mg to about 20 mg/kg of body weight. In some embodiments, the dosage of the polypeptide or agent is about 0.1 mg/kg of body weight. In some embodiments, the dosage of the polypeptide or agent is about 0.25 mg/kg of body weight. In some embodiments, the dosage of the polypeptide or agent is about 0.5 mg/kg of body weight. In some embodiments, the dosage of the polypeptide or agent is about 1 mg/kg of body weight. In some embodiments, the dosage of the polypeptide or agent is about 1.5 mg/kg of body weight. In some embodiments, the dosage of the polypeptide or agent is about 2 mg/kg of body weight. In some embodiments, the dosage of the polypeptide or agent is about 2.5 mg/kg of body weight. In some embodiments, the dosage of the polypeptide or agent is about 5 mg/kg of body weight. In some embodiments, the dosage of the polypeptide or agent is about 7.5 mg/kg of body weight. In some embodiments, the dosage of the polypeptide or agent is about 10 mg/kg of body weight. In some embodiments, the dosage of the polypeptide or agent is about 12.5 mg/kg of body weight. In some embodiments, the dosage of the polypeptide or agent is about 15 mg/kg of body weight. In certain embodiments, the dosage can be given once or more daily, weekly, monthly, or yearly. In certain embodiments, the polypeptide or agent is given once every week, once every two weeks, once every three weeks, or once every four weeks.

In some embodiments, a polypeptide or agent may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

In some embodiments, the dosing schedule may be limited to a specific number of administrations or "cycles". In some embodiments, the polypeptide or agent is administered for 3, 4, 5, 6, 7, 8, or more cycles. For example, the polypeptide or agent is administered every 2 weeks for 6 cycles, the polypeptide or agent is administered every 3 weeks for 6 cycles, the polypeptide or agent is administered every 2 weeks for 4 cycles, the polypeptide or agent is administered every 3 weeks for 4 cycles, etc. Dosing schedules can be decided upon and subsequently modified by those skilled in the art.

Thus, the present invention provides methods of administering to a subject the polypeptides or agents described herein comprising using an intermittent dosing strategy for administering one or more agents, which may reduce side effects and/or toxicities associated with administration of a polypeptide or agent, chemotherapeutic agent, etc. In some embodiments, a method for treating cancer in a human subject comprises administering to the subject a therapeutically effective dose of a polypeptide or agent in combination with a therapeutically effective dose of a chemotherapeutic agent, wherein one or both of the agents are administered according to an intermittent dosing strategy. In some embodiments, the intermittent dosing strategy comprises administering an initial dose of a polypeptide or agent to the subject, and administering subsequent doses of the polypeptide or agent about once every 2 weeks. In some embodiments, the intermittent dosing strategy comprises administering an initial dose of a polypeptide or agent to the subject, and administering subsequent doses of the polypeptide or agent about once every 3 weeks. In some embodiments, the intermittent dosing strategy comprises administering an initial dose of a polypeptide or agent to the subject, and administering subsequent doses of the polypeptide or agent about once every 4 weeks. In some embodiments, the polypeptide or agent is administered using an intermittent dosing strategy and the chemotherapeutic agent is administered weekly.

V. Screening

The present invention provides screening methods to identify agents that modulate the immune response. In some embodiments, the present invention provides methods for screening candidate agents, including but not limited to, proteins, antibodies, peptides, peptidomimetics, small molecules, compounds, or other drugs, which modulate the immune response.

In some embodiments, a method of screening for a candidate agent that modulates the immune response comprises determining if the polypeptide or agent has an effect on immune response cells. In some embodiments, a method of screening for a candidate agent that modulates the immune response comprises determining if the polypeptide or agent is capable of increasing the activity of immune cells. In some embodiments, a method of screening for a candidate agent that modulates the immune response comprises determining if the polypeptide or agent is capable of increasing the activity of cytolytic cells, such as CTLs and/or NK cells. In some embodiments, a method of screening for a candidate agent that modulates the immune response comprises determining if the polypeptide or agent is capable of inhibiting the activity of suppressor cells, such as Tregs and/or MDSCs.

VI. Kits Comprising Agents Described Herein

The present invention provides kits that comprise the polypeptides or agents described herein and that can be used to perform the methods described herein. In certain embodiments, a kit comprises at least one purified agent in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed agents of the present invention can be readily incorporated into one of the established kit formats which are well known in the art.

Further provided are kits that comprise a polypeptide or agent as well as at least one additional therapeutic agent. In certain embodiments, the second (or more) therapeutic agent is a chemotherapeutic agent. In certain embodiments, the second (or more) therapeutic agent is an angiogenesis inhibitor.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

Generation of Single Chain GITRL Trimer Constructs

As discussed herein hGITRL proteins organize into a homotrimer at the surface of cells and interact and/or engage with three GITR molecules. A representative diagram of a GITRL trimer on a cell surface is shown in FIG. 1A. The crystal structure of a human GITRL trimer was examined by the inventors and it was observed that the N-terminal amino acid residues from one monomer and the C-terminal amino acid residues from a second monomer were in close proximity to each other. This suggested that a very short span of amino acid residues, for example only 3-7 residues, might be sufficient to bridge the distance between each monomer and thereby enable a single chain GITRL trimer to be produced. Upon further analysis of the structure and sequence of GITRL, it was observed that there exists a span of several amino acids between the transmembrane domain and the TNF homology domain of the GITRL protein, this span is referred to as the "stalk" region (see FIGS. 1A and 1B). The inventors hypothesized that it would be possible to utilize this short stalk region to bridge the distance from the C-terminus of a GITRL monomer to the N-terminus of an adjacent GITRL monomer and in this fashion construct a single chain GITRL trimer that was devoid of exogenous peptide linker sequences.

Figure 1D:
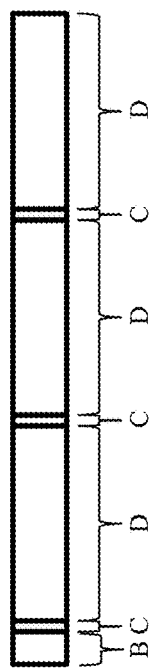

A membrane-bound single chain hGITRL trimer construct was generated using the transmembrane region (signal-anchor sequence—amino acids 51-70 of SEQ ID NO:1) and three copies of the stalk region and TNF family domain (amino acids 71-199 of SEQ ID NO:1; also SEQ ID NO:3). The sequence encompassing the stalk region and the TNF family domain is also referred to herein as the extracellular domain of GITRL. A representative diagram is shown in FIG. 1D.

Figure 1E:
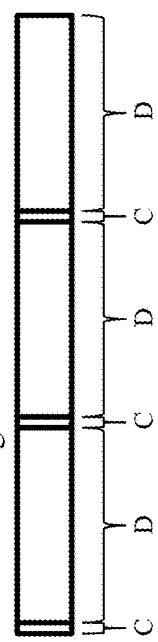
Figure 1F:
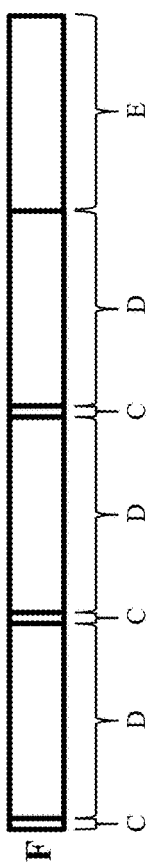

A soluble single chain hGITRL trimer construct was also generated (FIG. 1E). An additional construct was generated that comprised three copies of the extracellular domain of human GITRL linked to a human IgG1 Fc region (336B11; SEQ ID NO:6 with signal sequence and SEQ ID NO:7 without signal sequence). A representative diagram is shown in FIG. 1F.

The general outline disclosed herein for generating the GITRL trimer construct can be followed to produce other TNFSF trimer constructs. For example, the inventors have generated several OX40L trimers (SEQ ID NO:43, SEQ ID NO:44, SEQ ID NO:71; and SEQ ID NO:72), OX40L trimer-Fc proteins (SEQ ID NO:45, SEQ ID NO:46, SEQ ID NO:47, and SEQ ID NO:48), CD40L trimers (SEQ ID NO:85 and SEQ ID NO:88), and CD40L trimer-Fc proteins (SEQ ID NO:89, SEQ ID NO:90, SEQ ID NO:91 and SEQ ID NO:92).

Example 2

FACS Analysis of GITRL Trimer Binding to GITR

To test the ability of a single chain hGITRL trimer to bind human GITR, binding studies were conducted. Human HEK-293 cells were transiently co-transfected with expression vectors encoding (1) the membrane bound single chain hGITRL trimer construct described above and (2) green fluorescent protein (GFP) as a transfection marker. Twenty-four hours post-transfection, the cells were incubated with hGITR-Fc or a control fusion protein. The cells were stained with a PE-conjugated anti-human Fc secondary antibody and analyzed by flow cytometry.

Figure 2:
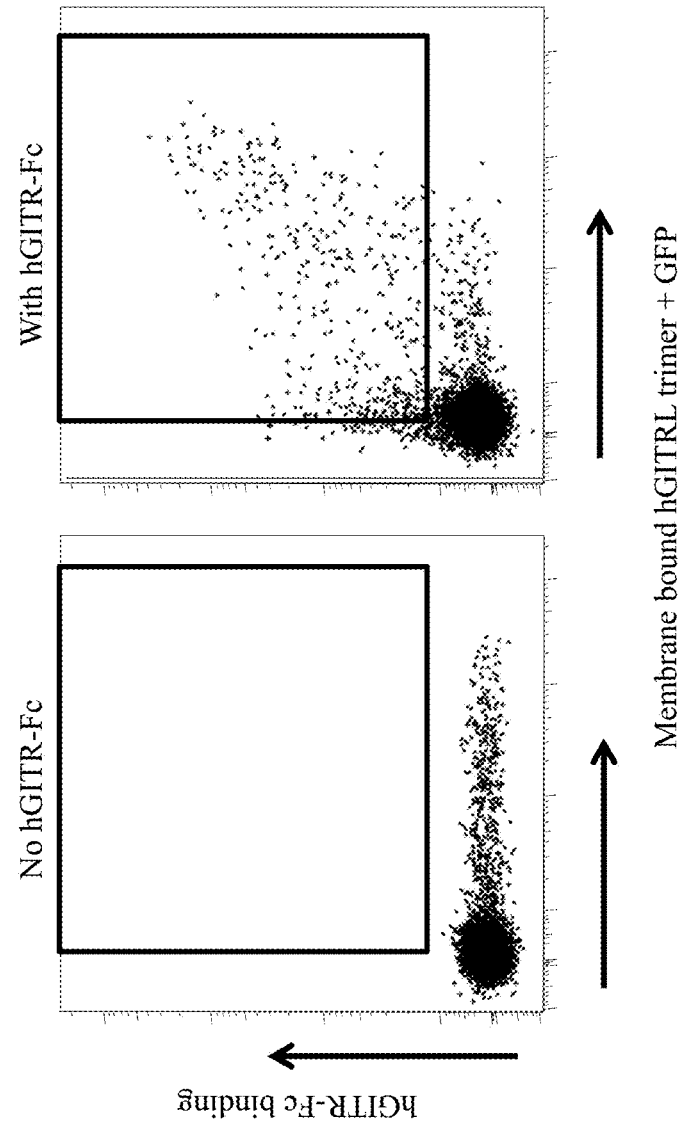
FIG. 2. FACS analysis of a membrane bound single chain GITRL trimer and soluble GITR. HEK293 cells were transiently transfected with an expression vector encoding a membrane bound single chain human GITRL trimer and a second expression vector encoding green fluorescent protein (GFP). Transfected cells were incubated with soluble human GITR-Fc fusion protein and analyzed by flow cytometry. Positive binding is determined by observation of cells within the inset box of the FACS plot.

As shown in FIG. 2, hGITR-Fc was able to bind to the single chain hGITRL trimer on the cell surface. These results demonstrated that the single chain hGITRL construct formed into a biologically functional trimeric structure and was able to interact with hGITR.

Example 3

GITRL Trimer Fusion Proteins and Binding

The inventors hypothesized that a soluble single chain GITRL trimer could be generated using an immunoglobulin Fc region backbone and that the GITRL trimer could potentially be linked to the N-terminus of the Fc region or the C-terminus of the Fc region. This would generate a molecule containing two GITRL trimers and could offer increased activity. The structural flexibility of the Fc region backbone could also allow generation of bispecific homodimeric agents. For example, an antibody-GITRL fusion protein could be designed wherein the single chain GITRL trimer is linked to an immunoglobulin heavy chain. To form an antigen binding site, the immunoglobulin heavy chain could be associated with an immunoglobulin light chain. An antibody-GITRL fusion protein could comprise an antibody heavy chain and a light chain as part of a single chain immunoglobulin. In a different design, an antibody-GITRL fusion protein could comprise a heavy chain variable region and a light chain variable region, such as a Fab or scFv.

Alternatively, one could design bispecific heterodimeric agents wherein one arm comprises a Fc fusion protein that comprises a single chain GITRL trimer and a second arm comprises a second Fc fusion protein that comprises an immunoglobulin heavy chain. As described above, to form an antigen binding site, the immunoglobulin heavy chain could be associated with an immunoglobulin light chain. The second arm could comprise an antibody heavy chain and a light chain as part of a single chain immunoglobulin or a Fc region linked to heavy chain variable region and a light chain variable region, such as a Fab or scFv. Schematic representations of some of these formats are shown in FIG. 3.

Several of these formats were produced as recombinant proteins using mouse IgG1 or IgG2 Fc regions, human IgG1 or IgG2 Fc regions, and mouse IgG1 or IgG2 antibodies. A pair of human IgG2 CH3 domain variants that preferentially heterodimerize were used to produce bispecific heterodimeric agents. 336B3 is a single chain mouse GITRL trimer linked to the C-terminus of a mouse IgG2a Fc region. 336B10 is a single chain mouse GITRL trimer linked to the N-terminus of a mouse IgG2a Fc region. 336B11 is a single chain human GITRL trimer linked to the N-terminus of a human IgG1 region. 336B11 comprises a fusion protein encoded by the plasmid "hGITRL-hIgG1" deposited with ATCC at 10801 University Boulevard, Manassas, Va., USA, under the conditions of the Budapest Treaty on Apr. 21, 2015 and assigned designation number PTA-122112. 336B1 is a single chain mouse GITRL trimer linked to a mouse IgG1 antibody. 336B2 is a single chain mouse GITRL trimer linked to a mouse IgG2a antibody. 336B4 is a heterodimeric agent wherein one arm is a mouse GITRL trimer linked to a human IgG2 Fc region and the second arm is a mouse antibody variable region linked to a human IgG2 Fc region.

To test the ability of these fusion proteins to interact with GITR, binding studies were conducted. Human HEK-293 cells were transiently co-transfected with expression vectors encoding (1) a full-length mouse GITR (cell surface expression) and (2) GFP as a transfection marker. Twenty-four hours post-transfection, the cells were incubated with the GITRL fusion proteins or control proteins. The cells were stained with a PE-conjugated anti-human or anti-mouse Fc secondary antibody and analyzed by flow cytometry.

Figure 4:
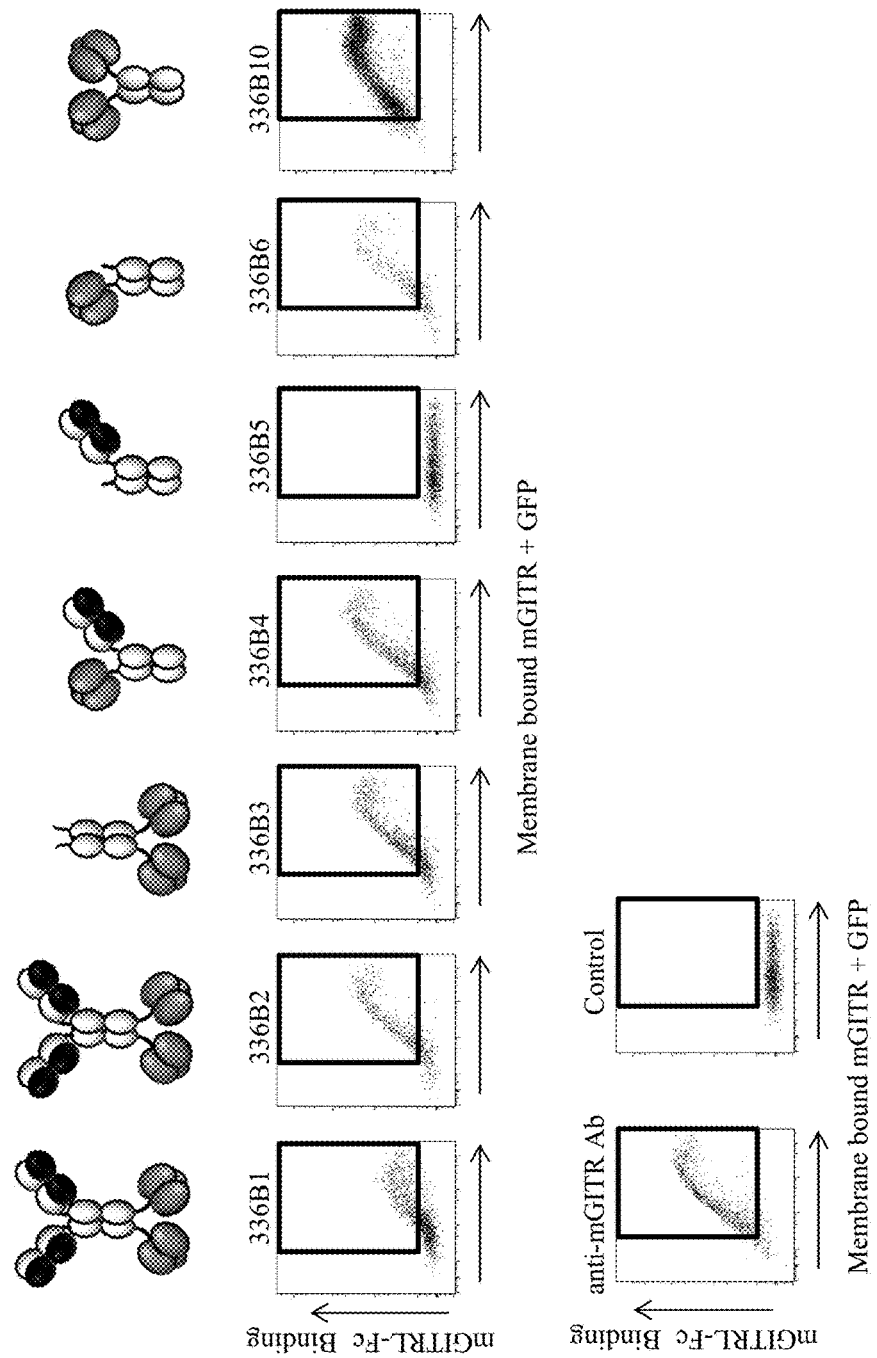
FIG. 4. FACS analysis of a membrane-bound GITR and soluble single chain GITRL trimer-Fc fusion polypeptides. HEK293 cells were transiently transfected with an expression vector encoding full-length mouse GITR and GFP. Transfected cells were incubated with mouse GITRL fusion polypeptides 336B1, 336B2, 336B3, 336B4, 336B6, 336B10, non-GITRL fusion polypeptide 336B5, and anti-GITR antibody DTA-1 and analyzed by flow cytometry. Positive binding is determined by observation of cells within the inset box of the FACS plot.

As shown in FIG. 4, Fc fusion proteins comprising GITRL trimer(s) strongly bind to GITR expressed at the cell surface. The results demonstrated that the GITRL trimer could bind GITR when linked at either the N-terminus or the C-terminus of the Fc protein and that GITRL could bind GITR when expressed as a single trimer or when multiple trimers were present. In addition, the GITRL trimers were functional when fused to Fc regions or antibodies of different isotypes. Importantly, the GITRL trimer also bound GITR in the context of a bispecific homodimeric or heterodimeric molecule.

A comparison of a single chain mGITRL trimer-Fc (336B10) and a single chain hGITRL trimer-Fc (336B11) to bind mouse GITR and human GITR, respectively, was undertaken. Human HEK-293 cells were transiently co-transfected with expression vectors encoding (1) a full-length mouse or human GITR (cell surface expression) and (2) GFP as a transfection marker. Twenty-four hours post-transfection, the cells were incubated with mGITRL trimer- Fc 336B10 or hGITRL trimer-Fc 336B11 over a range of concentrations (2-fold dilutions 20 μg/ml to 0.156 μg/ml). The cells were stained with a PE-conjugated anti-human or anti-mouse Fc secondary antibody and analyzed by flow cytometry.

Figure 5:
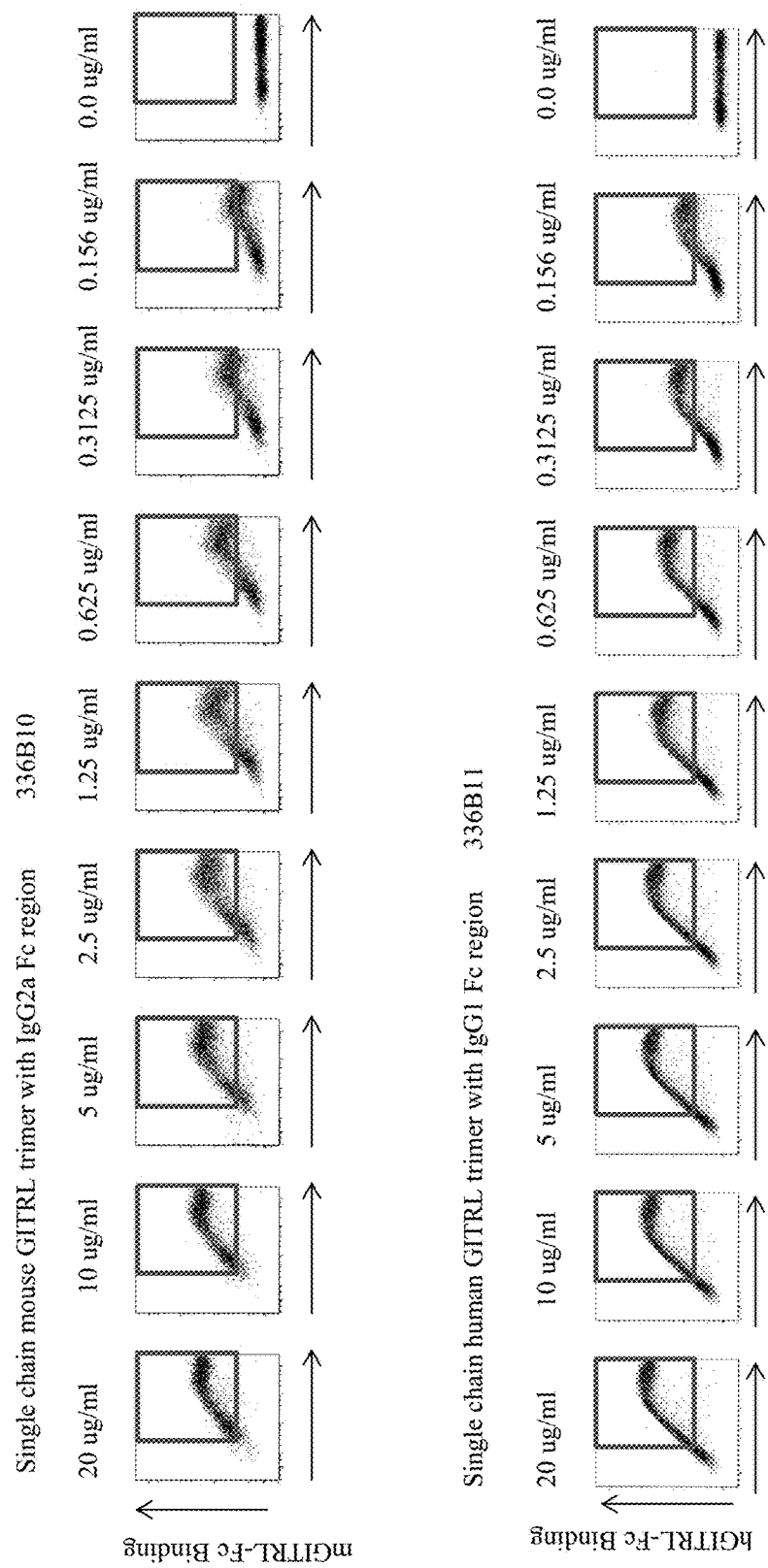
FIG. 5. Dose response of binding of murine GITRL trimer and human GITRL trimer fusion polypeptides to GITR. Shown is a flow cytometry binding analysis of single chain murine GITRL trimer with murine IgG2a Fc domain and single chain human GITRL trimer with human IgG1 Fc domain. HEK293 cells were transiently transfected with an expression vector encoding either human or murine GITR and GFP. Transfected cells were incubated with the indicated fusion protein and analyzed by flow cytometry. Positive binding is determined by observation of cells within the inset box of the FACS plot.

As shown in FIG. 5, single chain mGITRL trimer-Fc and single chain hGITRL trimer-Fc strongly bind to their respective GITRs and show similar dose responses for binding.

Additional studies have shown that human GITRL trimer-Fc 336B11 binds cynomolgus monkey GITR.

Example 4

Activation of GITR Signaling by GITRL Trimer-Fc

To determine whether the single chain GITRL trimer-Fc proteins would induce signaling through GITR, luciferase reporter assays were conducted. A HEK-293 cell line which contains a stably transfected NF-kB-luciferase reporter gene and mouse GITR cDNA was used. Cells were plated into a 96 well plate and incubated with single chain mGITRL-Fc fusion protein 336B3, single chain mGITRL-Fc fusion protein 336B6, anti-GITR antibody DTA-1, or a control antibody over a range of concentrations (5-fold dilutions 20 μg/ml to 0.01 μg/ml). 336B3 is a homodimer of the mGITRL trimer-Fc with the trimer linked at the C-terminus of an IgG2A Fc region ("two-trimer" version). 336B6 has only one of the Fc regions linked to a GITRL trimer linked at the N-terminus of an IgG2A Fc region (a "one-armed" or "one-trimer" version). DTA-1 is an agonist antibody targeting GITR and was included as a positive control.

Figure 6:
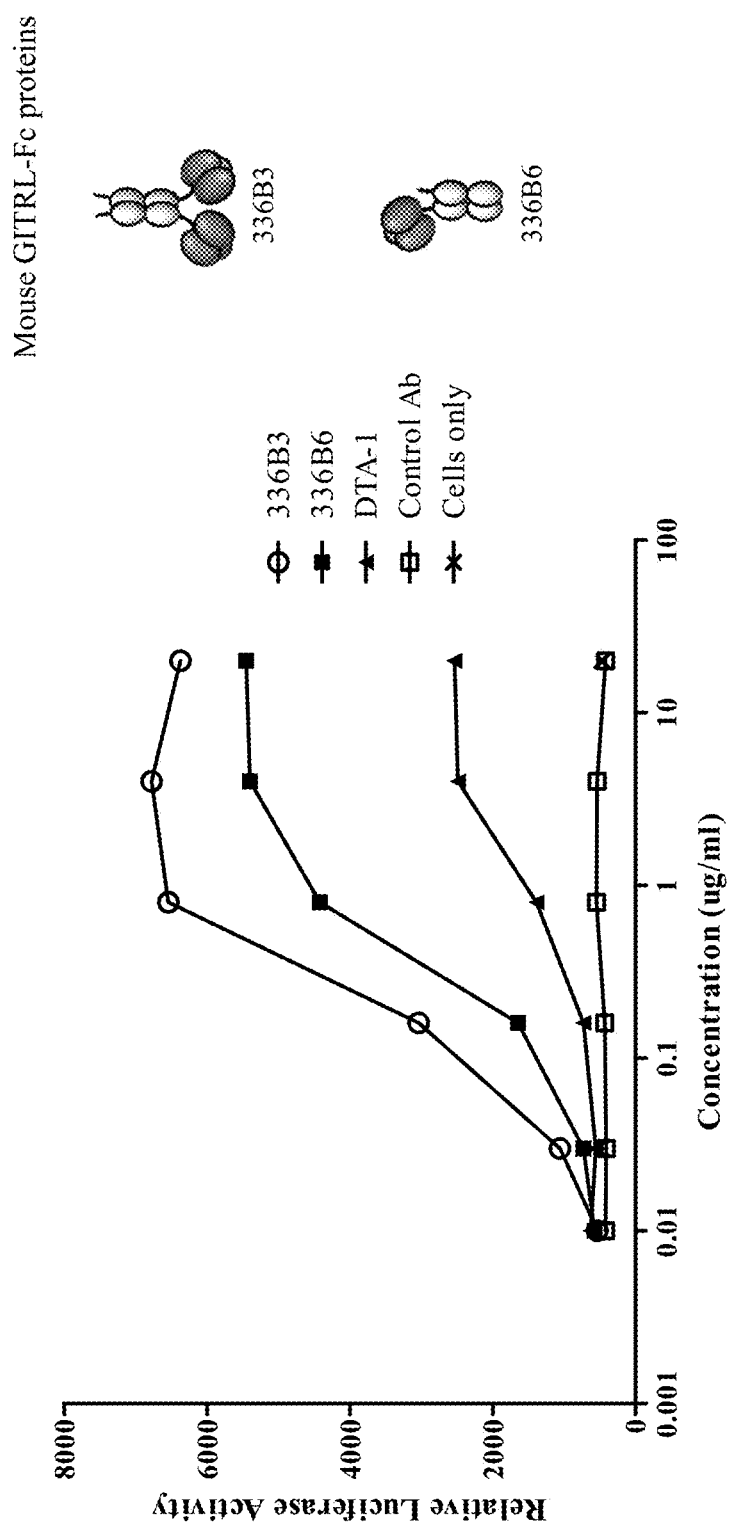
FIG. 6. Activation of GITR signaling. Shown is an analysis of the ability of single chain mGITRL trimer-Fc fusion proteins to activate mGITR signaling. HEK293 cells stably transfected with a NF-κB-luciferase reporter gene and mGITR cDNA were plated into a 96-well plate and incubated with single chain mouse GITRL trimer-Fc fusion 336B3, single chain mouse GITRL trimer-Fc fusion 336B6, anti-mGITR antibody DTA-1, or control antibody. After 24 hours luciferase activity was determined. DTA-1 is an agonist antibody and was included as a positive control.

As shown in FIG. 6, a Fc fusion protein containing a single GITRL trimer (336B6) and a Fc fusion protein containing two GITRL trimers (336B3) were able to robustly stimulate luciferase. These results suggest that the GITRL trimers are able to strongly induce GITR signaling in a biologically relevant manner. Interestingly, the single chain GITRL trimer formats were able to induce more robust GITR signaling than the agonist anti-GITR antibody. Furthermore, in this study a fusion protein containing two copies of the single chain GITRL trimer (336B3) was able to provide a higher maximal stimulation than a fusion protein containing only one GITRL trimer (336B6). These results are consistent with our hypothesis that the single chain GITRL trimer format could be more potent than an agonist antibody format for achieving activation of GITR and that multiple copies of GITRL trimers could function as a "supercluster" to achieve even more potent GITR activation.

These experiments were repeated with a human GITRL trimer-Fc fusion protein (336B11) and HEK-293 cells stably transfected with the NF-kB-luciferase reporter gene and human GITR cDNA. Cells were plated into a 96 well plate and incubated with single chain hGITRL-Fc fusion protein 336B11 over a range of concentrations (3-fold dilutions 20 μg/ml to 0.08 μg/ml).

Figure 7:
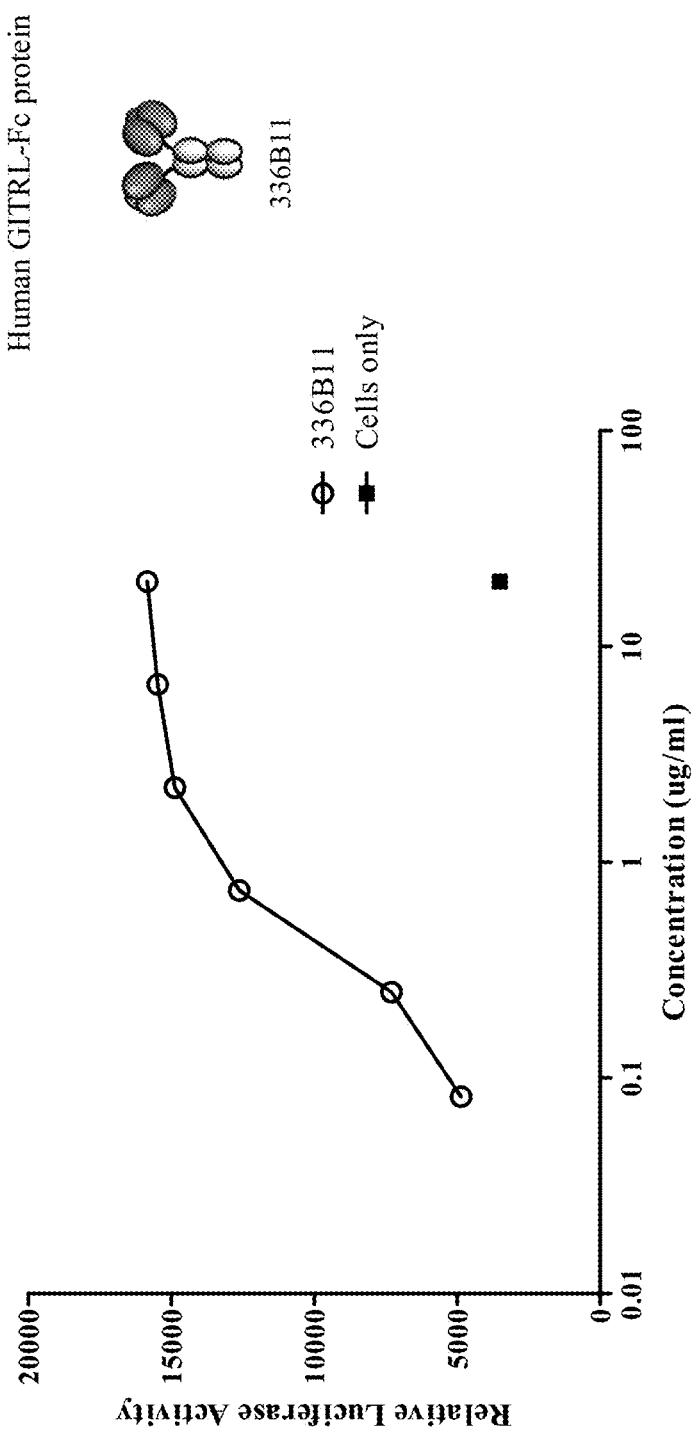
FIG. 7. Activation of GITR signaling. Shown is an analysis of the ability of single chain hGITRL trimer-Fc fusion proteins to activate hGITR signaling. HEK293 cells stably transfected with a NF-κB-luciferase reporter gene and GITR cDNA were plated into a 96-well plate and incubated with single chain human GITRL trimer-Fc fusion 336B11. After 24 hours luciferase activity was determined.

As shown in FIG. 7, the single chain human GITRL trimer-Fc protein 336B11 protein was able to robustly stimulate luciferase. These results are comparable to the results obtained with murine GITRL trimers and indicate that the human GITRL trimer is able to stimulate GITR signaling.

Example 5

In Vivo Tumor Growth Inhibition by Single Chain GITRL Trimer-Fc Protein

The murine colon tumor line CT26.WT was implanted subcutaneously (25,000 cells/mouse) in Balb/c mice. Mice were treated with 0.25 mg/mouse of single chain mGITRL trimer-Fc 336B3, agonist anti-GITR antibody DTA-1, or a control antibody (n=10 per group). Mice were dosed by intraperitoneal injection on days 7, 10, 14, and 17. Tumor growth was monitored and tumor volumes were measured with electronic calipers at the indicated time points.

Figure 8B:
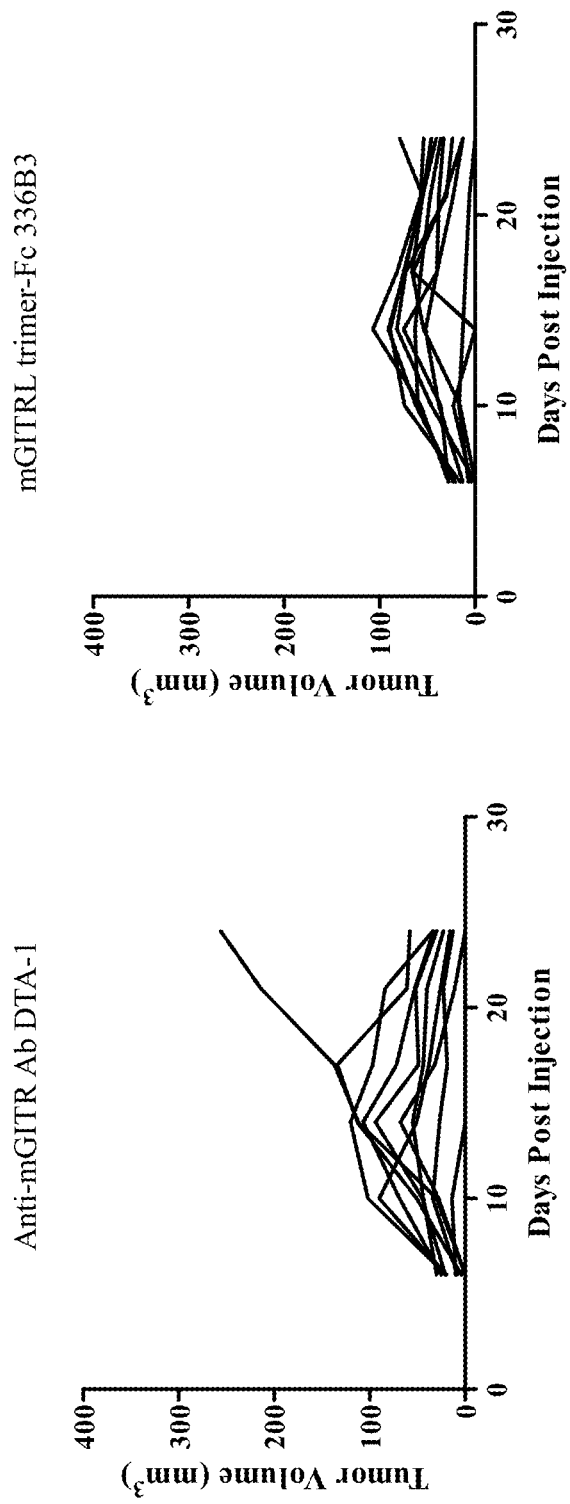

As is shown in FIG. 8A, treatment with mGITRL trimer-Fc 336B3 strongly inhibited and/or prevented growth of the CT26.WT tumors. Treatment with the agonist anti-GITR antibody DTA-1 also inhibited tumor growth. A more nuanced picture of the difference between 336B3 and DTA-1 can be seen by looking at the results from the individual mice within each group. As shown in FIG. 8B, treatment with 336B3 inhibited tumor growth in all ten mice while it appeared that treatment with DTA-1 inhibited tumor growth to a lesser extent and failed to block tumor growth in one of ten mice. These results indicate that the single chain GITRL trimer is active as an immunotherapeutic agent and could be more potent in achieving suppression of tumor growth than an agonist GITR antibody.

Example 6

ELISpot Assay for IFN-Gamma and IL-10

ELISpot is a highly sensitive immunoassay for the detection of cytokine-secreting cells. Briefly, an ELISpot assay employs a capture antibody specific for a desired cytokine, pre-coated onto the wells of a microplate. Cells are dispensed into the wells and the immobilized antibody in the immediate vicinity of any cytokine-secreting cell binds the secreted cytokine. Standard wash steps and incubation with appropriate detection reagents follow. For example, a biotinylated detection antibody followed by streptavidin conjugated to alkaline-phosphatase and a colored substrate solution are commonly used. A colored precipitate forms at the sites of cytokine localization and appears as a spot, with each individual spot representing an individual cytokine-secreting cell. The spots may be counted with an automated reader system or manually using a microscope.

Interferon (IFN)-gamma secreting cells were detected using a mouse IFN-gamma ELISpot kit (MabTech, Cincinnati, Ohio). Cells were isolated from the spleens of CT26.WT tumor-bearing mice treated with mGITRL trimer-Fc 336B, anti-mGITR antibody DTA-1, or a control, as described above in Example 5. Splenocytes from each mouse ($2\times10^5$ cells/well) were dispensed into the provided plates, which were pre-coated with a capture antibody specific for murine IFN-gamma. The cells were cultured in the presence or the absence of a tumor specific CD8+ T-cell peptide (AH-1) and incubated at 37° C. The sequence of the AH-1 peptide (SPSYVYHQF; SEQ ID NO:54) is the $H2-L^d$-restricted epitope (amino acids 6-14) of the gp70 envelope protein of an ecotropic murine leukemia provirus endogenous to the CT26.WT cell line. After 48 hours, cells secreting IFN-gamma were detected following the manufacturer's instructions. Spots were counted using a 6000 F-z Bioreader (Biosys, Miami, Fla.). Data are expressed as the mean±S.E.M spots/well.

Figure 9A:
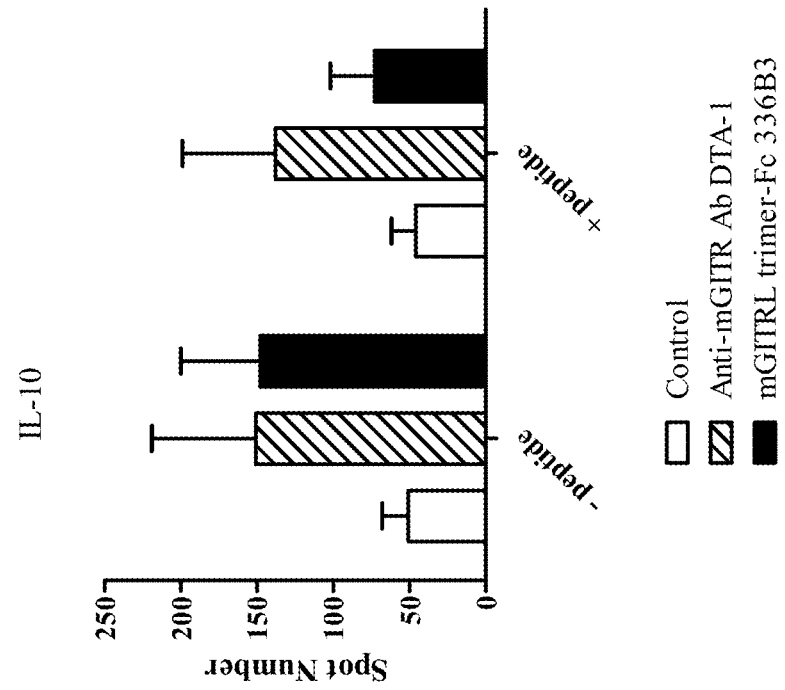
FIGS. 9A and 9B. ELISpot assays for IFN-gamma and IL-10. Cells were harvested from the spleens of CT26.WT-tumor bearing mice treated with anti-mGITR antibody DTA-1, mGITRL trimer-Fc 336B3, or a control.

As shown in FIG. 9A, tumor-specific IFN-gamma-secreting CD8+ T-cells were increased in mice treated with mGITRL trimer-Fc 336B3 and with anti-mGITR antibody DTA-1 when cells were incubated with the AH-1 peptide. The increase was greater with 336B3, approximately 2.5-fold increase versus an approximate 1.9-fold increase with DTA-1. Furthermore, in the mice treated with 336B3 the number of IFN-gamma secreting T-cells was increased even in the absence of a tumor-specific peptide. This increase was not seen with the anti-GITR antibody DTA-1.

IFN-gamma is generally produced by NK cells, Th1 CD4+ T-cells, CD8+ T-cells, antigen presenting cells, and B-cells. Studies have suggested a role for IFN-gamma in tumor immunity and that it may be a regulator of anti-tumor activity mediated by other cytokines, in particular IL-12 and IL-2. Thus, treatment with a GITRL trimer-Fc that results in an increase in IFN-gamma should enhance anti-tumor immunity.

IL-10 secreting cells were detected using a mouse IL-10 ELISPOT kit (MabTech). Cells were isolated from the spleens of CT26.WT tumor-bearing mice treated with mGITRL trimer-Fc 336B, anti-mGITR antibody DTA-1, or a control. Splenocytes ($5\times10^5$/well) from each mouse within each treatment group were dispensed into a 96-well plate coated with an antibody specific for mouse IL-10. The cells were cultured in the presence or the absence of a tumor specific CD8+ T-cell peptide (AH-1) and incubated at 37° C. After 48 hours cells secreting IL-10 were detected following the manufacturer's instructions. Images were captured using a Bioreader 6000 F-z instrument (BioSys) and spot number, spot area, and/or total optical density were determined. Data are expressed as the mean±S.E.M spots/well.

Figure 9B:
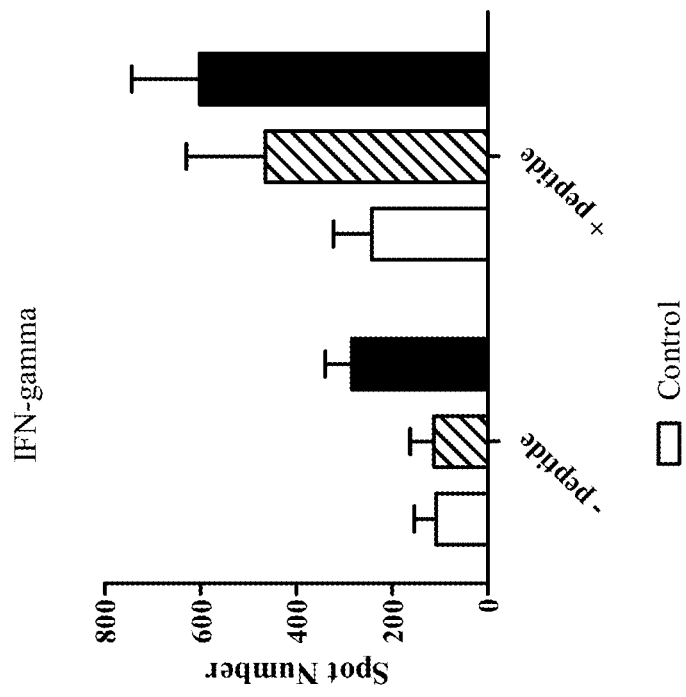

As shown in FIG. 9B, IL-10 secreting cells were significantly increased in mice treated with anti-mGITR antibody DTA-1 as compared to mice treated with a control whether the cells were incubated in the presence or absence of the tumor specific peptide. Interestingly, the number of IL-10 secreting cells from mice treated with mGITRL trimer-Fc 336B3 was significantly increased only when the tumor-specific peptide was not present, demonstrating only a small increase as compared to mice treated with control when the cells were stimulated with the tumor-specific peptide AH-1.

IL-10 is generally produced by Tregs and helper T-cells. IL-10 was originally recognized as a Th2 cytokine that modulates growth and/or differentiation of innate immune cells and suppresses the activation and effector functions of T-cells, particularly cytotoxic T-cells. More recently, IL-10 has been shown to have some immune stimulatory effects and thus is viewed as having pleiotropic functions. Since Th1 cytokines such as IFN-gamma counter-regulate production of Th2 cytokines including IL-10, 336B3 treatment may suppress IL-10 production by inducing significant production of IFN-gamma. Thus, in conjunction with increased IFN-gamma production, 336B3 treatment may promote anti-tumor immunity by suppressing IL-10 production.

These data suggest that the GITRL trimer-Fc can promote tumor-specific CD8+ T-cell activity by significantly producing IFN-gamma. These results may also suggest that the GITRL trimer-Fc can more efficiently induce anti-tumor immunity than an agonist anti-GITR antibody. Furthermore, these results may suggest that the mechanism by which the GITRL trimer-Fc is affecting immune cells and/or immune responses is different than the mechanism of the anti-GITR antibody.

Example 7

Cell Cytotoxicity Assay

Natural killer cells or NK cells are a type of cytotoxic lymphocyte critical to the innate immune system. NK cell activity in mice treated with mGITRL trimer-Fc 336B3 was assessed by measuring the cytotoxic activity of cells on tumor targets. Cells were harvested from the spleens of the CT26.WT tumor-bearing mice described above in Example 5. Cells were plated in 96-well V-bottom plates in RPMI 1640 culture medium (Gibco/Life Technologies, Grand Island, N.Y.) supplemented with 10% (v/v) fetal bovine serum (FBS), 2 mM L-glutamine, 100 U/ml penicillin, and 100 µg/ml streptomycin (Gibco). CT26.WT target cells were labeled with 10 µM calcein AM (Life Technologies) for 1 hour at 37° C. and then combined with the splenocytes at an effector:target (E:T) ratio of 25:1. Following a 4 hour incubation at 37° C., cell-free supernatants were harvested and calcein release was quantified on a fluorometer at an excitation of 485 nm and an emission of 535 nm. The percentage of specific cell lysis was determined as: % lysis=100×(ER−SR)/(MR−SR), where ER, SR, and MR represent experimental, spontaneous, and maximum calcein release, respectively. Spontaneous release is the fluorescence emitted by target cells incubated in media alone (i.e., in the absence of effector cells), while maximum release is determined by lysing target cells with an equal volume of 10% SDS.

Figure 10:
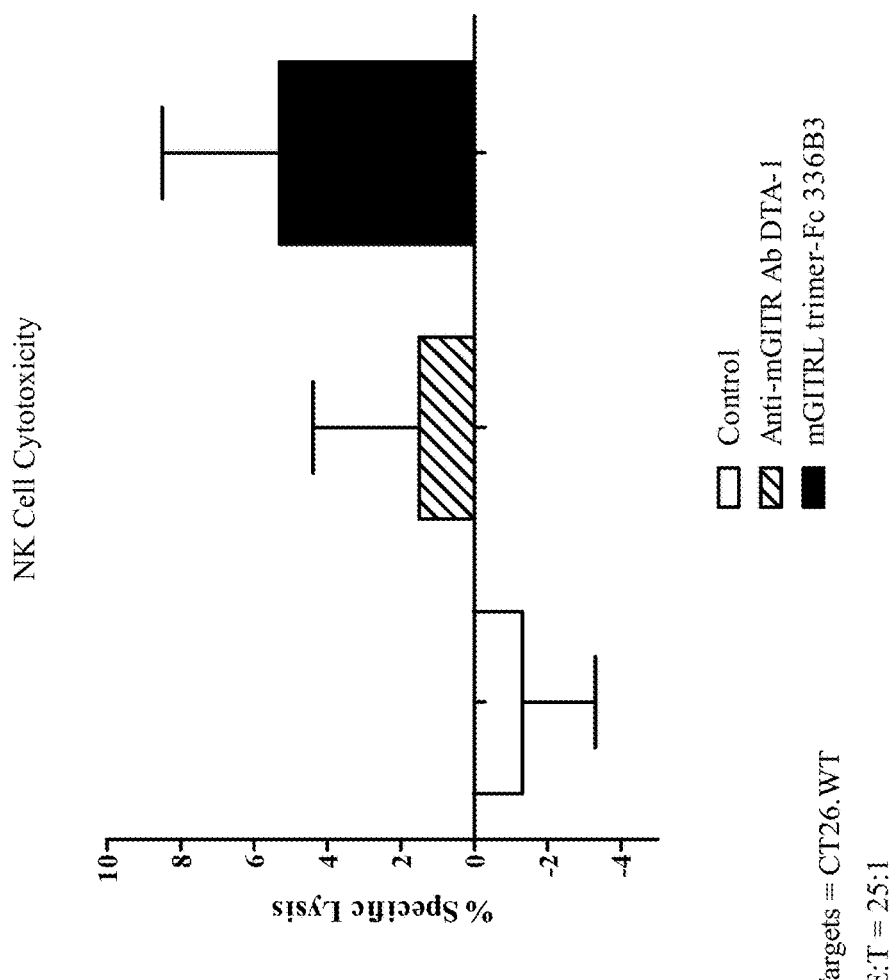
FIG. 10. NK cell cytotoxicity assay. Cells were harvested from the spleens of CT26.WT-tumor bearing mice treated with anti-mGITR antibody DTA-1, mGITRL trimer-Fc 336B3, or a control. CT26.WT target cells were labeled with 10 μM calcein AM mixed with the splenocytes at an E:T ratio of 25:1. Supernatants were harvested and calcein release was quantified on a fluorometer at an excitation of 485 nm and an emission of 535 nm.

As shown in FIG. 10, NK cells from CT26.WT tumor-bearing mice demonstrated an increased ability to kill CT26.WT target cells when the mice had been treated with mGITRL trimer-Fc 336B3 as compared to cells from mice treated with control antibody. This effect was greater than any effect seen with the anti-mGITR antibody DTA-1. Although the amount of lysis was low, these results suggest that treatment with the mGITRL trimer-Fc can increase NK activity and enhance anti-tumor immune responses. Furthermore, the effect with mGITRL trimer-Fc was more potent that what was observed with an anti-GITR antibody.

Example 8

Regulatory T-Cell (Treg) Assay

Regulatory T-cells (Tregs) play an essential role in the maintenance of homeostasis and prevention of autoimmune responses. Tregs are a small subset of T-cells, most which are CD4+ cells and express CD25 (an IL-2 receptor alpha chain) and other Treg cell-related molecular markers. Foxp3, a transcription factor, has been recognized to be a factor for Treg cell development and function. Foxp3 has also been considered as a specific marker to define and identify Treg cells from other T cell subpopulations although this has been challenged on its specificity in human Treg cells. In addition to CD4+ Treg cells, CD8+ Treg cells represent another cell population and Foxp3 may not be so crucial for their development and function when compared to CD4+ Treg cells.

The functionality of Tregs in mice treated with mGITRL trimer-Fc 336B3 was evaluated by determining the effect Tregs had on proliferation of naïve CD4+ or CD8+ T-cells. Naïve T-cells were purified from the spleens of untreated mice using a mouse CD3+ T-cell enrichment column (R&D Systems). These purified T-cells were labeled with 5 µM violet tracking dye (VTD; Life Technologies). $2\times10^5$ VTD-labeled T-cells were incubated with anti-CD3 and anti-CD28 antibody-coated beads to stimulate cell proliferation. Tregs were isolated from the spleens of CT26.WT tumor-bearing mice (see Example 5) treated with mGITRL trimer-Fc 336B3, anti-mGITR antibody DTA-1, or control using a mouse Treg isolation kit (Miltenyi Biotec). To determine the impact of Tregs on T-cell proliferation, the stimulated VTD-labeled T-cells (effectors) were co-cultured with the isolated splenic Tregs (Effector:Treg ratio of 1:0.5). On day 4, cells were washed, and incubated with anti-mouse CD4 or anti-mouse CD8 antibodies. Cells were evaluated by FACS analysis using a BD FACSCanto II instrument and BD FACSDiva software v6.1.3. VTD signals are reduced by half as the labeled cells divide, therefore the analysis gate was set between the maximum signal obtained with no Treg cells in the assay and the minimum signal obtained with no anti-CD3/CD28 stimulation. The percentage of cells within this region (reduced VTD expression) on CD4+ T-cells and CD8+ T-cells was used to calculate CD4+ and CD8+ T-cell proliferation. Percent suppression was calculated as [maximum signal−(sample signal/maximum signal)]×100.

Figure 11:
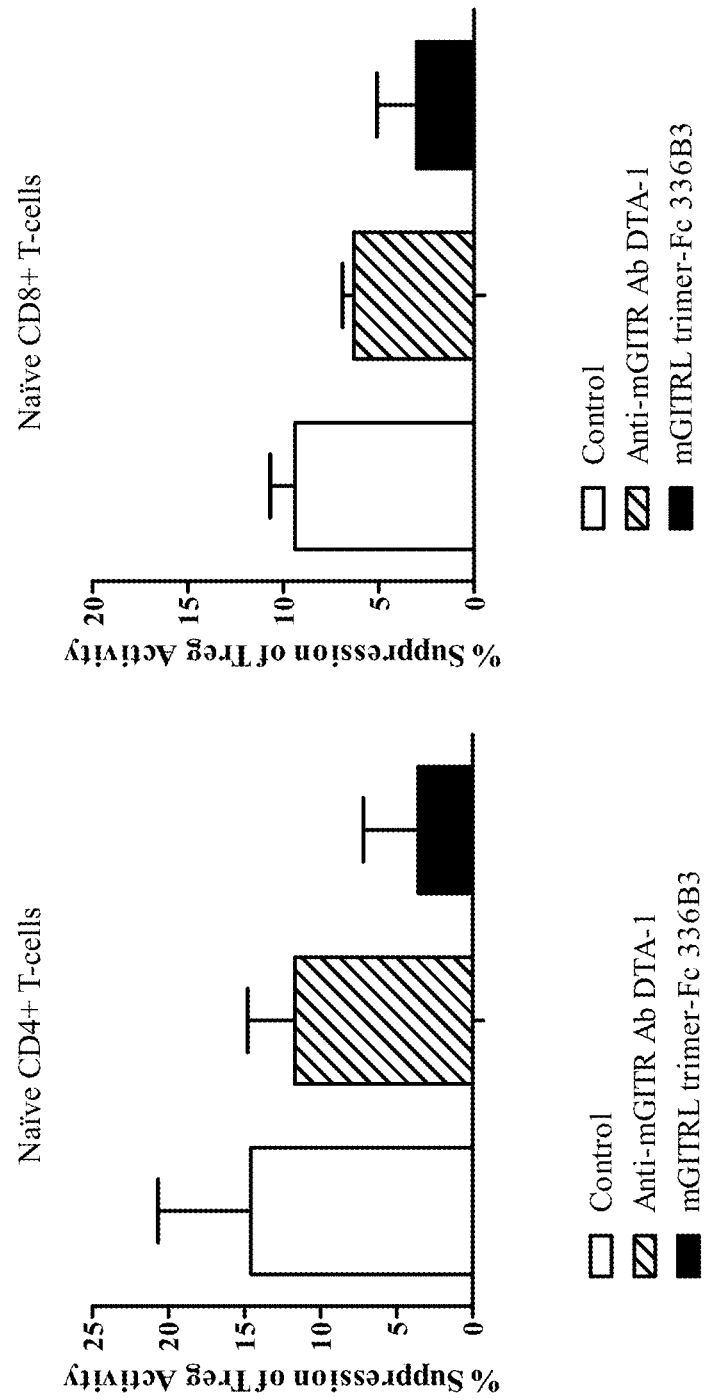
FIG. 11. Regulatory T-cell (Treg) assay. Naïve T-cells were purified from the spleens of untreated mice. These purified T-cells were labeled with 5 μM violet tracking dye. $2\times10^5$ VTD-labeled T-cells were incubated with anti-CD3 and anti-CD28 antibody-coated beads to stimulate cell proliferation. Tregs were isolated from the spleens of CT26WT tumor-bearing mice treated with mGITRL trimer-Fc 336B3, anti-mGITR antibody DTA-1, or control using a mouse Treg isolation kit. To determine the impact of Tregs on T-cell proliferation, the stimulated VTD-labeled T-cells (effectors) were co-cultured with the isolated splenic Tregs at an effector:Treg ratio of 1:0.5. On day 4, cells were washed, and incubated with anti-mouse CD4 or anti-mouse CD8 antibodies. Cells were evaluated by FACS analysis using a BD FACSCanto II instrument and BD FACSDiva software v6.1.3.

As shown in FIG. 11, treatment with mGITRL trimer-Fc 336B3 strongly decreased the suppressive function of Tregs on naïve CD4+ T-cell proliferation as compared to suppression seen with Tregs from mice treated with anti-mGITR antibody DTA-1 or control. Similarly, treatment with 336B3 reduced the suppressive function of Tregs on naïve CD8+ T-cell proliferation as compared to suppression seen with Tregs from mice treated with DTA-1 or control.

These results suggest that treatment with mGITRL trimer-Fc can lead to reduced Treg function and/or suppression. This effect can be thought of as "taking the brake off" the immune response. Thus, a reduction of Treg function could enhance total anti-tumor immune responses.

Example 9

Myeloid-Derived Suppressor Cell (MDSC) Assay

Studies have identified myeloid-origin cells that are potent suppressors of tumor immunity and therefore a significant impediment to cancer immunotherapy (see, for example, Ostrand-Rosenberg et al., 2009, *J. Immunol.*, 182: 4499-4506). Myeloid-derived suppressor cells (MDSCs) accumulate in the blood, lymph nodes, bone marrow, and at tumor sites in most patients and experimental animals with cancer. MDSCs have been shown to inhibit both adaptive and innate immunity.

It is believed that MDSCs facilitate cancer progression by inhibiting anti-tumor immune responses, promoting angiogenesis, and creating a pre-metastatic environment. MDSCs suppress the proliferation and activation of CD4+ T-cells and CD8+ T-cells, thereby inhibiting anti-tumor immunity. Importantly, MDSCs facilitate the generation of Tregs.

MDSCs are a heterogeneous family of myeloid cells. In mice, MDSCs are characterized by the cell surface expression of the myeloid lineage differentiation antigens Gr1 and CD11b. MDSCs can be divided into two subpopulations: granulocytic MDSCs (G-MDSC) and monocytic MDSCs (M-MDSC). G-MDSCs typically have multi-lobed nuclei and a CD11b+Ly6G+Ly6C$^{low}$ phenotype, whereas M-MDSCs have a monocytic morphology and a CD11b+Ly6G$^{+/-}$Ly6C$^{high}$ phenotype. Both populations of MDSCs have been shown to suppress T-cell responses by multiple mechanisms including increased production of arginase, inducible nitric oxide synthase (iNOS), nitric oxide, and reactive oxygen species. Thus, MDSCs contribute to an immunosuppressive tumor microenvironment and may limit the effects of anti-tumor immune responses.

The functionality of MDSCs in mice treated with mGITRL trimer-Fc 336B3 was evaluated by determining the effect MDSCs had on proliferation of naïve CD4+ or CD8+ T-cells. Naïve T-cells were purified from the spleens of untreated mice using a mouse CD3+ T-cell enrichment column (R&D Systems). These purified T-cells were labeled with 5 µM violet tracking dye (VTD; Life Technologies). 2×10$^5$ VTD-labeled T-cells were incubated with anti-CD3 and anti-CD28 antibody-coated beads to stimulate cell proliferation. MDSCs were isolated from the spleens of CT26.WT tumor-bearing mice (see Example 5) treated with mGITRL trimer-Fc 336B3, anti-mGITR antibody DTA-1, or control using a mouse MDSC isolation kit (Miltenyi Biotec). To determine the impact of MDSC on T-cell proliferation, the stimulated VTD-labeled T-cells (effectors) were co-cultured with the isolated splenic MDSCs (effector:MDSC ratio of 1:1). On day 4, cells were washed, and incubated with anti-mouse CD4 or anti-mouse CD8 antibodies. Cells were evaluated by FACS analysis using a BD FACSCanto II instrument and BD FACSDiva software v6.1.3. VTD signals are reduced by half as the labeled cells divide, therefore the analysis gate was set between the maximum signal obtained with no MDSCs in the assay and the minimum signal obtained with no anti-CD3/CD28 stimulation. The percentage of cells within this region (reduced VTD expression) on CD4+ T-cells and CD8+ T-cells was used to calculate CD4+ and CD8+ T-cell proliferation. Percent suppression was calculated as [maximum signal−(sample signal/maximum signal)]×100.

Figure 12:
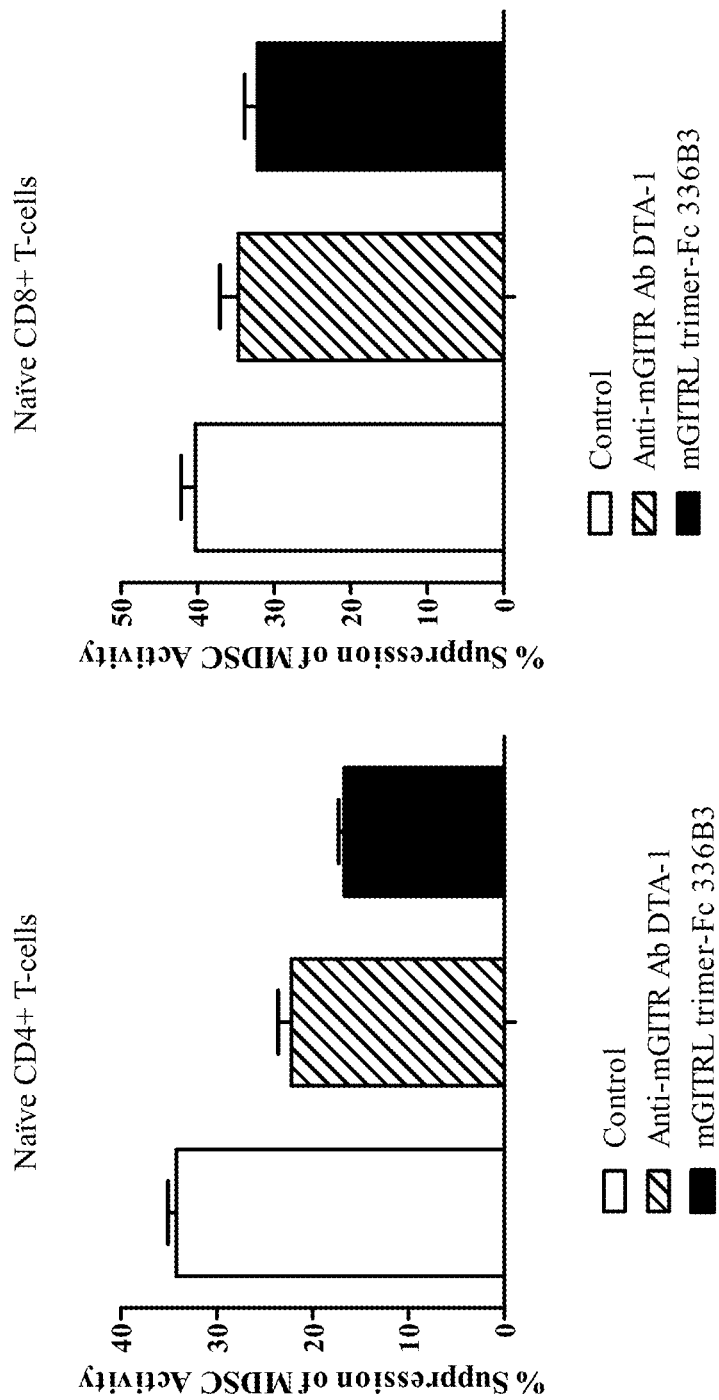
FIG. 12. Myeloid-derived suppressor cell (MDSC) assay. Naïve T-cells were purified from the spleens of untreated mice. These purified T-cells were labeled with 5 μM violet tracking dye. $2\times10^5$ VTD-labeled T-cells were incubated with anti-CD3 and anti-CD28 antibody-coated beads to stimulate cell proliferation. MDSCs were isolated from the spleens of CT26.WT tumor-bearing mice treated with mGITRL trimer-Fc 336B3, anti-mGITR antibody DTA-1, or control using a mouse MDSC isolation kit. The stimulated VTD-labeled T-cells (effectors) were co-cultured with the isolated splenic MDSCs at an effector:MDSC ratio of 1:1). On day 4, cells were washed, and incubated with anti-mouse CD4 or anti-mouse CD8 antibodies. Cells were evaluated by FACS analysis using a BD FACSCanto II instrument and BD FACSDiva software v6.1.3.

As shown in FIG. 12, treatment with mGITRL trimer-Fc 336B3 strongly decreased the suppressive function of MDSCs on naïve CD4+ T-cell proliferation as compared to suppression seen with MDSCs from mice treated with control. The reduction was less pronounced in cells from mice treated with the anti-GITR antibody. In contrast, treatment with 336B3 had only a slight effect on the suppressive function of MDSCs on naïve CD8+ T-cell proliferation as compared to suppression seen with MDSCs from mice treated with control.

These results suggest that treatment with mGITRL trimer-Fc may have some effect on MDSC function and/or suppression. A reduction of MDSC function could further enhance total anti-tumor immune responses.

Example 10

In Vivo Tumor Growth Inhibition by Single Chain GITRL Trimer-Fc Protein

Renca is a Balb/c-derived renal adenocarcinoma cell line obtained from ATCC. Renca cells were implanted subcutaneously (5×10$^5$ cells/mouse) in Balb/c mice and allowed to grow for seven days reaching an average size of approximately 78 mm$^3$. Mice were treated with 0.25 mg/mouse of single chain mGITRL trimer-Fc 336B3, agonist anti-GITR antibody DTA-1, or a control antibody (n=10 per group). Mice were dosed by intraperitoneal injection on days 7, 11, and 14. Tumor growth was monitored and tumor volumes were measured with electronic calipers at the indicated time points.

Figure 13:
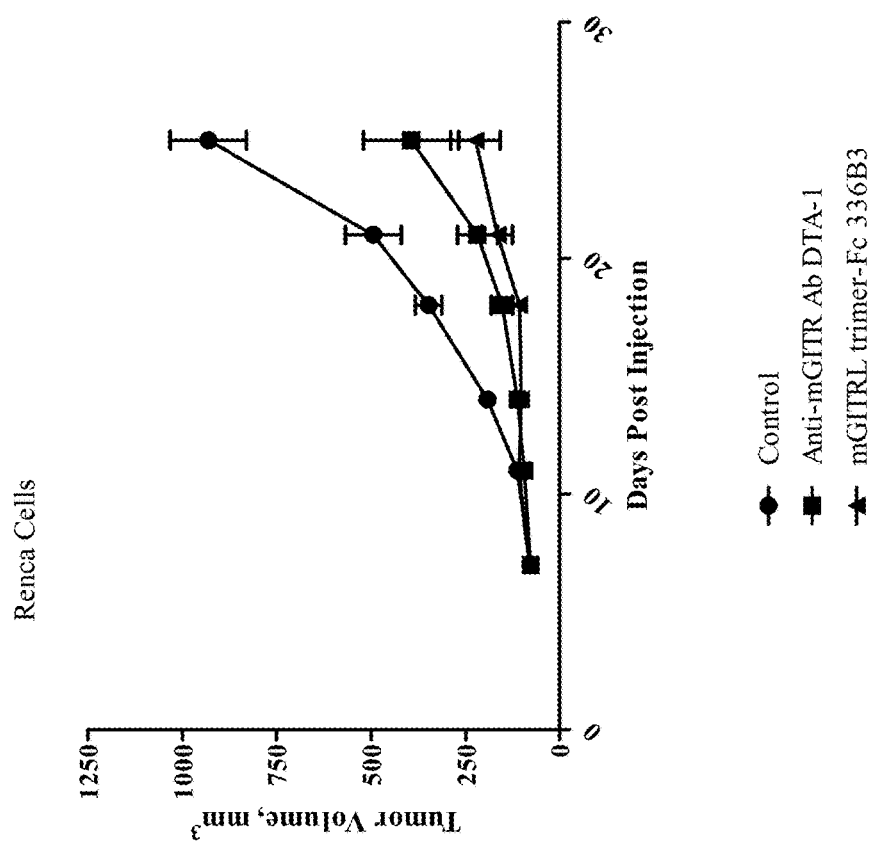
FIG. 13. Inhibition of tumor growth by single chain GITRL trimer-Fc fusion polypeptide. Renca cells were implanted subcutaneously into Balb/c mice (n=10 mice/group). Mice were injected on days 7, 11, and 14 with 0.25 mg/mouse of single chain mGITRL trimer-Fc fusion protein 336B3, anti-mGITR antibody DTA-1, or a control antibody. Tumor growth was monitored and tumor volumes were measured with electronic calipers at the indicated time points. Data is shown as tumor volume (mm$^3$) over days post injection.

As is shown in FIG. 13, treatment with mGITRL trimer-Fc 336B3 strongly inhibited growth of the Renca tumors. Treatment with the agonist anti-GITR antibody DTA-1 also inhibited tumor growth but to a lesser extent than 336B3. When results were assessed at an individual mouse level, tumors regressed to a size smaller than the size at the first treatment in 9 of 20 mice (45%) treated with 336B3, with three mice having undetectable tumors by Day 25. In contrast, tumors regressed to a size smaller than the size at the first treatment in only 5 of 20 mice (25%) treated with DTA-1, with four mice having undetectable tumors by Day 25.

These results support the idea that the single chain GITRL trimer is active as an immuno-oncologic agent in tumors of different origin and that it may be more potent in achieving inhibition of tumor growth than an agonist GITR antibody.

Example 11

Cell Cytotoxicity Assays

For natural killer (NK) cytotoxicity assays, the mouse lymphoblast cell line YAC-1 was used. Cells were cultured in RPMI 1640 culture medium (Gibco/Life Technologies, Grand Island, N.Y.) supplemented with 10% (v/v) fetal *bovine* serum (FBS), 2 mM L-glutamine, 100 U/ml penicillin, and 100 µg/ml streptomycin (Gibco) at 37° C. in a humidified atmosphere of 5% CO2. YAC-1 cells are known to be sensitive to NK cell activity and are a good target for NK cell assays.

Cells were harvested from the spleens of the mice described above in Example 10. Cells were plated in 96-well V-bottom plates in RPMI 1640 culture medium (Gibco/Life Technologies, Grand Island, N.Y.) supplemented with 10% (v/v) fetal *bovine* serum (FBS), 2 mM L-glutamine, 100 U/ml penicillin, and 100 µg/ml streptomycin (Gibco). YAC-1 target cells were labeled with 10 µM calcein AM (Life Technologies) for 1 hour at 37° C. and then combined with the splenocytes at an effector:target ratio of 25:1 or 50:1. Following a 4 hour incubation at 37° C., cell-free supernatants were harvested and calcein release was quantified on a fluorometer at an excitation of 485 nm and an emission of 535 nm. The percentage of specific cell lysis was determined as: % lysis=100×(ER−SR)/(MR−SR), where ER, SR, and MR represent experimental, spontaneous, and maximum calcein release, respectively. Spontaneous release is the fluorescence emitted by target cells incubated in media alone (i.e., in the absence of effector cells), while maximum release is determined by lysing target cells with an equal volume of 10% SDS.

NK cells from Renca cell-injected mice demonstrated an increased ability to kill YAC-1 target cells when the mice had been treated with mGITRL trimer-Fc 336B3 as compared to cells from mice treated with control. Treatment with anti-mGITR antibody DTA-1 also had an increased ability to kill target cells but to a smaller extent than 336B3 (FIG. 14A).

A CD8+ T-cell specific MHC class I tumor peptide sequence is not known for the Renca cell line, therefore the Renca cells were used as stimulators. Renca cells were treated with 25 µg/ml mitomycin C (Sigma-Aldrich) for 30 minutes at 37° C., washed, and resuspended at $10^7$ cells/ml in RPMI-1640 media containing 10% FCS, 2 mM L-glutamine, and antibiotics. Splenocytes were co-cultured with the mitomycin-treated Renca cells in the presence of IL-2 (2 ng/ml ), incubated for 5 days at 37° C., harvested, counted, and used in cytotoxicity assays as described above. Calcein AM-labeled Renca cells were used as targets at an effector:target ratio of 25:1. Calcein release was determined after 4 hours and specific lysis was calculated as described above.

Figure 14B:
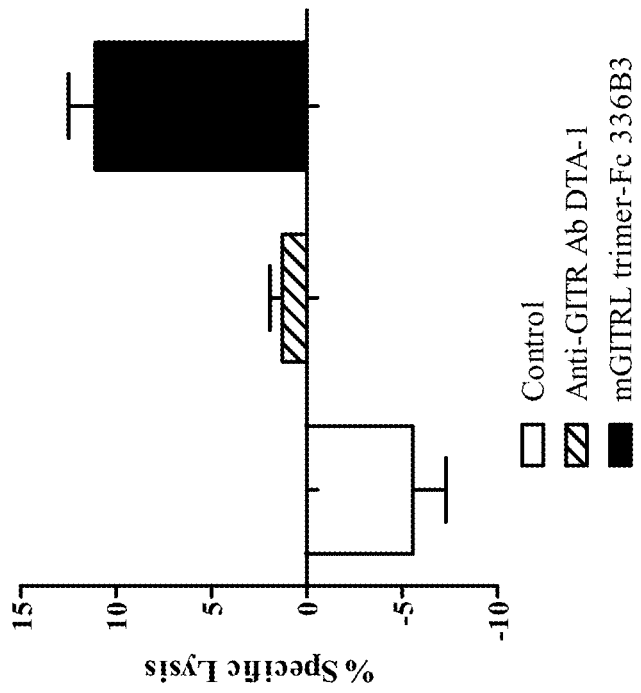
FIGS. 14A and 14B. Cell cytotoxicity assay.
Figure 14A:
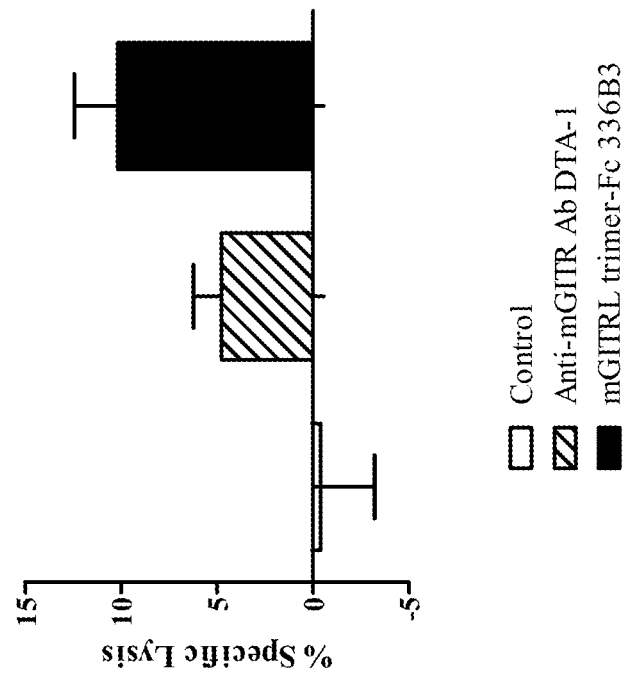

As shown in FIG. 14B, CD8+ cytotoxic cells from Renca cell-injected mice demonstrated an increased ability to kill Renca target cells when the mice had been treated with mGITRL trimer-Fc 336B3 as compared to cells from mice treated with anti-GITR antibody or control.

Example 12

Characterization of hGITRL Trimer-Fc Proteins with and without Exogenous Peptide Linkers A human GITRL trimer-Fc (IgG1) fusion protein was generated that replaced the stalk region (LQLETAK; SEQ ID NO:32) was an exogenous peptide linker consisting of the amino acid sequence GGGSGGG (SEQ ID NO:57). This "hGITRL trimer-Fc with linkers" construct was named 336B13 (SEQ ID NO:62 with signal sequence and SEQ ID NO:63 without signal sequence) and was used in stability studies with hGITRL trimer-Fc 336B11. The proteins were formulated in a buffer consisting of 20 mM histidine, 40 mM NaCl, 5% sucrose, and 0.01% polysorbate 20 at three different pHs (5.5, 6.0, and 6.5). The samples were stored at room temperature with analyses scheduled at time points 0, 2 weeks, and 3 months.

The samples were analyzed using Size Exclusion Chromatography-High Performance Liquid Chromatography (SEC-HPLC). This analytical assay is used to quantitate the relative purity of a protein by assessing the abundance of intact, monomeric protein versus higher molecular weight protein aggregates and/or smaller protein fragments in a sample by separating protein species by their relative size. 50 µg of protein was injected onto a Tosoh Biosciences TSK G3000SW-x1 size exclusion chromatography column (7.8 mm I.D.×30 cm) and a Waters 2695 Separations Module HPLC instrument was used to run the assays.

TABLE 1

| Molecule | pH | % Monomer T = 0 | % Aggregate T = 0 | % Monomer T = 2 weeks | % Aggregate T = 2 weeks | Change in Aggregate (%) |
|---|---|---|---|---|---|---|
| 336B11 | 5.5 | 96.09 | 3.91 | 96.69 | 3.31 | −15.3 |
|  | 6.0 | 95.85 | 4.15 | 96.28 | 3.72 | −10.4 |
|  | 6.5 | 95.78 | 4.22 | 96.35 | 3.65 | −13.5 |
| 336B13 | 5.5 | 97.20 | 2.81 | 96.9 | 3.11 | 10.7 |
|  | 6.0 | 97.03 | 2.97 | 96.79 | 3.22 | 8.4 |
|  | 6.5 | 96.85 | 3.15 | 96.55 | 3.44 | 9.2 |

As shown in Table 1, although the changes in aggregation at the 2 week time point were fairly small, it appeared that hGITRL trimer-Fc 336B11 (with native stalk region) was more stable than hGITRL trimer-Fc 336B13 (with peptide linkers). 336B11 actually had less aggregates at all pHs at the 2 week time point than it did at the 0 time point. In contrast, 336B13 (with exogenous linkers) had an increased percentage of aggregates at the 2 week time point (at all pHs).

The samples were also analyzed using polyacrylamide gel electrophoresis (SDS-PAGE). This analytical assay is used to separate proteins according to their size and no other physical feature. Once the proteins are separated, the quantity of intact, monomeric protein versus higher molecular weight protein aggregates and/or smaller protein fragments in a sample can be assessed. 4 µg of protein for each sample was run on 4-20% SDS-PAGE gels under non-reduced conditions. Gel bands were detected using a Typhoon Trio imaging instrument (GE Healthcare) and quantitated by densitometry using ImageQuant TL (GE Healthcare) software. On these PAGE gels, the main, dominant band is the monomeric GITRL trimer-Fc protein, while any bands larger than the main band are aggregates and any bands smaller than the main band are fragments of the protein.

TABLE 2

| Molecule | pH | % Monomer T = 0 | % Monomer T = 2 weeks |
|---|---|---|---|
| 336B11 | 5.5 | 98.35 | 94.14 |
|  | 6.0 | 98.06 | 94.12 |
|  | 6.5 | 97.70 | 94.49 |
| 336B13 | 5.5 | 95.75 | 76.19 |
|  | 6.0 | 95.79 | 77.27 |
|  | 6.5 | 95.83 | 77.06 |

Non-reduced SDS-PAGE analysis showed little change in the percentage of the main gel band of hGITRL trimer-Fc 336B11 (with native stalk region) over the two week period at all three pHs (Table 2). In contrast, the percentage of the main gel band of hGITRL trimer-Fc 336B13 (with peptide linkers) was decreased approximately 20%, with a corresponding increase in higher and lower molecular weight bands at all three pHs (Table 2).

These results support the idea that the GITRL trimer-Fc fusion protein with the native stalk region linking the individual GITRL domains is more stable than a GITRL trimer-Fc fusion protein with exogenous peptide linkers between the individual GITRL domains and without the native stalk region.

Example 13

In Vivo Tumor Growth Inhibition by Single Chain GITRL Trimer-Fc Protein—Dose Study Since the single chain GITRL trimer-Fc had been shown to be effective in inhibiting tumor growth, a dose range study was conducted. The murine colon tumor line CT26.WT was implanted subcutaneously (25,000 cells/mouse) in Balb/c mice and tumors were allowed to grow to an average size of approximately 115 mm$^3$. Mice were treated with 30, 12.5, 6.25, 3, or 0.5 mg/kg of mGITRL trimer-Fc 336B3 or were untreated (n=10 per group). Mice were dosed by intraperitoneal injection twice a week for a total of 6 doses. Tumor growth was monitored and tumor volumes were measured with electronic calipers at the indicated time points.

FIGS. 15A-15F show the tumor volumes of individual mice within each treatment group and FIG. 15G shows the average tumor volume of each treatment group. Treatment with mGITRL trimer-Fc 336B3 strongly inhibited growth of CT26.WT tumors at each dose including at the lowest level of 0.5 mg/kg. As shown in Table 3, at Day 18 tumors had regressed to an undetectable size in at least 50% of the mice treated with 30, 12.5, 6.25, and 3 mg/kg 336B3. Even at the lowest dose of 0.5 mg/kg, total tumor regression was observed in 3 of 10 mice.

TABLE 3

| Dose in mg/kg | Untreated | 30 | 12.5 | 6.25 | 3 | 0.5 |
|---|---|---|---|---|---|---|
| No. of mice with undetectable tumors at Day 18 | 0/10 | 6/10 | 5/10 | 5/10 | 5/10 | 3/10 |

Additional experiments were undertaken to evaluate the effect of frequency of dosing on inhibition of tumor growth by GITRL trimer. As described above, CT26.WT tumor cells were implanted subcutaneously (25,000 cells/mouse) in Balb/c mice and tumors were allowed to grow to an average size of approximately 104 mm$^3$. Mice were treated with 2.5 mg/kg of mGITRL trimer-Fc 336B3, 12.5 mg/kg of mGITRL trimer-Fc, or were untreated (n=10 per group). Mice were treated with a single dose at 2.5 mg/kg, treated once every 2 weeks at 2.5 mg/kg, treated once every week at 2.5 mg/kg, treated twice a week at 2.5 mg/kg, or treated twice a week at 12.5 mg/kg for only 3 doses.

Figure 16A:
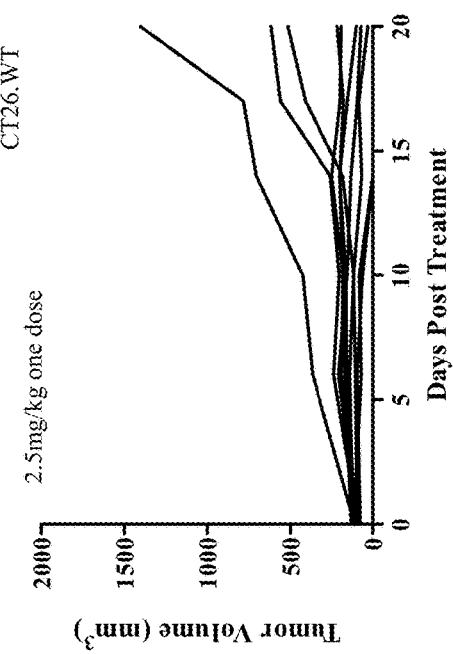
FIGS. 16A-16G. Inhibition of tumor growth by single chain GITRL trimer-Fc fusion polypeptide—a dose study. The murine colon tumor line CT26.WT was implanted subcutaneously into Balb/c mice (n=10 mice/group). Mice were treated with 2.5 mg/kg of mGITRL trimer-Fc 336B3, 12.5 mg/kg of mGITRL trimer-Fc, or were untreated (n=10 per group). Mice were treated with a single dose at 2.5 mg/kg, treated once every 2 weeks at 2.5 mg/kg, treated once every week at 2.5 mg/kg, treated twice a week at 2.5 mg/kg, or treated twice a week at 12.5 mg/kg for only 3 doses.
Figure 16B:
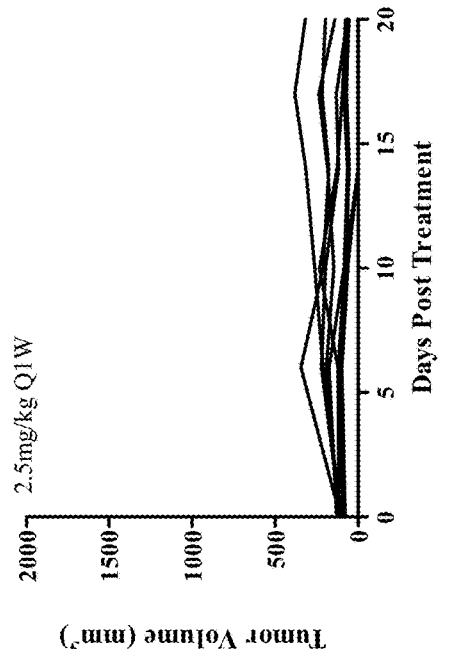
Figure 16C:
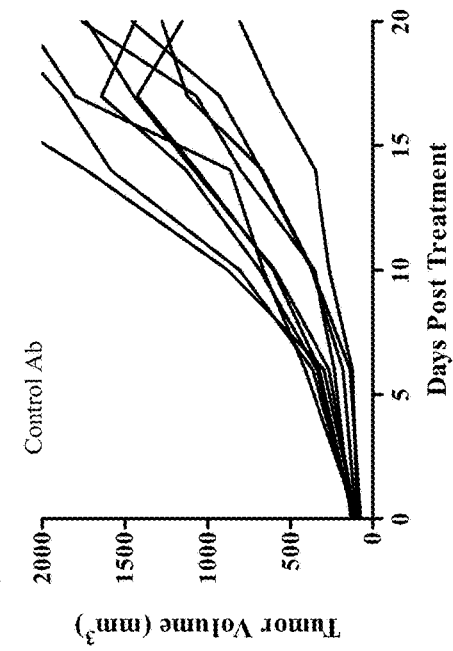
Figure 16D:
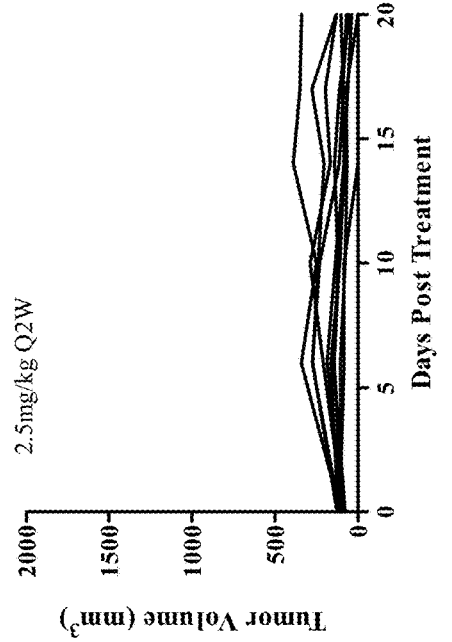
Figure 16F:
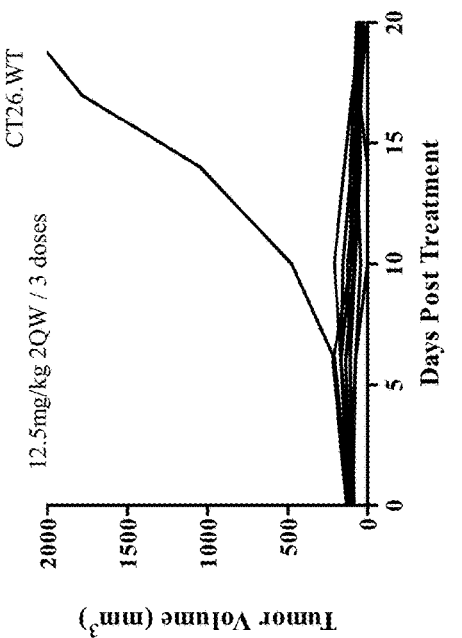
Figure 16E:
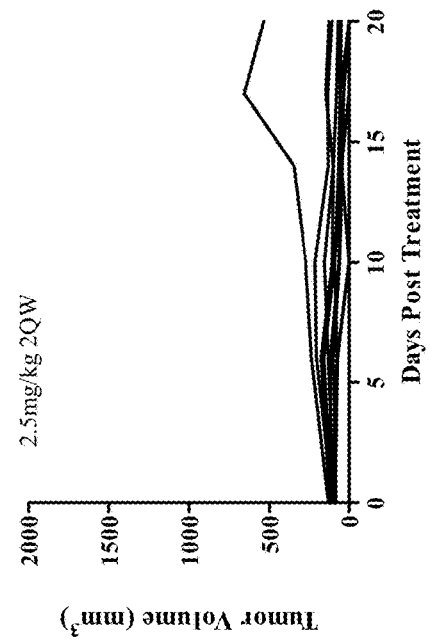
Figure 16G:
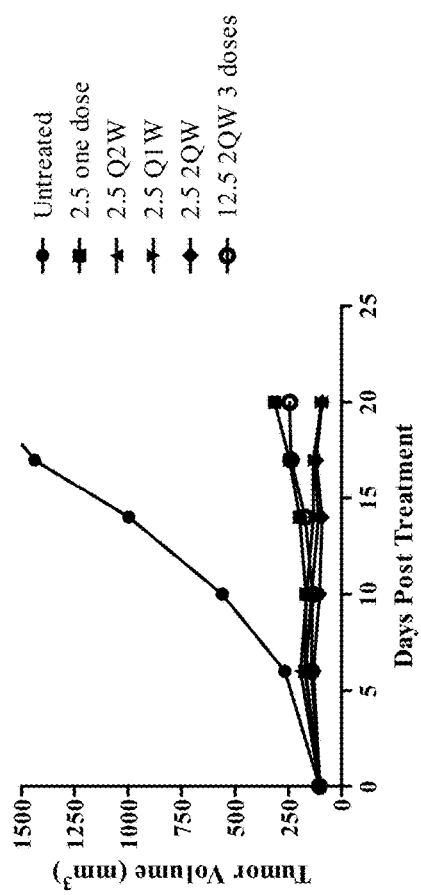

FIGS. 16A-16F show the tumor volumes of individual mice within each treatment group and FIG. 16G shows the average tumor volume of each treatment group. Treatment with mGITRL trimer-Fc 336B3 strongly inhibited growth of CT26.WT tumors at each dose interval. As shown in Table 4, at Day 20 tumors had regressed to an undetectable size in at least 20% of the mice treated with 2.5 mg/kg 336B3 at all dosing intervals. Even with a single dose of 336B3 at 2.5 mg/mg tumor growth was strongly inhibited and 2 mice had undetectable tumors.

TABLE 4

| | | Dose Interval | | | | |
|---|---|---|---|---|---|---|
| Dose in mg/kg | Untreated | Once 2.5 | Q2W 2.5 | Q1W 2.5 | 2QW 2.5 | 2QW* 12.5 |
| No. of mice with undetectable tumors at Day 20 | 0/10 | 2/10 | 2/10 | 2/10 | 4/10 | 2/10 |

*Mice received only 3 doses

These results demonstrate the potency of the single chain GITRL trimer as an immunotherapeutic agent. In general, these results are surprising in regard to the small amount of GITRL trimer-Fc needed to see a significant anti-tumor effect and furthermore that a significant effect is seen with limited doses. These results were unexpected, especially in light of the fact that preliminary data suggests that 336B3 has a non-linear PK and a half-life of only about 12 hours at 2 mg/kg.

Example 14

In Vivo Tumor Growth Inhibition by Single Chain GITRL Trimer-Fc Protein in Immune Cell-Depleted Mice Experiments were conducted to evaluate which immune cell populations were involved in the inhibition of tumor growth by GITRL trimer. For in vivo depletion of specific cell populations, Balb/c mice were given an intraperitoneal injection of anti-CD4 antibody (500 ug/dose), anti-CD8 antibody (500 ug/dose), a combination of anti-CD4 and anti-CD8 antibodies (500 ug/dose each), anti-asialo GM-1 antibody (25 ul), or a control IgG2 antibody (LFT-2; 500 ug/dose) 2 days and 1 day prior to tumor cell implantation, and then additional injections were given 1 day after implantation and twice a week during the experiment. The murine colon tumor line CT26.WT was implanted subcutaneously (30,000 cells/mouse) in the cell-depleted mice. Mice were treated on Day 7 post-implantation with 0.25 mg/mouse of mGITRL trimer-Fc 336B3 or a control antibody (n=10 per group). At Day 7, average tumor size ranged from approximately 20-50 mm$^3$, depending on the group of cell-depleted mice. Mice were dosed by intraperitoneal injection twice a week. Tumor growth was monitored and tumor volumes were measured with electronic calipers at the indicated time points.

Anti-asialo GM-1 antibody was used to deplete NK cells in the treated mice, although it is known that this antibody also binds to other cells in addition to NK cells. The results from mice treated with the anti-asialo GM1 antibody are not shown as these mice were sick and all were euthanized before Day 19.

Figure 17B:
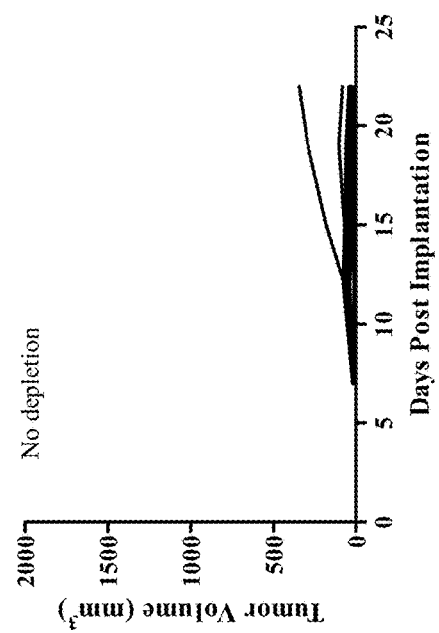
FIGS. 17A-17F. In vivo tumor growth inhibition by single chain GITRL trimer-Fc protein in immune cell-depleted mice. For in vivo depletion of specific cell populations, Balb/c mice were given an intraperitoneal injection of anti-CD4 antibody (500 ug/dose), anti-CD8 antibody (500 ug/dose), a combination of anti-CD4 and anti-CD8 antibodies (500 ug/dose each), anti-asialo GM-1 antibody (25 ul), or a control IgG2 antibody (LFT-2; 500 ug/dose) 2 days and 1 day prior to tumor cell implantation, and then additional injections were given 1 day after implantation and twice a week during the experiment. The murine colon tumor line CT26.WT was implanted subcutaneously (30,000 cells/mouse) in the cell-depleted mice. Mice were treated with 0.25 mg/mouse of mGITRL trimer-Fc 336B3 or a control antibody (n=10 per group). Mice were dosed by intraperitoneal injection twice a week. Tumor growth was monitored and tumor volumes were measured with electronic calipers at the indicated time points.
Figure 17D:
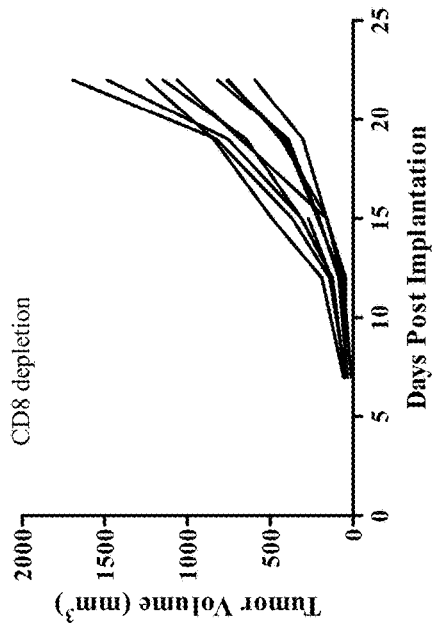
Figure 17A:
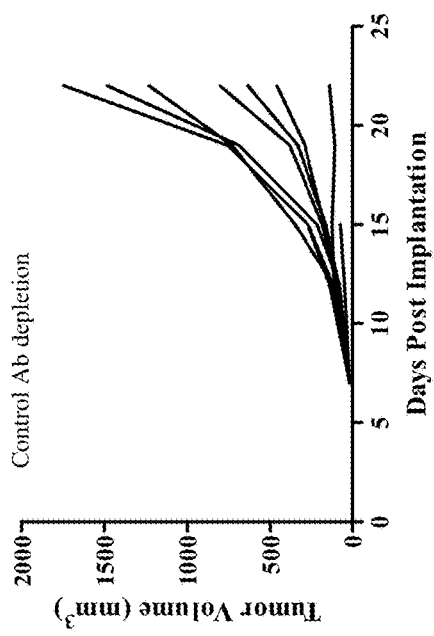
Figure 17C:
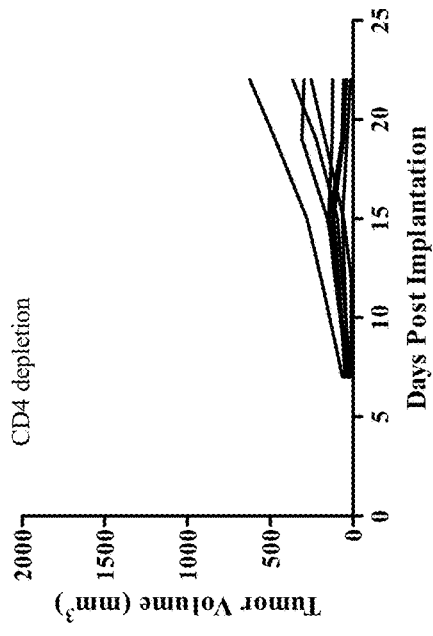
Figure 17F:
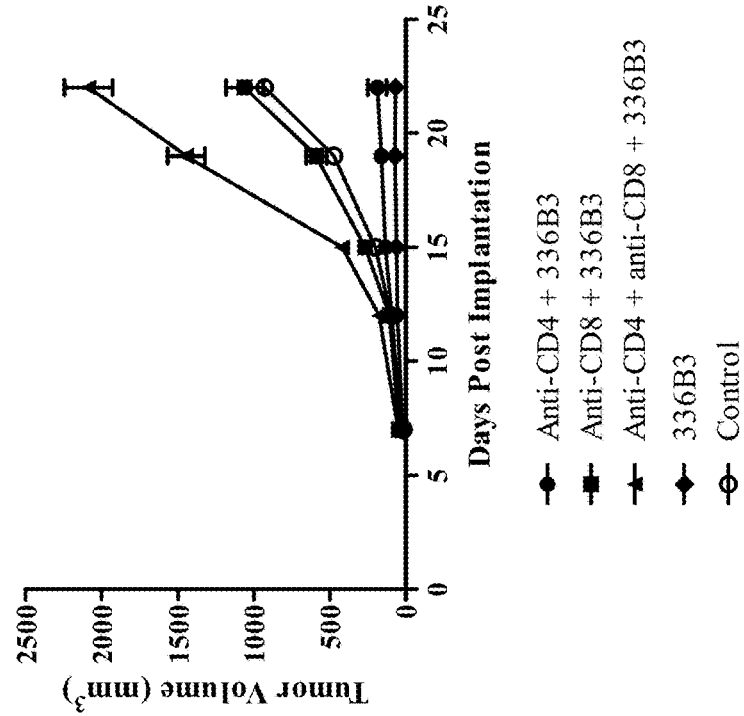
Figure 17E:
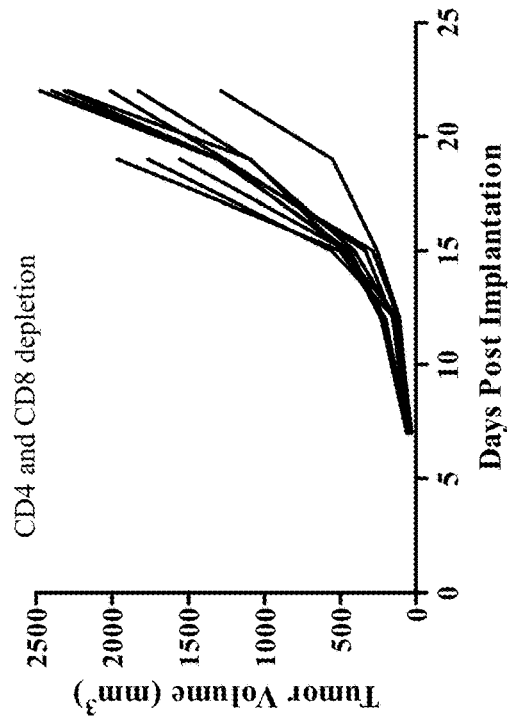

FIG. 17F shows the mean tumor volume in each group of mice and FIGS. 17A-17E show tumor volume of individual mice in each group. As seen in previous experiments, treatment with GITRL trimer-Fc 336B3 significantly inhibited tumor growth (FIG. 17B). Depletion of CD4+ cells only minimally reduced the effectiveness of GITRL-trimer-Fc 336B3 (FIG. 17C). In contrast depletion of CD8+ cells significantly affected the effectiveness of GITRL trimer-Fc 336B3 where the tumor volumes observed in the individual mice were very similar to tumor volumes seen in mice treated with the control (FIG. 17D and FIG. 17A, respectively). A higher level of tumor growth was seen in mice depleted of both CD4+ and CD8+ cells than in mice treated with control (FIG. 17E as compared to FIG. 17A).

These results demonstrate that functional CD8+ cells play a dominant role in the anti-tumor activity of the GITRL trimer-Fc 336B3. The higher level of tumor growth seen in CD4+CD8+ depleted mice indicates that the CD4+ T-cells enhance and/or are necessary for the ability of CD8+ T-cells to reduce tumor growth in the mice treated with 336B3. This result points to the importance of functional CD4+ helper T-cells for effective anti-tumor CTL activity induced by the GITRL trimer-Fc.

Example 15

In Vivo Tumor Growth Inhibition by Single Chain GITRL Trimer-Fc Protein and Anti-PD-1 Antibody The murine adenocarcinoma cell line Renca was implanted subcutaneously ($5 \times 10^5$ cells/mouse) in Balb/c mice and on the first day of treatment (Day 7 post-implantation) the tumors were an average size of approximately 52 mm$^3$. Mice were treated with 12.5 mg/kg of single chain mGITRL trimer-Fc 336B3, an anti-PD-1 antibody, a combination of 336B3 and anti-PD-1 antibody, or a control antibody (n=20 per group). Mice were administered 336B3 by intraperitoneal injection twice a week for only 3 doses and anti-PD-1 antibody was administered twice a week for 3 weeks. Tumor growth was monitored and tumor volumes were measured with electronic calipers.

Figure 18A:
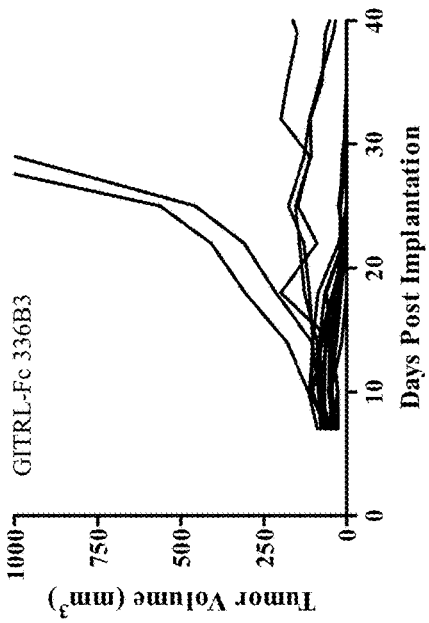
FIGS. 18A-18D. In vivo tumor growth inhibition by single chain GITRL trimer-Fc protein and anti-PD-1 antibody. The murine adenocarcinoma cell line Renca was implanted subcutaneously (5×10$^5$ cells/mouse) in Balb/c mice. Mice were treated with 12.5 mg/kg of single chain mGITRL trimer-Fc 336B3, an anti-PD-1 antibody, a combination of 336B3 and anti-PD-1 antibody, or a control antibody (n=20 per group). Mice were administered 336B3 by intraperitoneal injection twice a week for only 3 doses and anti-PD-1 antibody was administered twice a week for 3 weeks. Tumor growth was monitored and tumor volumes were measured with electronic calipers at the indicated time points.
Figure 18B:
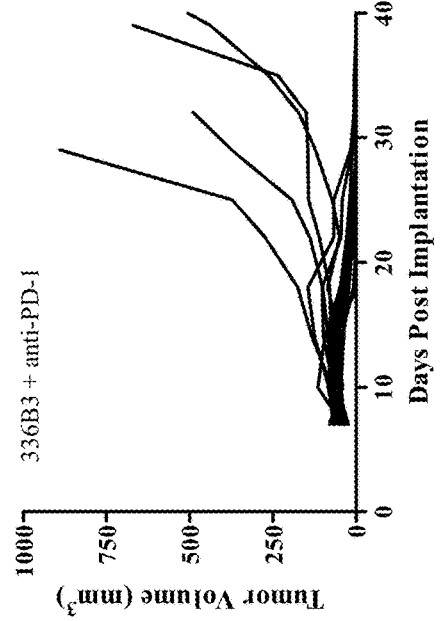
Figure 18C:
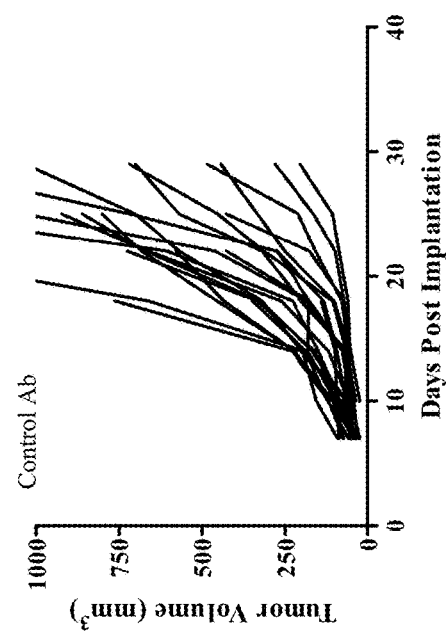
Figure 18D:
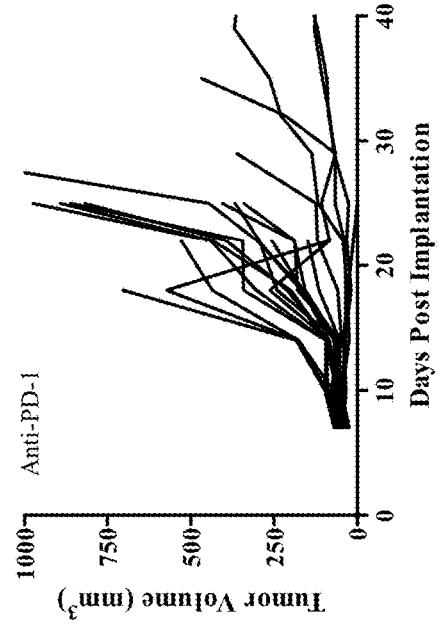

As is shown in FIG. 18B, treatment with mGITRL trimer-Fc 336B3 strongly inhibited growth of the Renca tumors in a high percentage of the mice. As seen in earlier examples, treatment with 336B3 is not only able to inhibit growth of the tumors, but is able to induce regression of tumors, often to undetectable levels. Treatment with the anti-PD-1 antibody was much less successful at inhibiting tumor growth as a single agent (FIG. 18C). Treatment with the combination of GITRL trimer-Fc 336B3 and an anti-PD-1 antibody had similar results as 336B3 as a single agent (FIG. 18D).

These results support the idea that the single chain GITRL trimer is a very potent immunotherapeutic agent, even when administered as a single agent and for only a short time. In addition, the efficacy of a GITRL trimer-Fc protein may be further enhanced by combining it with other immunotherapeutic agents.

Example 16

In Vivo Tumor Growth Inhibition by Single Chain GITRL Trimer-Fc Protein and Anti-PD-L1 Antibody The murine colon tumor line CT26.WT was implanted subcutaneously (30,000 cells/mouse) in Balb/c mice and on the first day of treatment (Day 10 post-implantation) the tumors were an average size of approximately 105 mm$^3$. Mice were treated with 0.25 mg/mouse of single chain mGITRL trimer-Fc 336B3, an anti-PD-L1 antibody, a combination of 336B3 and anti-PD-L1 antibody, or a control antibody (n=10-20 per group). Mice were administered 336B3 by intraperitoneal injection twice a week for only 3 doses and anti-PD-L1 antibody was administered twice a week for 3 weeks. Tumor growth was monitored and tumor volumes were measured with electronic calipers.

Figure 19A:
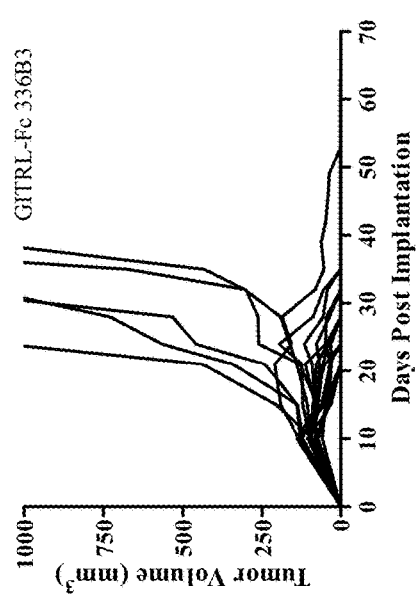
FIGS. 19A-19E. In vivo tumor growth inhibition by single chain GITRL trimer-Fc protein and anti-PD-L1 antibody. The murine colon tumor line CT26.WT was implanted subcutaneously (30,000 cells/mouse) in Balb/c mice. Mice were treated with 0.25 mg/mouse of single chain mGITRL trimer-Fc 336B3, an anti-PD-L1 antibody, a combination of 336B3 and anti-PD-L1 antibody, or a control antibody (n=10-20 per group). Mice were administered 336B3 by intraperitoneal injection twice a week for only 3 doses and anti-PD-L1 antibody was administered twice a week for 3 weeks. Tumor growth was monitored and tumor volumes were measured with electronic calipers at the indicated time points.
Figure 19B:
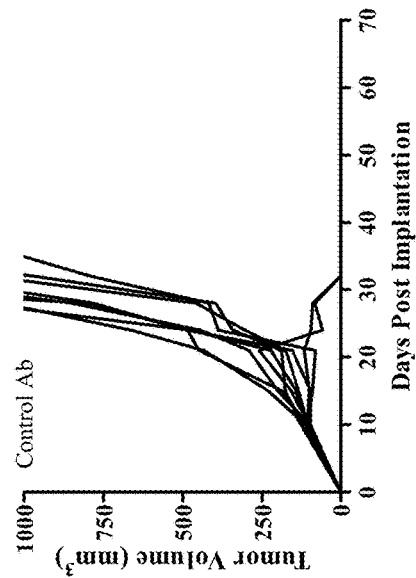
Figure 19C:
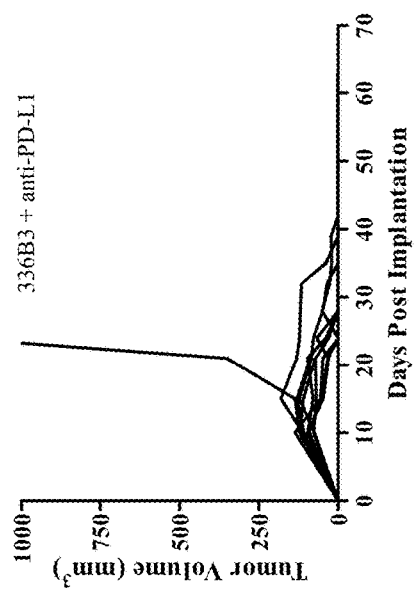
Figure 19D:
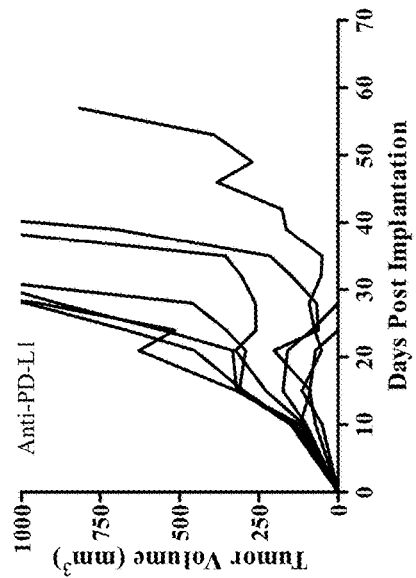

As is shown in FIG. 19B, treatment with mGITRL trimer-Fc 336B3 strongly inhibited growth of the CT26.WT tumors in a high percentage of the mice. As seen in earlier examples, treatment with 336B3 is not only able to inhibit growth of the tumors, but is able to induce regression of tumors, often to undetectable levels. Treatment with the anti-PD-L1 antibody was much less successful at inhibiting tumor growth as a single agent (FIG. 19C). Treatment with the combination of GITRL trimer-Fc 336B3 and an anti-PD-L1 antibody had similar results as 336B3 as a single agent (FIG. 19D). The results of the combination treatment may be better than the GITRL trimer alone other a longer period of time.

One method of evaluating the presence and/or functionally of an anti-tumor memory cell population is to re-challenge previously treated mice with fresh tumor cells. Mice (from the studies described above) previously treated with GITRL-Fc 336B3, anti-mPD-L1 antibody, or a combination of 336B3 and anti-mPD-L1 antibody were used for a re-challenge study. Mice whose tumors had regressed completely and were undetectable at least 128 days after the first tumor injection were re-challenged with CT26.WT tumor cells (30,000 cells). The mice subjected to tumor re-challenge had received a last treatment dose 100 days prior to re-challenge. Naïve Balb/c mice (n=10) were injected with CT26.WT tumor cells (30,000 cells) as a control group. Tumor growth was monitored and tumor volumes were measured with electronic calipers at the indicated time points. Data are expressed as mean±S.E.M.

Figure 19E:
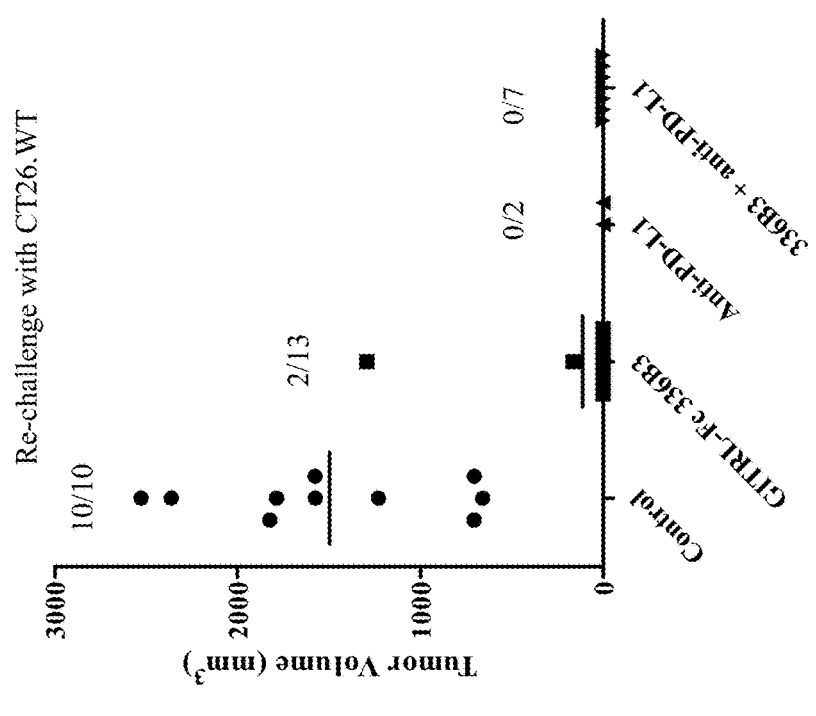

The average tumor volume of CT26.WT tumors in naive mice grew steadily up to Day 28 with an average tumor volume of approximately 1750 mm$^3$. From the previous experiment there were only two mice with completely regressed tumors that had been previously treated with the anti-PD-L1 antibody, but these two mice demonstrated complete immunity to the tumor re-challenge. There were 13 mice with completely regressed tumors that had been previously treated with GITRL-Fc and tumors grew in only 2 of these mice after re-challenge. The other 11 mice demonstrated complete immunity to the tumor re-challenge. In addition, there were 7 mice with completely regressed tumors that had been previously treated with the combination of 336B3 and an anti-PD-L1 antibody and these mice demonstrated complete immunity to the tumor challenge. These results (as of Day 28) are shown in FIG. 19E.

The mice treated with GITRL-Fc 336B3, either as a single agent or in combination with an anti-PD-L1 antibody, appeared to be strongly protected from re-challenge with the CT26.WT tumor cells. These results suggest the existence of immunogenic memory after treatment with GITRL-Fc 336B3, either as a single agent or in combination with a checkpoint inhibitor.

Example 17

In Vivo Tumor Growth Inhibition by Single Chain GITRL Trimer-Fc Protein and Anti-PD-1 Antibody The murine melanoma cell line B16-F10 is a poorly immunogenic tumor that originally developed in C57BL/6 mice and is thought to reflect the poor immunogenicity of metastatic tumors in humans. These cells have been shown to be unresponsive to several different types of anti-cancer therapies and therefore the B16-F10 tumor is considered to be a "high bar" model. B16-F10 cells were implanted subcutaneously (5000 cells/mouse) in C57BL/6 mice and on the first day of treatment (Day 8 post-implantation) the tumors were an average size of approximately 51 mm$^3$. Mice were treated with 5 mg/kg of single chain mGITRL trimer-Fc 336B3, 10 mg/kg of an anti-mPD-1 antibody, a combination of 336B3 and anti-mPD-1 antibody, or a control antibody (n=10 per group). Mice were administered 336B3, anti-mPD-1 antibody, or control antibody by intraperitoneal injection twice a week. Tumor growth was monitored and tumor volumes were measured with electronic calipers at the indicated time points.

Figure 20A:
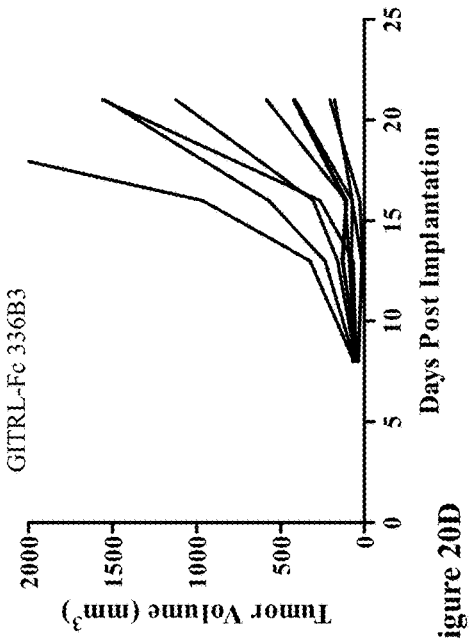
FIGS. 20A-20E. In vivo tumor growth inhibition by single chain GITRL trimer-Fc protein and anti-PD-1 antibody. The murine melanoma cell line B16-F10 cells were implanted subcutaneously (5000 cells/mouse) in C57BL/6 mice. Mice were treated with 5 mg/kg of single chain mGITRL trimer-Fc 336B3, 10 mg/kg of an anti-mPD-1 antibody, a combination of 336B3 and anti-mPD-1 antibody, or a control antibody (n=10 per group). Mice were administered 336B3, anti-mPD-1 antibody, or control antibody by intraperitoneal injection twice a week. Tumor growth was monitored and tumor volumes were measured with electronic calipers at the indicated time points.
Figure 20B:
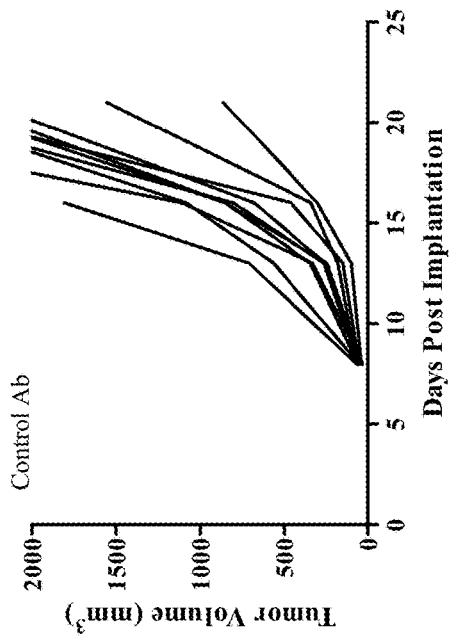
Figure 20C:
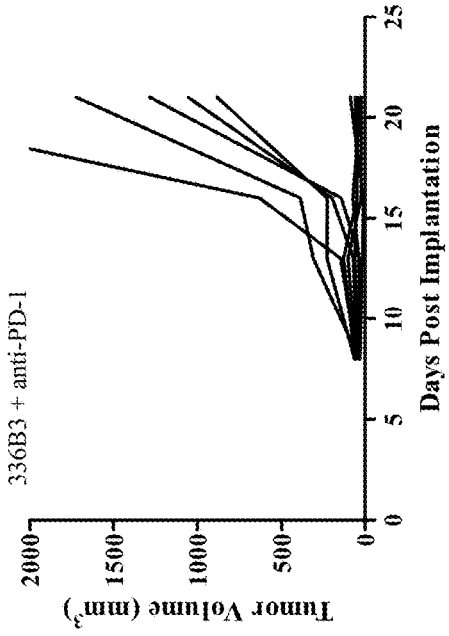
Figure 20D:
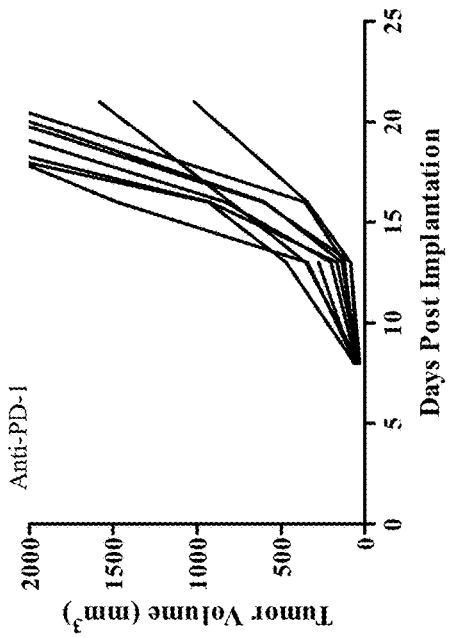
Figure 20E:
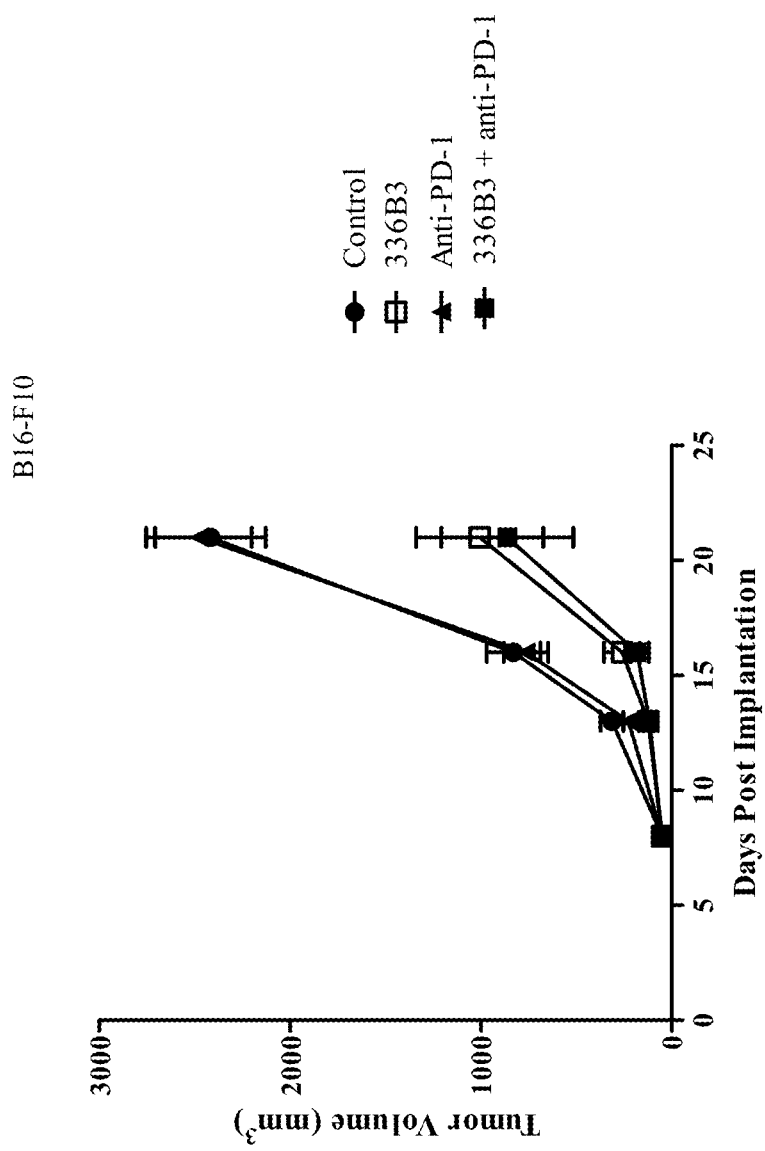

FIG. 20E shows the mean tumor volume in each group of mice and FIGS. 20A-20D show tumor volumes of individual mice in each group. Although treatment with the anti-PD-1 antibody had no effect on tumor growth in the B16-F10 model, treatment with GITRL trimer-Fc 336B3 was shown to have substantial efficacy in this model. When viewing the results as average tumor volume of each group, it appeared that there was only a slight increase in anti-tumor activity with the combination of 336B6 and anti-PD-1 antibody. However, when viewing the results of the individual mice, it is clear that treatment with the combination of 336B3 and anti-PD-1 inhibited tumor growth to a significant amount in 50% of the treated mice (FIG. 20D).

A follow-up study was conducted to evaluate the effective dose range of GITRL trimer-Fc 336B3 in the B16-F10 tumor model. B16-F10 cells were injected subcutaneously in C57BL/6 mice and on the first day of treatment the tumors were an average size of approximately 84 mm$^3$. Mice were treated with 0.5 mg/kg of anti-mGITR antibody DTA-1, 30, 10, 2.5, 0.5, and 0.05 mg/kg of single chain mGITRL trimer-Fc 336B3, two different control antibodies, or saline (n=10 per group). Mice were administered 336B3, antibodies, or saline by intraperitoneal injection once a week. Tumor growth was monitored and tumor volumes were measured with electronic calipers.

Figure 22:
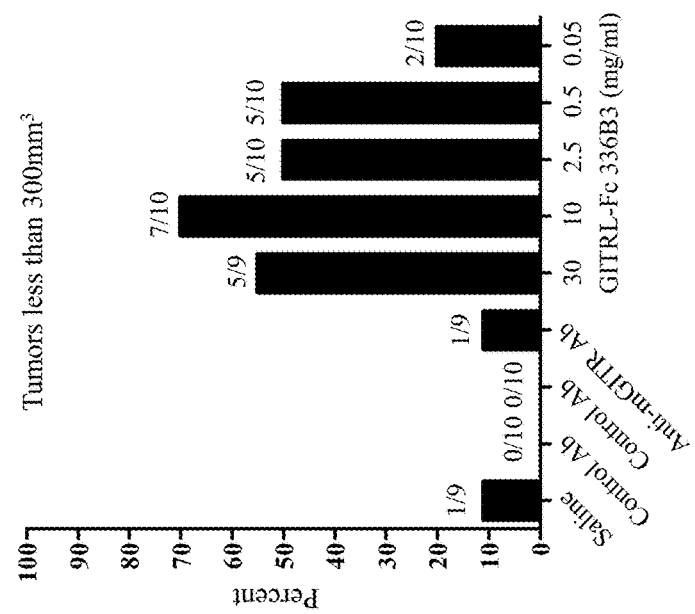
FIG. 22. Inhibition of tumor growth by single chain GITRL trimer-Fc fusion polypeptide—a dose study in B16-B10 mouse model. B16-F10 cells were injected subcutaneously in C57BL/6 mice and were allowed to reach an average size of approximately 84 mm$^3$. Mice were treated with 0.5 mg/kg of anti-mGITR antibody DTA-1, 30, 10, 2.5, 0.5, and 0.05 mg/kg of single chain mGITRL trimer-Fc 336B3, two different control antibodies, or saline (n=10 per group). Mice were administered 336B3, antibodies, or saline by intraperitoneal injection once a week. Tumor growth was monitored and tumor volumes were measured with electronic calipers. The results as shown percent of tumors that were less than 300 mm$^3$ in each treatment group.
Figure 23A:
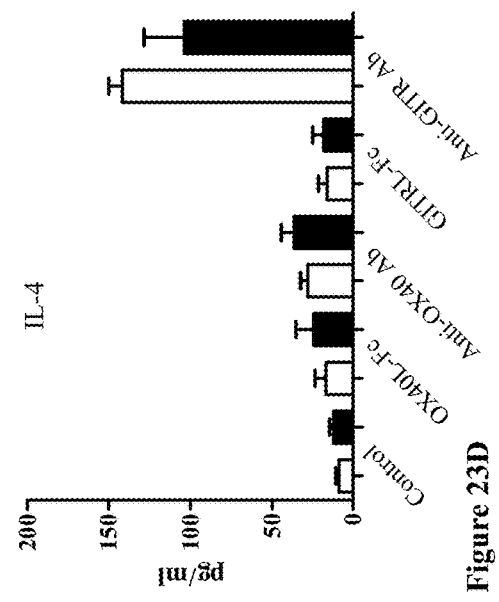
FIG. 23A-23L. Cytokine production. The murine colon tumor line CT26.WT was implanted subcutaneously into Balb/c mice (n=10 mice/group). Mice were injected twice a week for 3 doses with 0.25 mg/mouse of single chain mOX40L trimer-Fc fusion protein, anti-mOX40 antibody, mGITRL trimer-Fc, anti-mGITR antibody DTA-1, or a control antibody. Tumor growth was monitored and tumor volumes were measured with electronic calipers at the indicated time points. Cells were harvested on Day 26 from the spleens of the mice in each treatment group. The cells were cultured in the presence or the absence of the tumor specific CD8+ T-cell peptide AH-1. After 48 hours, cytokine levels in cell supernatants were measured using a multiplex panel for the Luminex® platform (ThermoFisher Scientific) following the manufacturer's instructions.
Figure 23B:
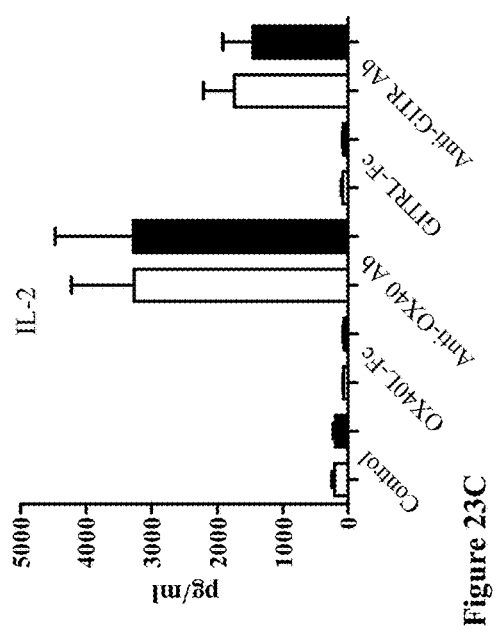
Figure 23C:
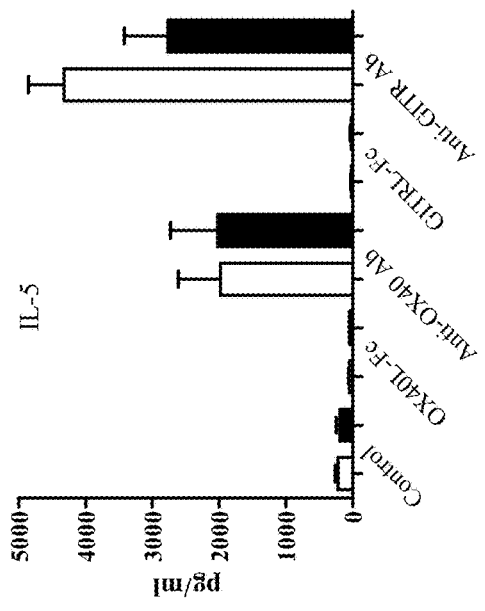
Figure 23D:
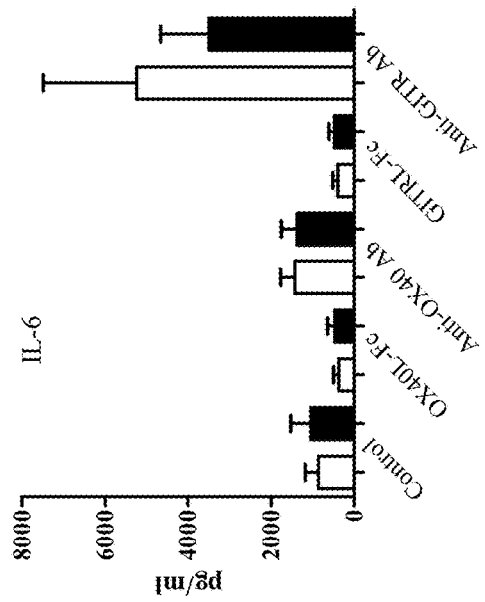
Figure 23F:
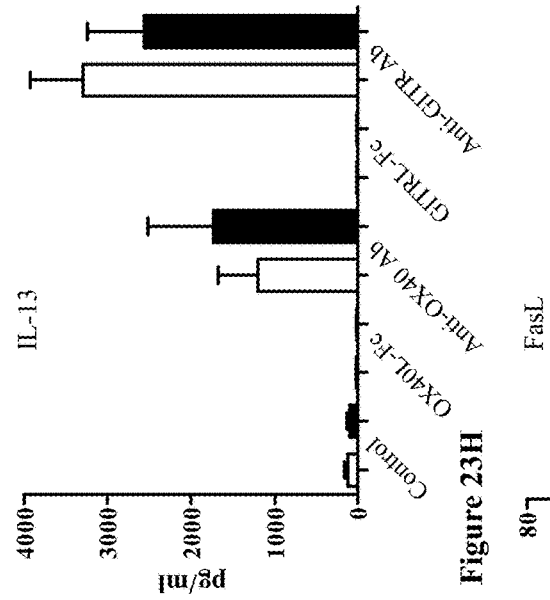
Figure 23H:
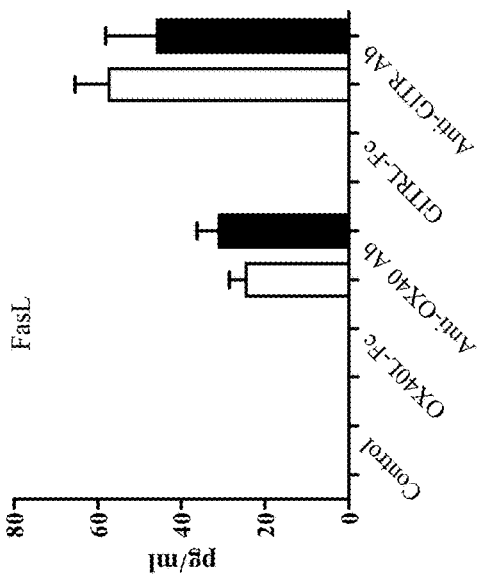
Figure 23E:
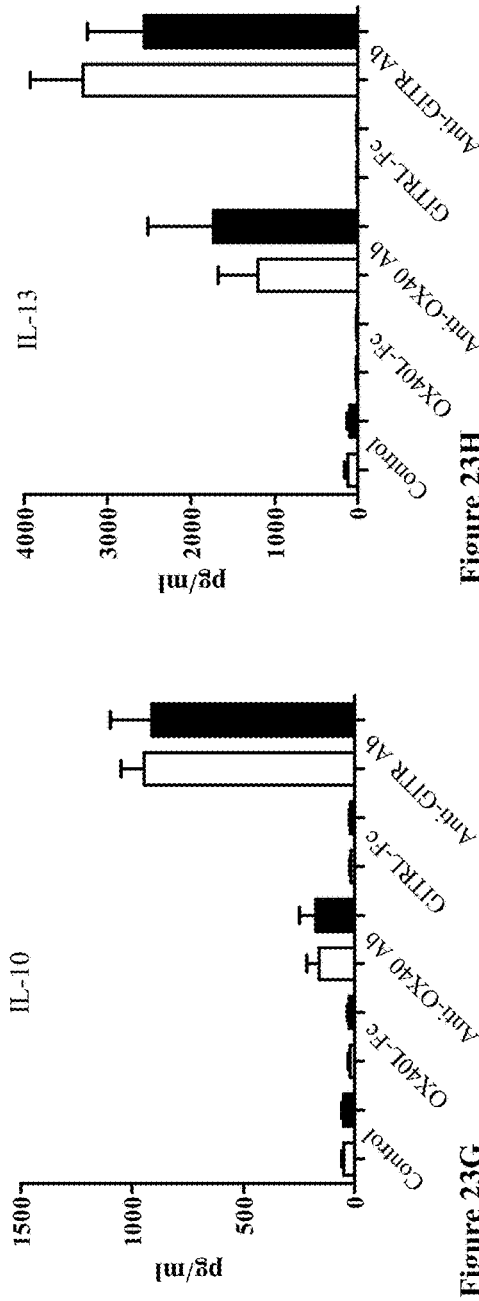
Figure 23G:
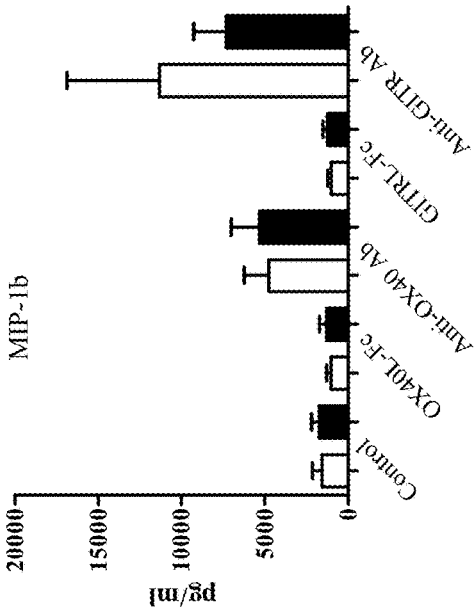
Figure 23J:
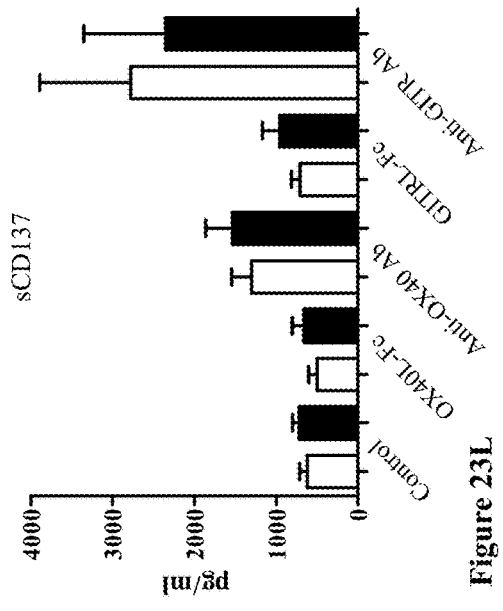
Figure 23L:
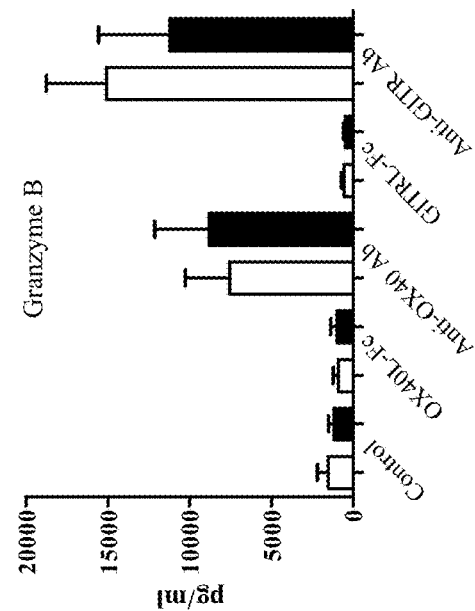
Figure 23I:
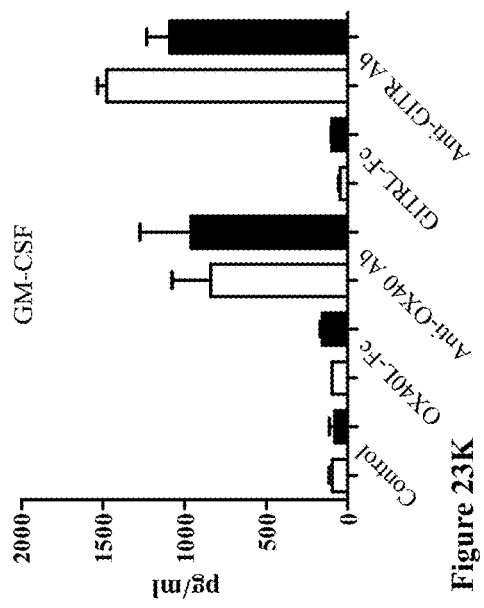
Figure 23K:
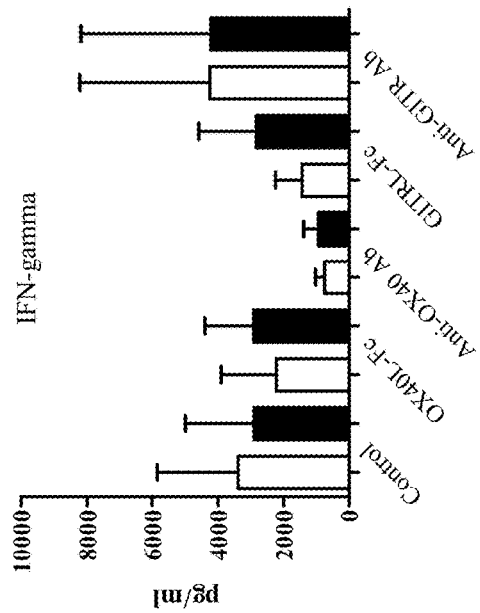

The percent of mice with tumors less than 300 mm$^3$ at study termination (Day 18) is shown in FIG. 22. Treatment with GITRL trimer-Fc 336B3 was observed to inhibit tumor growth of individual tumors at every dosage tested, including at the lowest dose of 0.05 mg/kg. In addition, in the group treated with 10 mg/kg, tumors had completely regressed in 3 mice and in the group treated with 2.5 mg/kg the tumor had completely regressed in 1 mouse.

These results are further evidence of the potent activity of the single chain GITRL trimer, even when assessed in what is considered a poorly immunogenic, "high bar" murine model.

Example 18

In Vivo Tumor Growth Inhibition by Single Chain OX40L Trimer-Fc Protein

The murine colon tumor line CT26.WT was implanted subcutaneously (30,000 cells/mouse) in Balb/c mice. Tumors were allowed to grow for 7 days reaching an average size of approximately 77 mm$^3$. Mice were treated with 0.25 mg/mouse of single chain mOX40L trimer-Fc 338F2, an agonist anti-OX40 antibody, single chain mGITRL trimer-Fc, agonist anti-GITR antibody DTA-1, or a control antibody (n=10 per group). Mice were dosed twice a week for a total of 3 doses. Tumor growth was monitored and tumor volumes were measured with electronic calipers at the indicated time points.

Figure 21B:
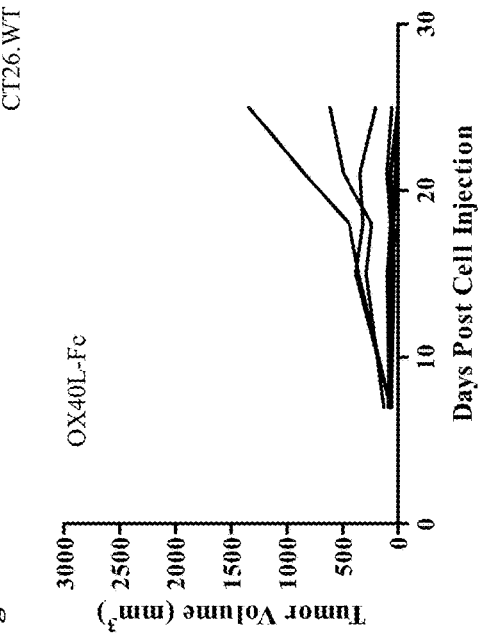
FIGS. 21A-21E. Inhibition of tumor growth by single chain GITRL trimer-Fc and OX40L trimer-Fc fusion polypeptide. The murine colon tumor line CT26.WT was implanted subcutaneously into Balb/c mice (n=10 mice/group). Mice were injected twice a week for 3 doses with 0.25 mg/mouse of single chain mOX40L trimer-Fc fusion protein, anti-mOX40 antibody, mGITRL trimer-Fc, anti-mGITR antibody DTA-1, or a control antibody. Tumor growth was monitored and tumor volumes were measured with electronic calipers at the indicated time points.
Figure 21D:
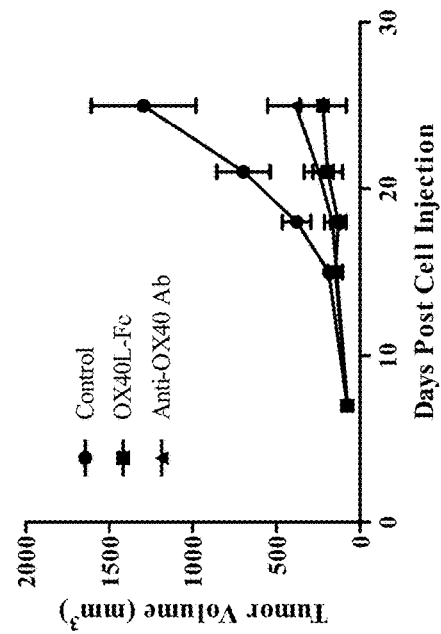
Figure 21A:
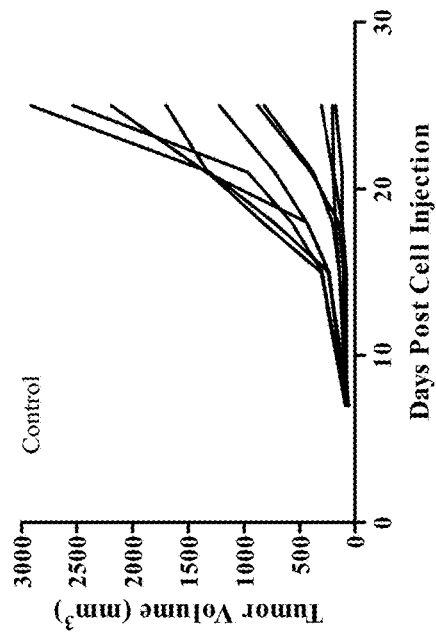
Figure 21C:
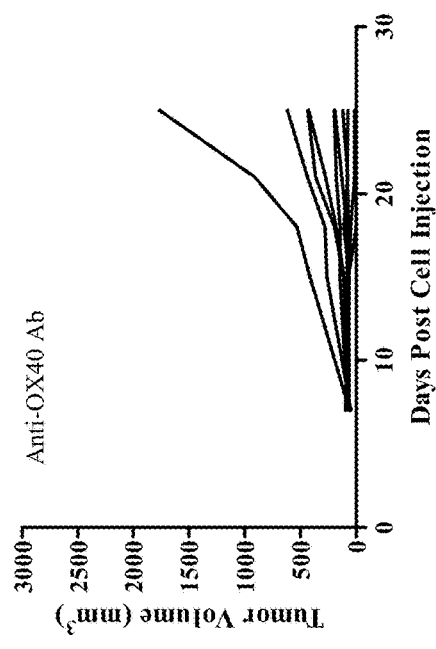
Figure 21E:
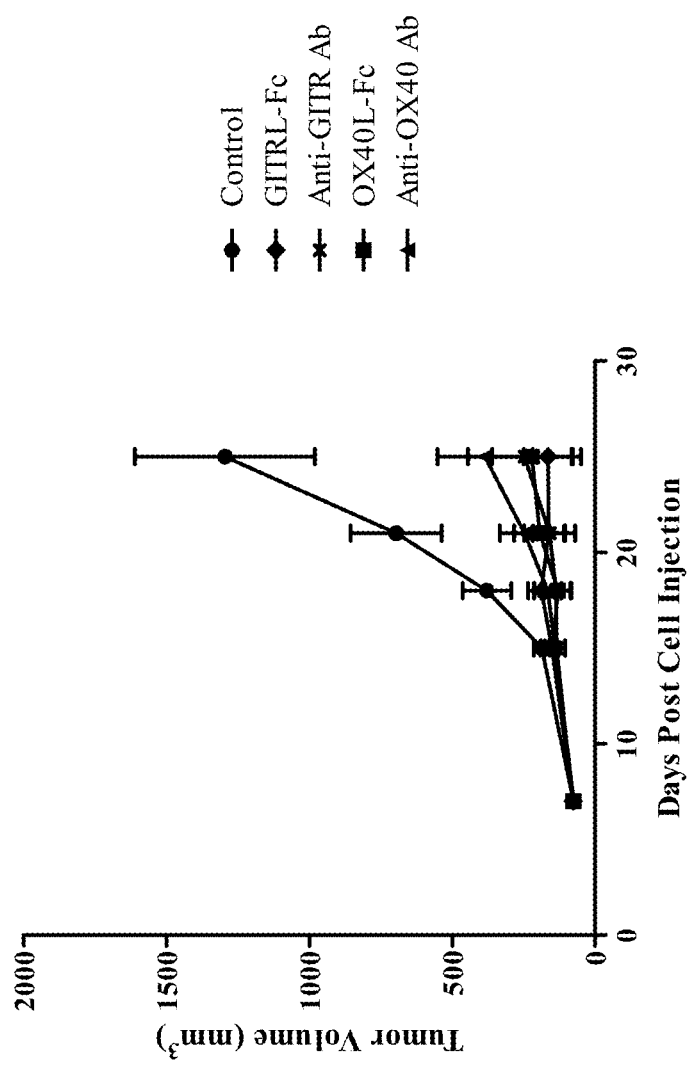

As is shown in FIGS. 21D and 21E, treatment with mOX40L trimer-Fc strongly inhibited and/or prevented growth of the CT26.WT tumors. Treatment with the agonist anti-OX40 antibody also inhibited tumor growth, but to a lesser extent than the OX40L trimer-Fc molecule. A more nuanced picture of the difference in tumor growth from treatment with OX40L trimer-Fc and an OX40 antibody can be seen by looking at the results from the individual mice within each group. As shown in FIG. 21B, tumors were undetectable in 6/10 mice treated with the OX40L trimer-Fc molecule while only one mouse had an undetectable tumor in the group treated with the anti-OX40 antibody.

Similar to the results seen with GITRL trimer-Fc 336B3, these results indicate that the single chain OX40L trimer-Fc is very active as an immunotherapeutic agent and could be more potent in achieving suppression of tumor growth than an agonist OX40 antibody.

Example 19

Cytokine Production

Cytokine production after treatment with GITRL trimer-Fc, OX40L trimer-Fc protein, anti-GITR antibody, or anti-OX40 antibody was evaluated. Cells were harvested on Day 26 from the spleens of the mice described above in Example 18. The cells were cultured in the presence or the absence of the tumor specific CD8+ T-cell peptide AH-1. After 48 hours, cytokine levels in cell supernatants were measured using a multiplex panel for the Luminex® platform (ThermoFisher Scientific) following the manufacturer's instructions.

As shown in FIGS. 23A-23L, almost all of the cytokines measured (IL-2, IL-4, IL-5, IL-6, IL-10, IL-13, MIP-1b, FasL, GM-CSF, sCD137, granzyme B) were produced in high amounts from mice treated with agonist anti-GITR or anti-OX40 antibodies relative to the cytokine amounts from mice treated with the control antibody. This is in stark contrast to the cytokine levels produced from mice treated with the GITRL trimer-Fc or OX40L trimer-Fc proteins. Cytokine levels produced from mice treated with the GITRL-Fc or OX40L-Fc were not increased relative to control and in most cases the cytokine levels were lower than controls. In addition, preliminary analysis of plasma samples from the treated mice have shown a similar trend of increased cytokine production in mice treated with agonist anti-GITR or anti-OX40 antibodies as compared to GITRL-Fc or OX40L-Fc treated mice.

These results indicate a striking difference in impact upon immune function with the GITRL trimer-Fc and OX40L trimer-Fc proteins, compared with agonist antibodies targeting GITR and OX40. Notably, whereas the treatment with GITRL-Fc and OX40L-Fc proteins did not result in elevated levels of cytokine production by splenocytes, the broad array of cytokines which were observed to be markedly elevated following treatment with the agonist GITR and OX40 antibodies is an unanticipated immunologic result that is indicative of substantial disruption of normal immune function. Many of the cytokines observed to be upregulated following agonist antibody treatment, including IL4, IL-5, IL-6, IL-10, and IL-13 possess biological functions that would tend to decrease the capacity of the immune system to mount an appropriate Th1-type immune response that is required to develop a durable anti-tumor immune response. Importantly, elevated levels of these powerful cytokines can contribute undesirable toxicities (i.e., a cytokine storm) that may reduce the therapeutic index of the agonist antibody. As the results were similar with both the anti-GITR antibody and the anti-OX40 antibody, this finding suggests that there may be a "class-effect" common to all agonist antibodies that impact GITR or OX-40, and potentially other TNFR family members.

Example 20

In Vivo Tumor Growth Inhibition by Single Chain GITRL Trimer-Fc Protein

The murine colon tumor line CT26.WT was implanted subcutaneously (30,000 cells/mouse) in Balb/c mice. To study the effect of the GITRL trimer-Fc protein on larger, established tumor cell masses, tumors were allowed to grow until reaching an average size of approximately 300 mm³. Mice were treated with 0.25 mg/mouse of single chain mGITRL trimer-Fc 336B3, agonist anti-GITR antibody DTA-1, or a control antibody (n=17 per group). Mice were dosed twice a week for a total of 3 doses by intraperitoneal injection. Tumor growth was monitored and tumor volumes were measured with electronic calipers. As possible, mice were followed beyond 80 days to assess long-term survival.

Figure 24B:
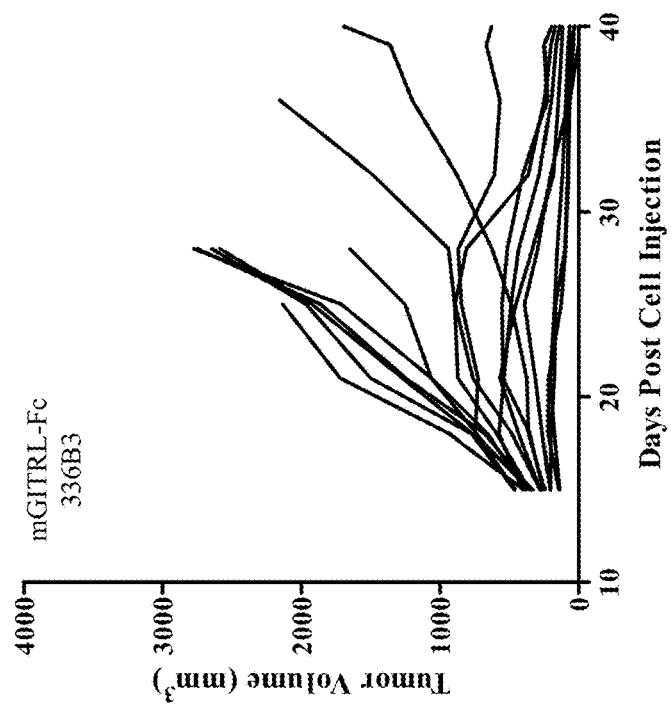
FIG. 24A-24D. Inhibition of tumor growth by single chain GITRL trimer-Fc protein. CT26.WT cells were implanted subcutaneously (30,000 cells/mouse) in Balb/c mice and allowed to grow until tumors were an average size of approximately 300 mm$^3$. Mice were treated with 0.25 mg/mouse of single chain mGITRL trimer-Fc 336B3, agonist anti-GITR antibody DTA-1, or a control antibody (n =17 per group). Mice were dosed twice a week for a total of 3 doses by intraperitoneal injection. Tumor growth was monitored and tumor volumes were measured with electronic calipers. As possible, mice were followed beyond 80 days to assess long-term survival.
Figure 24A:
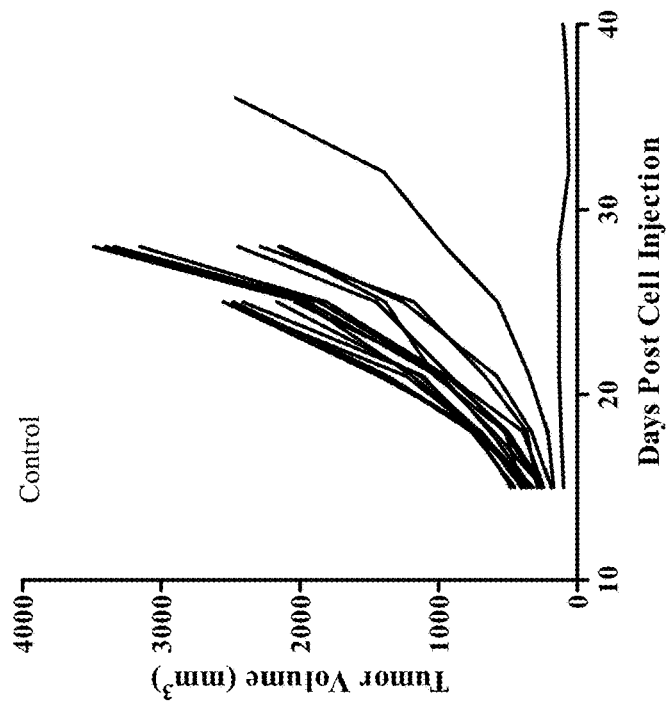
Figure 24C:
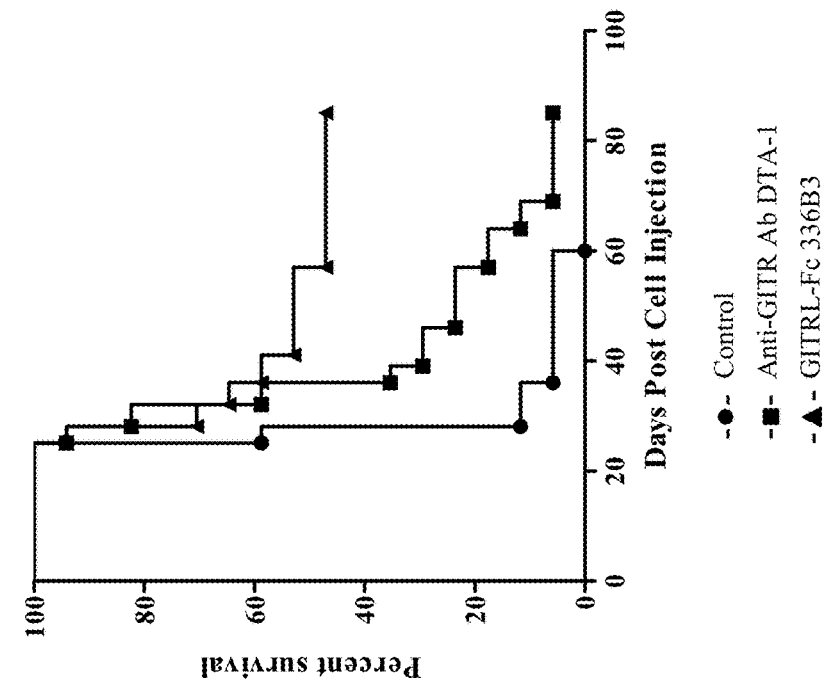
Figure 24D:
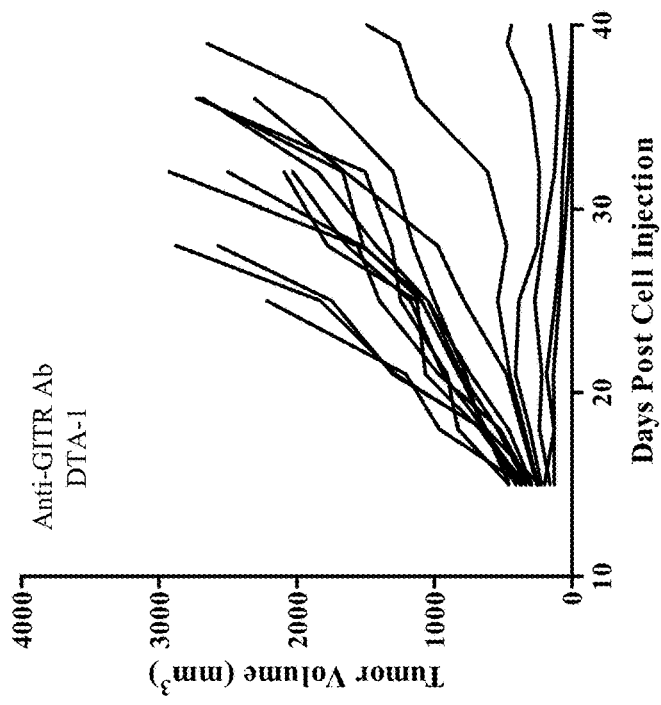

Tumor growth for the individual mice in each group up to Day 40 is shown in FIGS. 24A-C and percent survival is shown in FIG. 24D. The growth of CT26.WT tumors was strongly inhibited and/or prevented in the mice treated with mGITRL trimer-Fc 336B3. In at least 50% of the treated mice, tumors had regressed to a size smaller than tumor size prior to treatment (FIG. 24B). The agonist anti-GITR antibody DTA-1 inhibited tumor growth in only a small number of the treated mice (FIG. 24C). Tumor growth progressed very rapidly in untreated mice with 15 mice euthanized by Day 28. The survival curve shown in FIG. 24D clearly demonstrates the effectiveness of GITRL trimer-Fc 336B3 as compared to an agonist anti-GITR antibody.

These results indicate that the single chain GITRL trimer is active as an immunotherapeutic agent even against large, established tumors and is more potent in achieving suppression of tumor growth, regression of established tumors, and increasing survival than an agonist GITR antibody.

Example 21

In Vivo Tumor Growth Inhibition in Humanized Mice by Human GITRL Trimer-Fc Protein A humanized mouse model was used to study the efficacy of treatment with a human GITRL trimer-Fc protein on a human tumor. The humanized mice were obtained from Jackson Laboratories. These mice are created by injecting human hematopoietic stem cells (CD34+ cells) into irradiated NSG mice. After 15 weeks, the presence of mature human lymphocytes is confirmed by flow cytometry. Each mouse was injected subcutaneously with patient-derived melanoma tumor cells (OMP-M9, 75,000 cells/mouse). Tumors were allowed to grow 16 days until they had reached an average volume of approximately 60 mm³. Tumor-bearing mice were randomized into 2 groups (n=3 mice per group). Tumor-bearing mice were treated with either a control protein or hGITRL trimer-Fc OMP-336B11. Mice were dosed twice weekly at 10 mg/kg. Tumor growth was monitored and tumor volumes were measured with electronic calipers at the indicated time points.

Figure 25:
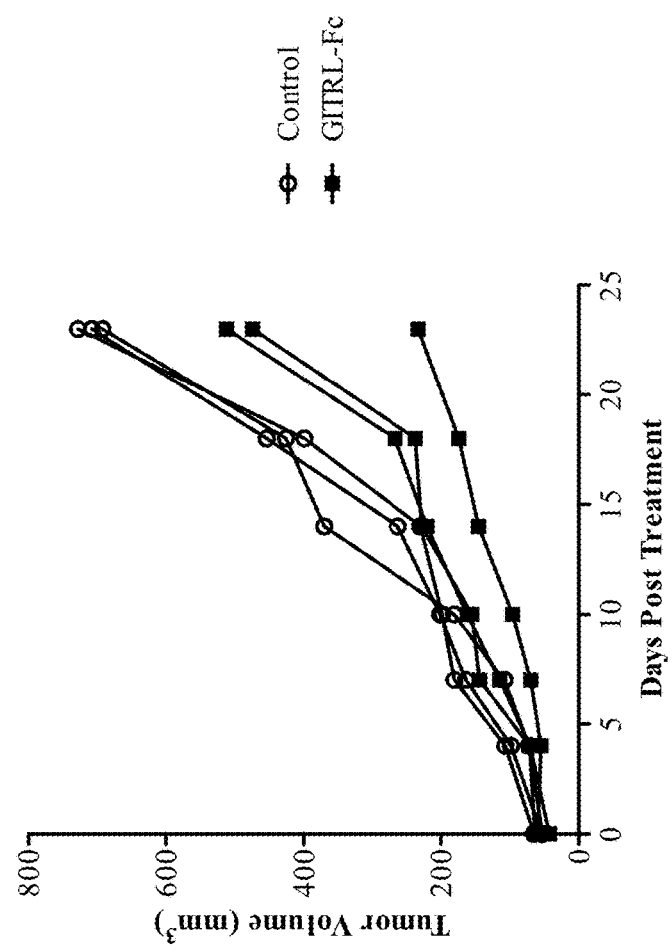
FIG. 25. Inhibition of tumor growth by single chain GITRL trimer-Fc protein in a humanized mouse model. Humanized mice were injected subcutaneously with patient-derived melanoma tumor cells (OMP-M9, 75,000 cells/mouse). Tumors were allowed to grow 16 days until they had reached an average volume of approximately 60 mm$^3$. Tumor-bearing mice were randomized into 2 groups (n=3 mice per group). Tumor-bearing mice were treated with either a control protein or hGITRL trimer-Fc OMP-336B11. Mice were dosed twice weekly at 10 mg/kg. Tumor growth was monitored and tumor volumes were measured with electronic calipers at the indicated time points.

As shown in FIG. 25, tumor growth was inhibited in the mice treated with human GITRL trimer-Fc as compared to control. These results show that the human GITRL trimer-Fc OMP-336B11 was effective at augmenting an anti-tumor immune response of human lymphocytes and contributing to inhibiting human tumor growth in vivo. Thus, these results demonstrated that humanized mouse models bearing patient-derived xenografts can be used to study the human GITRL trimer-Fc molecule in parallel with pre-clinical studies carried out with the surrogate mouse GITRL trimer-Fc protein and murine tumor models.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

Sequences disclosed in the application are:

```
Human GITRL (TNFSF18) amino acid sequence
                                                          (SEQ ID NO: 1)
MTLHPSPITCEFLFSTALISPKMCLSHLENMPLSHSRTQGAQRSSWKLWLFCSIVMLLFLCSFSWLIFIFLQLETAKE

PCMAKFGPLPSKWQMASSEPPCVNKVSDWKLEILQNGLYLIYGQVAPNANYNDVAPFEVRLYKNKDMIQTLTNKSKIQ

NVGGTYELHVGDTIDLIFNSEHQVLKNNTYWGIILLANPQFIS

Human GITRL signal/anchor region and extracellular domain amino acid sequence
                                                          (SEQ ID NO: 2)
FCSIVMLLFLCSFSWLIFIFLQLETAKEPCMAKFGPLPSKWQMASSEPPCVNKVSDWKLEILQNGLYLIYGQVAPNAN

YNDVAPFEVRLYKNKDMIQTLTNKSKIQNVGGTYELHVGDTIDLIFNSEHQVLKNNTYWGIILLANPQFIS

Human GITRL extracellular domain amino acid sequence
                                                          (SEQ ID NO: 3)
LQLETAKEPCMAKFGPLPSKWQMASSEPPCVNKVSDWKLEILQNGLYLIYGQVAPNANYNDVAPFEVRLYKNKDMIQT

LTNKSKIQNVGGTYELHVGDTIDLIFNSEHQVLKNNTYWGIILLANPQFIS

Human single chain GITRL trimer amino acid sequence with signal sequence
underlined
                                                          (SEQ ID NO: 4)
MEWGYLLEVTSLLAALLLLQRSPIVHALQLETAKEPCMAKFGPLPSKWQMASSEPPCVNKVSDWKLEILQNGLYLIYG

QVAPNANYNDVAPFEVRLYKNKDMIQTLTNKSKIQNVGGTYELHVGDTIDLIFNSEHQVLKNNTYWGIILLANPQFIS

LQLETAKEPCMAKFGPLPSKWQMASSEPPCVNKVSDWKLEILQNGLYLIYGQVAPNANYNDVAPFEVRLYKNKDMIQT

LTNKSKIQNVGGTYELHVGDTIDLIFNSEHQVLKNNTYWGIILLANPQFISLQLETAKEPCMAKFGPLPSKWQMASSE
```

```
PPCVNKVSDWKLEILQNGLYLIYGQVAPNANYNDVAPFEVRLYKNKDMIQTLTNKSKIQNVGGTYELHVGDTIDLIFN

SEHQVLKNNTYWGIILLANPQFIS
```

Human single chain GITRL trimer amino acid sequence without signal sequence (SEQ ID NO: 5)

```
LQLETAKEPCMAKFGPLPSKWQMASSEPPCVNKVSDWKLEILQNGLYLIYGQVAPNANYNDVAPFEVRLYKNKDMIQT

LTNKSKIQNVGGTYELHVGDTIDLIFNSEHQVLKNNTYWGIILLANPQFISLQLETAKEPCMAKFGPLPSKWQMASSE

PPCVNKVSDWKLEILQNGLYLIYGQVAPNANYNDVAPFEVRLYKNKDMIQTLINKSKIQNVGGIYELHVGDTIDLIFN

SEHQVLKNNTYWGIILLANPQFISLQLETAKEPCMAKFGPLPSKWQMASSEPPCVNKVSDWKLEILQNGLYLIYGQVA

PNANYNDVAPFEVRLYKNKDMIQTLTNKSKIQNVGGTYELHVGDTIDLIFNSEHQVLKNNTYWGIILLANPQFIS
```

336B11 Human single chain GITRL trimer-Fc (IgG1) amino acid sequence with signal sequence underlined (SEQ ID NO: 6)

```
MEWGYLLEVTSLLAALLLLQRSPIVHALQLETAKEPCMAKFGPLPSKWQMASSEPPCVNKVSDWKLEILQNGLYLIYG

QVAPNANYNDVAPFEVRLYKNKDMIQTLTNKSKIQNVGGTYELHVGDTIDLIFNSEHQVLKNNTYWGIILLANPQFIS

LQLETAKEPCMAKFGPLPSKWQMASSEPPCVNKVSDWKLEILQNGLYLIYGQVAPNANYNDVAPFEVRLYKNKDMIQT

LTNKSKIQNVGGTYELHVGDTIDLIFNSEHQVLKNNTYWGIILLANPQFISLQLETAKEPCMAKFGPLPSKWQMASSE

PPCVNKVSDWKLEILQNGLYLIYGQVAPNANYNDVAPFEVRLYKNKDMIQTLTNKSKIQNVGGTYELHVGDTIDLIFN

SEHQVLKNNTYWGIILLANPQFISDKTHTCPPCPAPELLGGPSVFLFPPKPKDTLMISRIPEVTCVVVDVSHEDPEVK

FNWYVDGVEVHNAKTKPREEQYNSTYRVVSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDGSFFLYSKLTVDKSRWQQGNVFSCSVMHE

ALHNHYTQKSLSLSPGK
```

336B11 Human single chain GITRL trimer-Fc (IgG1) amino acid sequence without signal sequence (SEQ ID NO: 7)

```
LQLETAKEPCMAKFGPLPSKWQMASSEPPCVNKVSDWKLEILQNGLYLIYGQVAPNANYNDVAPFEVRLYKNKDMIQT

LTNKSKIQNVGGTYELHVGDTIDLIFNSEHQVLKNNTYWGIILLANPQFISLQLETAKEPCMAKFGPLPSKWQMASSE

PPCVNKVSDWKLEILQNGLYLIYGQVAPNANYNDVAPFEVRLYKNKDMIQTLTNKSKIQNVGGTYELHVGDTIDLIFN

SEHQVLKNNTYWGIILLANPQFISLQLETAKEPCMAKFGPLPSKWQMASSEPPCVNKVSDWKLEILQNGLYLIYGQVA

PNANYNDVAPFEVRLYKNKDMIQTLTNKSKIQNVGGTYELHVGDTIDLIFNSEHQVLKNNTYWGIILLANPQFISDKT

HTCPPCPAPELLGGPSVFLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHYTQKSLSLSPGK
```

336B14 Human single chain GITRL trimer-Fc (IgG2) amino acid sequence with signal sequence underlined (SEQ ID NO: 8)

```
MEWGYLLEVTSLLAALLLLQRSPIVHALQLETAKEPCMAKFGPLPSKWQMASSEPPCVNKVSDWKLEILQNGLYLIYG

QVAPNANYNDVAPFEVRLYKNKDMIQTLTNKSKIQNVGGTYELHVGDTIDLIFNSEHQVLKNNTYWGIILLANPQFIS

LQLETAKEPCMAKFGPLPSKWQMASSEPPCVNKVSDWKLEILQNGLYLIYGQVAPNANYNDVAPFEVRLYKNKDMIQT

LTNKSKIQNVGGTYELHVGDTIDLIFNSEHQVLKNNTYWGIILLANPQFISLQLETAKEPCMAKFGPLPSKWQMASSE

PPCVNKVSDWKLEILQNGLYLIYGQVAPNANYNDVAPFEVRLYKNKDMIQTLTNKSKIQNVGGTYELHVGDTIDLIFN

SEHQVLKNNTYWGIILLANPQFISVERKSCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDSDGSFFLYSKLTVDKSRWQQGNVFSCSVM

HEALHNHYTQKSLSLSPGK
```

336B14 Human single chain GITRL trimer-Fc (IgG2) amino acid sequence without
signal sequence (SEQ ID NO: 9)

LQLETAKEPCMAKFGPLPSKWQMASSEPPCVNKVSDWKLEILQNGLYLIYGQVAPNANYNDVAPFEVRLYKNKDMIQT

LTNKSKIQNVGGTYELHVGDTIDLIFNSEHQVLKNNTYWGIILLANPQFISLQLETAKEPCMAKFGPLPSKWQMASSE

PPCVNKVSDWKLEILQNGLYLIYGQVAPNANYNDVAPFEVRLYKNKDMIQTLTNKSKIQNVGGTYELHVGDTIDLIFN

SEHQVLKNNTYWGIILLANPQFISLQLETAKEPCMAKFGPLPSKWQMASSEPPCVNKVSDWKLEILQNGLYLIYGQVA

PNANYNDVAPFEVRLYKNKDMIQTLTNKSKIQNVGGTYELHVGDTIDLIFNSEHQVLKNNTYWGIILLANPQFISVER

KSCVECPPCPAPPVAGPSVFLFPPKPKDTLMISRTPEVTCVVVDVSHEDPEVQFNWYVDGVEVHNAKTKPREEQFNST

FRVVSVLTVVHQDWLNGKEYKCKVSNKGLPAPIEKTISKTKGQPREPQVYTLPPSREEMTKNQVSLTCLVKGFYPSDI

AVEWESNGQPENNYKTTPPMLDSDGSFFLYSKLTVDKSRWQQGNVFSCSVMHEALHNHYTQKSLSLSPGK

Human IgG1 Fc region (SEQ ID NO: 10)

DKTHTCPPCPAPELLGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCSVMHEALHNHYTQKSLSLSPGK

Human IgG1 Fc region (SEQ ID NO: 11)

KSSDKTHTCPPCPAPELLGGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFSCSVMHEALHNHYTQKSLSLSPGK

Human IgG1 Fc region (SEQ ID NO: 12)

EPKSSDKTHTCPPCPAPELLGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHYTQKSLSLSPGK

Human IgG2 Fc region (SEQ ID NO: 13)

CVECPPCPAPPVAGPSVFLFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKNQVSLTCLVKGFYPSDIAV

EWESNGQPENNYKTTPPMLDSDGSFFLYSKLTVDKSRWQQGNVFSCSVMHEALHNHYTQKSLSLSPGK

Human IgG2 Fc region (SEQ ID NO: 14)

VERKSCVECPPCPAPPVAGPSVFLFPPKPKDTLMISRTPEVTCVVVDVSHEDPEVQFNWYVDGVEVHNAKTKPREEQF

NSTFRVVSVLTVVHQDWLNGKEYKCKVSNKGLPAPIEKTISKTKGQPREPQVYTLPPSREEMTKNQVSLTCLVKGFYP

SDIAVEWESNGQPENNYKTTPPMLDSDGSFFLYSKLTVDKSRWQQGNVFSCSVMHEALHNHYTQKSLSLSPGK

Human IgG1 Heavy chain constant region (SEQ ID NO: 15)

ASTKGPSVFPLAPSSKSTSGGTAALGCLVKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSDGSFFLYSKLTVDKSRWQQGNVFSCSVMH

EALHNHYTQKSLSLSPGK

Human IgG2 Heavy chain constant region (SEQ ID NO: 16)

ASTKGPSVFPLAPCSRSTSESTAALGCLVKDYFPEPVTVSWNSGALTSGVHTFPAVLQSSGLYSLSSVVTVPSSNFGT

QTYTCNVDHKPSNTKVDKTVERKCCVECPPCPAPPVAGPSVFLFPPKPKDTLMISRTPEVTCVVVDVSHEDPEVQFNW

YVDGVEVHNAKTKPREEQFNSTFRVVSVLTVVHQDWLNGKEYKCKVSNKGLPAPIEKTISKTKGQPREPQVYTLPPSR

EEMTKNQVSLTCLVKGFYPSDIAVEWESNGQPENNYKTTPPMLDSDGSFFLYSKLTVDKSRWQQGNVFSCSVMHEALH
NHYTQKSLSLSPGK

Human IgG3 Heavy chain constant region
(SEQ ID NO: 17)
ASTKGPSVFPLAPCSRSTSGGTAALGCLVKDYFPEPVTVSWNSGALTSGVHTFPAVLQSSGLYSLSSVVTVPSSSLGT
QTYTCNVNHKPSNTKVDKRVELKTPLGDTTHTCPRCPEPKSCDTPPPCPRCPEPKSCDTPPPCPRCPEPKSCDTPPPC
PRCPAPELLGGPSVFLFPPKPKDTLMISRTPEVTCVVVDVSHEDPEVQFKWYVDGVEVHNAKTKPREEQYNSTFRVVS
VLTVLHQDWLNGKEYKCKVSNKALPAPIEKTISKTKGQPREPQVYTLPPSREEMTKNQVSLTCLVKGFYPSDIAVEWE
SSGQPENNYNTTPPMLDSDGSFFLYSKLTVDKSRWQQGNIFSCSVMHEALHNRFTQKSLSLSPGK Human IgG4 Heavy chain constant region
(SEQ ID NO: 18)
ASTKGPSVFPLAPCSRSTSESTAALGCLVKDYFPEPVTVSWNSGALTSGVHTFPAVLQSSGLYSLSSVVTVPSSSLGT
KTYTCNVDHKPSNTKVDKRVESKYGPPCPSCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVDKSRWQEGNVFSCSVMHEAL
HNHYTQKSLSLSLGK Human GITRL nucleotide sequence
(SEQ ID NO: 19)
ATGACATTGCATCCTTCACCCATCACTTGTGAATTTTTGTTTTCCACAGCTCTCATTTCTCCAAAAATGTGTTTGAGC
CACTTGGAAAATATGCCTTTAAGCCATTCAAGAACTCAAGGAGCTCAGAGATCATCCTGGAAGCTGTGGCTCTTTTGC
TCAATAGTTATGTTGCTATTTCTTTGCTCCTTCAGTTGGCTAATCTTTATTTTTCTCCAATTAGAGACTGCTAAGGAG
CCCTGTATGGCTAAGTTTGGACCATTACCCTCAAAATGGCAAATGGCATCTTCTGAACCTCCTTGCGTGAATAAGGTG
TCTGACTGGAAGCTGGAGATACTTCAGAATGGCTTATATTTAATTTATGGCCAAGTGGCTCCCAATGCAAACTACAAT
GATGTAGCTCCTTTTGAGGTGCGGCTGTATAAAAACAAAGACATGATACAAACTCTAACAAACAAATCTAAAATCCAA
AATGTAGGAGGGACTTATGAATTGCATGTTGGGGACACCATAGACTTGATATTCAACTCTGAGCATCAGGTTCTAAAA
AATAATACATACTGGGGTATCATTTTACTAGCAAATCCCCAATTCATCTCCTAG Human GITRL signal/anchor region and extracellular domain nucleotide sequence
(SEQ ID NO: 20)
TTTTGCTCAATAGTTATGTTGCTATTTCTTTGCTCCTTCAGTTGGCTAATCTTTATTTTTCTCCAATTAGAGACTGCT
AAGGAGCCCTGTATGGCTAAGTTTGGACCATTACCCTCAAAATGGCAAATGGCATCTTCTGAACCTCCTTGCGTGAAT
AAGGTGTCTGACTGGAAGCTGGAGATACTTCAGAATGGCTTATATTTAATTTATGGCCAAGTGGCTCCCAATGCAAAC
TACAATGATGTAGCTCCTTTTGAGGTGCGGCTGTATAAAAACAAAGACATGATACAAACTCTAACAAACAAATCTAAA
ATCCAAAATGTAGGAGGGACTTATGAATTGCATGTTGGGGACACCATAGACTTGATATTCAACTCTGAGCATCAGGTT
CTAAAAAATAATACATACTGGGGTATCATTTTACTAGCAAATCCCCAATTCATCTCCTAG Human GITRL extracellular domain nucleotide sequence
(SEQ ID NO: 21)
CTCCAATTAGAGACTGCTAAGGAGCCCTGTATGGCTAAGTTTGGACCATTACCCTCAAAATGGCAAATGGCATCTTCT
GAACCTCCTTGCGTGAATAAGGTGTCTGACTGGAAGCTGGAGATACTTCAGAATGGCTTATATTTAATTTATGGCCAA
GTGGCTCCCAATGCAAACTACAATGATGTAGCTCCTTTTGAGGTGCGGCTGTATAAAAACAAAGACATGATACAAACT
CTAACAAACAAATCTAAAATCCAAAATGTAGGAGGGACTTATGAATTGCATGTTGGGGACACCATAGACTTGATATTC
AACTCTGAGCATCAGGTTCTAAAAAATAATACATACTGGGGTATCATTTTACTAGCAAATCCCCAATTCATCTCCTAG Human single chain GITRL trimer without signal sequence nucleotide sequence
(SEQ ID NO: 22)
CTGCAACTGGAAACCGCTAAGGAGCCCTGTATGGCTAAGTTCGGCCCACTGCCTTCCAAATGGCAGATGGCATCTAGT
GAGCCACCCTGTGTTAATAAAGTTAGCGATTGGAAACTGGAGATCCTGCAAAACGGGCTCTACCTGATTTACGGACAA
GTTGCTCCTAATGCTAACTACAATGATGTGGCTCCTTTTGAAGTTAGGCTGTATAAAAACAAAGACATGATCCAAACT -continued

CTCACTAACAAAAGCAAAATCCAAAATGTCGGTGGGACTTATGAGCTCCATGTTGGGGACACCATCGACCTGATTTTC

AACTCTGAGCATCAGGTTCTCAAAAATAATACATACTGGGGAATCATTCTCCTCGCGAATCCACAATTCATCTCTCTC

CAACTGGAAACCGCTAAAGAACCTTGCATGGCCAAATTTGGACCTCTCCCAAGCAAATGGCAAATGGCTTCTTCTGAA

CCTCCTTGCGTGAATAAGGTGTCTGACTGGAAGCTGGAGATTCTGCAGAATGGCCTCTATCTGATTTATGGGCAAGTT

GCACCTAACGCTAATTATAACGACGTCGCACCATTCGAAGTTCGCCTCTACAAAAATAAGGACATGATTCAAACACTG

ACTAATAAATCCAAATTCAAAACGTTGGGGGCACATACGAACTGCACGTCGGCGATACTATTGATCTCATCTTTAAT

TCCGAACACCAGGTCCTCAAAAACAATACCTATTGGGGGATCATCCTCCTGGCTAACCCACAATTTATATCTCTCCAA

CTCGAAACAGCCAAGGAACCATGTATGGCAAAGTTTGGTCCCCTCCCATCCAAGTGGCAAATGGCCAGTTCTGAACCC

CCATGCGTTAATAAGGTTTCCGACTGGAAACTGGAGATCCTGCAAAATGGTCTGTACCTCATCTATGGTCAAGTTGCA

CCAAACGCCAATTACAATGATGTTGCACCATTTGAAGTTCGCCTGTACAAAAACAAAGATATGATCCAAACCCTCACT

AACAAATCTAAAATCCAAAATGTTGGTGGTACTTACGAACTGCATGTGGGTGACACCATCGACCTCATCTTCAATTCC

GAGCATCAGGTGCTCAAAAACAATACATATTGGGGCATAATTCTGCTCGCAAATCCACAATTCATCTCT

Human single chain GITRL trimer with signal sequence nucleotide sequence
(SEQ ID NO: 23)
ATGGAGTGGGGTTATCTGCTCGAAGTGACCTCCCTGCTGGCCGCCCTGCTCCTGCTGCAACGCTCTCCTATCGTGCAC

GCCCTGCAACTGGAAACCGCTAAGGAGCCCTGTATGGCTAAGTTCGGCCCACTGCCTTCCAAATGGCAGATGGCATCT

AGTGAGCCACCCTGTGTTAATAAAGTTAGCGATTGGAAACTGGAGATCCTGCAAAACGGGCTCTACCTGATTTACGGA

CAAGTTGCTCCTAATGCTAACTACAATGATGTGGCTCCTTTTGAAGTTAGGCTGTATAAAAACAAAGACATGATCCAA

ACTCTCACTAACAAAAGCAAAATCCAAAATGTCGGTGGGACTTATGAGCTCCATGTTGGGGACACCATCGACCTGATT

TTCAACTCTGAGCATCAGGTTCTCAAAAATAATACATACTGGGGAATCATTCTCCTCGCGAATCCACAATTCATCTCT

CTCCAACTGGAAACCGCTAAAGAACCTTGCATGGCCAAATTTGGACCTCTCCCAAGCAAATGGCAAATGGCTTCTTCT

GAACCTCCTTGCGTGAATAAGGTGTCTGACTGGAAGCTGGAGATTCTGCAGAATGGCCTCTATCTGATTTATGGGCAA

GTTGCACCTAACGCTAATTATAACGACGTCGCACCATTCGAAGTTCGCCTCTACAAAAATAAGGACATGATTCAAACA

CTGACTAATAAATCCAAAATTCAAAACGTTGGGGGCACATACGAACTGCACGTCGGCGATACTATTGATCTCATCTTT

AATTCCGAACACCAGGTCCTCAAAAACAATACCTATTGGGGGATCATCCTCCTGGCTAACCCACAATTTATATCTCTC

CAACTCGAAACAGCCAAGGAACCATGTATGGCAAAGTTTGGTCCCCTCCCATCCAAGTGGCAAATGGCCAGTTCTGAA

CCCCCATGCGTTAATAAGGTTTCCGACTGGAAACTGGAGATCCTGCAAAATGGTCTGTACCTCATCTATGGTCAAGTT

GCACCAAACGCCAATTACAATGATGTTGCACCATTTGAAGTTCGCCTGTACAAAAACAAAGATATGATCCAAACCCTC

ACTAACAAATCTAAAATCCAAAATGTTGGTGGTACTTACGAACTGCATGTGGGTGACACCATCGACCTCATCTTCAAT

TCCGAGCATCAGGTGCTCAAAAACAATACATATTGGGGCATAATTCTGCTCGCAAATCCACAATTCATCTCT

336B11 Human single chain GITRL trimer-Fc (IgG1) nucleotide sequence
(SEQ ID NO: 24)
ATGGAGTGGGGTTATCTGCTCGAAGTGACCTCCCTGCTGGCCGCCCTGCTCCTGCTGCAACGCTCTCCTATCGTGCAC

GCCCTGCAACTGGAAACCGCTAAGGAGCCCTGTATGGCTAAGTTCGGCCCACTGCCTTCCAAATGGCAGATGGCATCT

AGTGAGCCACCCTGTGTTAATAAAGTTAGCGATTGGAAACTGGAGATCCTGCAAAACGGGCTCTACCTGATTTACGGA

CAAGTTGCTCCTAATGCTAACTACAATGATGTGGCTCCTTTTGAAGTTAGGCTGTATAAAAACAAAGACATGATCCAA

ACTCTCACTAACAAAAGCAAAATCCAAAATGTCGGTGGGACTTATGAGCTCCATGTTGGGGACACCATCGACCTGATT

TTCAACTCTGAGCATCAGGTTCTCAAAAATAATACATACTGGGGAATCATTCTCCTCGCGAATCCACAATTCATCTCT

CTCCAACTGGAAACCGCTAAAGAACCTTGCATGGCCAAATTTGGACCTCTCCCAAGCAAATGGCAAATGGCTTCTTCT

GAACCTCCTTGCGTGAATAAGGTGTCTGACTGGAAGCTGGAGATTCTGCAGAATGGCCTCTATCTGATTTATGGGCAA

GTTGCACCTAACGCTAATTATAACGACGTCGCACCATTCGAAGTTCGCCTCTACAAAAATAAGGACATGATTCAAACA

CTGACTAATAAATCCAAAATTCAAAACGTTGGGGGCACATACGAACTGCACGTCGGCGATACTATTGATCTCATCTTT

AATTCCGAACACCAGGTCCTCAAAAACAATACCTATTGGGGGATCATCCTCCTGGCTAACCCACAATTTATATCTCTC

-continued

```
CAACTCGAAACAGCCAAGGAACCATGTATGGCAAAGTTTGGTCCCCTCCCATCCAAGTGGCAAATGGCCAGTTCTGAA
CCCCCATGCGTTAATAAGGTTTCCGACTGGAAACTGGAGATCCTGCAAAATGGTCTGTACCTCATCTATGGTCAAGTT
GCACCAAACGCCAATTACAATGATGTTGCACCATTTGAAGTTCGCCTGTACAAAAACAAAGATATGATCCAAACCCTC
ACTAACAAATCTAAAATCCAAAATGTTGGTGGTACTTACGAACTGCATGTGGGTGACACCATCGACCTCATCTTCAAT
TCCGAGCATCAGGTGCTCAAAAACAATACATATTGGGGCATAATTCTGCTCGCAAATCCACAATTCATCTCTGACAAG
ACCCACACCTGCCCTCCCTGCCCTGCCCCTGAGCTGCTGGGCGGACCTTCCGTGTTCCTGTTCCCTCCTAAGCCTAAG
GACACCCTGATGATCTCCCGGACCCCTGAAGTGACATGCGTGGTGGTGGACGTGTCCCACGAGGACCCTGAGGTGAAG
TTCAACTGGTATGTGGACGGCGTGGAGGTGCACAACGCTAAGACCAAGCCTAGGGAGGAGCAGTACAACTCCACCTAC
CGGGTGGTGTCTGTGCTGACCGTGCTGCACCAGGACTGGCTGAACGGCAAAGAATACAAGTGCAAGGTCTCCAACAAG
GCCCTGCCCGCTCCCATCGAGAAAACCATCAGCAAGGCAAAGGGCCAGCCTCGCGAGCCTCAGGTGTACACCCTGCCA
CCCAGCCGGGAGGAGATGACCAAGAACCAGGTGTCCCTGACCTGTCTGGTGAAGGGCTTTTACCCTTCCGATATTGCC
GTGGAGTGGGAGTCTAACGGCCAGCCCGAGAACAACTACAAGACCACCCCTCCTGTGCTGGACTCCGACGGCTCCTTC
TTCCTGTACTCCAAGCTGACCGTGGACAAGTCCCGGTGGCAGCAGGGCAACGTGTTCTCCTGCTCCGTGATGCACGAG
GCCCTGCACAACCACTACACCCAGAAGAGCCTGTCTCTGTCTCCTGGCAAGTGA
```

336B14 Human single chain GITRL trimer-Fc (IgG2) nucleotide sequence (SEQ ID NO: 25)
```
ATGGAGTGGGGTTATCTGCTCGAAGTGACCTCCCTGCTGGCCGCCCTGCTCCTGCTGCAACGCTCTCCTATCGTGCAC
GCCCTGCAACTGGAAACCGCTAAGGAGCCCTGTATGGCTAAGTTCGGCCCACTGCCTTCCAAATGGCAGATGGCATCT
AGTGAGCCACCCTGTGTTAATAAAGTTAGCGATTGGAAACTGGAGATCCTGCAAAACGGGCTCTACCTGATTTACGGA
CAAGTTGCTCCTAATGCTAACTACAATGATGTGGCTCCTTTTGAAGTTAGGCTGTATAAAAACAAAGACATGATCCAA
ACTCTCACTAACAAAAGCAAAATCCAAAATGTCGGTGGGACTTATGAGCTCCATGTTGGGGACACCATCGACCTGATT
TTCAACTCTGAGCATCAGGTTCTCAAAAATAATACATACTGGGGAATCATTCTCCTCGCGAATCCACAATTCATCTCT
CTCCAACTGGAAACCGCTAAAGAACCTTGCATGGCCAAATTTGGACCTCTCCCAAGCAAATGGCAAATGGCTTCTTCT
GAACCTCCTTGCGTGAATAAGGTGTCTGACTGGAAGCTGGAGATTCTGCAGAATGGCCTCTATCTGATTTATGGGCAA
GTTGCACCTAACGCTAATTATAACGACGTCGCACCATTCGAAGTTCGCCTCTACAAAAATAAGGACATGATTCAAACA
CTGACTAATAAATCCAAAATTCAAAACGTTGGGGGCACATACGAACTGCACGTCGGCGATACTATTGATCTCATCTTT
AATTCCGAACACCAGGTCCTCAAAAACAATACCTATTGGGGGATCATCCTCCTGGCTAACCCACAATTTATATCTCTC
CAACTCGAAACAGCCAAGGAACCATGTATGGCAAAGTTTGGTCCCCTCCCATCCAAGTGGCAAATGGCCAGTTCTGAA
CCCCCATGCGTTAATAAGGTTTCCGACTGGAAACTGGAGATCCTGCAAAATGGTCTGTACCTCATCTATGGTCAAGTT
GCACCAAACGCCAATTACAATGATGTTGCACCATTTGAAGTTCGCCTGTACAAAAACAAAGATATGATCCAAACCCTC
ACTAACAAATCTAAAATCCAAAATGTTGGTGGTACTTACGAACTGCATGTGGGTGACACCATCGACCTCATCTTCAAT
TCCGAGCATCAGGTGCTCAAAAACAATACATATTGGGGCATAATTCTGCTCGCAAATCCACAATTCATCTCTGTTGAG
CGCAAATCTTGTGTCGAGTGCCCACCTTGCCCAGCACCACCTGTGGCAGGACCTTCAGTCTTCCTCTTCCCCCCAAAA
CCCAAGGACACCCTCATGATCTCCCGGACCCCTGAGGTCACATGCGTGGTGGTGGACGTGAGCCACGAAGACCCCGAG
GTCCAGTTTAATTGGTATGTCGACGGCGTGGAGGTGCATAATGCCAAGACAAAGCCACGGGAGGAGCAGTTCAACAGC
ACATTCAGGGTGGTCAGCGTCCTCACCGTTGTGCACCAGGACTGGCTGAACGGCAAGGAGTACAAGTGCAAGGTGTCC
AACAAAGGCCTCCCAGCCCCCATCGAGAAAACCATCTCCAAAACCAAAGGGCAGCCCAGAGAACCACAGGTGTACACC
CTGCCCCCATCCCGGGAGGAGATGACCAAGAACCAGGTCAGCCTGACCTGCCTGGTGAAGGGATTTTATCCTTCCGAC
ATCGCCGTGGAGTGGGAGAGCAATGGGCAGCCTGAGAACAACTACAAGACCACACCTCCCATGCTGGACTCCGACGGC
TCCTTCTTCCTGTATTCCAAACTCACCGTGGACAAGAGCAGGTGGCAGCAGGGGAACGTCTTCTCATGCTCCGTGATG
CATGAGGCTCTGCACAACCACTACACACAGAAGAGCCTCTCCCTGTCCCCTGGGAAAGTGA
```

-continued

Human IgG2 Fc region (13A Version)
(SEQ ID NO: 26)
CVECPPCPAPPVAGPSVFLFPPKPKDTLMISRTPEVTCVVVDVSHEDPEVQFNTNYVDGVEVHNAKTKPREEQFNSTF
RVVSVLTVVHQDTNLNGKEYKCKVSNKGLPAPIEKTISKTKGQPREPQVYTLPPSREKMTKNQVSLTCLVKGFYPSDI
AVEWESNGQPENNYKTTPPMLKSDGSFFLYSKLTVDKSRWQQGNVFSCSVMHEALHNHYTQKSLSLSPGK Human IgG2 Fc region (13B Version)
(SEQ ID NO: 27)
CVECPPCPAPPVAGPSVFLFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKNQVSLTCLVEGFYPSDIAV
EWESNGQPENNYKTTPPMLDSDGSFFLYSELTVDKSRWQQGNVFSCSVMHEALHNHYTQKSLSLSPGK Human IgG2 Fc region (13A Version)
(SEQ ID NO: 28)
TKVDKTVERKCCVECPPCPAPPVAGPSVFLFPPKPKDTLMISRTPEVTCVVVDVSHEDPEVQFNWYVDGVEVHNAKTK
PREEQFNSTFRVVSVLTVVHQDWLNGKEYKCKVSNKGLPAPIEKTISKTKGQPREPQVYTLPPSREKMTKNQVSLTCL
VKGFYPSDIAVEWESNGQPENNYKTTPPMLKSDGSFFLYSKLTVDKSRWQQGNVFSCSVMHEALHNHYTQKSLSLSPG
K Human IgG2 Fc region (13A Version)
(SEQ ID NO: 29)
TKVDKTVERKSCVECPPCPAPPVAGPSVFLFPPKPKDTLMISRTPEVTCVVVDVSHEDPEVQFNWYVDGVEVHNAKTK
PREEQFNSTFRVVSVLTVVHQDWLNGKEYKCKVSNKGLPAPIEKTISKTKGQPREPQVYTLPPSREKMTKNQVSLTCL
VKGFYPSDIAVEWESNGQPENNYKTTPPMLKSDGSFFLYSKLTVDKSRWQQGNVFSCSVMHEALHNHYTQKSLSLSPG
K Human IgG2 Fc region (13B Version)
(SEQ ID NO: 30)
TKVDKTVERKCCVECPPCPAPPVAGPSVFLFPPKPKDTLMISRTPEVTCVVVDVSHEDPEVQFNWYVDGVEVHNAKTK
PREEQFNSTFRVVSVLTVVHQDWLNGKEYKCKVSNKGLPAPIEKTISKTKGQPREPQVYTLPPSREEMTKNQVSLTCL
VEGFYPSDIAVEWESNGQPENNYKTTPPMLDSDGSFFLYSELTVDKSRWQQGNVFSCSVMHEALHNHYTQKSLSLSPG
K Human IgG2 Fc region (13B Version)
(SEQ ID NO: 31)
TKVDKTVERKSCVECPPCPAPPVAGPSVFLFPPKPKDTLMISRTPEVTCVVVDVSHEDPEVQFNWYVDGVEVHNAKTK
PREEQFNSTFRVVSVLTVVHQDWLNGKEYKCKVSNKGLPAPIEKTISKTKGQPREPQVYTLPPSREEMTKNQVSLTCL
VEGFYPSDIAVEWESNGQPENNYKTTPPMLDSDGSFFLYSELTVDKSRWQQGNVFSCSVMHEALHNHYTQKSLSLSPG
K Human GITRL Stalk Region
(SEQ ID NO: 32)
LQLETAK Human GITRL TNF Homology Domain
(SEQ ID NO: 33)
KWQMASSEPPCVNKVSDWKLEILQNGLYLIYGQVAPNANYNDVAPFEVRLYKNKDMIQTLTNKSKIQNVGGTYELHVG
DTIDLIFNSEHQVLKNNTYWGIILL Linker
(SEQ ID NO: 34)
ESGGGGVT Linker
(SEQ ID NO: 35)
LESGGGGVT Linker
(SEQ ID NO: 36)
GRAQVT Linker
(SEQ ID NO: 37)
WRAQVT

```
Linker                                                                  (SEQ ID NO: 38)
ARGRAQVT FLAGTag                                                                 (SEQ ID NO: 39)
DYKDDDDK Human OX40L (TNFSF4) amino acid sequence
                                                                        (SEQ ID NO: 40)
MERVQPLEENVGNAARPRFERNKLLLVASVIQGLGLLLCFTYICLHFSALQVSHRY-
PRIQSIKVQFTEYKKEKGFILT

SQKEDEIMKVQNNSVIINCDGFYLISLKGYFSQEVNISLHYQKDEEPLFQLKKVRS-
VNSLMVASLTYKDKVYLNVTTD

NTSLDDFHVNGGELILIHQNPGEFCVL

Human OX40L transmembrane and extracellular domain amino acid sequence
                                                                        (SEQ ID NO: 41)
LLLVASVIQGLGLLLCFTYICLHFSALQVSHRYPRIQSIKVQFTEYKKEKGFILTSQKEDEIMKVQNNSVIINCDGFY

LISLKGYFSQEVNISLHYQKDEEPLFQLKKVRSVNSLMVASLTYKDKVYLNVTTDNTSLDDFHVNGGELILIHQNPGE

FCVL

Human OX40L extracellular domain amino acid sequence
                                                                        (SEQ ID NO: 42)
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVL

Human single chain OX40L trimer amino acid sequence with signal sequence
underlined
                                                                        (SEQ ID NO: 43)
MEWGYLLEVTSLLAALLLLQRSPIVHAQVSHRYPRIQSIKVQFTEYKKEKGFILTSQKEDEIMKVQNNSVIINCDGFY

LISLKGYFSQEVNISLHYQKDEEPLFQLKKVRSVNSLMVASLTYKDKVYLNVTTDNTSLDDFHVNGGELILIHQNPGE

FCVLQVSHRYPRIQSIKVQFTEYKKEKGFILTSQKEDEIMKVQNNSVIINCDGFYLISLKGYFSQEVNISLHYQKDEE

PLFQLKKVRSVNSLMVASLTYKDKVYLNVTTDNTSLDDFHVNGGELILIHQNPGEFCVLQVSHRYPRIQSIKVQFTEY

KKEKGFILTSQKEDEIMKVQNNSVIINCDGFYLISLKGYFSQEVNISLHYQKDEEPLFQLKKVRSVNSLMVASLTYKD

KVYLNVTTDNTSLDDFHVNGGELILIHQNPGEFCVL

Human single chain OX40L trimer amino acid sequence without signal sequence
                                                                        (SEQ ID NO: 44)
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVLQVSHRYPRIQSIKVQFTEYKKEK

GFILTSQKEDEIMKVQNNSVIINCDGFYLISLKGYFSQEVNISLHYQKDEEPLFQLKKVRSVNSLMVASLTYKDKVYL

NVTTDNTSLDDFHVNGGELILIHQNPGEFCVLQVSHRYPRIQSIKVQFTEYKKEKGFILTSQKEDEIMKVQNNSVIIN

CDGFYLISLKGYFSQEVNISLHYQKDEEPLFQLKKVRSVNSLMVASLTYKDKVYLNVTTDNTSLDDFHVNGGELILIH

QNPGEFCVL

338F3 Human single chain OX40L trimer-Fc (IgG1) amino acid sequence with
signal sequence underlined
                                                                        (SEQ ID NO: 45)
MEWGYLLEVTSLLAALLLLQRSPIVHAQVSHRYPRIQSIKVQFTEYKKEKGFILTSQKEDEIMKVQNNSVIINCDGFY

LISLKGYFSQEVNISLHYQKDEEPLFQLKKVRSVNSLMVASLTYKDKVYLNVTTDNTSLDDFHVNGGELILIHQNPGE

FCVLQVSHRYPRIQSIKVQFTEYKKEKGFILTSQKEDEIMKVQNNSVIINCDGFYLISLKGYFSQEVNISLHYQKDEE

PLFQLKKVRSVNSLMVASLTYKDKVYLNVTTDNTSLDDFHVNGGELILIHQNPGEFCVLQVSHRYPRIQSIKVQFTEY

KKEKGFILTSQKEDEIMKVQNNSVIINCDGFYLISLKGYFSQEVNISLHYQKDEEPLFQLKKVRSVNSLMVASLTYKD

KVYLNVTTDNTSLDDFHVNGGELILIHQNPGEFCVLDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPAPIEKTISKAK
```

```
GQPREPQVYTLPPSREEMTKNQVSLTCLVKGFYPSDIAVEWESNGQPENNYKTTPPVLDSDGSFFLYSKLTVDKSRWQ

QGNVFSCSVMHEALHNHYTQKSLSLSPGK
```

338F3 Human single chain OX40L trimer-Fc (IgG1) amino acid sequence without
signal sequence (SEQ ID NO: 46)

```
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVLQVSHRYPRIQSIKVQFTEYKKEK

GFILTSQKEDEIMKVQNNSVIINCDGFYLISLKGYFSQEVNISLHYQKDEEPLFQLKKVRSVNSLMVASLTYKDKVYL

NVTTDNTSLDDFHVNGGELILIHQNPGEFCVLQVSHRYPRIQSIKVQFTEYKKEKGFILTSQKEDEIMKVQNNSVIIN

CDGFYLISLKGYFSQEVNISLHYQKDEEPLFQLKKVRSVNSLMVASLTYKDKVYLNVTTDNTSLDDFHVNGGELILIH

QNPGEFCVLDKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRWQQGNVFSCSVMHEALHNHYTQKSLSLSP

GK
```

Human single chain OX40L trimer-Fc (IgG2) amino acid sequence with signal
sequence underlined (SEQ ID NO: 47)

```
MEWGYLLEVTSLLAALLLLQRSPIVHAQVSHRYPRIQSIKVQFTEYKKEKGFILTSQKEDEIMKVQNNSVIINCDGFY

LISLKGYFSQEVNISLHYQKDEEPLFQLKKVRSVNSLMVASLTYKDKVYLNVTTDNTSLDDFHVNGGELILIHQNPGE

FCVLQVSHRYPRIQSIKVQFTEYKKEKGFILTSQKEDEIMKVQNNSVIINCDGFYLISLKGYFSQEVNISLHYQKDEE

PLFQLKKVRSVNSLMVASLTYKDKVYLNVTTDNTSLDDFHVNGGELILIHQNPGEFCVLQVSHRYPRIQSIKVQFTEY

KKEKGFILTSQKEDEIMKVQNNSVIINCDGFYLISLKGYFSQEVNISLHYQKDEEPLFQLKKVRSVNSLMVASLTYKD

KVYLNVTTDNTSLDDFHVNGGELILIHQNPGEFCVLVERKSCVECPPCPAPPVAGPSVFLFPPKPKDTLMISRTPEVT

CVVVDVSHEDPEVQFNWYVDGVEVHNAKTKPREEQFNSTFRVVSVLTVVHQDWLNGKEYKCKVSNKGLPAPIEKTISK

TKGQPREPQVYTLPPSREEMTKNQVSLTCLVKGFYPSDIAVEWESNGQPENNYKTTPPMLDSDGSFFLYSKLTVDKSR

WQQGNVFSCSVMHEALHNHYTQKSLSLSPGK
```

Human single chain OX40L trimer-Fc (IgG2) amino acid sequence without signal
sequence (SEQ ID NO: 48)

```
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVLQVSHRYPRIQSIKVQFTEYKKEK

GFILTSQKEDEIMKVQNNSVIINCDGFYLISLKGYFSQEVNISLHYQKDEEPLFQLKKVRSVNSLMVASLTYKDKVYL

NVTTDNTSLDDFHVNGGELILIHQNPGEFCVLQVSHRYPRIQSIKVQFTEYKKEKGFILTSQKEDEIMKVQNNSVIIN

CDGFYLISLKGYFSQEVNISLHYQKDEEPLFQLKKVRSVNSLMVASLTYKDKVYLNVTTDNTSLDDFHVNGGELILIH

QNPGEFCVLVERKSCVECPPCPAPPVAGPSVFLFPPKPKDTLMISRTPEVTCVVVDVSHEDPEVQFNWYVDGVEVHNA

KTKPREEQFNSTFRVVSVLTVVHQDWLNGKEYKCKVSNKGLPAPIEKTISKTKGQPREPQVYTLPPSREEMTKNQVSL

TCLVKGFYPSDIAVEWESNGQPENNYKTTPPMLDSDGSFFLYSKLTVDKSRWQQGNVF-
SCSVMHEALHNHYTQKSLSL

SPGK
```

Human OX40L nucleotide sequence (SEQ ID NO: 49)

```
ATGGAAAGGGTCCAACCCCTGGAAGAGAATGTGGGAAATGCAGCCAGGCCAAGATTCGAGAGGAACAAGCTATTGCTG

GTGGCCTCTGTAATTCAGGGACTGGGGCTGCTCCTGTGCTTCACCTACATCTGCCTGCACTTCTCTGCTCTTCAGGTA

TCACATCGGTATCCTCGAATTCAAAGTATCAAAGTACAATTTACCGAATATAAGAAGGAGAAAGGTTTCATCCTCACT

TCCCAAAAGGAGGATGAAATCATGAAGGTGCAGAACAACTCAGTCATCATCAACTGTGATGGGTTTTATCTCATCTCC

CTGAAGGGCTACTTCTCCCAGGAAGTCAACATTAGCCTTCATTACCAGAAGGATGAGGAGCCCCTCTTCCAACTGAAG
```

-continued

AAGGTCAGGTCTGTCAACTCCTTGATGGTGGCCTCTCTGACTTACAAAGACAAAGTCTACTTGAATGTGACCACTGAC

AATACCTCCCTGGATGACTTCCATGTGAATGGCGGAGAACTGATTCTTATCCATCAAAATCCTGGTGAATTCTGTGTC

CTTTGA

Human OX40L extracellular domain nucleotide sequence
(SEQ ID NO: 50)
CAGGTATCACATCGGTATCCTCGAATTCAAAGTATCAAAGTACAATTTACCGAATATAAGAAGGAGAAAGGTTTCATC

CTCACTTCCCAAAAGGAGGATGAAATCATGAAGGTGCAGAACAACTCAGTCATCATCAACTGTGATGGGTTTTATCTC

ATCTCCCTGAAGGGCTACTTCTCCCAGGAAGTCAACATTAGCCTTCATTACCAGAAGGATGAGGAGCCCCTCTTCCAA

CTGAAGAAGGTCAGGTCTGTCAACTCCTTGATGGTGGCCTCTCTGACTTACAAAGACAAAGTCTACTTGAATGTGACC

ACTGACAATACCTCCCTGGATGACTTCCATGTGAATGGCGGAGAACTGATTCTTATCCATCAAAATCCTGGTGAATTC

TGTGTCCTTTGA

Human single chain OX40L trimer with signal sequence nucleotide sequence
(SEQ ID NO: 51)
ATGGAGTGGGGTTATCTGCTCGAAGTGACCTCCCTGCTGGCCGCCCTGCTCCTGCTGCAACGCTCTCCTATCGTGCAC

GCCCAGGTCTCTCATAGATACCCACGCATACAATCAATCAAAGTCCAATTTACAGAATATAAGAAGGAAAAAGGATTC

ATTCTCACATCTCAGAAGGAGGACGAAATCATGAAAGTGCAAAATAACAGCGTGATAATTAATTGCGACGGTTTTTAC

CTGATCTCCCTGAAGGGGTATTTCTCCCAGGAGGTCAATATTTCTCTCCACTACCAAAAGGACGAGGAACCTCTCTTC

CAGCTCAAGAAAGTTAGAAGCGTCAATTCCCTGATGGTGGCCTCCCTGACTTATAAGGATAAAGTGTATCTCAATGTT

ACCACAGATAACACTTCTCTGGATGATTTCCATGTCAATGGTGGAGAGCTCATCCTCATTCACCAGAACCCTGGGGAG

TTCTGCGTACTGCAAGTCTCACACCGGTACCCGCGCATCCAAAGCATAAAAGTTCAATTCACCGAGTATAAAAAGAG

AAGGGTTTCATACTCACATCACAAAAGGAAGATGAAATTATGAAGGTTCAAAACAACTCTGTTATCATTAACTGCGAT

GGGTTCTATCTGATTTCACTGAAAGGTTACTTCAGCCAAGAGGTGAACATATCTCTGCATTATCAGAAAGATGAAGAG

CCCCTGTTCCAACTGAAGAAGGTCCGCTCAGTCAACTCACTGATGGTTGCATCCCTCACATATAAAGATAAGGTCTAT

CTGAATGTGACAACTGACAATACCTCACTGGATGACTTTCATGTTAACGGAGGCGAACTGATTCTCATACATCAGAAT

CCAGGAGAGTTCTGTGTCCTCCAAGTTTCCCATCGCTATCCTCGGATTCAATCTATCAAGGTTCAGTTTACTGAGTAC

AAAAAAGAAAAGGGATTTATTCTGACCTCTCAAAAAGAGGATGAGATAATGAAGGTCCAGAATAATTCCGTCATTATA

AACTGTGACGGCTTCTATCTCATATCCCTCAAGGGGTACTTTTCACAAGAAGTTAATATATCACTCCATTACCAAAAA

GATGAAGAGCCACTCTTTCAACTGAAAAAAGTCAGATCCGTCAACTCTCTCATGGTCGCTTCTCTCACCTACAAAGAC

AAAGTTTACCTGAACGTTACTACAGACAACACATCCCTGGACGACTTCCACGTGAATGGCGGGGAACTGATACTGATC

CACCAAAATCCCGGCGAATTTTGTGTGCTC

Human single chain OX40L trimer without signal sequence nucleotide sequence
(SEQ ID NO: 52)
CAGGTCTCTCATAGATACCCACGCATACAATCAATCAAAGTCCAATTTACAGAATATAAGAAGGAAAAAGGATTCATT

CTCACATCTCAGAAGGAGGACGAAATCATGAAAGTGCAAAATAACAGCGTGATAATTAATTGCGACGGTTTTTACCTG

ATCTCCCTGAAGGGGTATTTCTCCCAGGAGGTCAATATTTCTCTCCACTACCAAAAGGACGAGGAACCTCTCTTCCAG

CTCAAGAAAGTTAGAAGCGTCAATTCCCTGATGGTGGCCTCCCTGACTTATAAGGATAAAGTGTATCTCAATGTTACC

ACAGATAACACTTCTCTGGATGATTTCCATGTCAATGGTGGAGAGCTCATCCTCATTCACCAGAACCCTGGGGAGTTC

TGCGTACTGCAAGTCTCACACCGGTACCCGCGCATCCAAAGCATAAAAGTTCAATTCACCGAGTATAAAAAGAGAAG

GGTTTCATACTCACATCACAAAAGGAAGATGAAATTATGAAGGTTCAAAACAACTCTGTTATCATTAACTGCGATGGG

TTCTATCTGATTTCACTGAAAGGTTACTTCAGCCAAGAGGTGAACATATCTCTGCATTATCAGAAAGATGAAGAGCCC

CTGTTCCAACTGAAGAAGGTCCGCTCAGTCAACTCACTGATGGTTGCATCCCTCACATATAAAGATAAGGTCTATCTG

AATGTGACAACTGACAATACCTCACTGGATGACTTTCATGTTAACGGAGGCGAACTGATTCTCATACATCAGAATCCA

GGAGAGTTCTGTGTCCTCCAAGTTTCCCATCGCTATCCTCGGATTCAATCTATCAAGGTTCAGTTTACTGAGTACAAA

AAAGAAAAGGGATTTATTCTGACCTCTCAAAAAGAGGATGAGATAATGAAGGTCCAGAATAATTCCGTCATTATAAAC

-continued

TGTGACGGCTTCTATCTCATATCCCTCAAGGGGTACTTTTCACAAGAAGTTAATATATCACTCCATTACCAAAAAGAT
GAAGAGCCACTCTTTCAACTGAAAAAAGTCAGATCCGTCAACTCTCTCATGGTCGCTTCTCTCACCTACAAAGACAAA
GTTTACCTGAACGTTACTACAGACAACACATCCCTGGACGACTTCCACGTGAATGGCGGGGAACTGATACTGATCCAC
CAAAATCCCGGCGAATTTTGTGTGCTC

Human single chain OX40L-Fc (IgG1) trimer nucleotide sequence
(SEQ ID NO: 53)
ATGGAGTGGGGTTATCTGCTCGAAGTGACCTCCCTGCTGGCCGCCCTGCTCCTGCTGCAACGCTCTCCTATCGTGCAC
GCCCAGGTCTCTCATAGATACCCACGCATACAATCAATCAAAGTCCAATTTACAGAATATAAGAAGGAAAAAGGATTC
ATTCTCACATCTCAGAAGGAGGACGAAATCATGAAAGTGCAAAATAACAGCGTGATAATTAATTGCGACGGTTTTTAC
CTGATCTCCCTGAAGGGGTATTTCTCCCAGGAGGTCAATATTTCTCTCCACTACCAAAAGGACGAGGAACCTCTCTTC
CAGCTCAAGAAAGTTAGAAGCGTCAATTCCCTGATGGTGGCCTCCCTGACTTATAAGGATAAAGTGTATCTCAATGTT
ACCACAGATAACACTTCTCTGGATGATTTCCATGTCAATGGTGGAGAGCTCATCCTCATTCACCAGAACCCTGGGGAG
TTCTGCGTACTGCAAGTCTCACACCGGTACCCGCGCATCCAAAGCATAAAAGTTCAATTCACCGAGTATAAAAAAGAG
AAGGGTTTCATACTCACATCACAAAAGGAAGATGAAATTATGAAGGTTCAAAACAACTCTGTTATCATTAACTGCGAT
GGGTTCTATCTGATTTCACTGAAAGGTTACTTCAGCCAAGAGGTGAACATATCTCTGCATTATCAGAAAGATGAAGAG
CCCCTGTTCCAACTGAAGAAGGTCCGCTCAGTCAACTCACTGATGGTTGCATCCCTCACATATAAAGATAAGGTCTAT
CTGAATGTGACAACTGACAATACCTCACTGGATGACTTTCATGTTAACGGAGGCGAACTGATTCTCATACATCAGAAT
CCAGGAGAGTTCTGTGTCCTCCAAGTTTCCCATCGCTATCCTCGGATTCAATCTATCAAGGTTCAGTTTACTGAGTAC
AAAAAAGAAAGGGATTTATTCTGACCTCTCAAAAAGAGGATGAGATAATGAAGGTCCAGAATAATTCCGTCATTATA
AACTGTGACGGCTTCTATCTCATATCCCTCAAGGGGTACTTTTCACAAGAAGTTAATATATCACTCCATTACCAAAAA
GATGAAGAGCCACTCTTTCAACTGAAAAAAGTCAGATCCGTCAACTCTCTCATGGTCGCTTCTCTCACCTACAAAGAC
AAAGTTTACCTGAACGTTACTACAGACAACACATCCCTGGACGACTTCCACGTGAATGGCGGGGAACTGATACTGATC
CACCAAAATCCCGGCGAATTTTGTGTGCTCGACAAGACCCACACCTGCCCTCCCTGCCCTGCCCCTGAGCTGCTGGGC
GGACCTTCCGTGTTCCTGTTCCCTCCTAAGCCTAAGGACACCCTGATGATCTCCCGGACCCCTGAAGTGACATGCGTG
GTGGTGGACGTGTCCCACGAGGACCCTGAGGTGAAGTTCAACTGGTATGTGGACGGCGTGGAGGTGCACAACGCTAAG
ACCAAGCCTAGGGAGGAGCAGTACAACTCCACCTACCGGGTGGTGTCTGTGCTGACCGTGCTGCACCAGGACTGGCTG
AACGGCAAAGAATACAAGTGCAAGGTCTCCAACAAGGCCCTGCCCGCTCCCATCGAGAAAACCATCAGCAAGGCAAAG
GGCCAGCCTCGCGAGCCTCAGGTGTACACCCTGCCACCCAGCCGGGAGGAGATGACCAAGAACCAGGTGTCCCTGACC
TGTCTGGTGAAGGGCTTTTACCCTTCCGATATTGCCGTGGAGTGGGAGTCTAACGGCCAGCCCGAGAACAACTACAAG
ACCACCCCTCCTGTGCTGGACTCCGACGGCTCCTTCTTCCTGTACTCCAAGCTGACCGTGGACAAGTCCCGGTGGCAG
CAGGGCAACGTGTTCTCCTGCTCCGTGATGCACGAGGCCCTGCACAACCACTACACCCAGAAGAGCCTGTCTCTGTCT
CCTGGCAAGTGA AH-1 Peptide
(SEQ ID NO: 54)
SPSYVYHQF OX40L Stalk region
(SEQ ID NO: 55)
QVSHRYP OX40L TNF homology domain
(SEQ ID NO: 56)
EIMKVQNNSVIINCDGFYLISLKGYFSQEVNISLHYQKDEEPLFQLKKVRSVNSLMVASLTYKDKVYLNVTTDNTSLD
DFHVNGGELILIHQNPG Linker
(SEQ ID NO: 57)
GGGSGGG -continued Human IgG1 Fc region (13A Version)
(SEQ ID NO: 58)
DKTHTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDKLTKNQVSLTCLVKGFYPSD
IAVEWESNGQPENNYKTTPPVLKSDGSFFLYSKLTVDKSRWQQGNVFSCSVMHEALHNHYTQKSLSLSPGK Human IgG1 Fc region (13B Version)
(SEQ ID NO: 59)
DKTHTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVEGFYPSD
IAVEWESNGQPENNYKTTPPVLDSDGSFFLYSELTVDKSRWQQGNVFSCSVMHEALHNHYTQKSLSLSPGK Human IgG1 Fc region (13A Version)
(SEQ ID NO: 60)
EPKSSDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDKLTKNQVSLTCLVKG
FYPSDIAVEWESNGQPENNYKTTPPVLKSDGSFFLYSKLTVDKSRWQQGNVFSCSVMHEALHNHYTQKSLSLSPGK Human IgG1 Fc region (13B Version)
(SEQ ID NO: 61)
EPKSSDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTCLVEG
FYPSDIAVEWESNGQPENNYKTTPPVLDSDGSFFLYSELTVDKSRWQQGNVFSCSVMHEALHNHYTQKSLSLSPGK 336B13 Human single chain GITRL trimer-Fc (IgG1) with linkers with signal
sequence underlined
(SEQ ID NO: 62)
<u>MEWGYLLEVTSLLAALLLLQRSPIVHAL</u>QLETAKEPCMAKFGPLPSKWQMASSEPPCVNKVSDWKLEILQNGLYLIYG
QVAPNANYNDVAPFEVRLYKNKDMIQTLTNKSKIQNVGGTYELHVGDTIDLIFNSEHQVLKNNTYWGIILLANPQFIS
GGGSGGGEPCMAKFGPLPSKWQMASSEPPCVNKVSDWKLEILQNGLYLIYGQVAPNANYNDVAPFEVRLYKNKDMIQT
LTNKSKIQNVGGTYELHVGDTIDLIFNSEHQVLKNNTYWGIILLANPQFISGGGSGGGEPCMAKFGPLPSKWQMASSE
PPCVNKVSDWKLEILQNGLYLIYGQVAPNANYNDVAPFEVRLYKNKDMIQTLTNKSKIQNVGGTYELHVGDTIDLIFN
SEHQVLKNNTYWGIILLANPQFISDKTHTCPPCPAPELLGGPSVFLFPPKPKDTLMISRIPEVTCVVVDVSHEDPEVK
FNWYVDGVEVHNAKTKPREEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLTVDKSRWQQGNVFSCSVMHE
ALHNHYTQKSLSLSPGK 336B13 Human single chain GITRL trimer-Fc (IgG1) with linkers without
signal sequence
(SEQ ID NO: 63)
LQLETAKEPCMAKFGPLPSKWQMASSEPPCVNKVSDWKLEILQNGLYLIYGQVAPNANYNDVAPFEVRLYKNKDMIQT
LTNKSKIQNVGGTYELHVGDTIDLIFNSEHQVLKNNTYWGIILLANPQFISGGGSGGGEPCMAKFGPLPSKWQMASSE
PPCVNKVSDWKLEILQNGLYLIYGQVAPNANYNDVAPFEVRLYKNKDMIQTLINKSKIQNVGGTYELHVGDTIDLIFN
SEHQVLKNNTYWGIILLANPQFISGGGSGGGEPCMAKFGPLPSKWQMASSEPPCVNKVSDWKLEILQNGLYLIYGQVA
PNANYNDVAPFEVRLYKNKDMIQTLTNKSKIQNVGGTYELHVGDTIDLIFNSEHQVLKNNTYWGIILLANPQFISDKT
HTCPPCPAPELLGGPSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALHNHYTQKSLSLSPGK Human GITRL extracellular domain without stalk region amino acid sequence
(SEQ ID NO: 64)
EPCMAKFGPLPSKWQMASSEPPCVNKVSDWKLEILQNGLYLIYGQVAPNANYNDVAPFEVRLYKNKDMIQTLTNKSKI
QNVGGTYELHVGDTIDLIFNSEHQVLKNNTYWGIILLANPQFIS Human single chain GITRL trimer (2 stalk regions) amino acid sequence with
signal sequence underlined
(SEQ ID NO: 65)
<u>MEWGYLLEVTSLLAALLLLQRSPIVHA</u>EPCMAKFGPLPSKWQMASSEPPCVNKVSDWKLEILQNGLYLIYGQVAPNAN

YNDVAPFEVRLYKNKDMIQTLTNKSKIQNVGGTYELHVGDTIDLIFNSEHQVLKNNTYWGIILLANPQFISLQLETAK

EPCMAKFGPLPSKWQMASSEPPCVNKVSDWKLEILQNGLYLIYGQVAPNANYNDVAPFEVRLYKNKDMIQTLTNKSKI

QNVGGTYELHVGDTIDLIFNSEHQVLKNNTYWGIILLANPQFISLQLETAKEPCMAKFGPLPSKWQMASSEPPCVNKV

SDWKLEILQNGLYLIYGQVAPNANYNDVAPFEVRLYKNKDMIQTLTNKSKIQNVGGTYELHVGDTIDLIFNSEHQVLK

NNTYWGIILLANPQFIS

Human single chain GITRL trimer (2 stalk regions) amino acid sequence without
signal sequence
(SEQ ID NO: 66)
EPCMAKFGPLPSKWQMASSEPPCVNKVSDWKLEILQNGLYLIYGQVAPNANYNDVAPFEVRLYKNKDMIQTLTNKSKI

QNVGGTYELHVGDTIDLIFNSEHQVLKNNTYWGIILLANPQFISLQLETAKEPCMAKFGPLPSKWQMASSEPPCVNKV

SDWKLEILQNGLYLIYGQVAPNANYNDVAPFEVRLYKNKDMIQTLTNKSKIQNVGGTYELHVGDTIDLIFNSEHQVLK

NNTYWGIILLANPQFISLQLETAKEPCMAKFGPLPSKWQMASSEPPCVNKVSDWKLEILQNGLYLIYGQVAPNANYND

VAPFEVRLYKNKDMIQTLTNKSKIQNVGGTYELHVGDTIDLIFNSEHQVLKNNTYWGIILLANPQFIS

Human OX40L extracellular domain without stalk region amino acid sequence
(SEQ ID NO: 67)
RIQSIKVQFTEYKKEKGFILTSQKEDEIMKVQNNSVIINCDGFYLISLKGYFSQEVNISLHYQKDEEPLFQLKKVRSV

NSLMVASLTYKDKVYLNVTTDNTSLDDFHVNGGELILIHQNPGEFCVL

Human single chain OX40L trimer (2 stalk regions) amino acid sequence with
signal sequence underlined
(SEQ ID NO: 68)
<u>MEWGYLLEVTSLLAALLLLQRSPIVHA</u>RIQSIKVQFTEYKKEKGFILTSQKEDEIMKVQNNSVIINCDGFYLISLKGY

FSQEVNISLHYQKDEEPLFQLKKVRSVNSLMVASLTYKDKVYLNVTTDNTSLDDFHVNGGELILIHQNPGEFCVLQVS

HRYPRIQSIKVQFTEYKKEKGFILTSQKEDEIMKVQNNSVIINCDGFYLISLKGYFSQEVNISLHYQKDEEPLFQLKK

VRSVNSLMVASLTYKDKVYLNVTTDNTSLDDFHVNGGELILIHQNPGEFCVLQVSHRYPRIQSIKVQFTEYKKEKGFI

LTSQKEDEIMKVQNNSVIINCDGFYLISLKGYFSQEVNISLHYQKDEEPLFQLKKVRSVNSLMVASLTYKDKVYLNVT

IDNTSLDDFHVNGGELILIHQNPGEFCVL

Human single chain OX40L trimer (2 stalk regions) amino acid sequence without
signal sequence
(SEQ ID NO: 69)
RIQSIKVQFTEYKKEKGFILTSQKEDEIMKVQNNSVIINCDGFYLISLKGYFSQEVNISLHYQKDEEPLFQLKKVRSV

NSLMVASLTYKDKVYLNVTTDNTSLDDFHVNGGELILIHQNPGEFCVLQVSHRYPRIQSIKVQFTEYKKEKGFILTSQ

KEDEIMKVQNNSVIINCDGFYLISLKGYFSQEVNISLHYQKDEEPLFQLKKVRSVNSLMVASLTYKDKVYLNVTTDNT

SLDDFHVNGGELILIHQNPGEFCVLQVSHRYPRIQSIKVQFTEYKKEKGFILTSQKEDEIMKVQNNSVIINCDGFYLI

SLKGYFSQEVNISLHYQKDEEPLFQLKKVRSVNSLMVASLTYKDKVYLNVTTDNTSLDDFHVNGGELILIHQNPGEFC

VL

338F4 Human single chain OX40L trimer amino acid sequence without signal
sequence
(SEQ ID NO: 70)
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVLALQVSHRYPRIQSIKVQFTEYKK

EKGFILTSQKEDEIMKVQNNSVIINCDGFYLISLKGYFSQEVNISLHYQKDEEPLFQLKKVRSVNSLMVASLTYKDKV

YLNVTTDNTSLDDFHVNGGELILIHQNPGEFCVLALQVSHRYPRIQSIKVQFTEYKKEKGFILTSQKEDEIMKVQNNS

VIINCDGFYLISLKGYFSQEVNISLHYQKDEEPLFQLKKVRSVNSLMVASLTYKDKVYLNVTTDNTSLDDFHVNGGEL

ILIHQNPGEFCVL

338F5 Human single chain OX40L trimer amino acid sequence without signal
sequence (SEQ ID NO: 71)
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVLSHRYPRIQSIKVQFTEYKKEKGF

ILTSQKEDEIMKVQNNSVIINCDGFYLISLKGYFSQEVNISLHYQKDEEPLFQLKKVRSVNSLMVASLTYKDKVYLNV

TTDNTSLDDFHVNGGELILIHQNPGEFCVLSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKVYLNVTTDNTSLDDFHVNGGELILIHQNPG

EFCVL

338F6 Human single chain OX40L trimer amino acid sequence without signal
sequence (SEQ ID NO: 72)
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVLHRYPRIQSIKVQFTEYKKEKGFI

LTSQKEDEIMKVQNNSVIINCDGFYLISLKGYFSQEVNISLHYQKDEEPLFQLKKVRSVNSLMVASLTYKDKVYLNVT

TDNTSLDDFHVNGGELILIHQNPGEFCVLHRYPRIQSIKVQFTEYKKEKGFILTSQKEDEIMKVQNNSVIINCDGFYL

ISLKGYFSQEVNISLHYQKDEEPLFQLKKVRSVNSLMVASLTYKDKVYLNVTTDNTSLDDFHVNGGELILIHQNPGEF

CVL

338F5 Human single chain OX40L trimer nucleotide sequence without signal
sequence (SEQ ID NO: 73)
CAGGTCTCTCATAGATACCCACGCATACAATCAATCAAAGTCCAATTTACAGAATATAAGAAGGAAAAGGATTCATT

CTCACATCTCAGAAGGAGGACGAAATCATGAAAGTGCAAAATAACAGCGTGATAATTAATTGCGACGGTTTTTACCTG

ATCTCCCTGAAGGGGTATTTCTCCCAGGAGGTCAATATTTCTCTCCACTACCAAAAGGACGAGGAACCTCTCTTCCAG

CTCAAGAAAGTTAGAAGCGTCAATTCCCTGATGGTGGCCTCCCTGACTTATAAGGATAAAGTGTATCTCAATGTTACC

ACAGATAACACTTCTCTGGATGATTTCCATGTCAATGGTGGAGAGCTCATCCTCATTCACCAGAACCCTGGGGAGTTC

TGCGTACTGTCACACCGGTACCCGCGCATCCAAAGCATAAAAGTTCAATTCACCGAGTATAAAAAAGAGAAGGGTTTC

ATACTCACATCACAAAAGGAAGATGAAATTATGAAGGTTCAAAACAACTCTGTTATCATTAACTGCGATGGGTTCTAT

CTGATTTCACTGAAAGGTTACTTCAGCCAAGAGGTGAACATATCTCTGCATTATCAGAAAGATGAAGAGCCCCTGTTC

CAACTGAAGAAGGTCCGCTCAGTCAACTCACTGATGGTTGCATCCCTCACATATAAAGATAAGGTCTATCTGAATGTG

ACAACTGACAATACCTCACTGGATGACTTTCATGTTAACGGAGGCGAACTGATTCTCATACATCAGAATCCAGGAGAG

TTCTGTGTCCTCTCCCATCGCTATCCTCGGATTCAATCTATCAAGGTTCAGTTTACTGAGTACAAAAAGAAAAGGGA

TTTATTCTGACCTCTCAAAAAGAGGATGAGATAATGAAGGTCCAGAATAATTCCGTCATTATAAACTGTGACGGCTTC

TATCTCATATCCCTCAAGGGGTACTTTTCACAAGAAGTTAATATATCACTCCATTACCAAAAAGATGAAGAGCCACTC

TTTCAACTGAAAAAAGTCAGATCCGTCAACTCTCTCATGGTCGCTTCTCTCACCTACAAAGACAAAGTTTACCTGAAC

GTTACTACAGACAACACATCCCTGGACGACTTCCACGTGAATGGCGGGGAACTGATACTGATCCACCAAAATCCCGGC

GAATTTTGTGTGCTCTGA

OX40L Stalk region variant 1

(SEQ ID NO: 74)
ALQVSHRYP

OX40L Stalk region variant 2

(SEQ ID NO: 75)
SHRYP

OX40L Stalk region variant 3

(SEQ ID NO: 76)
HRYP

-continued

Human OX40L extracellular domain amino acid sequence variant 1
(SEQ ID NO: 77)
ALQVSHRYPRIQSIKVQFTEYKKEKGFILTSQKEDEIMKVQNNSVIINCDGFYLISLKGYFSQEVNISLHYQKDEEPL

FQLKKVRSVNSLMVASLTYKDKVYLNVTTDNTSLDDFHVNGGELILIHQNPGEFCVL

Human OX40L extracellular domain amino acid sequence variant 2
(SEQ ID NO: 78)
SHRYPRIQSIKVQFTEYKKEKGFILTSQKEDEIMKVQNNSVIINCDGFYLISLKGYFSQEVNISLHYQKDEEPLFQLK

KVRSVNSLMVASLTYKDKVYLNVTTDNTSLDDFHVNGGELILIHQNPGEFCVL

Human OX40L extracellular domain amino acid sequence variant 3
(SEQ ID NO: 79)
HRYPRIQSIKVQFTEYKKEKGFILTSQKEDEIMKVQNNSVIINCDGFYLISLKGYFSQEVNISLHYQKDEEPLFQLKK

VRSVNSLMVASLTYKDKVYLNVTTDNTSLDDFHVNGGELILIHQNPGEFCVL

338F5 Human single chain OX40L trimer-Fc (IgG1) amino acid sequence with
signal sequence underlined
(SEQ ID NO: 80)
<u>MEWGYLLEVTSLLAALLLLQRSPIVHA</u>QVSHRYPRIQSIKVQFTEYKKEKGFILTSQKEDEIMKVQNNSVIINCDGFY

LISLKGYFSQEVNISLHYQKDEEPLFQLKKVRSVNSLMVASLTYKDKVYLNVTTDNTSLDDFHVNGGELILIHQNPGE

FCVLSHRYPRIQSIKVQFTEYKKEKGFILTSQKEDEIMKVQNNSVIINCDGFYLISLKGYFSQEVNISLHYQKDEEPL

FQLKKVRSVNSLMVASLTYKDKVYLNVTTDNTSLDDFHVNGGELILIHQNPGEFCVLSHRYPRIQSIKVQFTEYKKEK

GFILTSQKEDEIMKVQNNSVIINCDGFYLISLKGYFSQEVNISLHYQKDEEPLFQLKKVRSVNSLMVASLTYKDKVYL

NVTTDNTSLDDFHVNGGELILIHQNPGEFCVLDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTTPPVLDSDGSFFLYSKLTVDKSRWQQGNV

FSCSVMHEALHNHYTQKSLSLSPGK

338F5 Human single chain OX40L trimer-Fc (IgG1) amino acid sequence without
signal sequence
(SEQ ID NO: 81)
QVSHRYPRIQSIKVQFTEYKKEKGFILTSQKEDEIMKVQNNSVIINCDGFYLISLKGYFSQEVNISLHYQKDEEPLFQ

LKKVRSVNSLMVASLTYKDKVYLNVTTDNTSLDDFHVNGGELILIHQNPGEFCVLSHRYPRIQSIKVQFTEYKKEKGF

ILTSQKEDEIMKVQNNSVIINCDGFYLISLKGYFSQEVNISLHYQKDEEPLFQLKKVRSVNSLMVASLTYKDKVYLNV

TTDNTSLDDFHVNGGELILIHQNPGEFCVLSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKVYLNVTTDNTSLDDFHVNGGELILIHQNPG

EFCVLDKTHTCPPCPAPELLGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLPPSREEMTKNQVSLTCLVKG

FYPSDIAVEWESNGQPENNYKTTPPVLDSDGSFFLYSKLTVDKSRWQQGNVFSCSVMHEALHNHYTQKSLSLSPGK

Human CD40L (TNFSF5) amino acid sequence
(SEQ ID NO: 82)
MIETYNQTSPRSAATGLPISMKIFMYLLTVFLITQMIGSALFAVYLHRRLDKIEDERNLHEDFVFMKTIQRCNTGERS

LSLLNCEEIKSQFEGFVKDIMLNKEETKKENSFEMQKGDQNPQIAAHVISEASSKTTSVLQWAEKGYYTMSNNLVTLE

NGKQLTVKRQGLYYIYAQVTFCSNREASSQAPFIASLCLKSPGRFERILLRAANTHSSAKPCGQQSIHLGGVFELQPG

ASVFVNVTDPSQVSHGTGFTSFGLLKL

Human CD40L extracellular domain amino acid sequence
(SEQ ID NO: 83)
HRRLDKIEDERNLHEDFVFMKTIQRCNTGERSLSLLNCEEIKSQFEGFVKDIMLNKEETKKENSFEMQKGDQNPQIAA

HVISEASSKTTSVLQWAEKGYYTMSNNLVTLENGKQLTVKRQGLYYIYAQVTFCSNREAS-
SQAPFIASLCLKSPGRFE

RILLRAANTHSSAKPCGQQSIHLGGVFELQPGASVFVNVTDPSQVSHGTGFTSFGLLKL

Human CD40L extracellular domain with stalk fragment 1 (aa 113-261)
(SEQ ID NO: 84)
MQKGDQNPQIAAHVISEASSKTTSVLQWAEKGYYTMSNNLVTLENGKQLTVKRQGLYYIYAQVTFCSNREASSQAPFI
ASLCLKSPGRFERILLRAANTHSSAKPCGQQSIHLGGVFELQPGASVFVNVTDPSQVSHGTGFTSFGLLKL Human single chain CD40L trimer amino acid sequence without signal sequence
(SEQ ID NO: 85)
MQKGDQNPQIAAHVISEASSKTTSVLQWAEKGYYTMSNNLVTLENGKQLTVKRQGLYYIYAQVTFCSNREASSQAPFI
ASLCLKSPGRFERILLRAANTHSSAKPCGQQSIHLGGVFELQPGASVFVNVTDPSQVSHGTGFTSFGLLKLMQKGDQN
PQIAAHVISEASSKTTSVLQWAEKGYYTMSNNLVTLENGKQLTVKRQGLYYIYAQVTFCSNREASSQAPFIASLCLKS
PGRFERILLRAANTHSSAKPCGQQSIHLGGVFELQPGASVFVNVTDPSQVSHGTGFTSFGLLKLMQKGDQNPQIAAHV
ISEASSKTTSVLQWAEKGYYTMSNNLVTLENGKQLTVKRQGLYYIYAQVTFCSNREASSQAPFIASLCLKSPGRFERI
LLRAANTHSSAKPCGQQSIHLGGVFELQPGASVFVNVTDPSQVSHGTGFTSFGLLKL Human single chain CD40L trimer nucleotide sequence without signal sequence
(SEQ ID NO: 86)
ATGCAAAAGGGGATCAGAATCCTCAAATTGCAGCACATGTCATATCTGAGGCCAGCTCAAAAACAACATCTGTGCTC
CAGTGGGCTGAAAAAGGATACTACACCATGAGCAACAACCTCGTTACCCTGGAAAATGGGAAACAGCTGACCGTTAAA
AGACAAGGACTCTATTATATCTATGCCCAAGTCACCTTCTGTTCCAATCGGGAAGCATCTTCACAAGCTCCATTTATC
GCCAGCCTCTGCCTCAAGTCCCCCGGTCGGTTCGAGAGAATCCTCCTCAGAGCTGCAAATACCCACTCTTCCGCCAAA
CCTTGCGGGCAACAATCCATTCACCTCGGAGGAGTTTTTGAACTGCAACCAGGGGCTTCTGTGTTTGTCAATGTGACT
GATCCAAGCCAAGTGTCTCATGGAACTGGCTTCACTTCCTTTGGCCTCCTCAAACTCATGCAGAAAGGGGACCAAAAC
CCCCAGATAGCCGCTCACGTTATTTCCGAAGCAAGCTCAAAAACAACATCTGTGCTCCAGTGGGCTGAAAAAGGATAC
TACACCATGAGCAACAACCTCGTTACCCTGGAGAACGGAAAGCAACTCACTGTGAAGCGGCAGGGGCTGTACTACATA
TACGCACAAGTGACTTTTTGCAGCAACAGGGAGGCATCCTCTCAGGCCCCTTTCATTGCCAGCCTCTGCCTGAAGTCC
CCCGGTAGATTCGAGAGAATCCTCCTCAGAGCTGCAAATACCCACTCCTCCGCAAAACCCTGTGGCCAGCAGAGCATC
CATCTGGGCGGCGTGTTCGAGCTCCAGCCTGGGGCCTCCGTCTTCGTGAACGTCACCGACCCTTCCCAAGTCAGCCAC
GGCACTGGCTTCACATCCTTTGGCCTCCTCAAACTCATGCAAAAAGGCGATCAGAATCCTCAAATTGCTGCACATGTC
ATTTCCGAAGCCTCATCCAAAACTACCTCCGTCCTGCAATGGGCCGAGAAGGGGTATTATACAATGTCAAATAACCTG
GTTACTCTGGAAAACGGCAAACAGCTCACTGTTAAGCGCCAAGGTCTCTACTATATATATGCACAAGTTACTTTCTGT
TCAAATCGCGAAGCATCATCACAAGCACCATTTATAGCATCACTCTGTCTCAAGTCACCAGGTCGCTTTGAACGCATA
CTGCTCCGCGCAGCAAATACTCACTCATCAGCAAAACCATGCGGTCAACAATCAATACACCTCGGTGGTGTTTTGAG
CTCCAACCAGGCGCTTCAGTTTTTGTTAATGTTACTGATCCATCACAAGTTTCACATGGTACAGGTTTCACTTCATTT
GGTCTGCTCAAACTCTAATAG Human CD40L anchor region and extracellular domain amino acid sequence
(SEQ ID NO: 87)
IFMYLLTVFLITQMIGSALFAVYLHRRLDKIEDERNLHEDFVFMKTIQRCNTGERSLSLLNCEEIKSQFEGFVKDIML
NKEETKKENSFEMQKGDQNPQIAAHVISEASSKTTSVLQWAEKGYYTMSNNLVTLENGKQLTVKRQGLYYIYAQVTFC
SNREASSQAPFIASLCLKSPGRFERILLRAANTHSSAKPCGQQSIHLGGVFELQPGASVFVNVTDPSQVSHGTGFTSF
GLLKL Human single chain CD40L trimer amino acid sequence with signal sequence
underlined
(SEQ ID NO: 88)
<u>MEWGYLLEVTSLLAALLLLQRSPIVHA</u>MQKGDQNPQIAAHVISEASSKTTSVLQWAEKGYYTMSNNLVTLENGKQLTV
KRQGLYYIYAQVTFCSNREASSQAPFIASLCLKSPGRFERILLRAANTHSSAKPCGQQSIHLGGVFELQPGASVFVNV
TDPSQVSHGTGFTSFGLLKLMQKGDQNPQIAAHVISEASSKTTSVLQWAEKGYYTMSNNLVTLENGKQLTVKRQGLYY
IYAQVTFCSNREASSQAPFIASLCLKSPGRFERILLRAANTHSSAKPCGQQSIHLGGVFELQPGASVFVNVTDPSQVS
HGTGFTSFGLLKLMQKGDQNPQIAAHVISEASSKTTSVLQWAEKGYYTMSNNLVTLENGKQLTVKRQGLYYIYAQVTF

CSNREASSQAPFIASLCLKSPGRFERILLRAANTHSSAKPCGQQSIHLGGVFELQPGASVFVNVTDPSQVSHGTGFTS

FGLLKL

Human single chain CD40L trimer-Fc (IgG1) amino acid sequence with signal
sequence underlined
(SEQ ID NO: 89)
MEWGYLLEVTSLLAALLLLQRSPIVHAMQKGDQNPQIAAHVISEASSKTTSVLQWAEKGYYTMSNNLVTLENGKQLTV

KRQGLYYIYAQVTFCSNREASSQAPFIASLCLKSPGRFERILLRAANTHSSAKPCGQQSIHLGGVFELQPGASVFVNV

TDPSQVSHGTGFTSFGLLKLMQKGDQNPQIAAHVISEASSKTTSVLQWAEKGYYTMSNNLVTLENGKQLTVKRQGLYY

IYAQVTFCSNREASSQAPFIASLCLKSPGRFERILLRAANTHSSAKPCGQQSIHLGGVFELQPGASVFVNVTDPSQVS

HGTGFTSFGLLKLMQKGDQNPQIAAHVISEASSKTTSVLQWAEKGYYTMSNNLVTLENGKQLTVKRQGLYYIYAQVTF

CSNREASSQAPFIASLCLKSPGRFERILLRAANTHSSAKPCGQQSIHLGGVFELQPGASVFVNVTDPSQVSHGTGFTS

FGLLKLDKTHTCPPCPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQGNVFSCSVMHEALHNHYTQKSLSLSPGK

Human single chain CD40L trimer-Fc (IgG1) amino acid sequence without signal
sequence
(SEQ ID NO: 90)
MQKGDQNPQIAAHVISEASSKTTSVLQWAEKGYYTMSNNLVTLENGKQLTVKRQGLYYIYAQVTFCSNREASSQAPFI

ASLCLKSPGRFERILLRAANTHSSAKPCGQQSIHLGGVFELQPGASVFVNVTDPSQVSHGTGFTSFGLLKLMQKGDQN

PQIAAHVISEASSKTTSVLQWAEKGYYTMSNNLVTLENGKQLTVKRQGLYYIYAQVTFCSNREASSQAPFIASLCLKS

PGRFERILLRAANTHSSAKPCGQQSIHLGGVFELQPGASVFVNVTDPSQVSHGTGFTSFGLLKLMQKGDQNPQIAAHV

ISEASSKTTSVLQWAEKGYYTMSNNLVTLENGKQLTVKRQGLYYIYAQVTFCSNREAS-
SQAPFIASLCLKSPGRFERI

LLRAANTHSSAKPCGQQSIHLGGVFELQPGASVFVNVTDPSQVSHGTGFTSFGLLKLDKTHTCPPCPAPELLGGPSVF

LFPPKPKDTLMISRTPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

Human single chain CD40L trimer-Fc (IgG2) amino acid sequence with signal
sequence underlined
(SEQ ID NO: 91)
<u>MEWGYLLEVTSLLAALLLLQRSPIVHA</u>MQKGDQNPQIAAHVISEASSKTTSVLQWAEKGYYTMSNNLVTLENGKQLTV

KRQGLYYIYAQVTFCSNREASSQAPFIASLCLKSPGRFERILLRAANTHSSAKPCGQQSIHLGGVFELQPGASVFVNV

TDPSQVSHGTGFTSFGLLKLMQKGDQNPQIAAHVISEASSKTTSVLQWAEKGYYTMSNNLVTLENGKQLTVKRQGLYY

IYAQVTFCSNREASSQAPFIASLCLKSPGRFERILLRAANTHSSAKPCGQQSIHLGGVFELQPGASVFVNVTDPSQVS

HGTGFTSFGLLKLMQKGDQNPQIAAHVISEASSKTTSVLQWAEKGYYTMSNNLVTLENGKQLTVKRQGLYYIYAQVTF

CSNREASSQAPFIASLCLKSPGRFERILLRAANTHSSAKPCGQQSIHLGGVFELQPGASVFVNVTDPSQVSHGTGFTS

FGLLKLVERKSCVECPPCPAPPVAGPSVFLFPPKPKDTLMISRIPEVTCVVVDVSHEDPEVQFNWYVDGVEVHNAKTK

PREEQFNSTFRVVSVLTVVHQDWLNGKEYKCKVSNKGLPAPIEKTISKTKGQPREPQVYTLPPSREEMTKNQVSLTCL

VKGFYPSDIAVEWESNGQPENNYKTTPPMLDSDGSFFLYSKLTVDKSRWQQGNVFSCSVMHEALHNHYTQKSLSLSPG

K

Human single chain CD40L trimer-Fc (IgG2) amino acid sequence without signal
sequence
(SEQ ID NO: 92)
MQKGDQNPQIAAHVISEASSKTTSVLQWAEKGYYTMSNNLVTLENGKQLTVKRQGLYYIYAQVTFCSNREASSQAPFI

ASLCLKSPGRFERILLRAANTHSSAKPCGQQSIHLGGVFELQPGASVFVNVTDPSQVSHGTGFTSFGLLKLMQKGDQN

PQIAAHVISEASSKTTSVLQWAEKGYYTMSNNLVTLENGKQLTVKRQGLYYIYAQVTFCSNREASSQAPFIASLCLKS

PGRFERILLRAANTHSSAKPCGQQSIHLGGVFELQPGASVFVNVTDPSQVSHGTGFTSFGLLKLMQKGDQNPQIAAHV

-continued

ISEASSKTTSVLQWAEKGYYTMSNNLVTLENGKQLTVKRQGLYYIYAQVTFCSNREAS-
SQAPFIASLCLKSPGRFERI

LLRAANTHSSAKPCGQQSIHLGGVFELQPGASVFVNVTDPSQVSHGTGFTSFGLLKLVERKSCVECPPCPAPPVAGPS

VFLFPPKPKDTLMISRTPEVTCVVVDVSHEDPEVQFNWYVDGVEVHNAKTKPREEQFNSTFRVVSVLTVVHQDWLNGK

EYKCKVSNKGLPAPIEKTISKTKGQPREPQVYTLPPSREEMTKNQVSLTCLVKGFYPSDIAVEWESNGQPENNYKTTP

PMLDSDGSFFLYSKLTVDKSRWQQGNVFSCSVMHEALHNHYTQKSLSLSPGK

Human CD40L Stalk Region
(SEQ ID NO: 93)
HRRLDKIEDERNLHEDFVFMKTIQRCNTGERSLSLLNCEEIKSQFEGFVKDIMLNKEETKKENSFEMQKGDQ Human CD40L TNF homology domain
(SEQ ID NO: 94)
IAAHVISEASSKTTSVLQWAEKGYYTMSNNLVTLENGKQLTVKRQGLYYIYAQVTFCSNREASSQAPFIASLCLKSPG

RFERILLRAANTHSSAKPCGQQSIHLGGVFELQPGASVFVNVTDPSQVSHGTGFTSFGLLKL

Human CD40Lextracellular domain without stalk region amino acid sequence
(SEQ ID NO: 95)
NPQIAAHVISEASSKTTSVLQWAEKGYYTMSNNLVTLENGKQLTVKRQGLYYIYAQVTFCSNREASSQAPFIASLCLK

SPGRFERILLRAANTHSSAKPCGQQSIHLGGVFELQPGASVFVNVTDPSQVSHGTGFTSFGLLKL

Human single chain CD40L trimer (2 stalks regions) amino acid sequence with
signal sequence underlined
(SEQ ID NO: 96)
<u>MEWGYLLEVTSLLAALLLLQRSPIVHA</u>NPQIAAHVISEASSKTTSVLQWAEKGYYTMSNNLVTLENGKQLTVKRQGLY

YIYAQVTFCSNREASSQAPFIASLCLKSPGRFERILLRAANTHSSAKPCGQQSIHLGGVFELQPGASVFVNVTDPSQV

SHGTGFTSFGLLKLMQKGDQNPQIAAHVISEASSKTTSVLQWAEKGYYTMSNNLVTLENGKQLTVKRQGLYYIYAQVT

FCSNREASSQAPFIASLCLKSPGRFERILLRAANTHSSAKPCGQQSIHLGGVFELQPGASVFVNVTDPSQVSHGTGFT

SFGLLKLMQKGDQNPQIAAHVISEASSKTTSVLQWAEKGYYTMSNNLVTLENGKQLTVKRQGLYYIYAQVTFCSNREA

SSQAPFIASLCLKSPGRFERILLRAANTHSSAKPCGQQSIHLGGVFELQPGASVFVNVTDPSQVSHGTGFTSFGLLKL

Human single chain CD40L trimer (2 stalks regions) amino acid sequence without
signal sequence
(SEQ ID NO: 97)
NPQIAAHVISEASSKTTSVLQWAEKGYYTMSNNLVTLENGKQLTVKRQGLYYIYAQVTFCSNREASSQAPFIASLCLK

SPGRFERILLRAANTHSSAKPCGQQSIHLGGVFELQPGASVFVNVTDPSQVSHGTGFTSFGLLKLMQKGDQNPQIAAH

VISEASSKTTSVLQWAEKGYYTMSNNLVTLENGKQLTVKRQGLYYIYAQVTFCSNREASSQAPFIASLCLKSPGRFER

ILLRAANTHSSAKPCGQQSIHLGGVFELQPGASVFVNVTDPSQVSHGTGFTSFGLLKLMQKGDQNPQIAAHVISEASS

KTTSVLQWAEKGYYTMSNNLVTLENGKQLTVKRQGLYYIYAQVTFCSNREASSQAPFIASLCLKSPGRFERILLRAAN

THSSAKPCGQQSIHLGGVFELQPGASVFVNVTDPSQVSHGTGFTSFGLLKL

Human CD40L Stalk Region-fragment 1
(SEQ ID NO: 98)
MQKGDQ

Human CD40L Stalk Region-fragment 2
(SEQ ID NO: 99)
FEMQKGDQ

Human CD40L Stalk Region-fragment 3
(SEQ ID NO: 100)
EMQKGDQ

Human CD40L Stalk Region-fragment 4
(SEQ ID NO: 101)
QKGDQ

Human CD40L Stalk Region-fragment 5
(SEQ ID NO: 102)
KGDQ

-continued

Human CD40L extracellular domain with stalk fragment 2 (aa 111-261)
(SEQ ID NO: 103)
FEMQKGDQNPQIAAHVISEASSKTTSVLQWAEKGYYTMSNNLVTLENGKQLTVKRQGLYYIYAQVTFCSNREASSQAP

FIASLCLKSPGRFERILLRAANTHSSAKPCGQQSIHLGGVFELQPGASVFVNVTDPSQVSHGTGFTSFGLLKL

Human CD40L extracellular domain with stalk fragment 3 (aa 112-261)
(SEQ ID NO: 104)
EMQKGDQNPQIAAHVISEASSKTTSVLQWAEKGYYTMSNNLVTLENGKQLTVKRQGLYYIYAQVTFCSNREASSQAPF

IASLCLKSPGRFERILLRAANTHSSAKPCGQQSIHLGGVFELQPGASVFVNVTDPSQVSHGTGFTSFGLLKL

Human CD40L extracellular domain with stalk fragment 4 (aa 114-261)
(SEQ ID NO: 105)
QKGDQNPQIAAHVISEASSKTTSVLQVAEKGYYTMSNNLVTLENGKQLTVKRQGLYYIYAQVTFCSNREASSQAPFIA

SLCLKSPGRFERILLRAANTHSSAKPCGQQSIHLGGVFELQPGASVFVNVTDPSQVSHGTGFTSFGLLKL

Human CD40L extracellular domain with stalk fragment 5 (aa 115-261)
(SEQ ID NO: 106)
KGDQNPQIAAHVISEASSKTTSVLQNAEKGYYTMSNNLVTLENGKQLTVKRQGLYYIYAQVTFCSNREASSQAPFIAS

LCLKSPGRFERILLRAANTHSSAKPCGQQSIHLGGVFELQPGASVFVNVTDPSQVSHGTGFTSFGLLKL

What is claimed is:

1. A method of treating cancer in a subject, comprising administering to a subject a therapeutically effective amount of a polypeptide comprising a first, second, and third copy of the extracellular domain of a human tumor necrosis factor receptor ligand superfamily (TNFSF) protein or a fragment thereof capable of binding a receptor of the TNFSF protein, wherein at least one of the first, second, or third copies of the extracellular domain or a fragment thereof comprises the stalk region of the TNFSF protein, wherein the polypeptide does not comprise a linker between the first and second or the second and third copies of the extracellular domain or fragment thereof, and wherein the polypeptide comprises the first, second, and third copy of the extracellular domain of the TNFSF protein or fragment thereof as a single chain polypeptide.

2. The method of claim 1, wherein the TNFSF protein is glucocorticoid-induced tumor necrosis factor receptor ligand (GITRL).

3. The method of claim 2, wherein the polypeptide comprises SEQ ID NO:5 or SEQ ID NO:66.

4. The method of claim 3, wherein the stalk region comprises SEQ ID NO:32.

5. The method of claim 2, wherein the polypeptide further comprises a human Fc region or an immunoglobulin heavy chain.

6. The method of claim 5, wherein the human Fc region is selected from the group consisting of: SEQ ID NO:10, SEQ ID NO:11, SEQ ID NO:12, SEQ ID NO:13, and SEQ ID NO:14.

7. The method of claim 3, wherein the polypeptide activates GITR and/or induces GITR activity.

8. The method of claim 1, wherein the polypeptide is encoded by the plasmid deposited with ATCC and assigned designation number PTA-122112.

9. The method of claim 1, wherein at least one of the first, second, or third copies of the extracellular domain or a fragment thereof comprises SEQ ID NO:3.

10. The method of claim 2, wherein the polypeptide comprises SEQ ID NO:66.

11. The method of claim 2, wherein the polypeptide comprises SEQ ID NO:5.

12. The method of claim 11, wherein the polypeptide further comprises a human Fc region or an immunoglobulin heavy chain.

13. The method of claim 2, wherein the cancer is selected from the group consisting of colorectal cancer, colon cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, head and neck cancer, lymphoma and leukemia.

14. The method of claim 2, which further comprises administering at least one additional therapeutic agent to the subject.

15. The method of claim 14, wherein the additional therapeutic agent is a chemotherapeutic agent or an agent that stimulates immune response.

16. The method of claim 14, wherein the additional therapeutic agent is an anti-PD-1 antibody, an anti-PD-L1 antibody, an anti-CTLA-4 antibody, or an anti-TIGIT antibody.

17. A method of treating cancer in a subject, comprising administering to a subject a therapeutically effective amount of a polypeptide comprising a first, second, and third copy of the extracellular domain of a human TNFSF protein or a fragment thereof capable of binding a receptor of the TNFSF protein,
    wherein at least one of the first, second, or third copies of the extracellular domain or a fragment thereof comprises the stalk region of the TNFSF protein,
    wherein the polypeptide does not comprise a linker between the first and second or the second and third copies of the extracellular domain or fragment thereof,
    wherein the polypeptide comprises the first, second, and third copy of the extracellular domain of the TNFSF protein or fragment thereof as a single chain polypeptide,
    wherein the TNFSF protein is GITRL, and
    wherein the polypeptide comprises SEQ ID NO:7.

18. A method of treating cancer in a subject, comprising administering to a subject a therapeutically effective amount of a homodimeric agent comprising a polypeptide comprising a first, second, and third copy of the extracellular domain of a human TNFSF protein or a fragment thereof capable of binding a receptor of the TNFSF protein, wherein at least one of the first, second, or third copies of the extracellular domain or a fragment thereof comprises the stalk region of the TNFSF protein, wherein the polypeptide does not comprise a linker between the first and second or the second and third copies of the extracellular domain or fragment thereof, and wherein the polypeptide comprises the first, second, and third copy of the extracellular domain of the TNFSF protein or fragment thereof as a single chain polypeptide.

* * * * *